United States Patent
Yen et al.

(10) Patent No.: US 11,629,140 B2
(45) Date of Patent: Apr. 18, 2023

(54) ORGANIC COMPOUND AND ORGANIC ELECTROLUMINESCENCE DEVICE USING THE SAME

(71) Applicants: Feng-Wen Yen, Taipei (TW); Li-Chieh Chuang, Nantou (TW)

(72) Inventors: Feng-Wen Yen, Taipei (TW); Li-Chieh Chuang, Nantou (TW)

(73) Assignee: LUMINESCENCE TECHNOLOGY CORP., Hsin-Chu (TW)

( * ) Notice: Subject to any disclaimer, the term of this patent is extended or adjusted under 35 U.S.C. 154(b) by 745 days.

(21) Appl. No.: 16/532,515

(22) Filed: Aug. 6, 2019

(65) Prior Publication Data
US 2021/0040075 A1    Feb. 11, 2021

(51) Int. Cl.
*C07D 413/04*    (2006.01)
*C07D 417/04*    (2006.01)
*C07D 265/38*    (2006.01)
*C07F 7/08*      (2006.01)
*C07D 279/36*    (2006.01)
*C07D 401/04*    (2006.01)
*H01L 51/00*     (2006.01)

(52) U.S. Cl.
CPC ......... *C07D 413/04* (2013.01); *C07D 265/38* (2013.01); *C07D 279/36* (2013.01); *C07D 401/04* (2013.01); *C07D 417/04* (2013.01); *C07F 7/0816* (2013.01); *H01L 51/0054* (2013.01); *H01L 51/0069* (2013.01); *H01L 51/0072* (2013.01)

(58) Field of Classification Search
None
See application file for complete search history.

(56) References Cited

FOREIGN PATENT DOCUMENTS

CN    106467531 A    *   3/2017
KR    10-2014-0034537    *   3/2014

OTHER PUBLICATIONS

Machine English Translation of Pyo et al. (KR-10-2014-0034537). Feb. 4, 2022.*
Machine English translation of Tang et al. (CN 106467531 A). Jun. 21, 2022.*

* cited by examiner

*Primary Examiner* — Jay Yang

(57) ABSTRACT

An organic compound is described. An organic electroluminescence device comprises the organic compound, as a host of an emissive layer, or as a hole blocking layer. The organic compound may increase a half-life or current efficiency of the organic electroluminescence device. The organic compound may lower a driving voltage of the organic electroluminescence device. The mentioned organic compound may have the following formula:

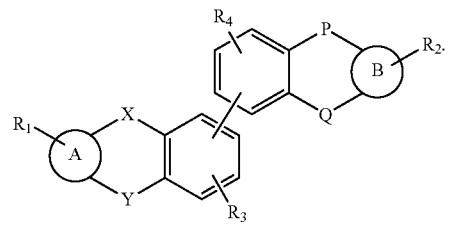

The same definition as described in the present invention.

6 Claims, 3 Drawing Sheets

ORGANIC COMPOUND AND ORGANIC ELECTROLUMINESCENCE DEVICE USING THE SAME

FIELD OF INVENTION

The present invention relates to an organic compound and, more particularly, to an organic electroluminescence device using the organic compound.

BACKGROUND OF THE INVENTION

Organic electroluminescence (organic EL) devices, i.e., organic light-emitting diodes (OLEDs) that make use of organic compounds, are becoming increasingly desirable than before. One of the organic compounds has the following formula:

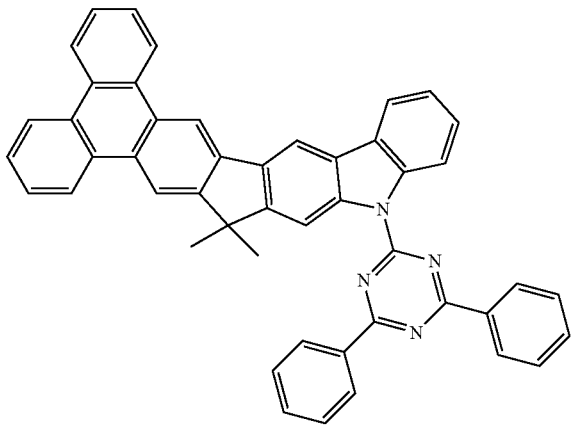

H1

For OLEDs, organic compounds may have performance advantages over conventional materials. For example, the wavelength at which an emissive layer emits light may generally be readily tuned with appropriate dopants. However, there is still a need for improvement of those organic compounds in an organic EL device, for example, in relation to the current efficiency, driving voltage or half-life of the organic EL device.

SUMMARY OF THE INVENTION

An object of the invention may be to provide an organic compound and an organic EL device using the same.

Another object of the present invention may be to improve an organic compound of an organic EL device, so that the organic EL device may have a higher current efficiency, a lower driving voltage, or a longer half-life.

According to the present invention, an organic compound which may be applied in an organic EL device is disclosed. The organic compound may have the following formula (C):

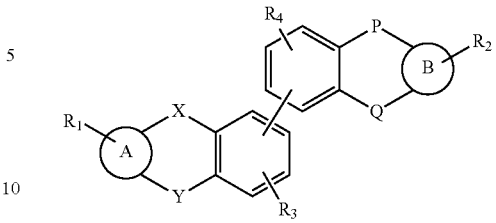

formual (C)

wherein P is a divalent bridge selected from the group consisting of NAr, O, S, $CR_5R_6$ and $SiR_7R_8$; Q is a single bond or a divalent bridge selected from the group consisting of NAr, O, S, $CR_5R_6$ and $SiR_7R_8$; at least one of X and Y is NAr; X is a divalent bridge selected from the group consisting of O, S, $CR_5R_6$ and $SiR_7R_8$ if X is not NAr; Y is a divalent bridge selected from the group consisting of O, S, $CR_5R_6$ and $SiR_7R_8$ if Y is not NAr; A represents a substituted or unsubstituted fused ring hydrocarbons unit having two rings; B represents a substituted or unsubstituted fused ring hydrocarbons unit having one or two rings; Ar represents a substituted or unsubstituted aryl group having 6 to 30 carbon atoms; and $R_1$ to $R_8$ are independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 7 to 30 carbon atoms; a substituted or unsubstituted arylamine group having 6 to 30 ring carbon atoms, and a substituted or unsubstituted heteroarylamine group having 5 to 30 ring carbon atoms.

The present invention further discloses an organic EL device. The organic EL device may comprise an anode, a cathode and one or more organic layers formed between the anode and the cathode. At least one of the organic layers comprises the organic compound of formula (C).

DESCRIPTION OF THE PREFERRED EMBODIMENTS

What probed into the invention is the organic compound and organic EL device using the organic compound. Detailed descriptions of the production, structure and elements will be provided as follows such that the invention can be fully understood. Obviously, the application of the invention is not confined to specific details familiar to those skilled in the art. On the other hand, the common elements and procedures that are known to everyone are not described in details to avoid unnecessary limits of the invention. Some preferred embodiments of the present invention will now be described in greater detail as follows. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

In a first embodiment of the present invention, an organic compound may have the following formula (C):

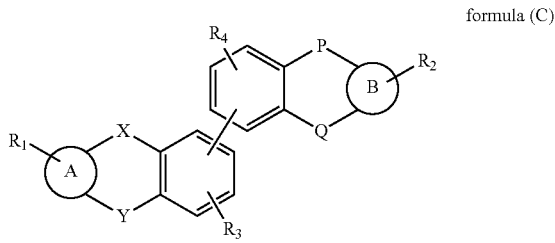

formula (C)

wherein P may be a divalent bridge selected from the group consisting of NAr, O, S, $CR_5R_6$ and $SiR_7R_8$. Q may be a single bond or a divalent bridge selected from the group consisting of NAr, O, S, $CR_5R_6$ and $SiR_7R_8$. At least one of X and Y may be NAr. X may be a divalent bridge selected from the group consisting of O, S, $CR_5R_6$ and $SiR_7R_8$ if X is not NAr. Y may be a divalent bridge selected from the group consisting of O, S, $CR_5R_6$ and $SiR_7R_8$ if Y is not NAr.

In formula (C), A may represent a substituted or unsubstituted fused ring hydrocarbons unit having two rings. B may represent a substituted or unsubstituted fused ring hydrocarbons unit having one or two rings.

Ar may represent a substituted or unsubstituted aryl group having 6 to 30 carbon atoms. $R_1$ to $R_8$ may be independently selected from the group consisting of a hydrogen atom, a halide, a substituted or unsubstituted alkyl group having 1 to 30 carbon atoms, a substituted or unsubstituted aryl group having 6 to 30 carbon atoms, a substituted or unsubstituted aralkyl group having 7 to 30 carbon atoms; a substituted or unsubstituted arylamine group having 6 to 30 ring carbon atoms, and a substituted or unsubstituted heteroarylamine group having 5 to 30 ring carbon atoms. The alkyl group, aralkyl group, aryl group, heteroaryl group, arylamine group, or heteroarylamine group is substituted by, for example, a halogen, an alkyl group, an aryl group, or a heteroaryl group.

Figure 1:
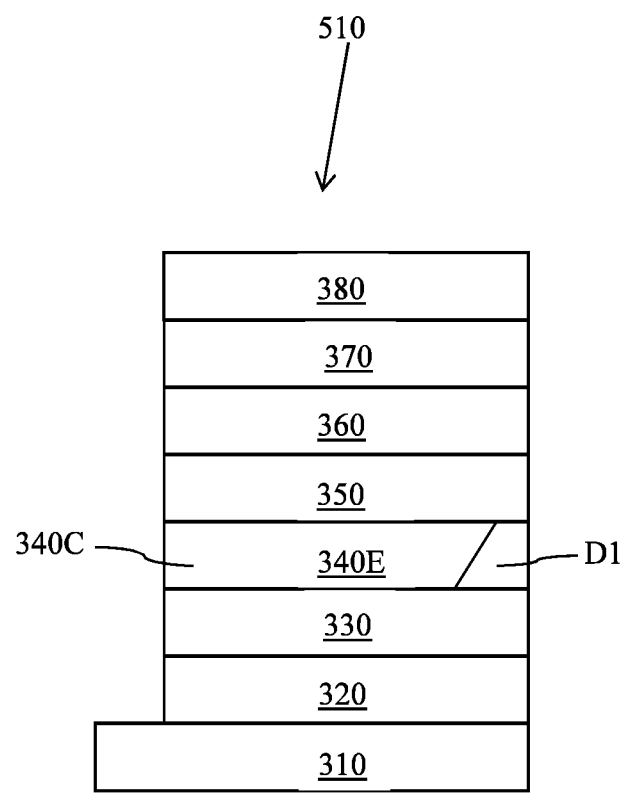
FIG. 1 is a cross-sectional view of a first organic EL device according to a second embodiment of the present invention.

In a second embodiment of the present invention, a first organic EL device using the organic compound of formula (C) is disclosed. FIG. 1 is a cross-sectional view of the first organic EL device. Referring to FIG. 1, the first organic EL device 510 may comprise the organic compound of formula (C) as a host 340C of an emissive layer 340E.

Figure 2:
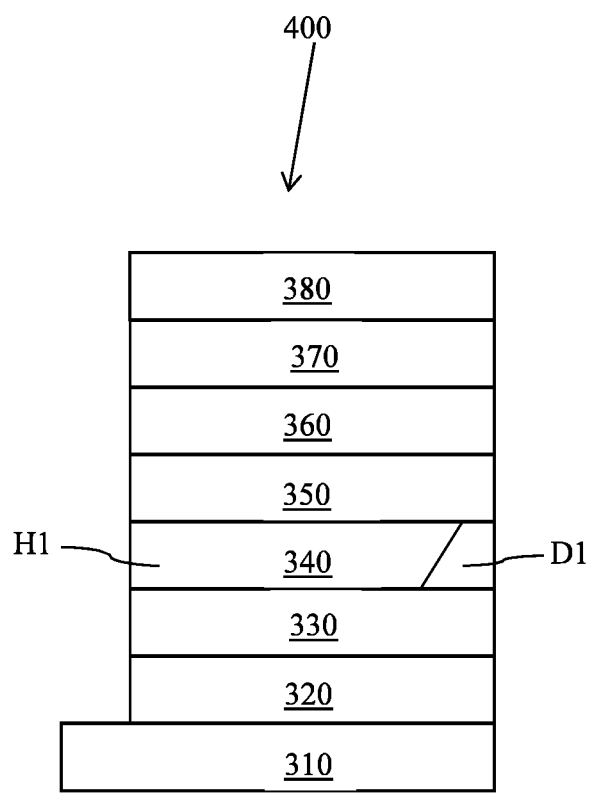
FIG. 2 is a cross-sectional view of an organic EL device without the host 340C of FIG. 1.

FIG. 2 is a cross-sectional view of an organic EL device without the organic compound of formula (C) (without 340C of FIG. 1). Referring to FIG. 2, the organic EL device 400 may have a driving voltage of about 5.1 V, a current efficiency of about 18 cd/A, or a half-life of about 350 hours.

Referring to FIG. 1, by comprising the organic compound of formula (C) as the host 340C, the first organic EL device 510 may have a driving voltage lower than that of the organic EL device 400 (FIG. 2). Moreover, by comprising the organic compound of formula (C) as the host 340C, the first organic EL device 510 of FIG. 1 may have a current efficiency higher than that of the organic EL device 400 (FIG. 2). Furthermore, by comprising the organic compound of formula (C) as the host 340C, the first organic EL device 510 of FIG. 1 may have a half-life longer than that of the organic EL device 400 (FIG. 2).

As the host 340C of the first organic EL device 510 of FIG. 1, the organic compound of formula (C) may lower the driving voltage to be about 2.8 V to about 4.5 V. Moreover, the organic compound of formula (C) may increase the current efficiency to be 25 cd/A to about 45 cd/A. Furthermore, the organic compound of formula (C) may increase the half-life to be about 430 hours to about 1000 hours.

Figure 3:
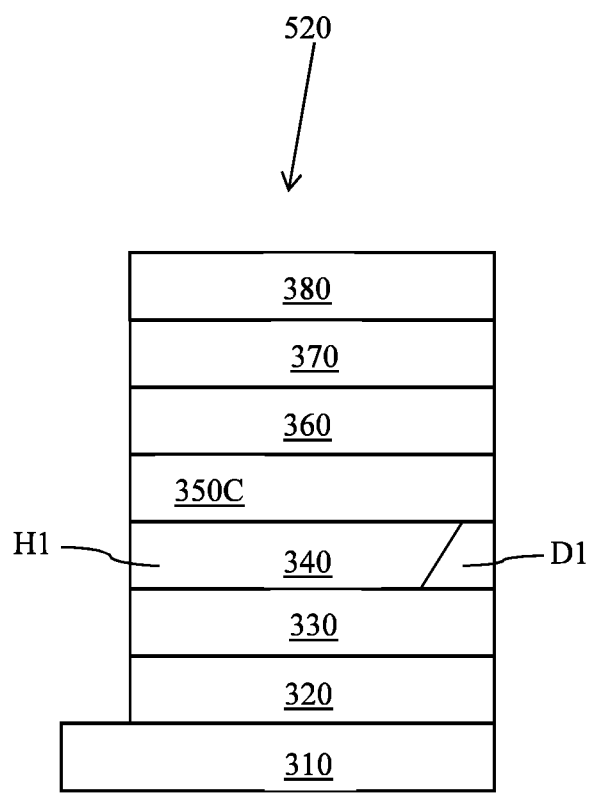
FIG. 3 is a cross-sectional view of a second organic EL device according to a third embodiment of the present invention.

In a third embodiment of the present invention, a second organic EL device using the organic compound of formula (C) is disclosed. FIG. 3 is a cross-sectional view of the second organic EL device. Referring to FIG. 3, the second organic EL device 520 may comprise the organic compound of formula (C) as a hole blocking layer 350C.

FIG. 2 is a cross-sectional view of an organic EL device without the organic compound of formula (C) (without 350C of FIG. 3). Referring to FIG. 2, the organic EL device 400 may have a driving voltage of about 5.1 V, a current efficiency of about 18 cd/A, or a half-life of about 350 hours.

Referring to FIG. 3, by comprising the organic compound of formula (C) as the hole blocking layer 350C, the second organic EL device 520 may have a driving voltage lower than that of the organic EL device 400 (FIG. 2). Moreover, by comprising the organic compound of formula (C) as the hole blocking layer 350C, the second organic EL device 520 of FIG. 3 may have a current efficiency higher than that of the organic EL device 400 (FIG. 2). Furthermore, by comprising the organic compound of formula (C) as the hole blocking layer 350C, the second organic EL device 520 of FIG. 3 may have a half-life longer than that of the organic EL device 400 (FIG. 2).

Referring to FIG. 3, as the hole blocking layer 350C of the second organic EL device 520, the organic compound of formula (C) may lower the driving voltage to be about 4.0 V to about 4.9 V. Moreover, the organic compound of formula (C) may increase the current efficiency to be about 20 cd/A to about 27 cd/A. Furthermore, the organic compound of formula (C) may increase the half-life to be about 380 hours to about 520 hours.

In formula (C), Ar may also represent a substituted or unsubstituted phenyl group, a substituted or unsubstituted biphenyl group, a substituted or unsubstituted fluorene group, a substituted or unsubstituted benzofluorene group, a substituted or unsubstituted naphthyl group, a substituted or unsubstituted anthracenyl group, a substituted or unsubstituted phenanthrenyl group, a substituted or unsubstituted pyrenyl group, a substituted or unsubstituted chrysenyl group, a substituted or unsubstituted triphenylenyl group.

The organic compound of the present invention may also have one of the following formula (3) to formula (26):

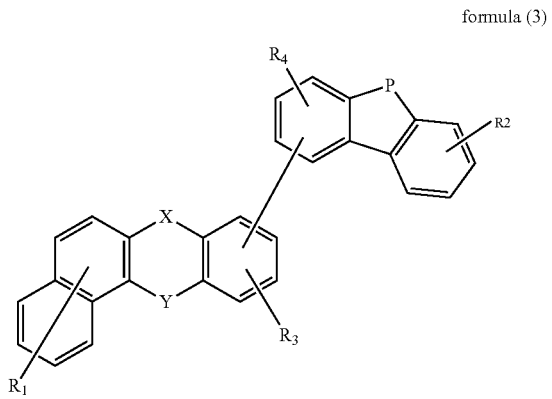

formula (3)

formula (4)
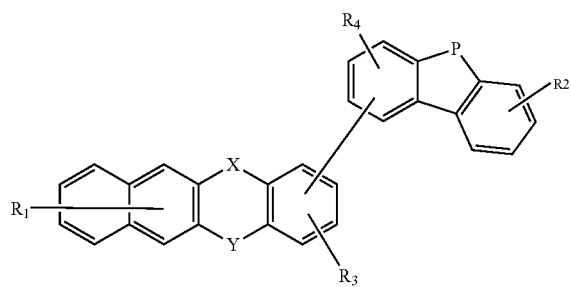
formula (5)
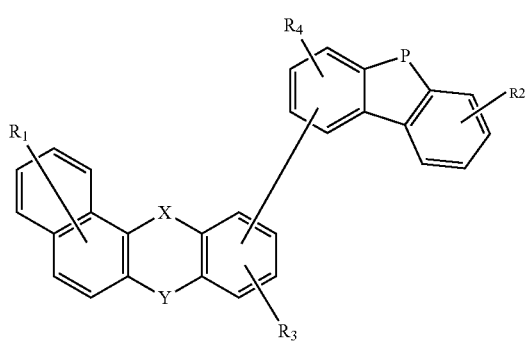
formula (6)
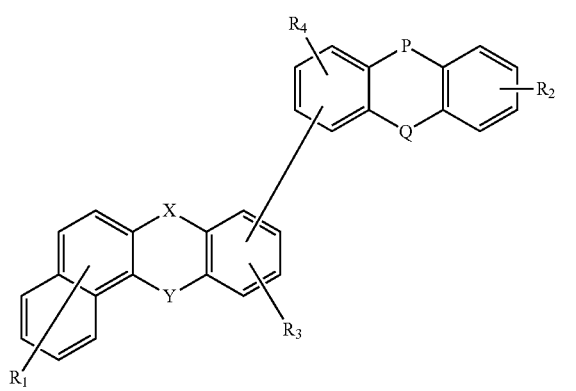
formula (7)
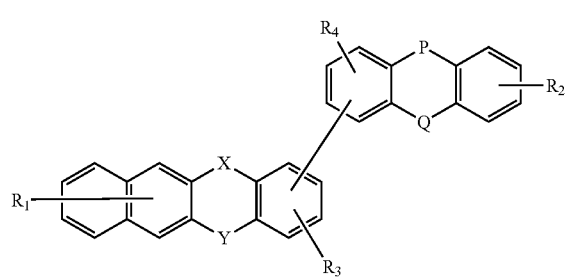
formula (8)
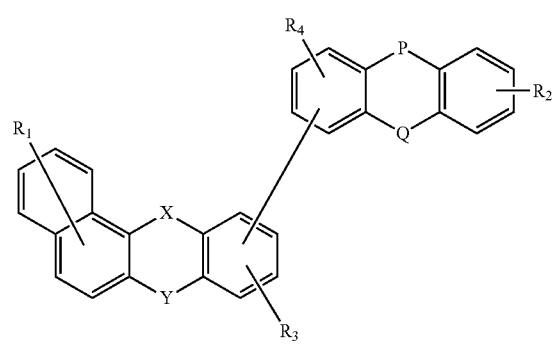
formula (9)
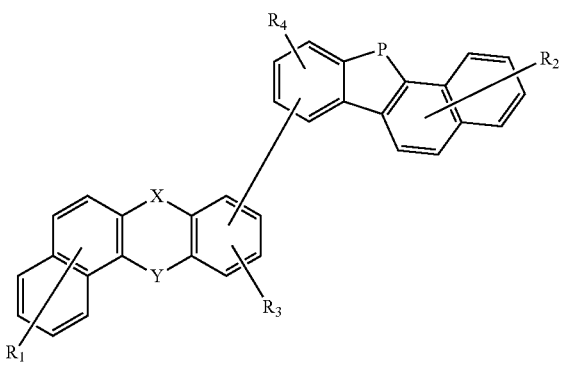
formula (10)
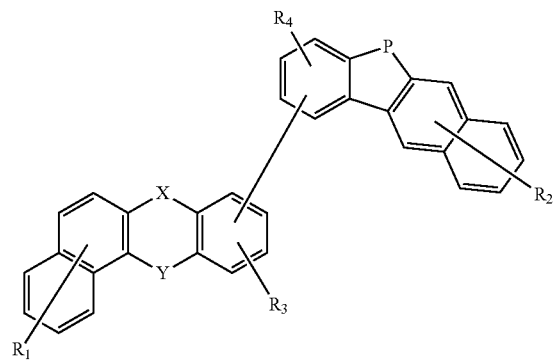
formula (11)
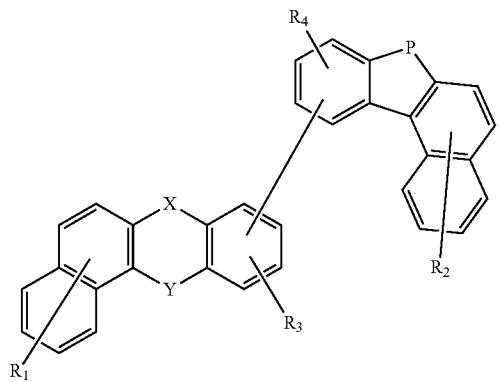

formula (12)
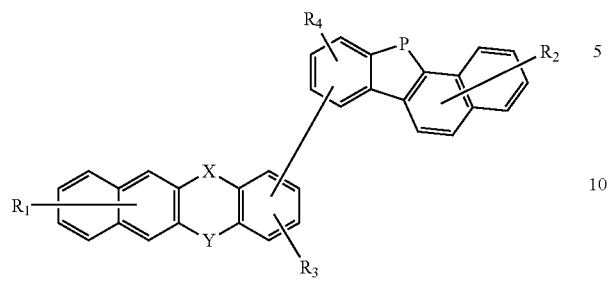
formula (13)
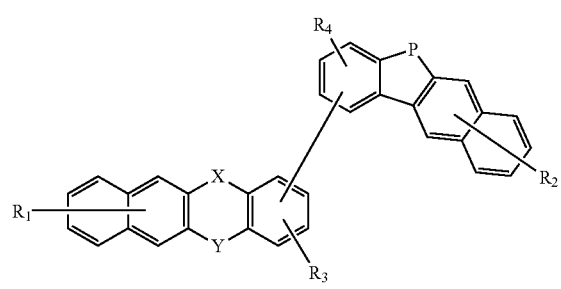
formula (14)
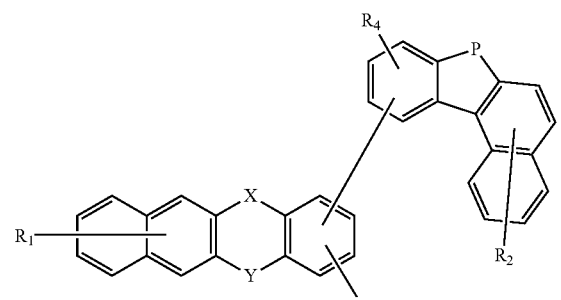
formula (15)
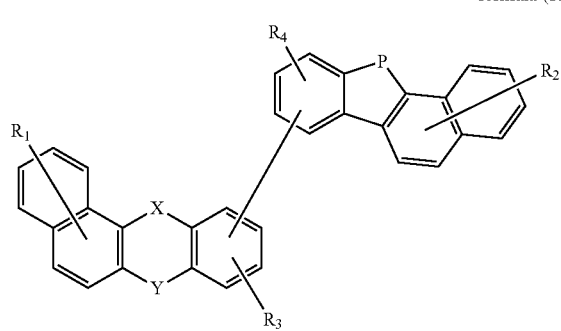
formula (16)
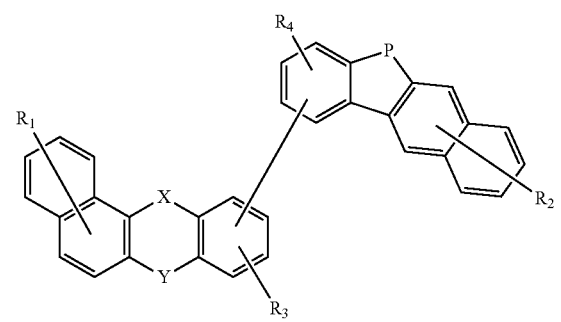
formula (17)
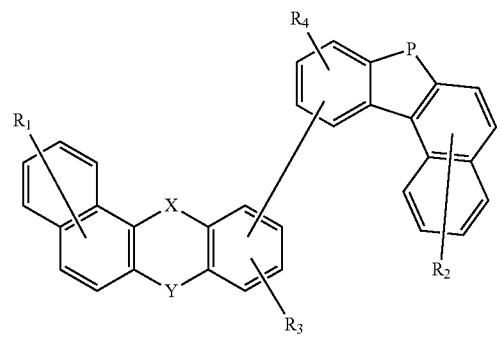
formula 18
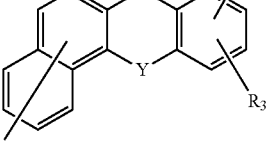
formula 19
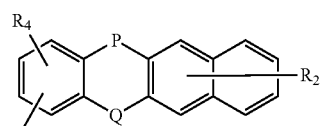
formula 20
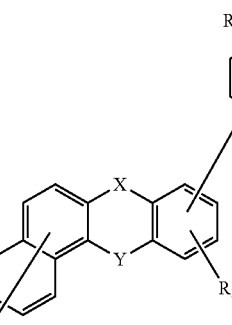

formula (21)
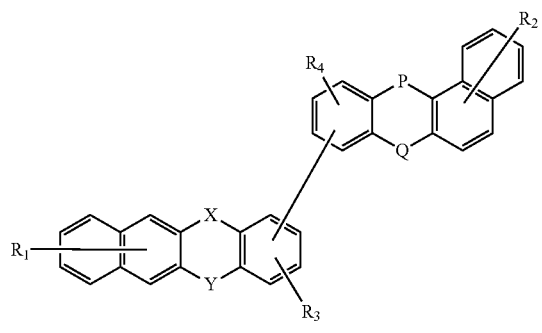
formula (22)
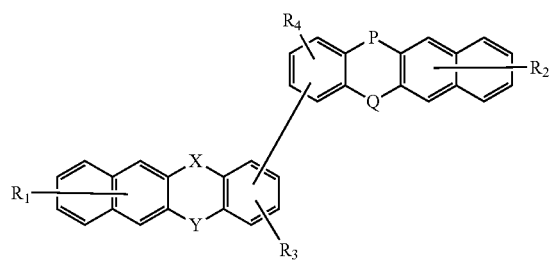
formula (23)
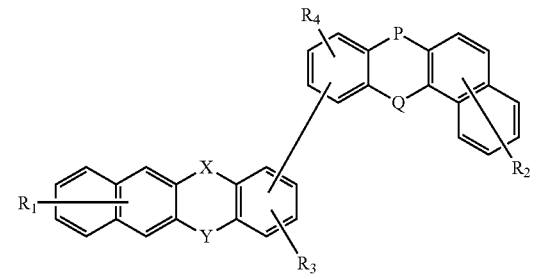
formula (24)
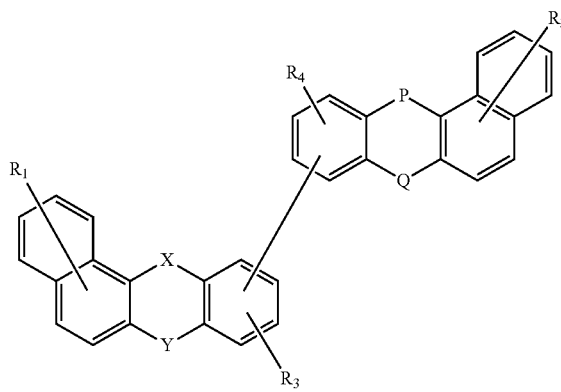
formula (25)
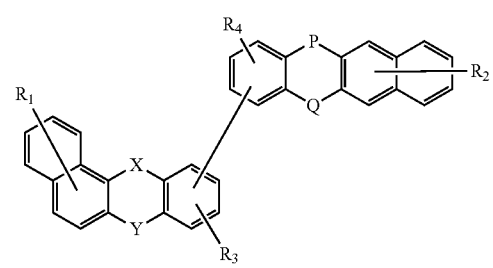
and
formula (26)
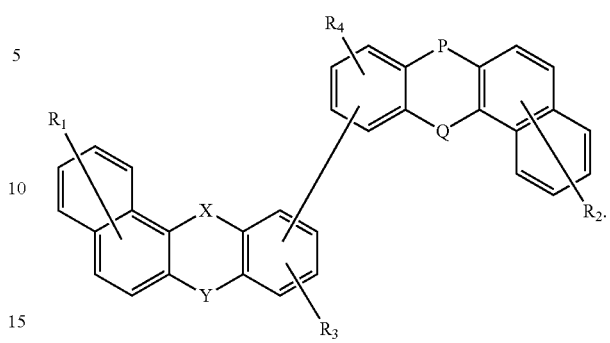
The same definition as described in the paragraph [0011] to paragraph [0027].
In formula (C), Ar may represent one of the following substituents:
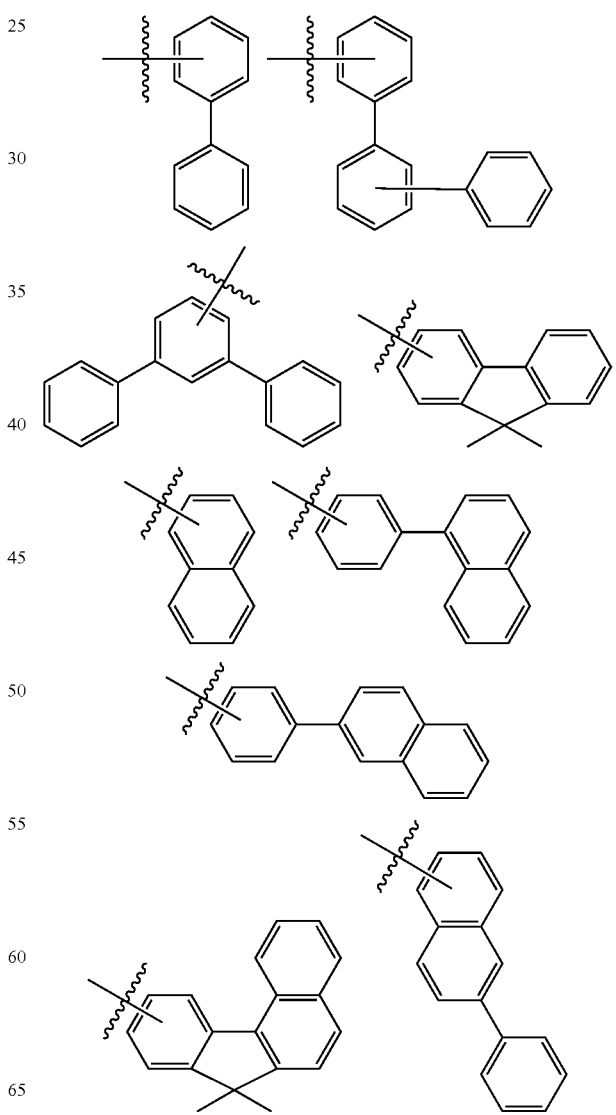

-continued
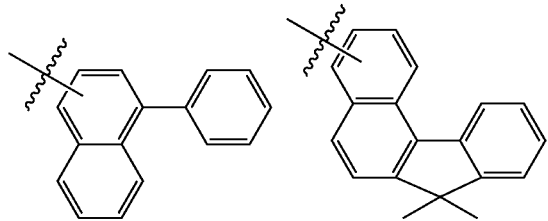
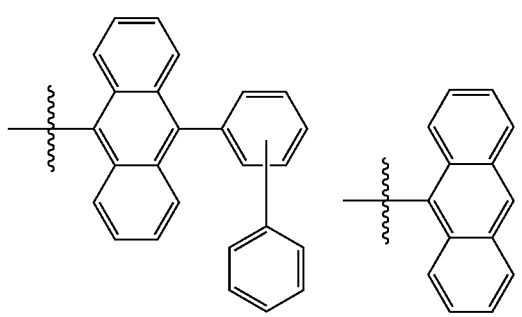
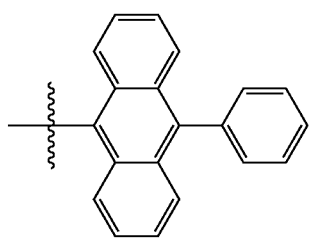
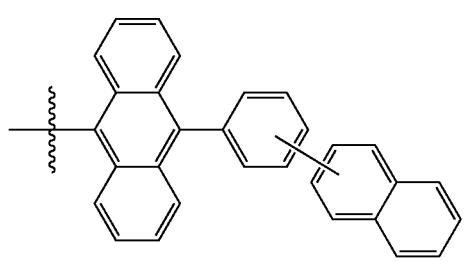
-continued
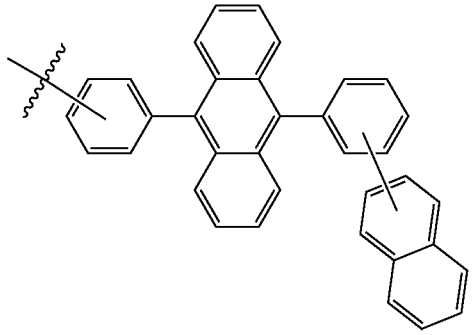
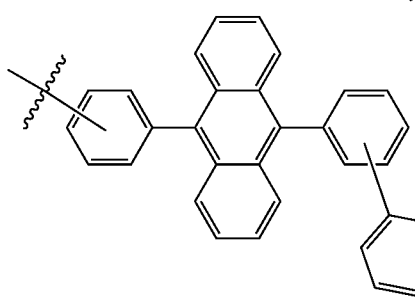
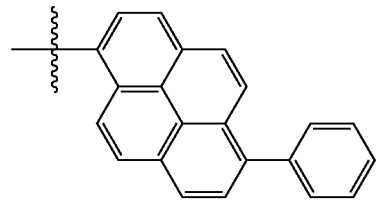
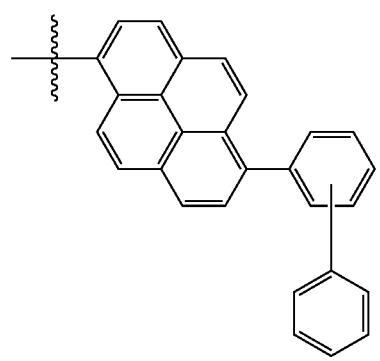
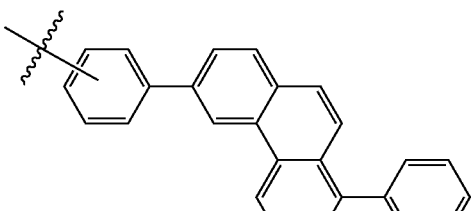
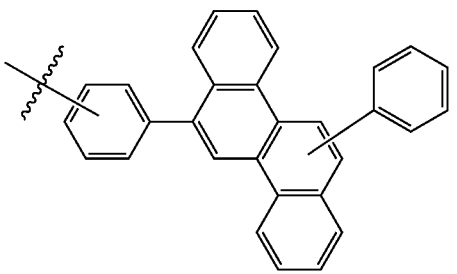

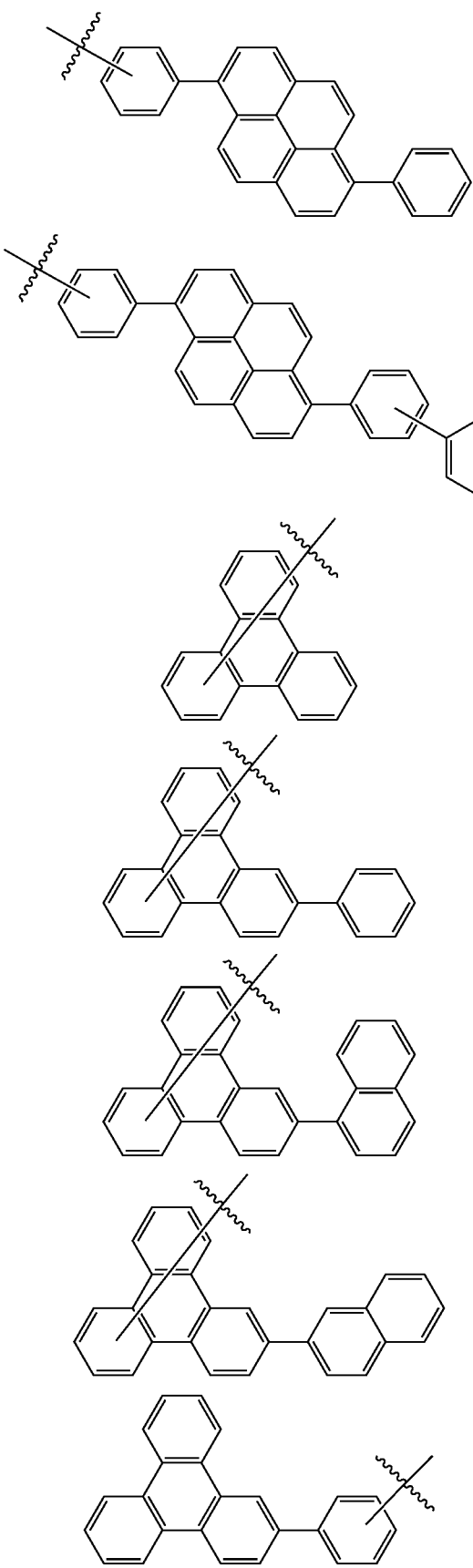
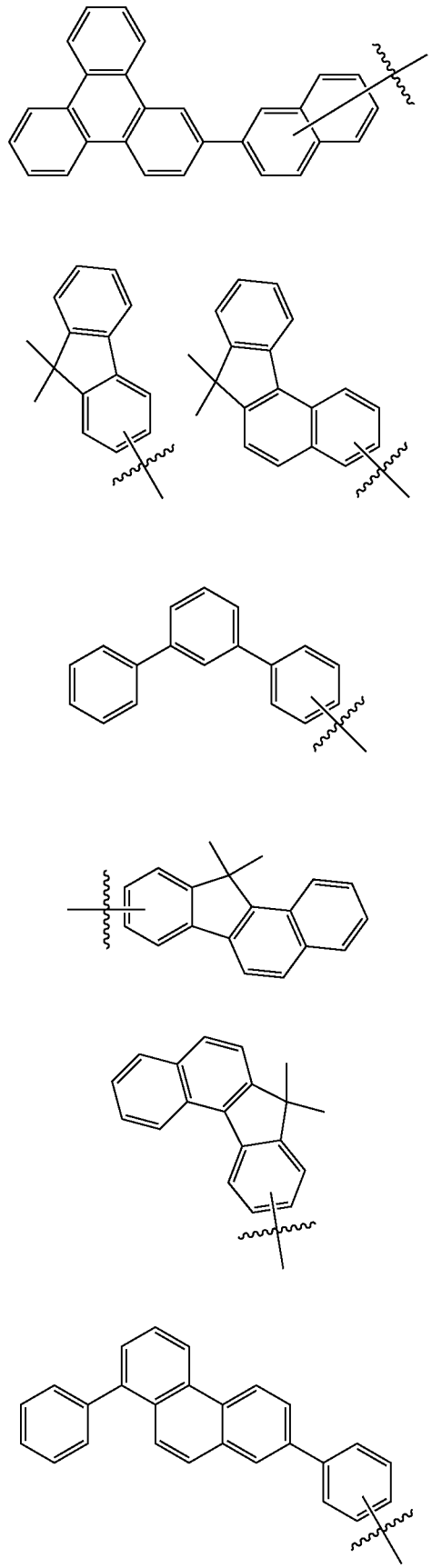

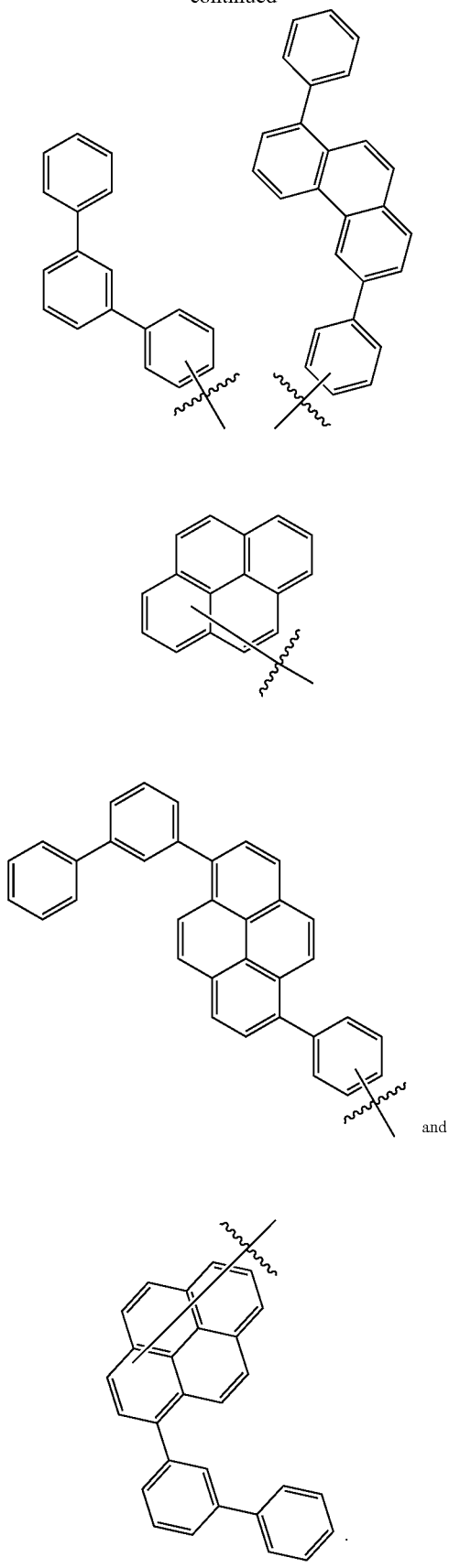
The organic compound of the present invention may also have one of the following formulas:
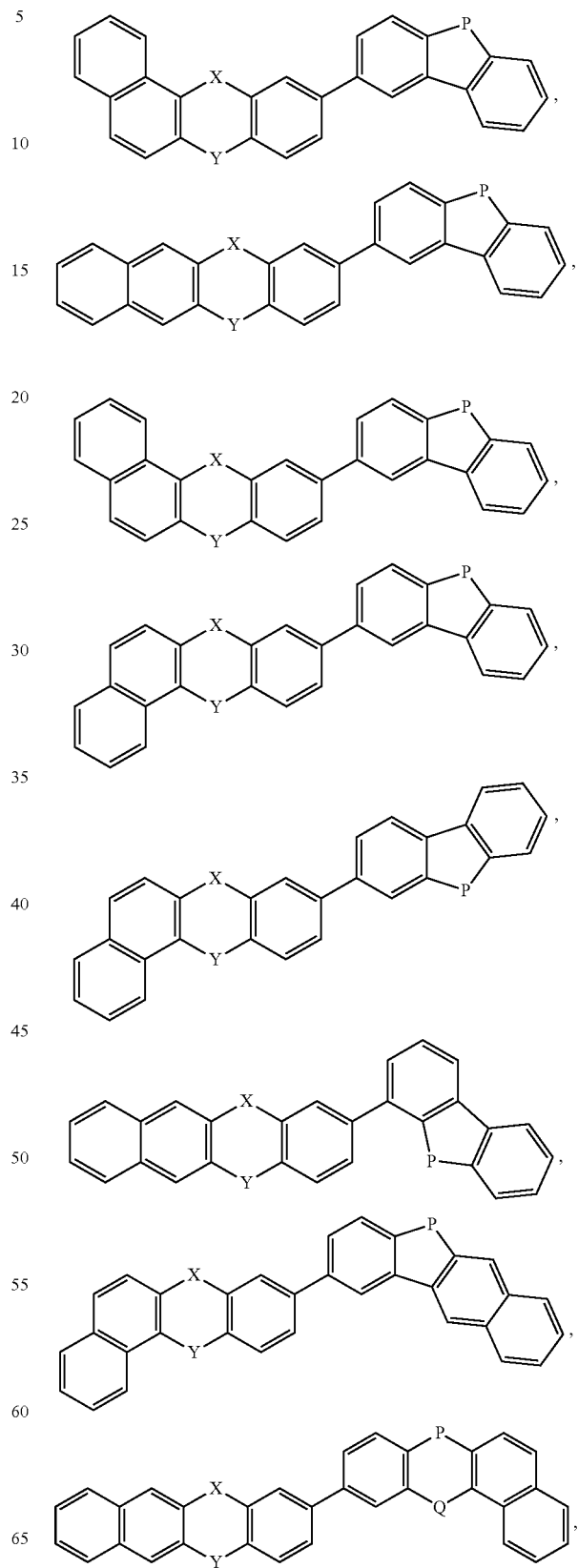

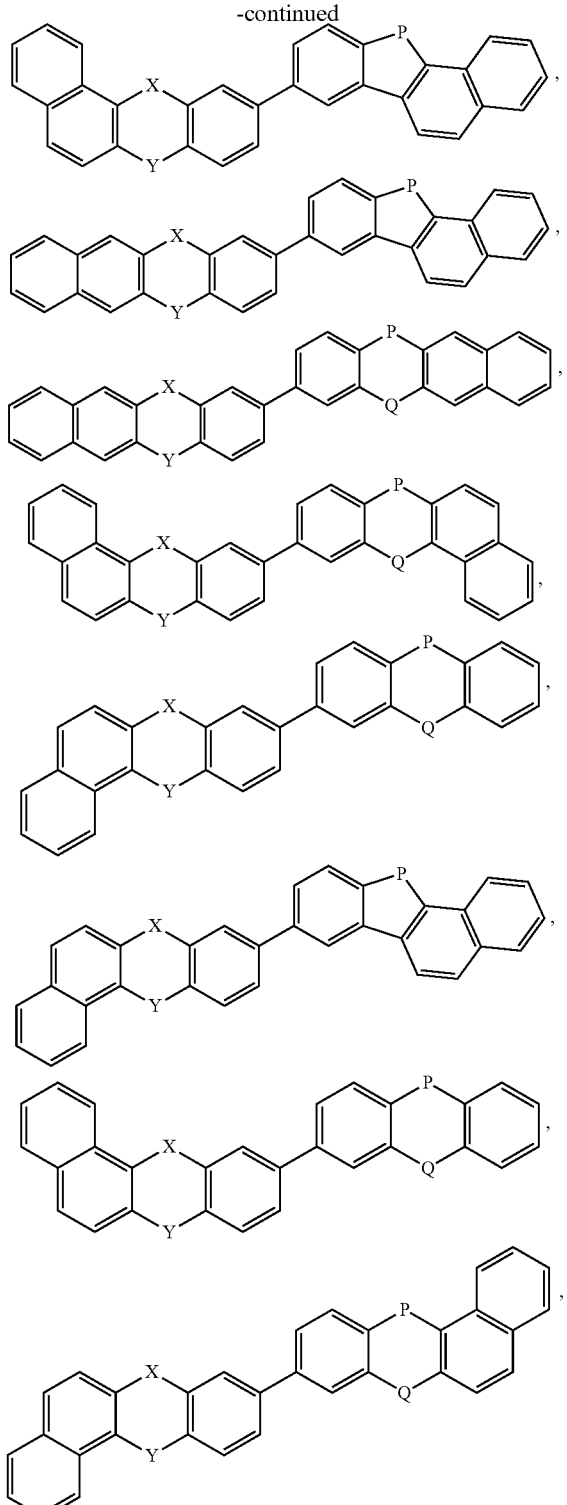
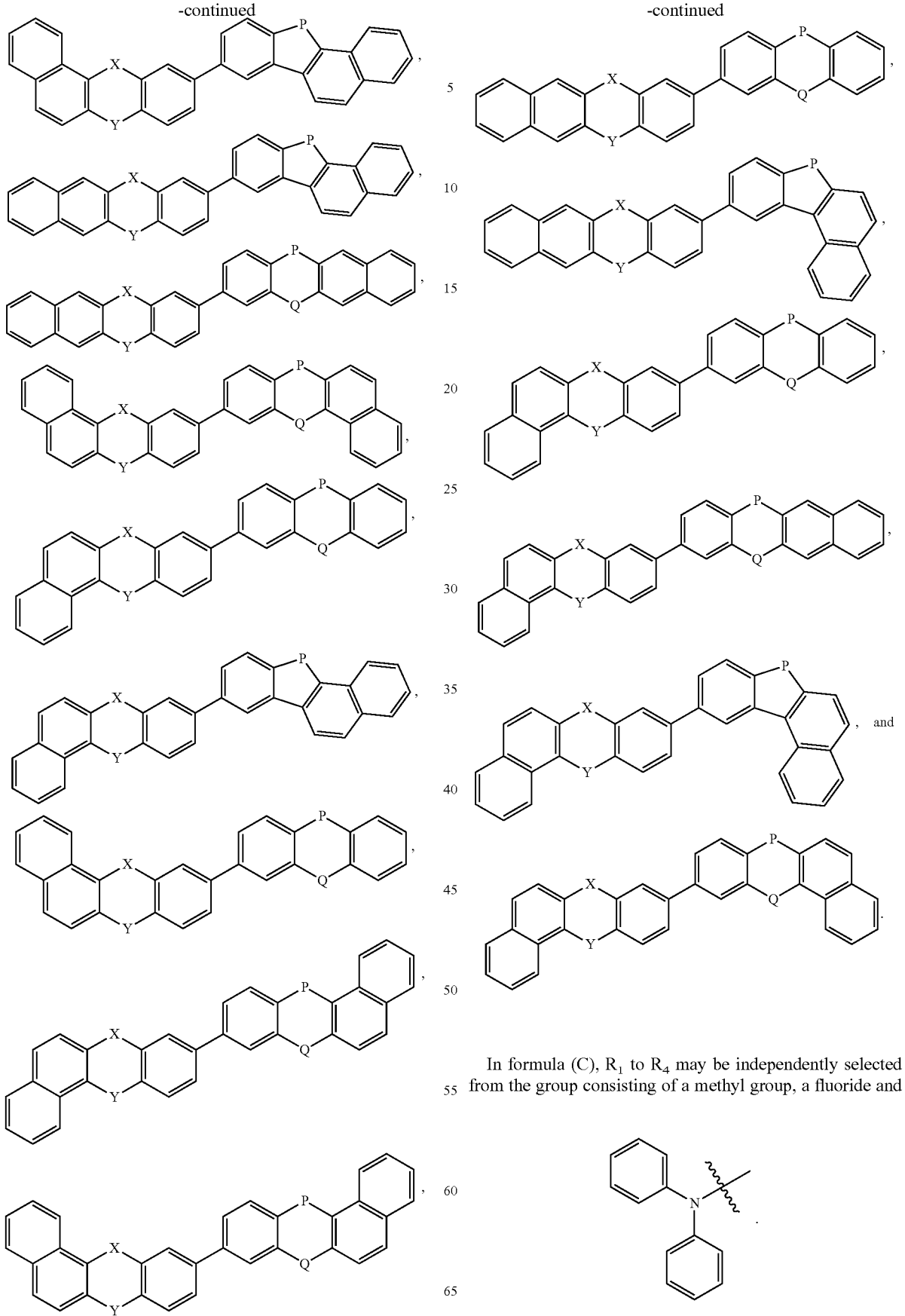
In formula (C), $R_1$ to $R_4$ may be independently selected from the group consisting of a methyl group, a fluoride and
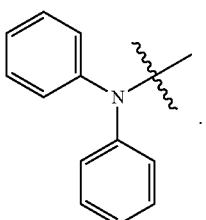

The organic compound of the present invention may be one of the following compounds:
compound 5
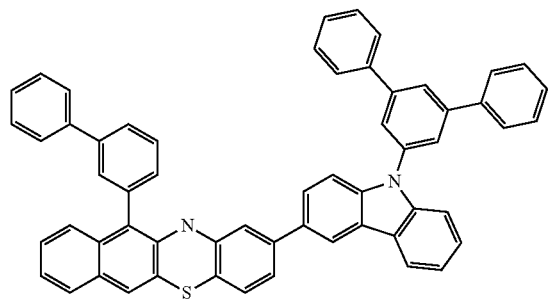
compound 6
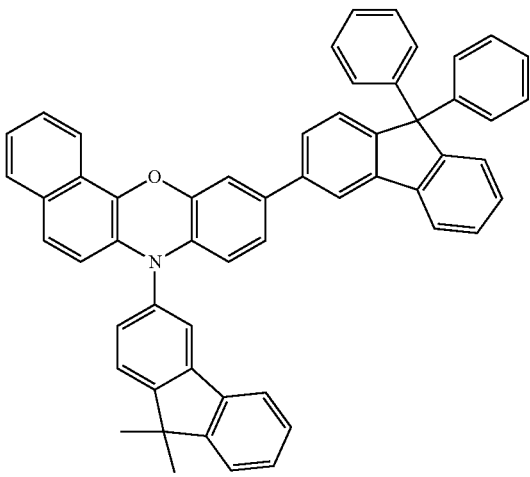
compound 7
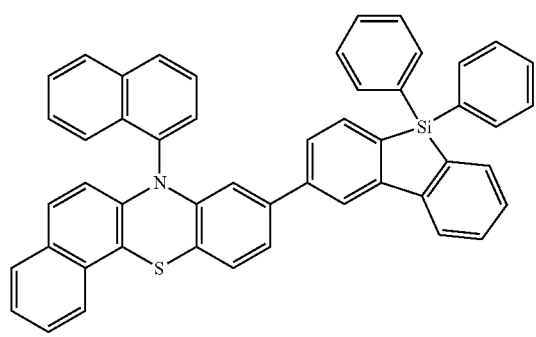
compound 8
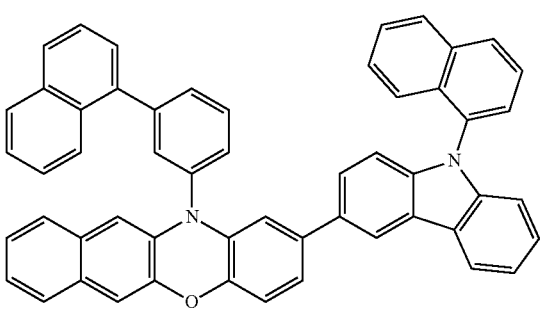
compound 9
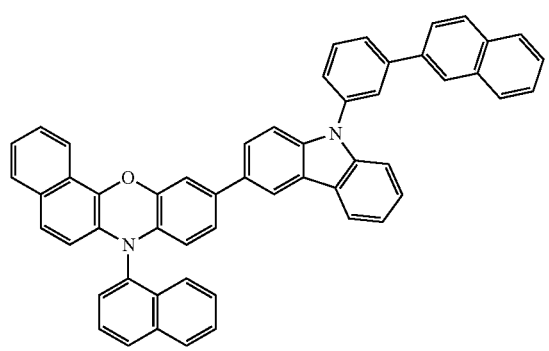
compound 10
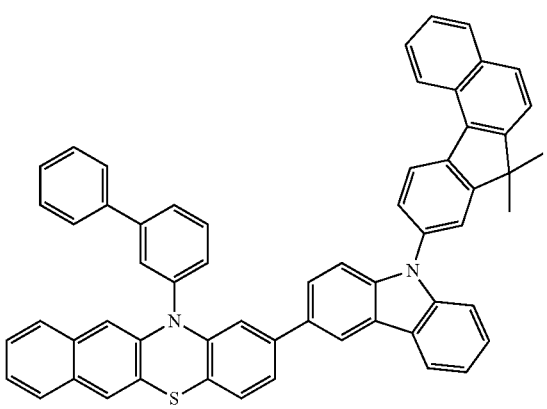

-continued
compound 11
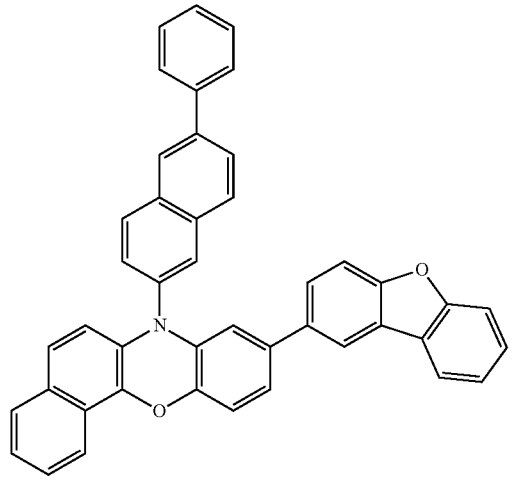
compound 12
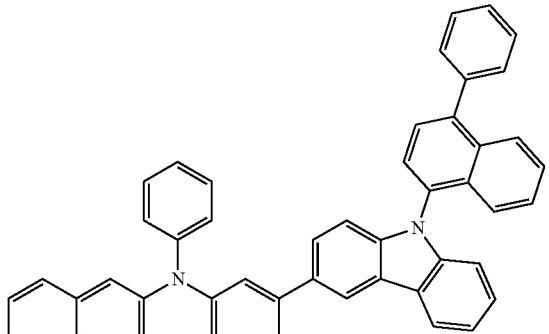
compound 13
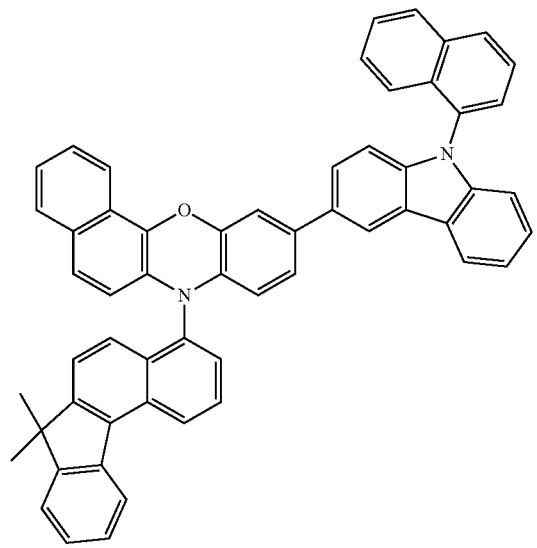
compound 14
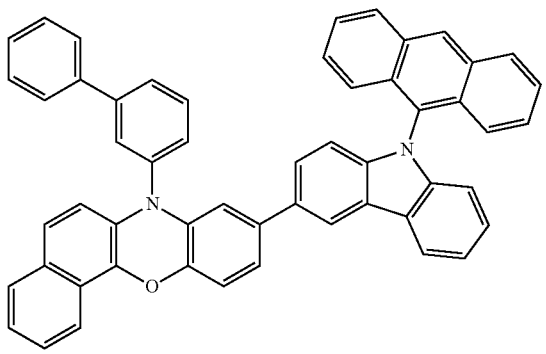
compound 15
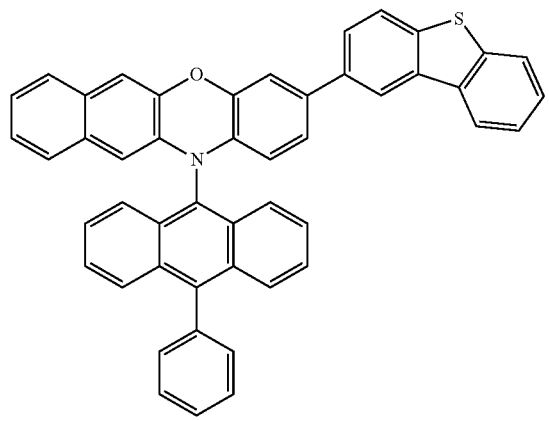
compound 16
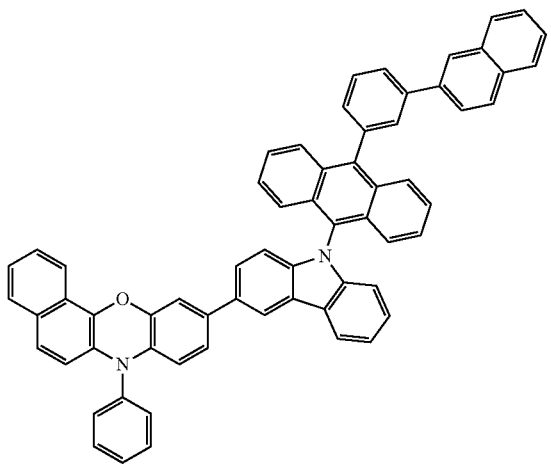

-continued
compound 17
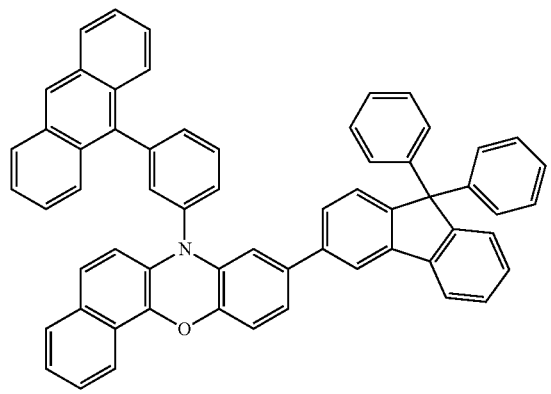
compound 18
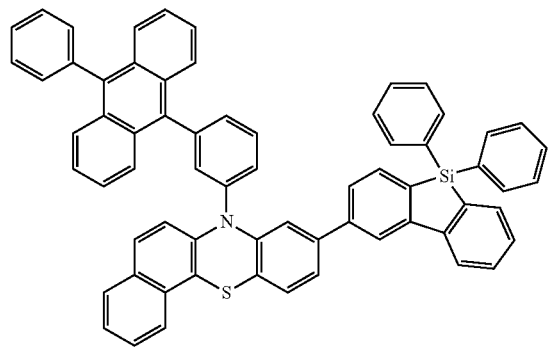
compound 19
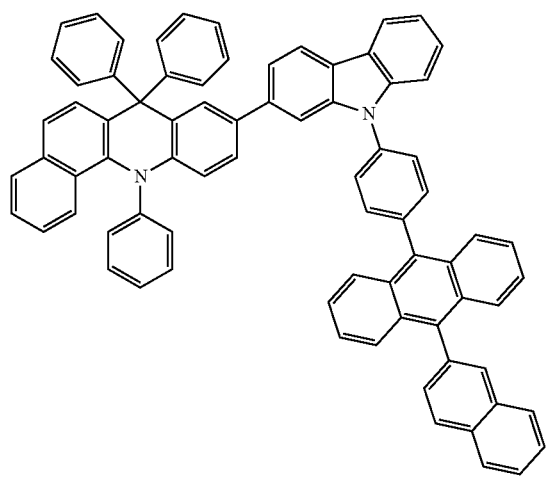
compound 20
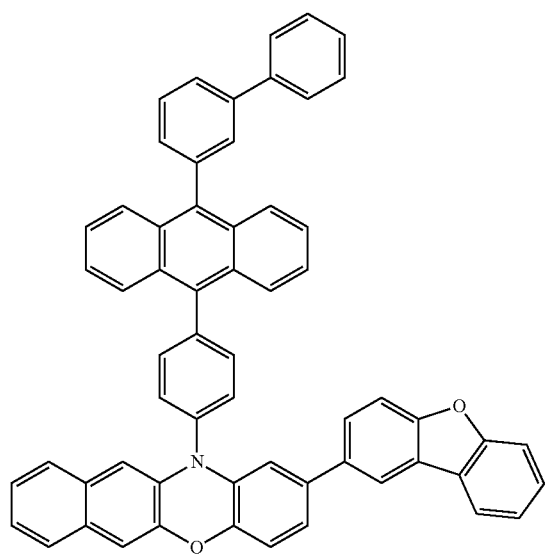
compound 21
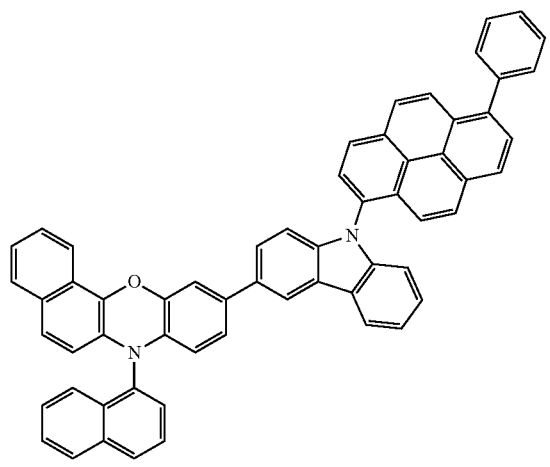
compound 22
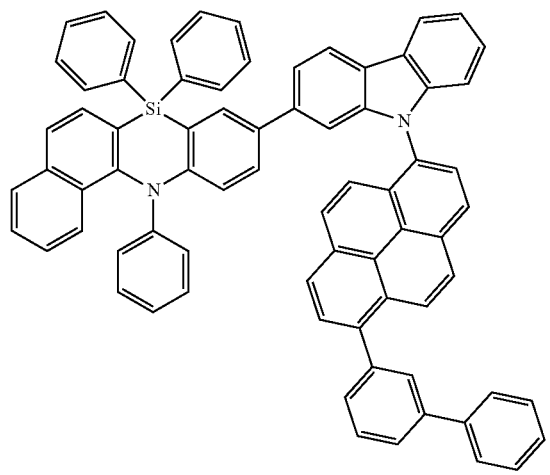

compound 23
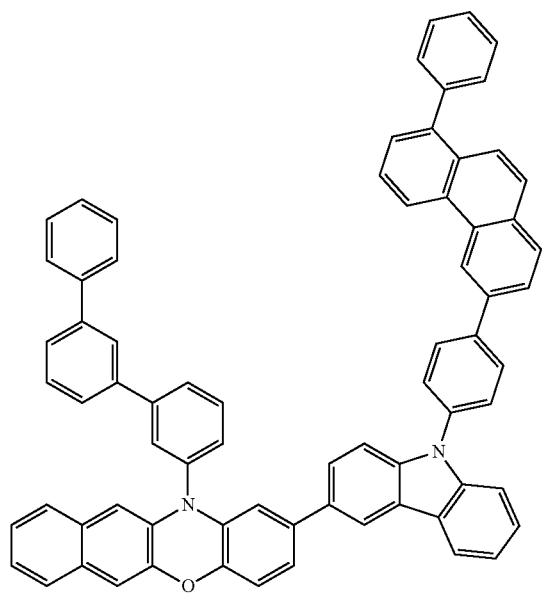
compound 24
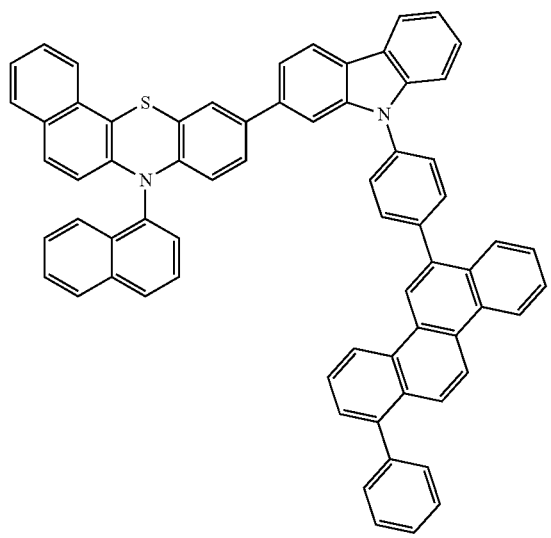
compound 25
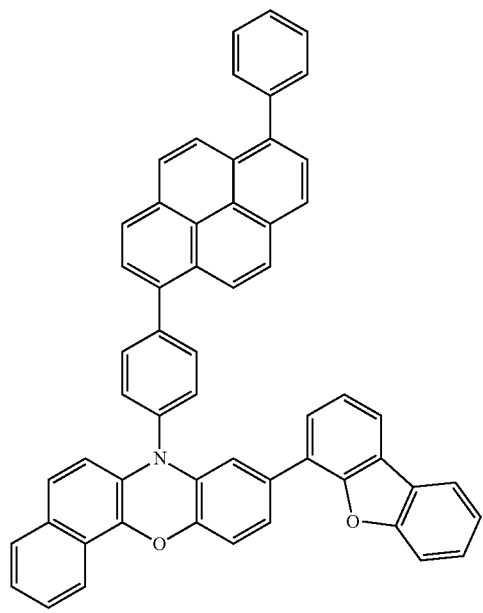
compound 26
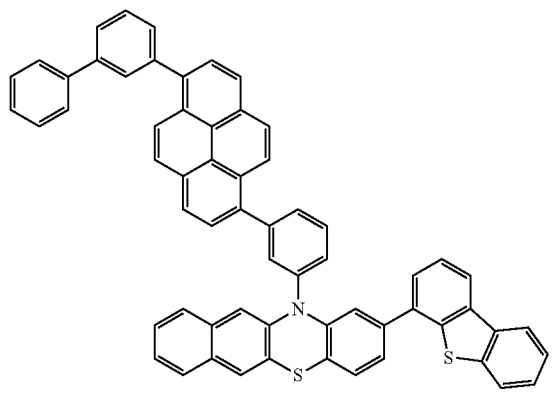

-continued
compound 27
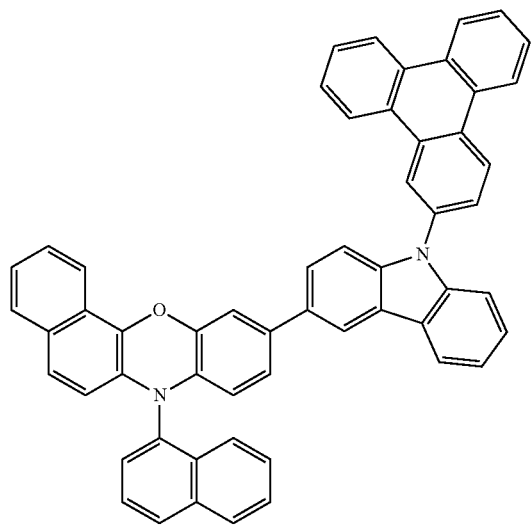
compound 28
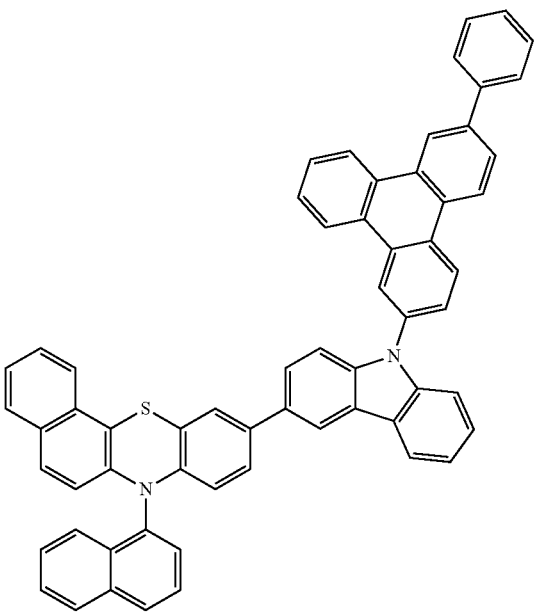
compound 29
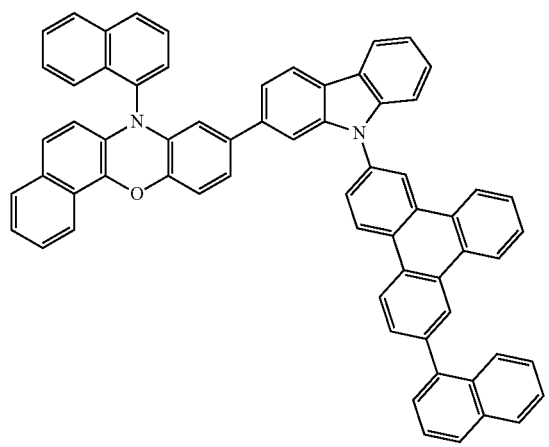
compound 30
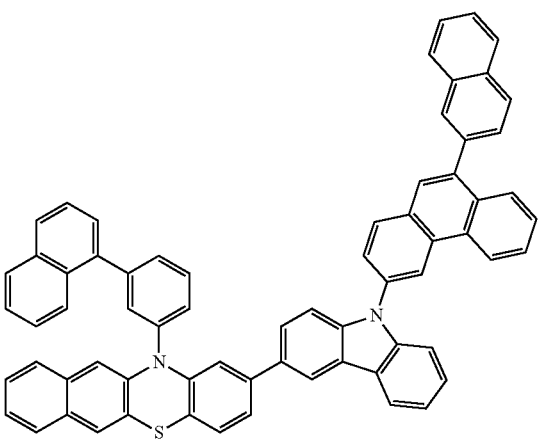
compound 31
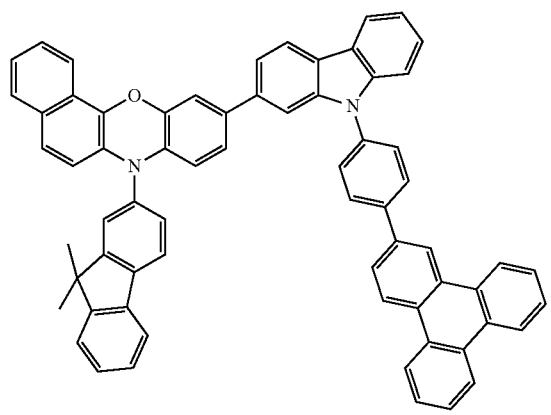
compound 32
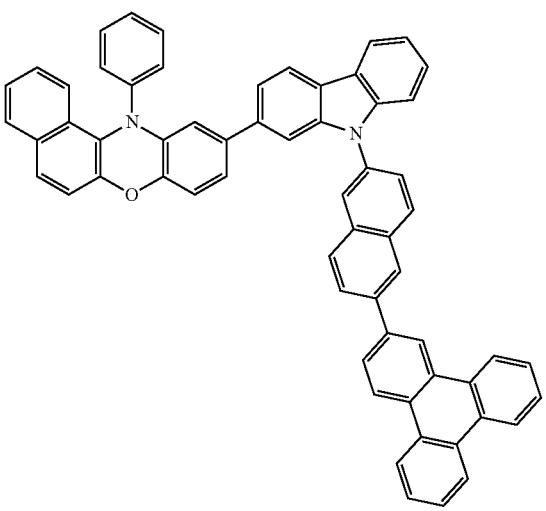

-continued
compound 33
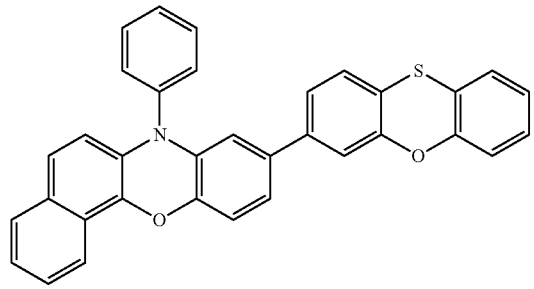
compound 34
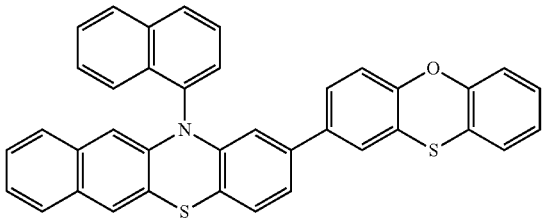
compound 35
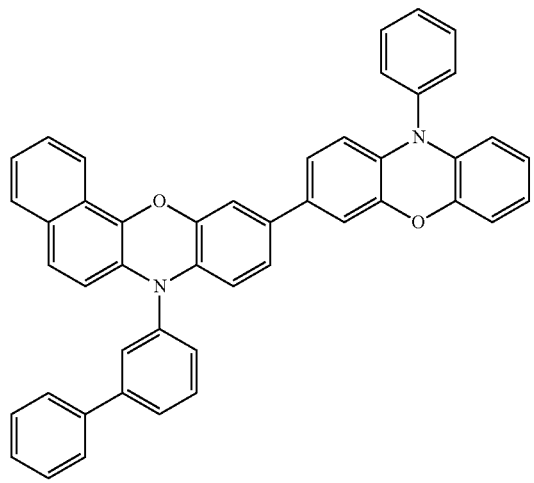
compound 36
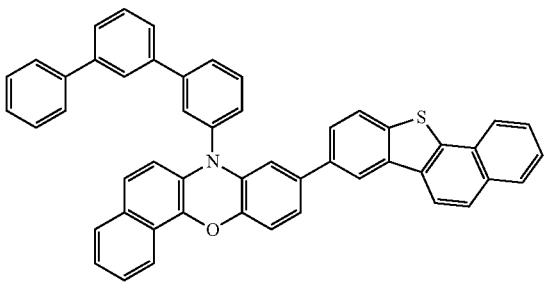
compound 37
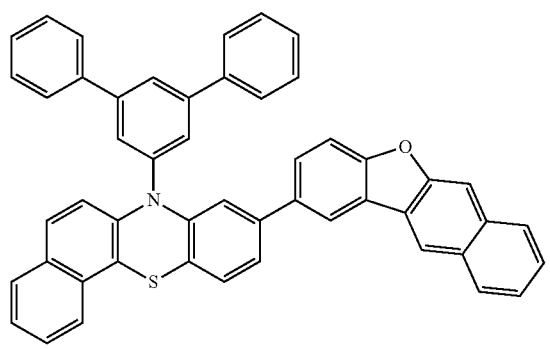
compound 38
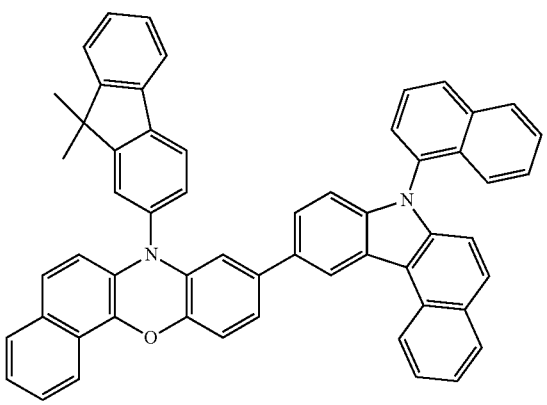
compound 39
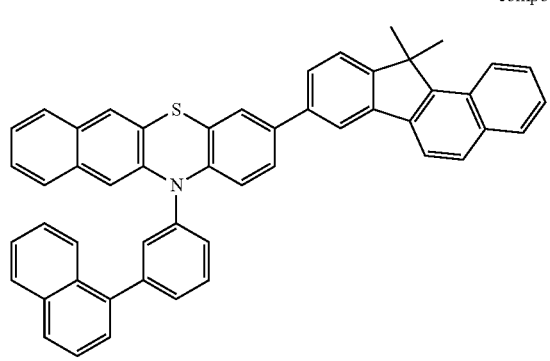
compound 40
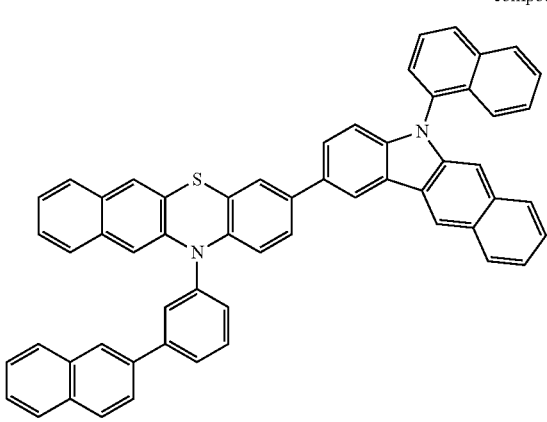

-continued
compound 41
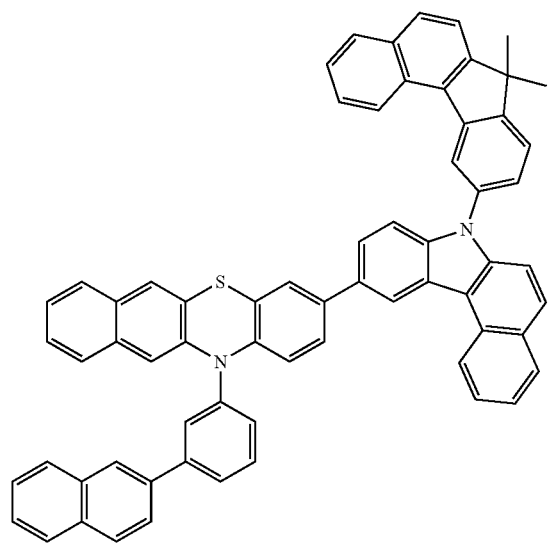
compound 42
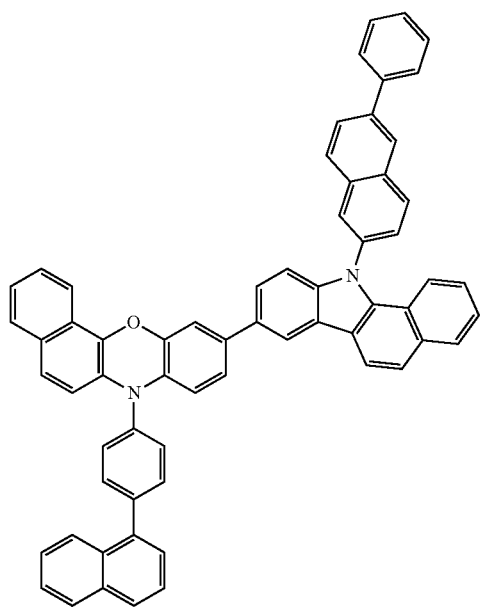
compound 43
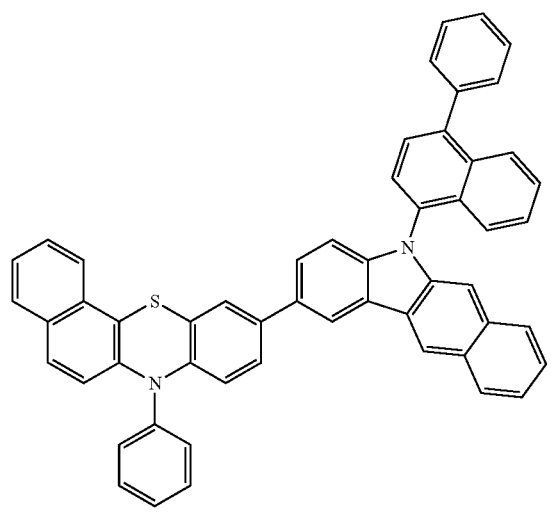
compound 44
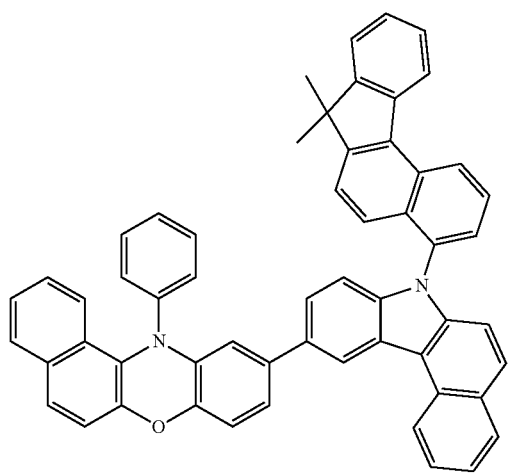

compound 45
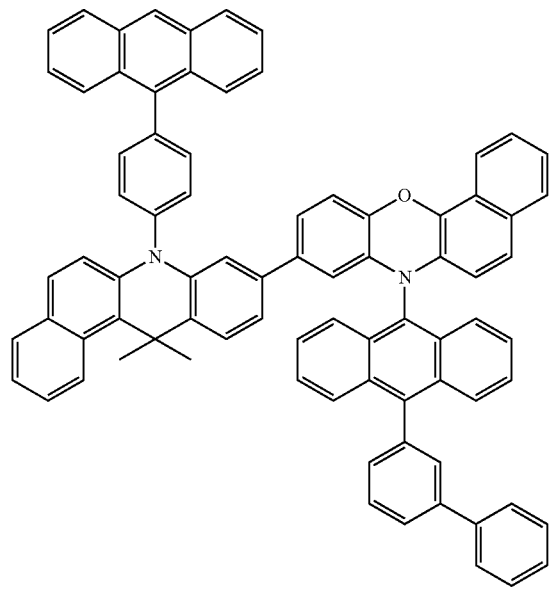
compound 46
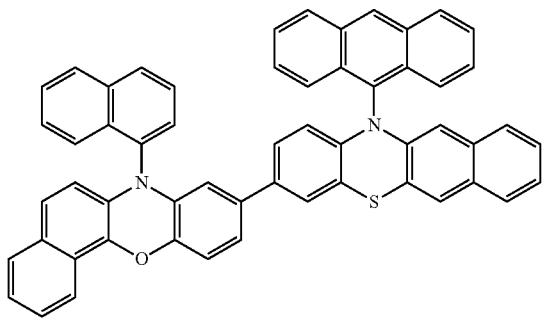
compound 47
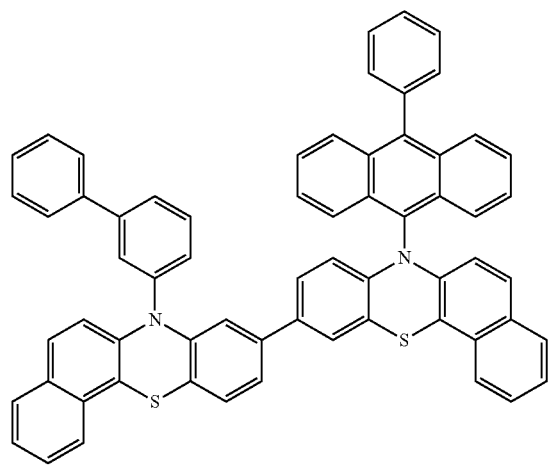
compound 48
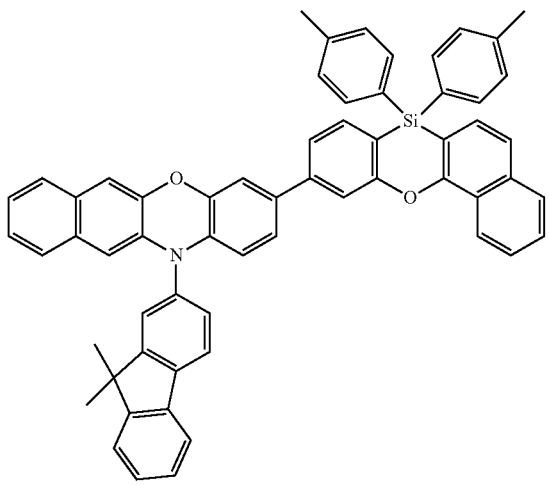
compound 49
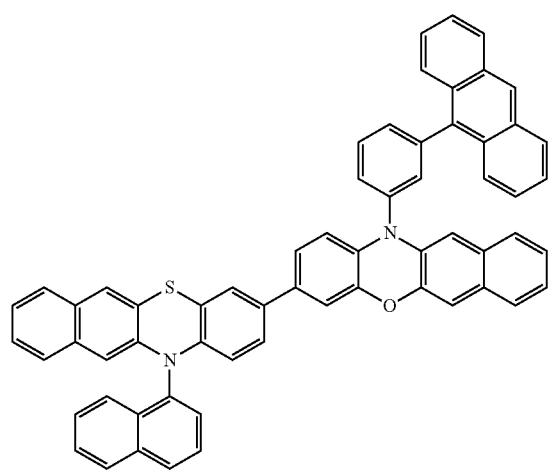
compound 50
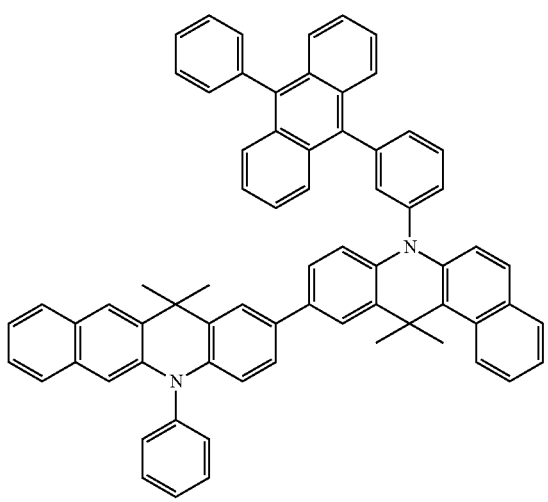

-continued
compound 51
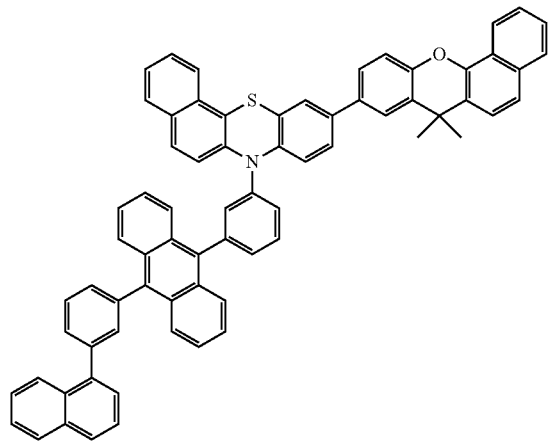
compound 52
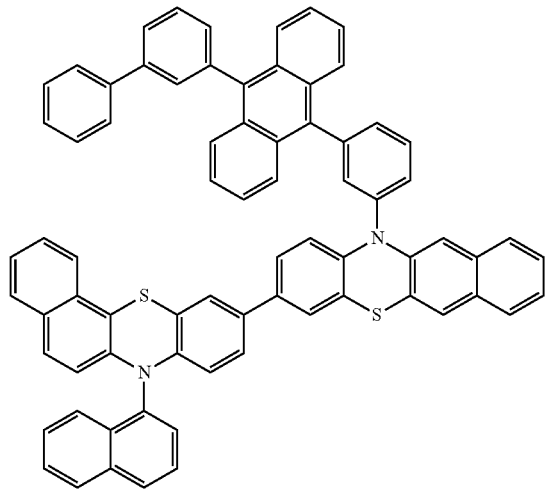
compound 53
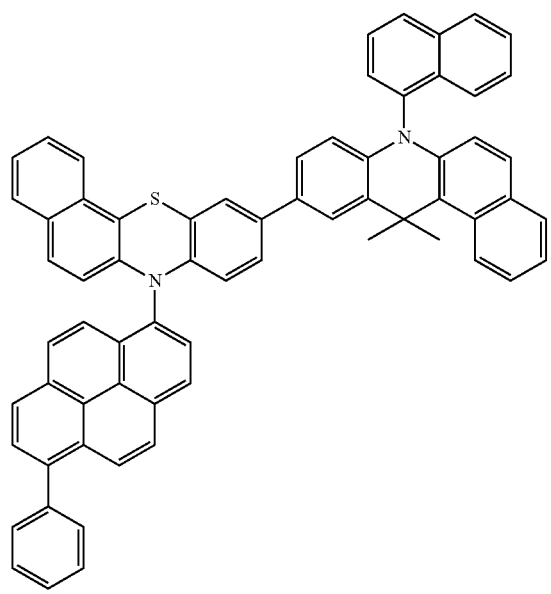
compound 54
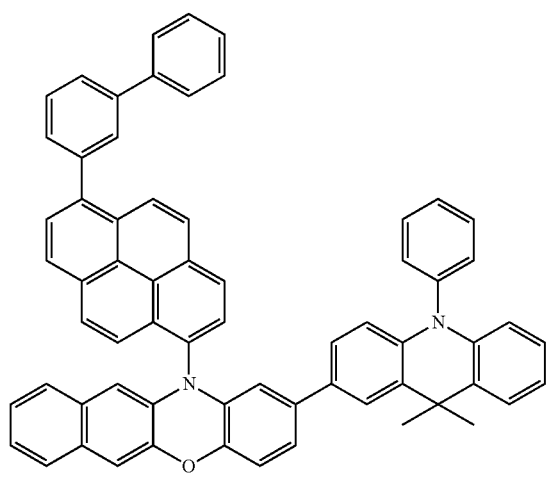

-continued
compound 55
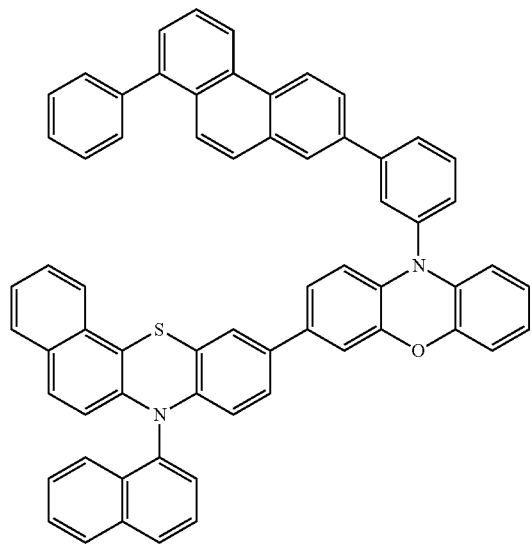
compound 56
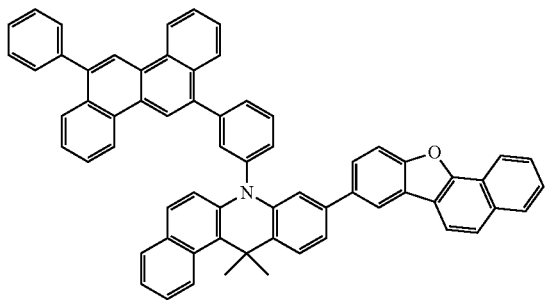
compound 57
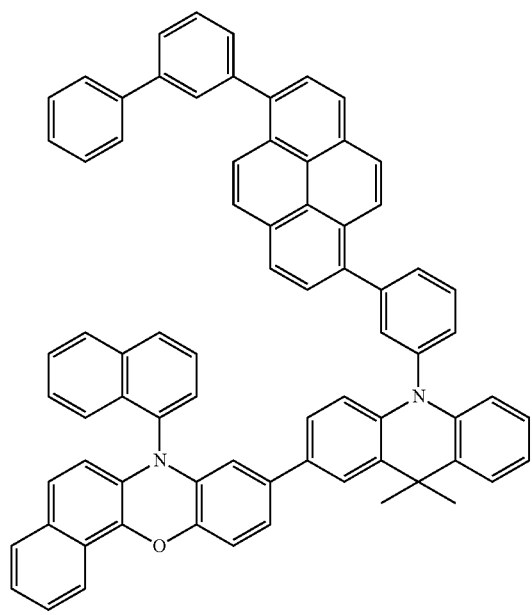
compound 58
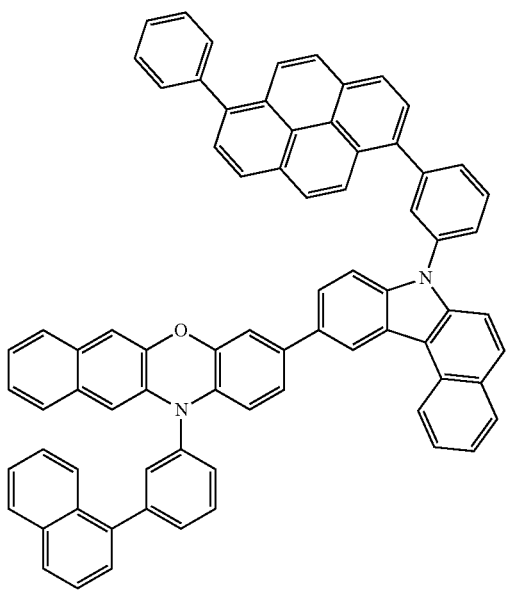

-continued
compound 59
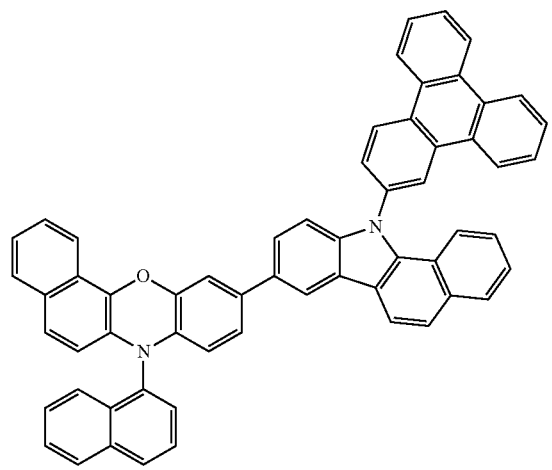
compound 60
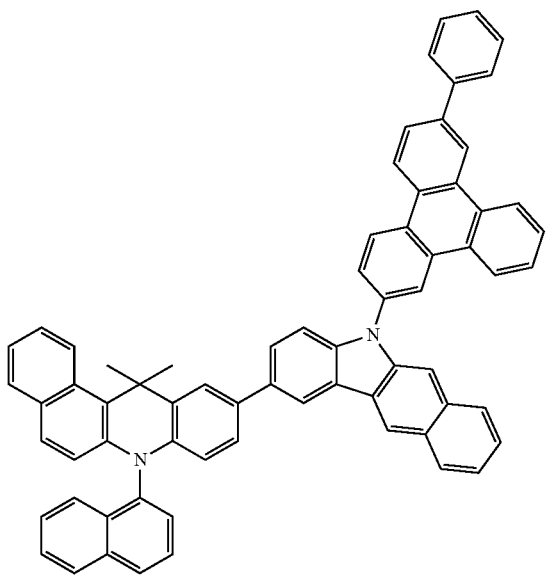
compound 61
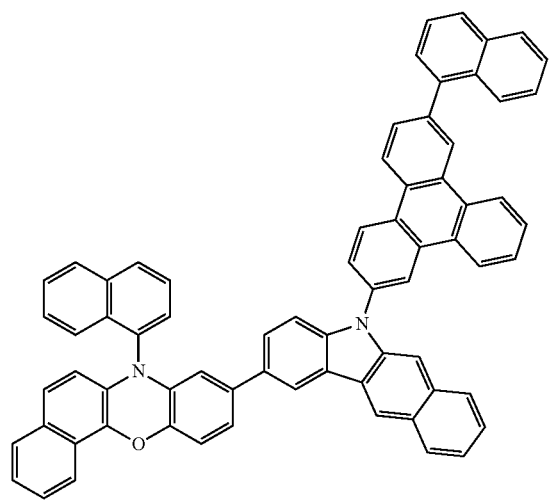
compound 62
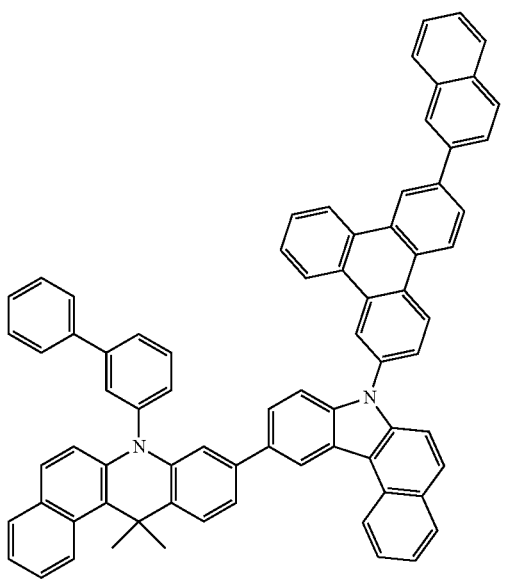

-continued
compound 63
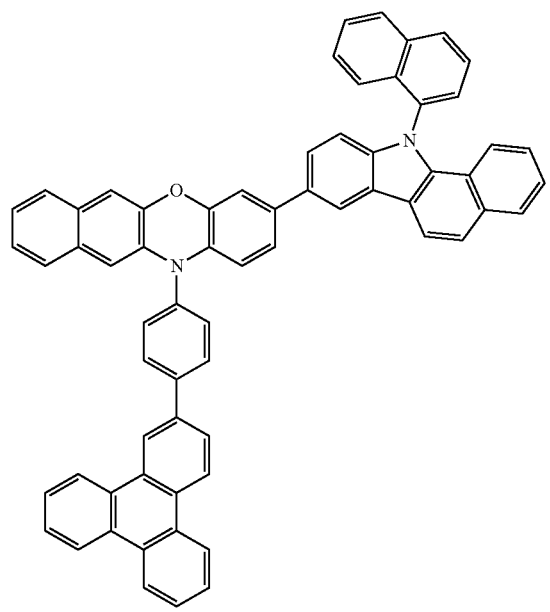
compound 64
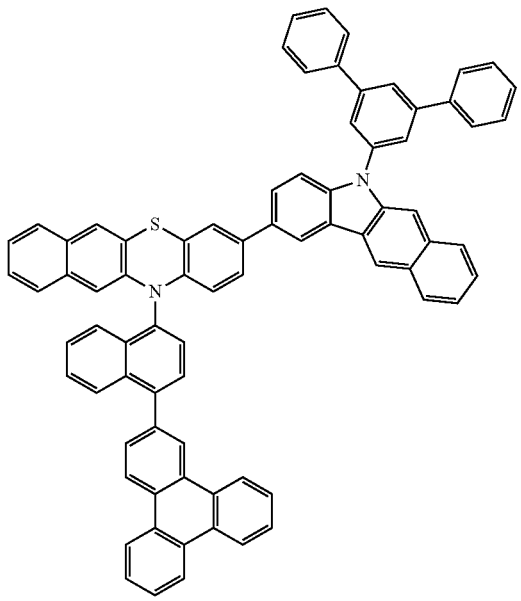
compound 65
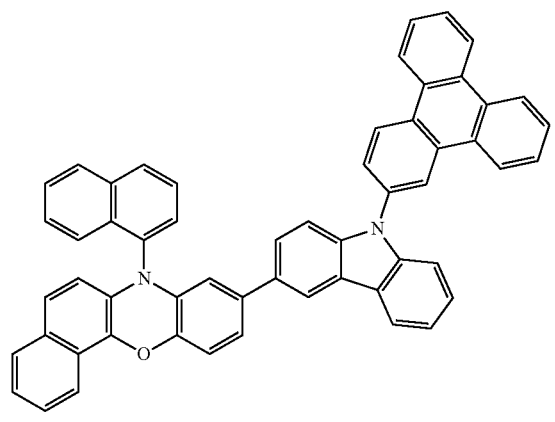
compound 66
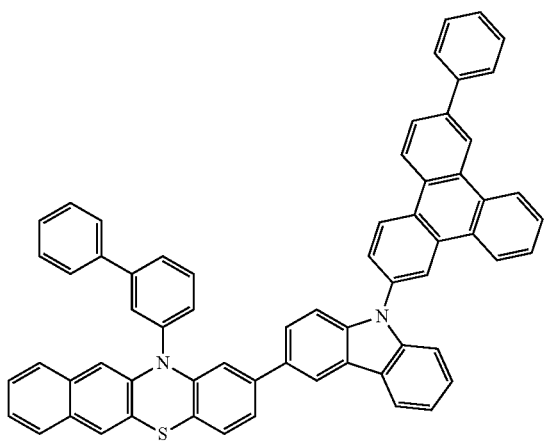

-continued
compound 67
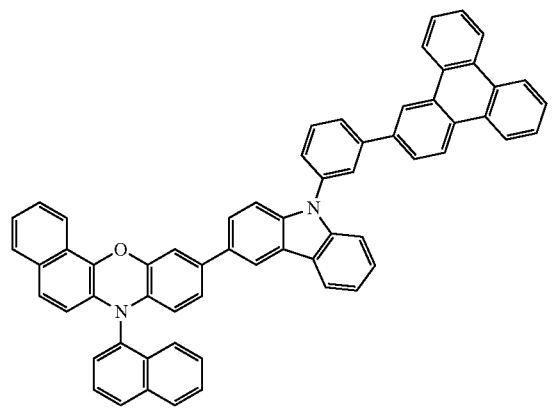
compound 68
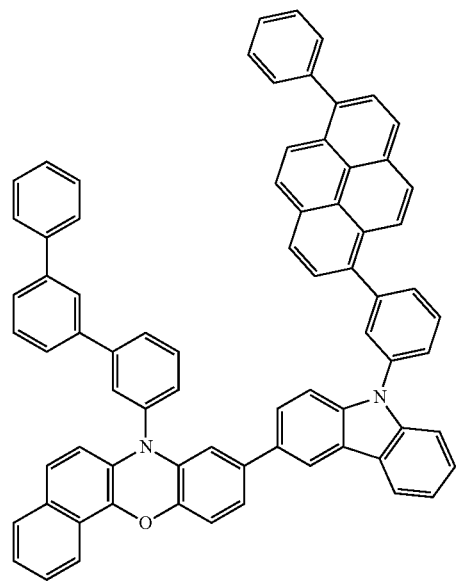
compound 69
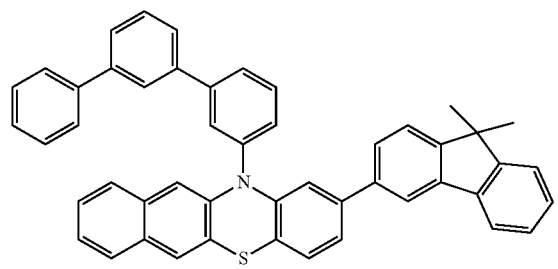
compound 70
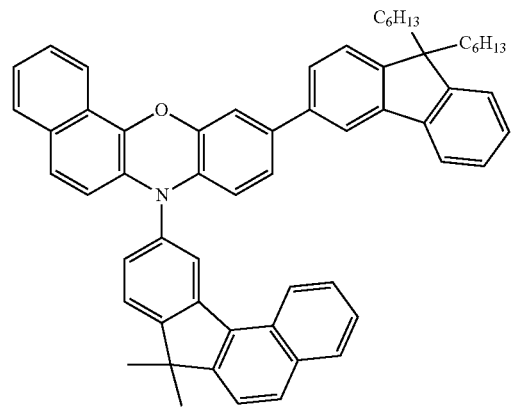
compound 71
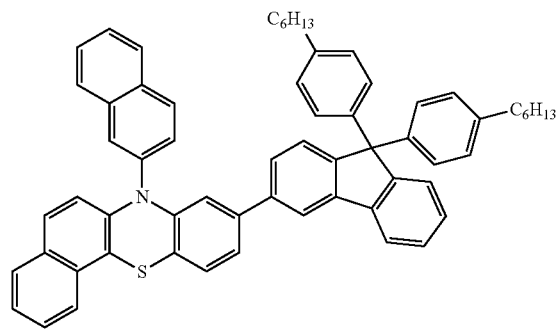
compound 72
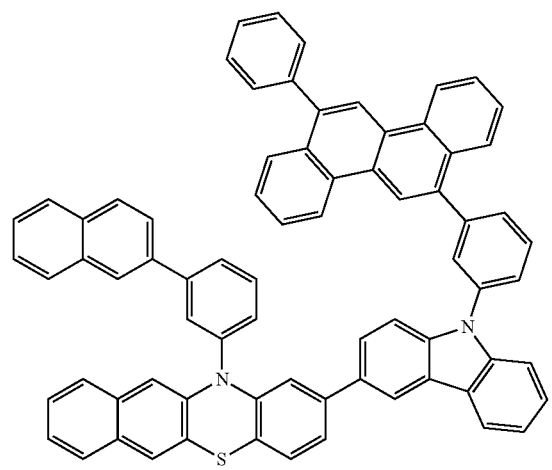

-continued
compound 73
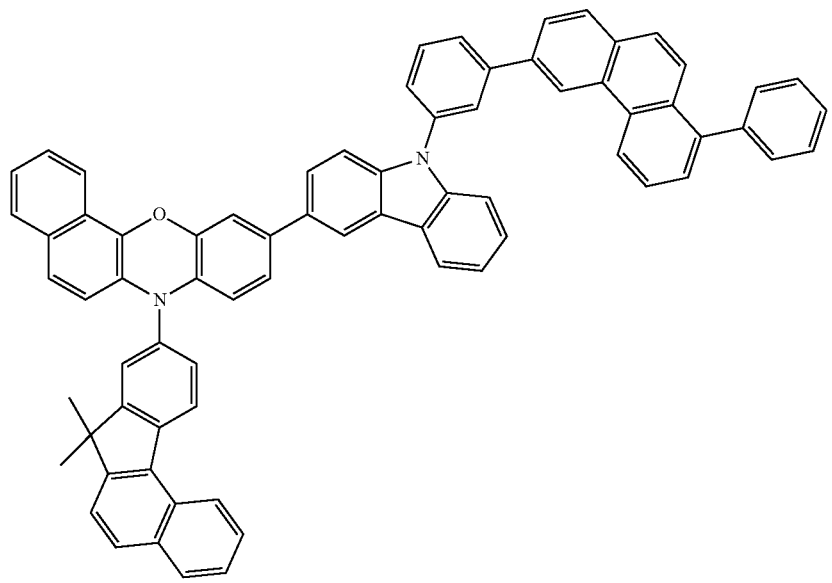
compound 74
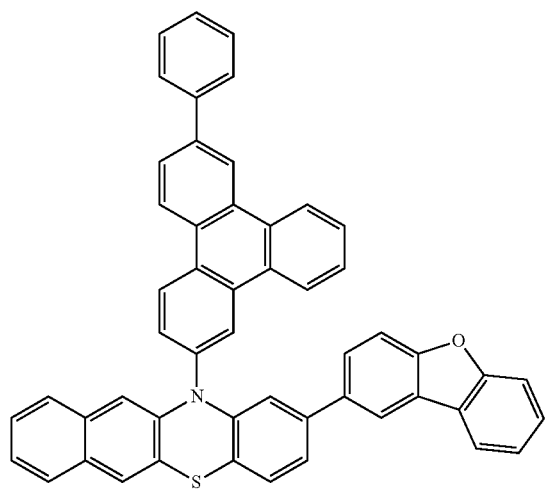
compound 75
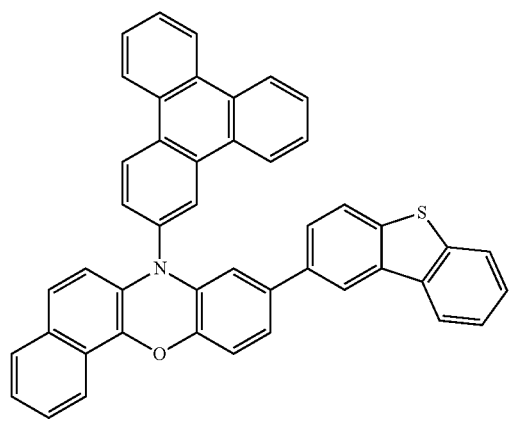
compound 76
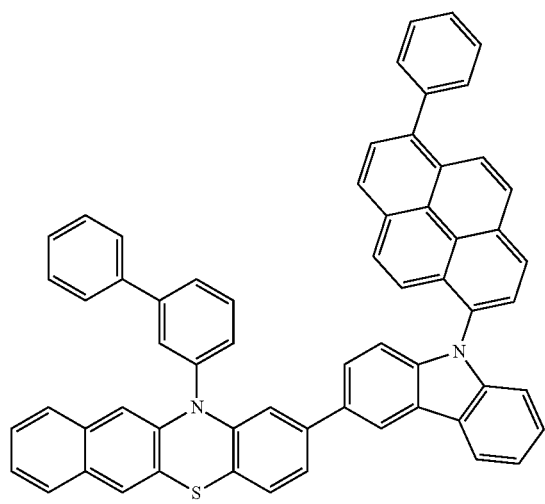
compound 77
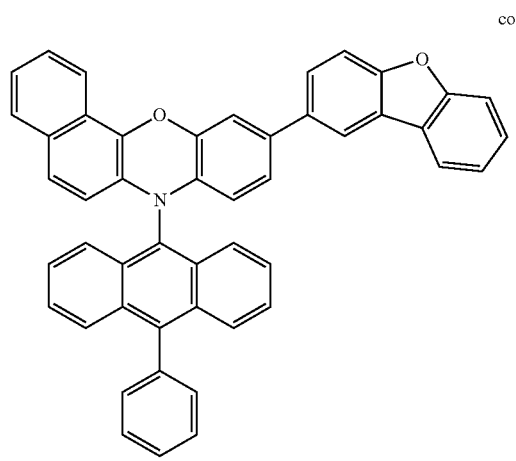

-continued
compound 78
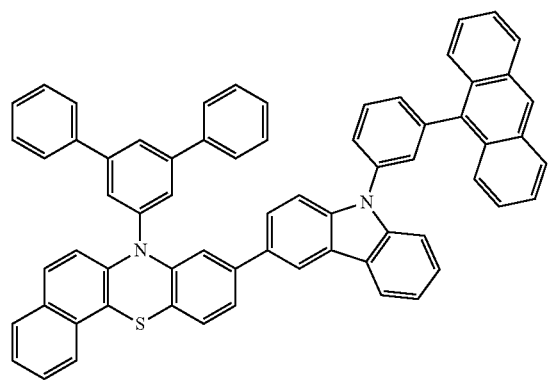
compound 79
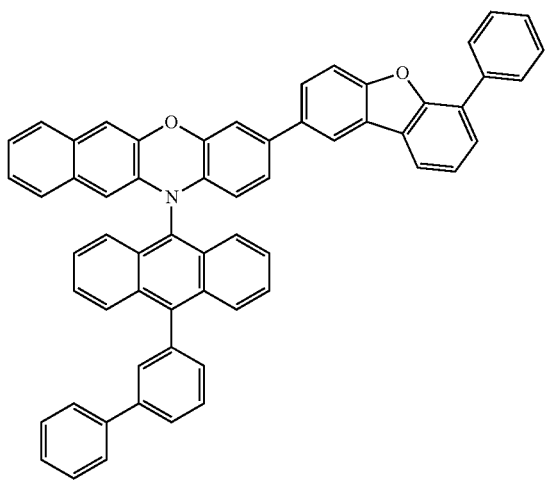
compound 80
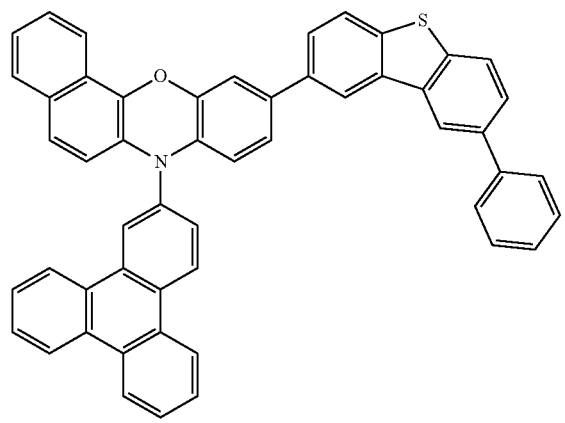
compound 81
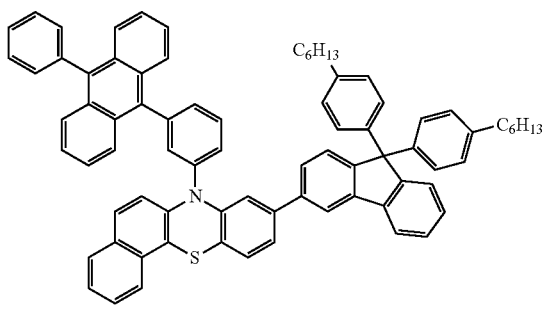
compound 82
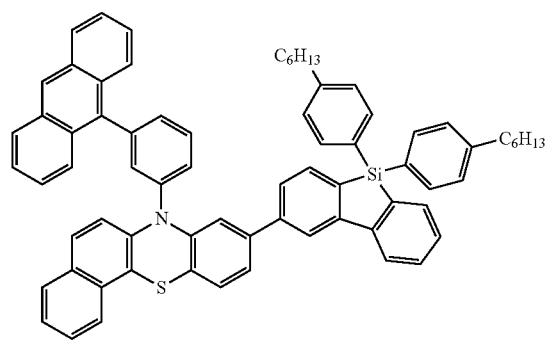
compound 83
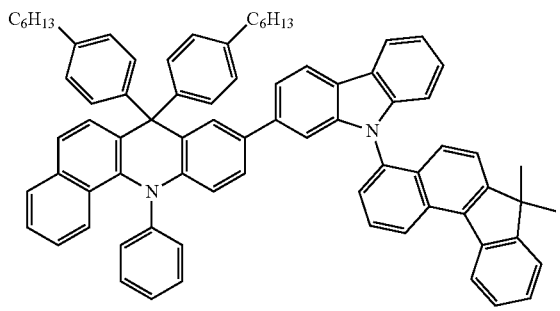

-continued
compound 84
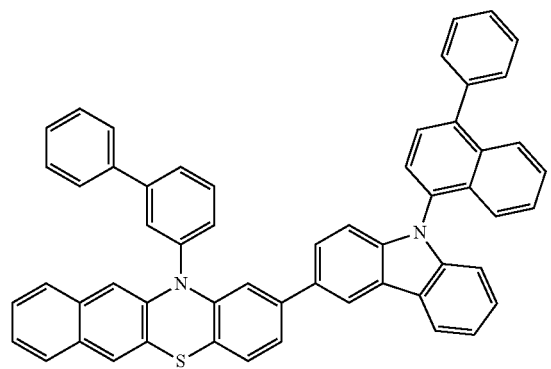
compound 85
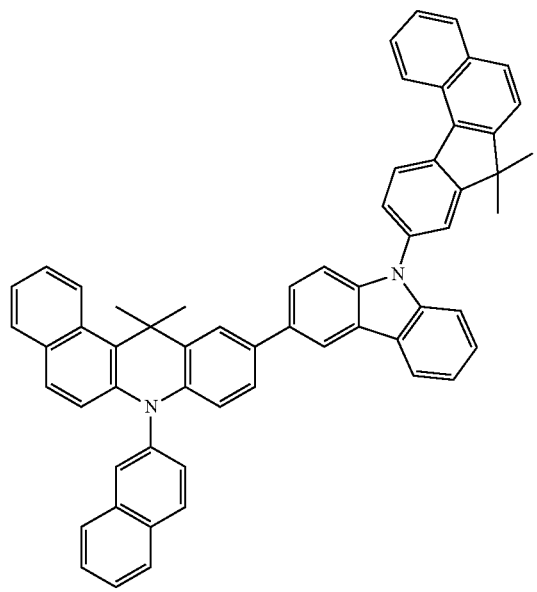
compound 86
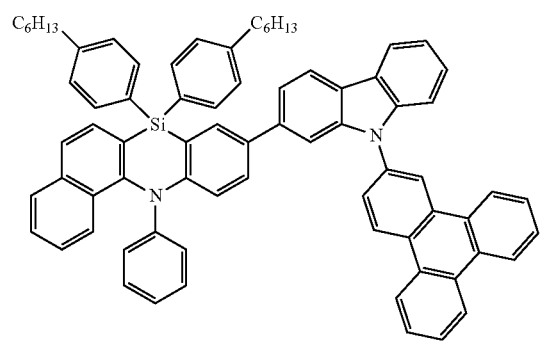
compound 87
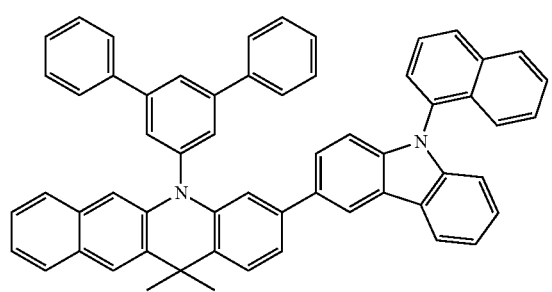
compound 88
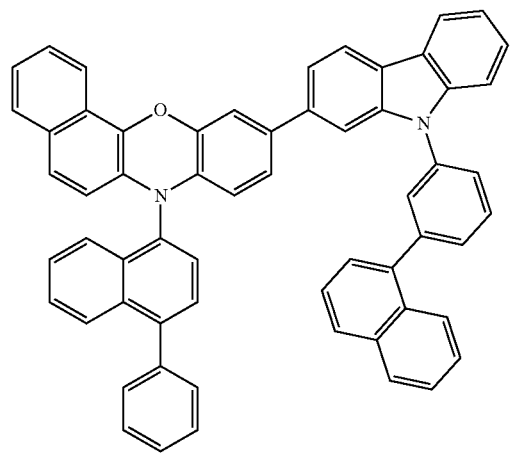
compound 89
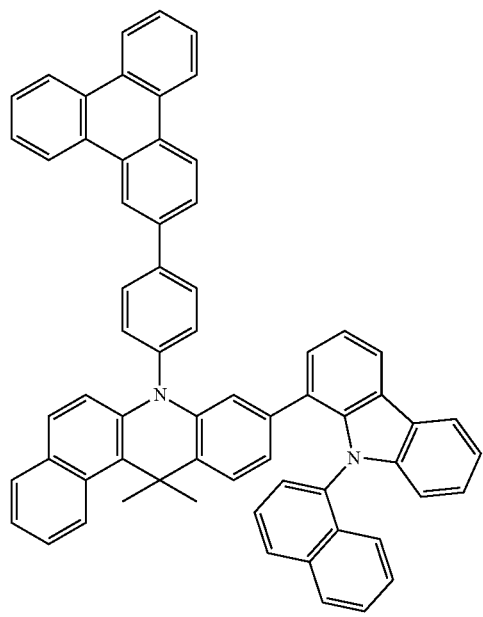

compound 90
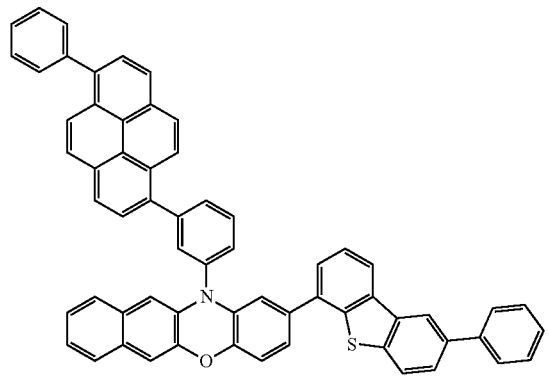
compound 91
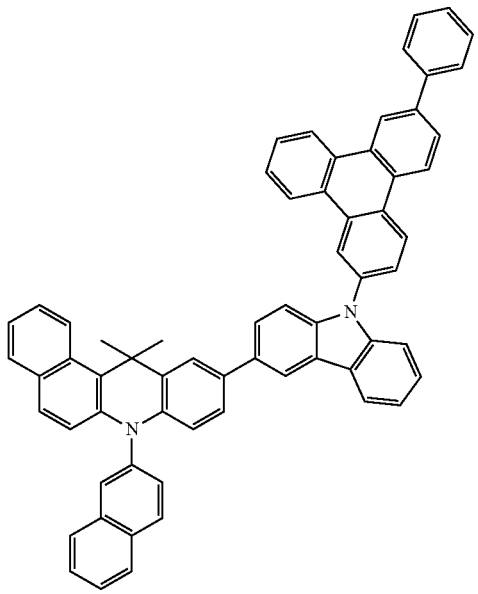
compound 92
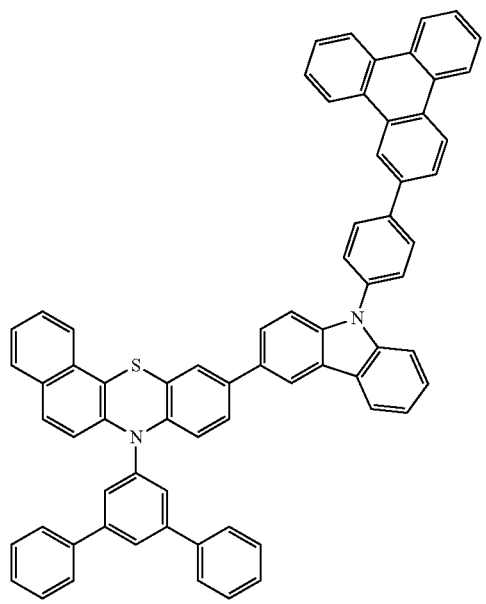
compound 93
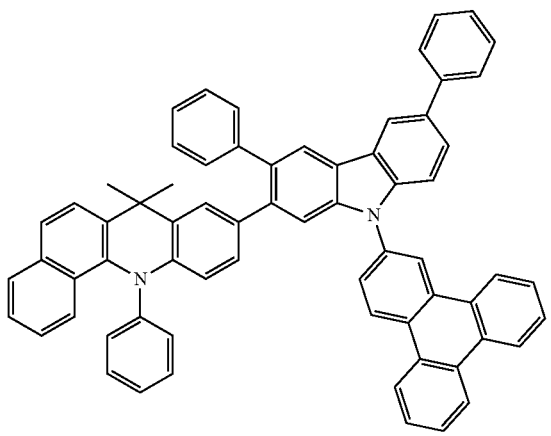

-continued
compound 94
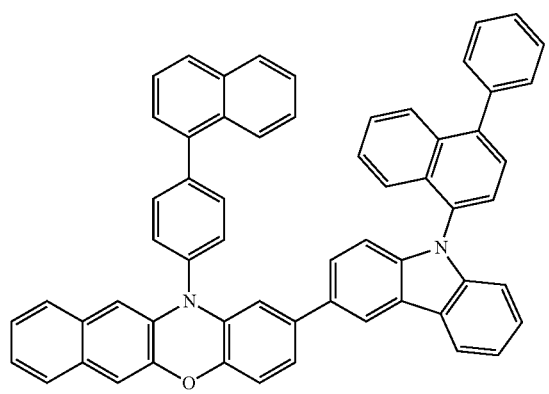
compound 95
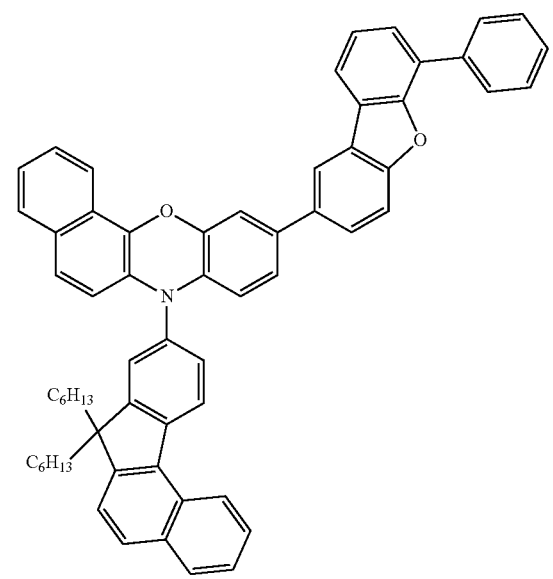
compound 96
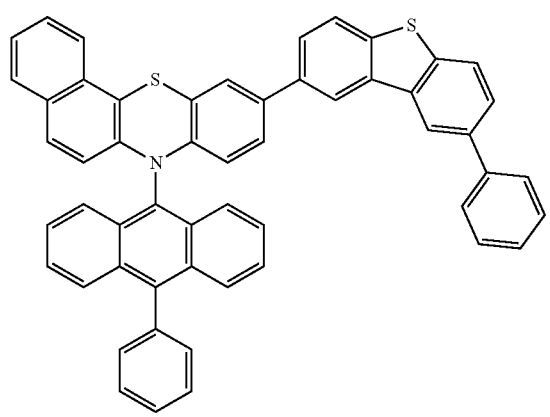
compound 97
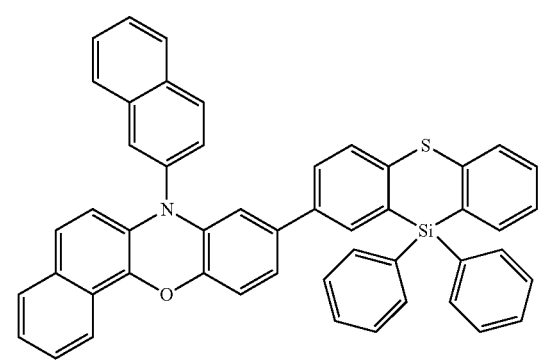
compound 98
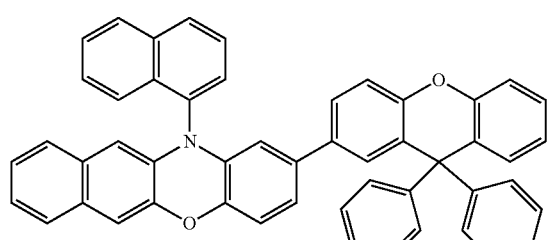
compound 99
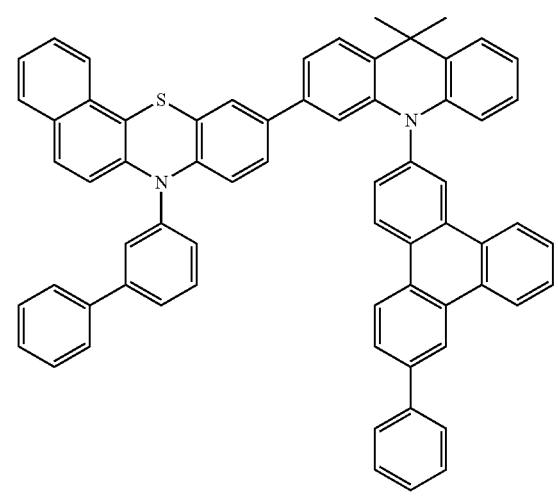

compound 100
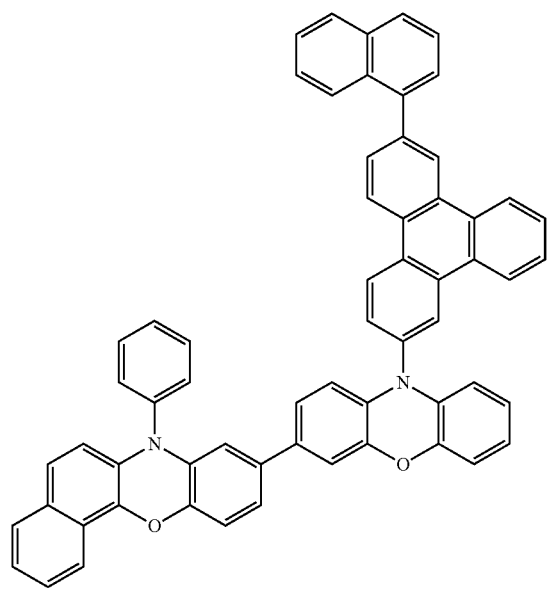
compound 101
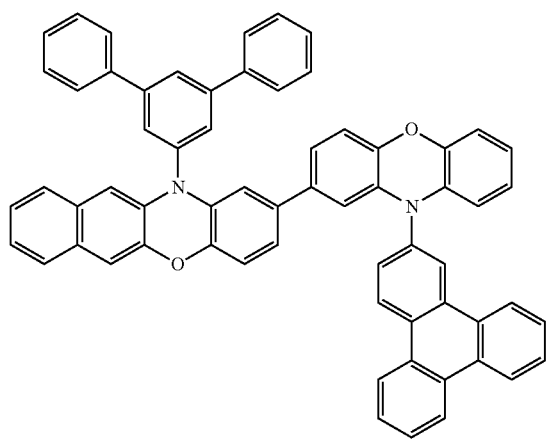
compound 102
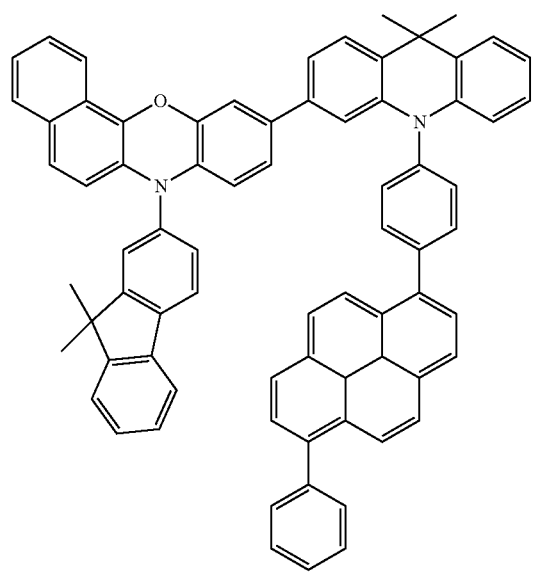
compound 103
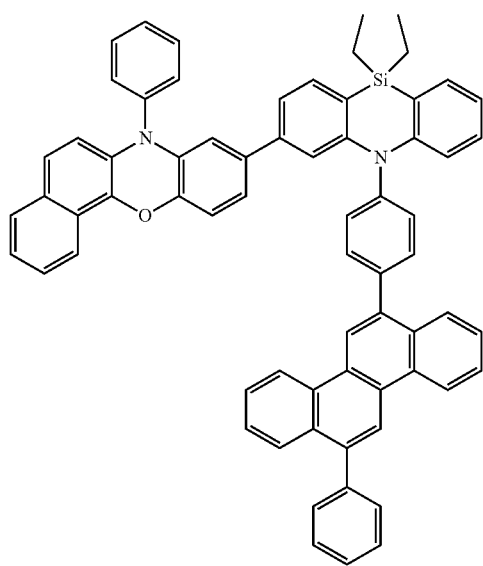

-continued
compound 104
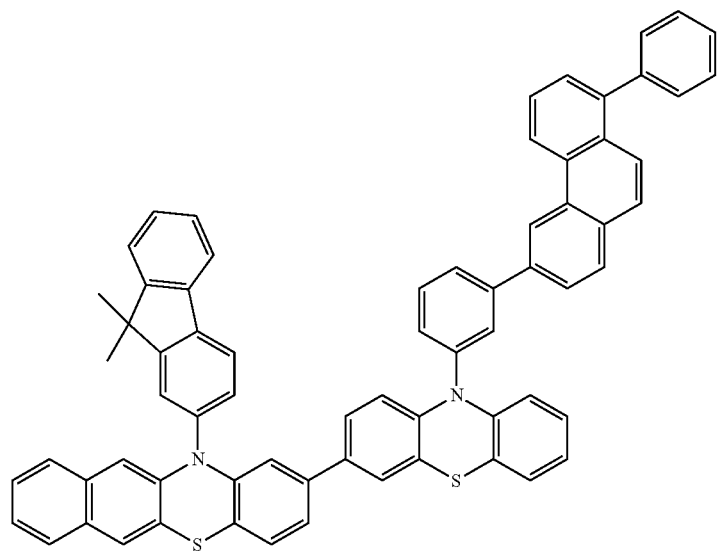
compound 105
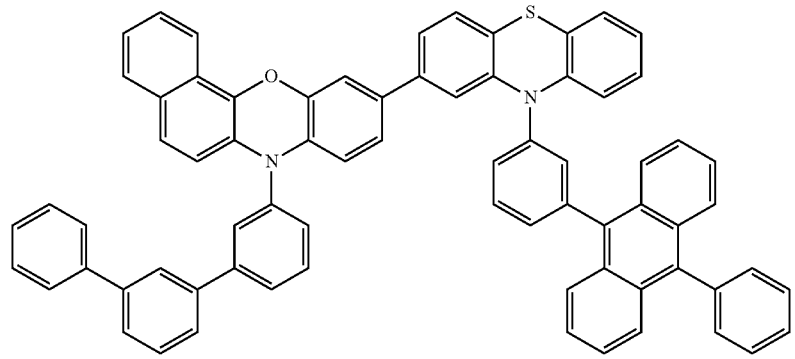
compound 106
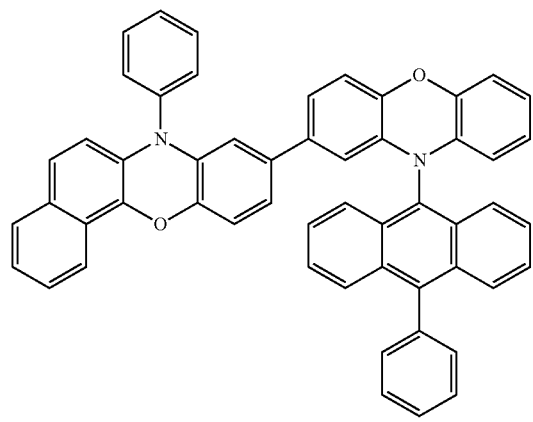
compound 107
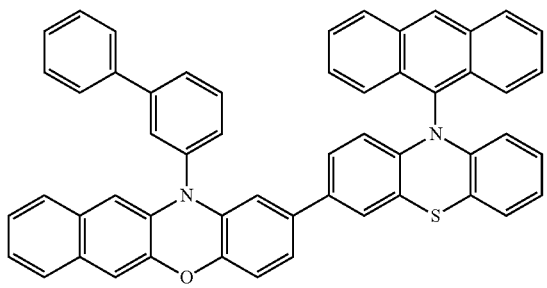

-continued
compound 108
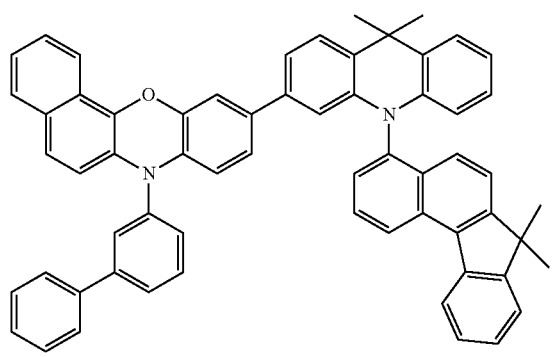
compound 109
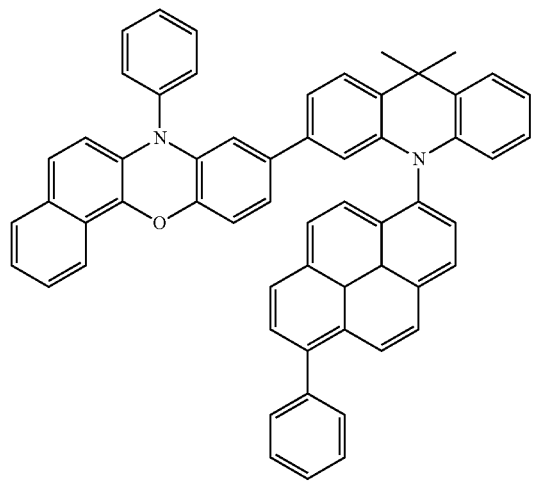
compound 111
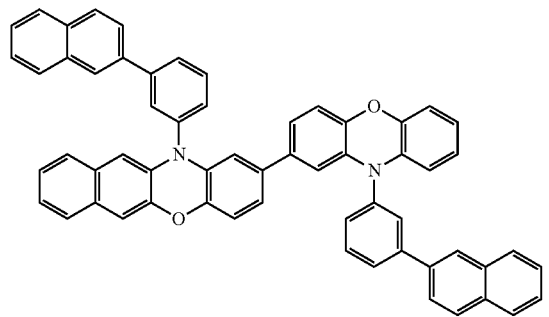
compound 110
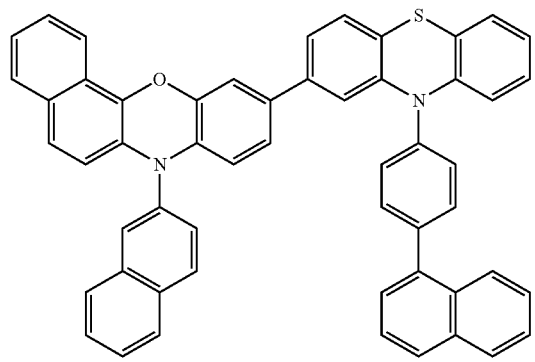
compound 112
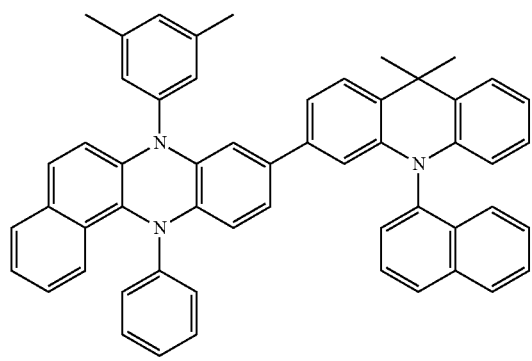
compound 113
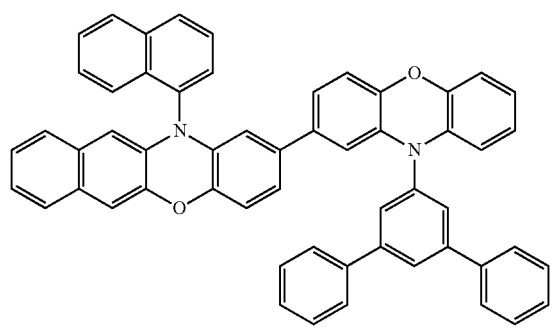

-continued
compound 114
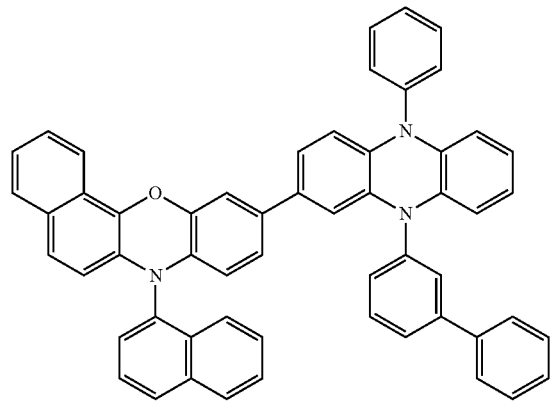
compound 115
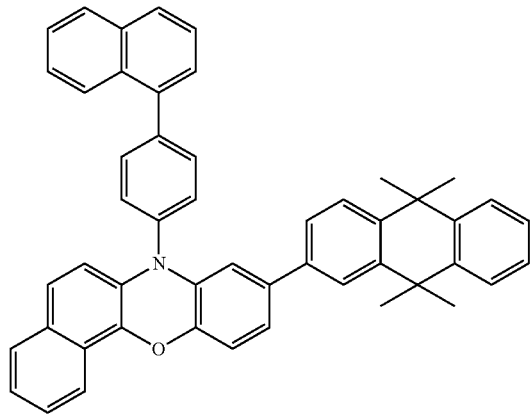
compound 116
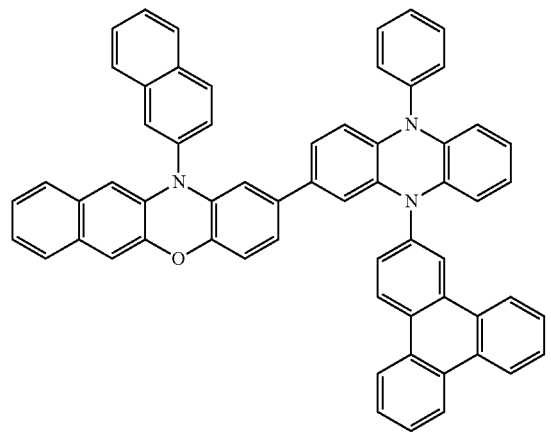
compound 117
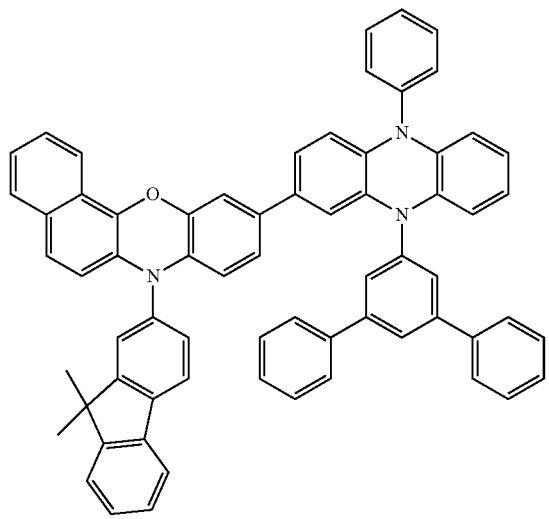
compound 118
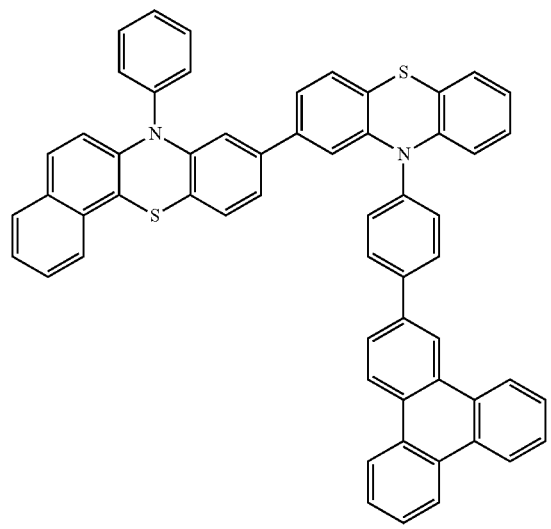
compound 119
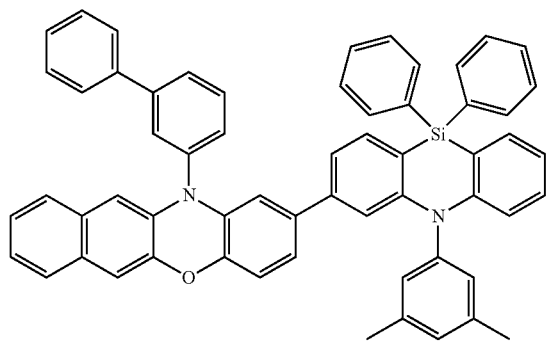

-continued
compound 120
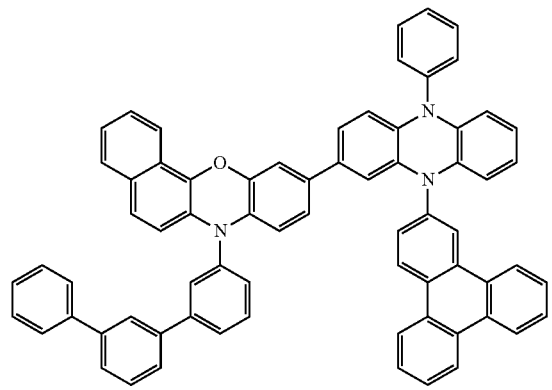
compound 121
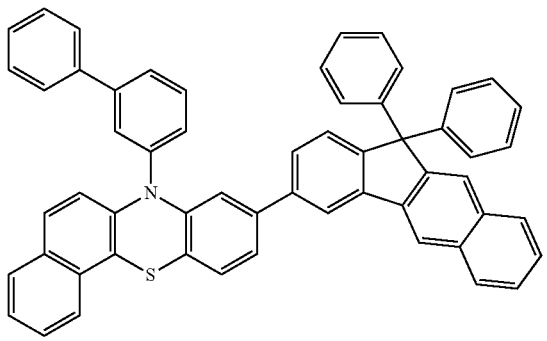
compound 122
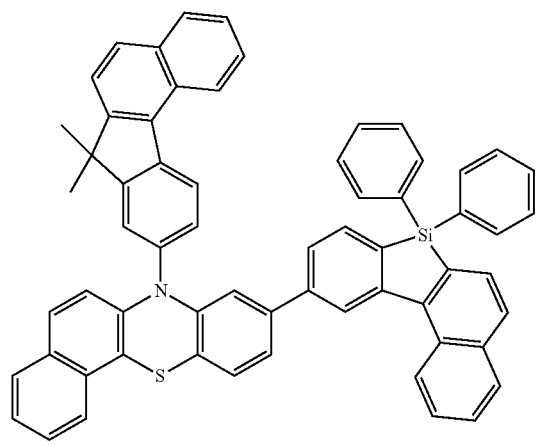
compound 123
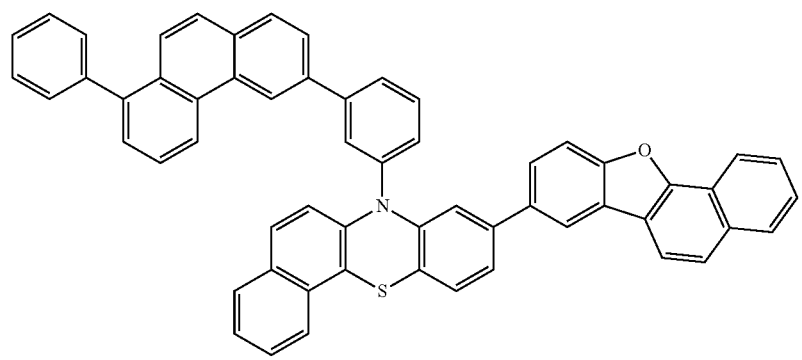

-continued
compound 124
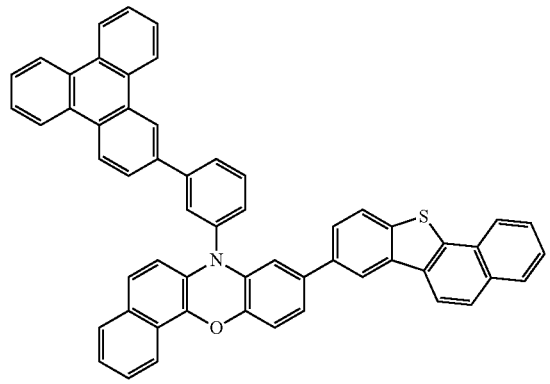
compound 125
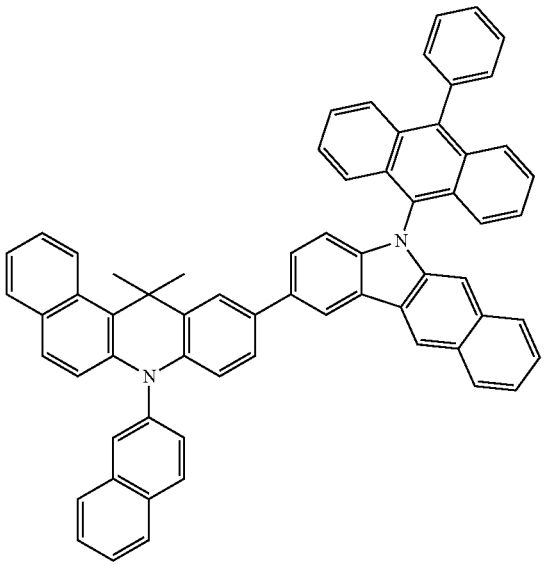
compound 126
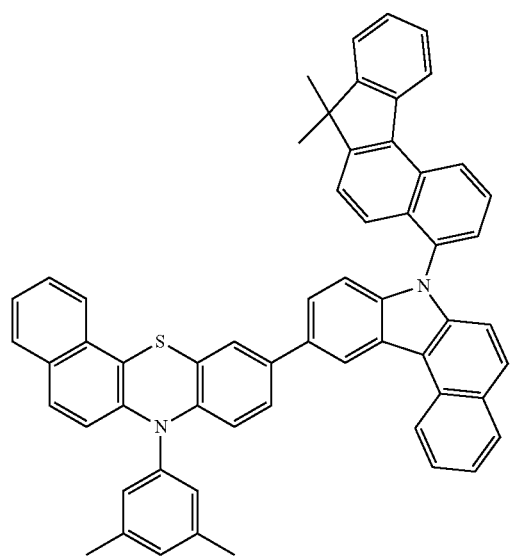
compound 127
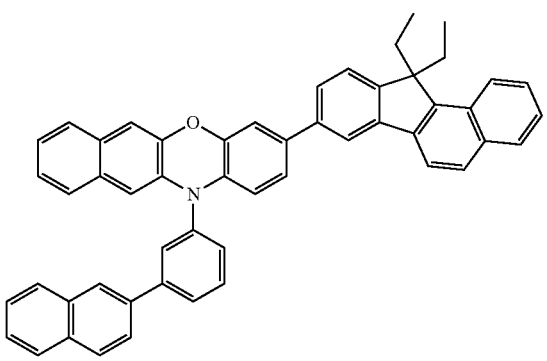

-continued
compound 128
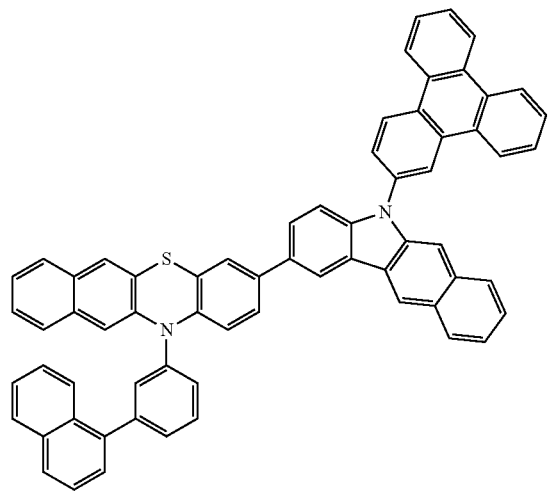
compound 129
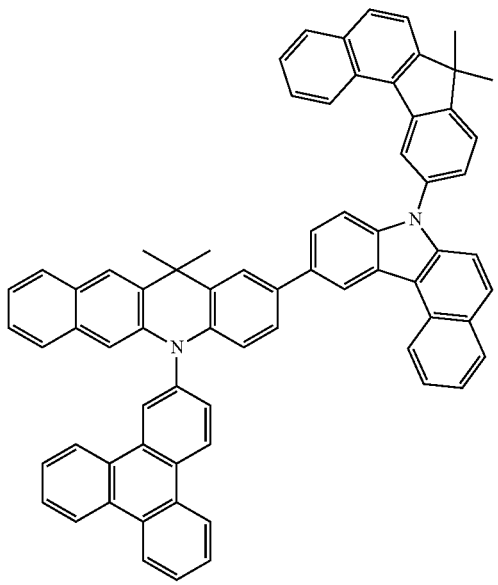
compound 130
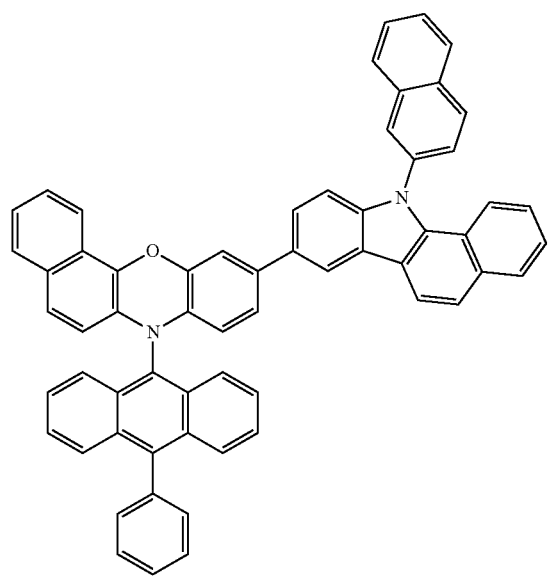
compound 131
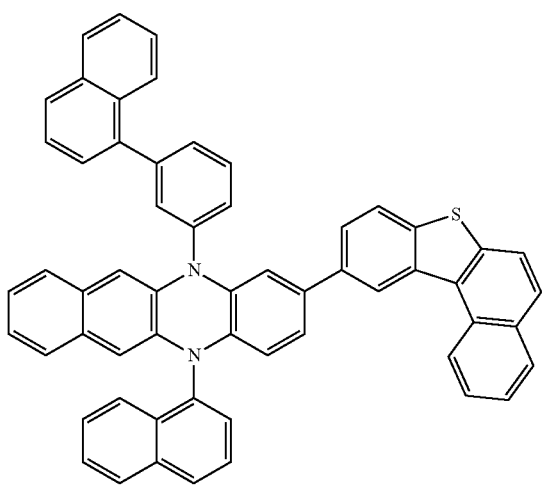
compound 132
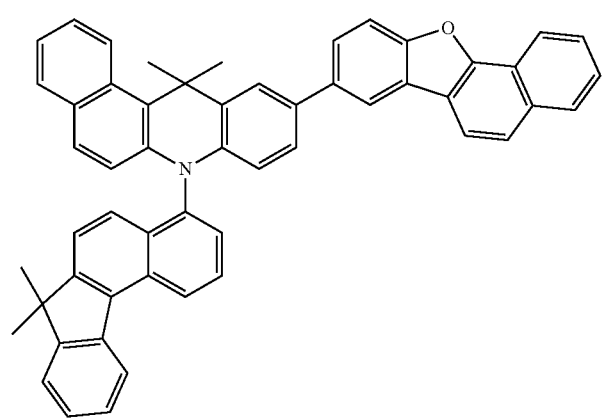
compound 133
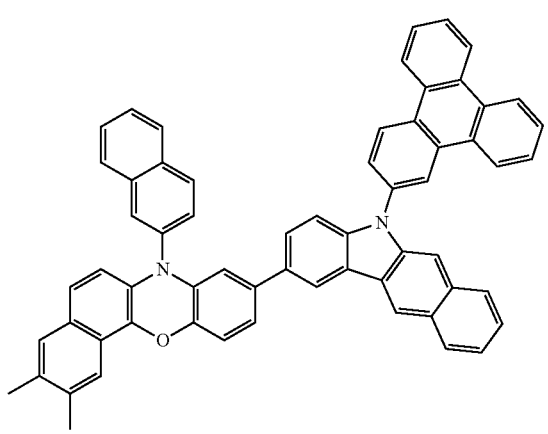

-continued
compound 134
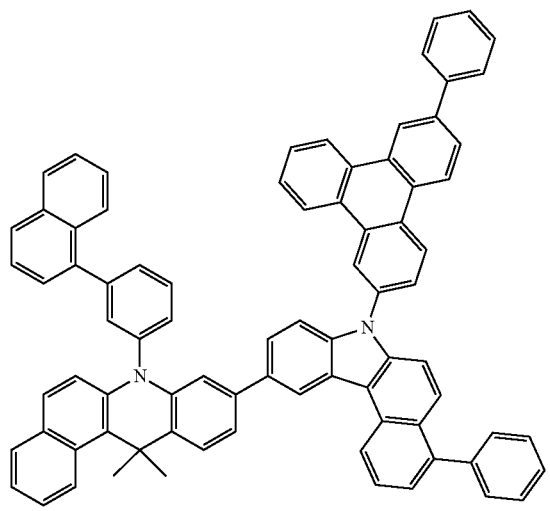
compound 135
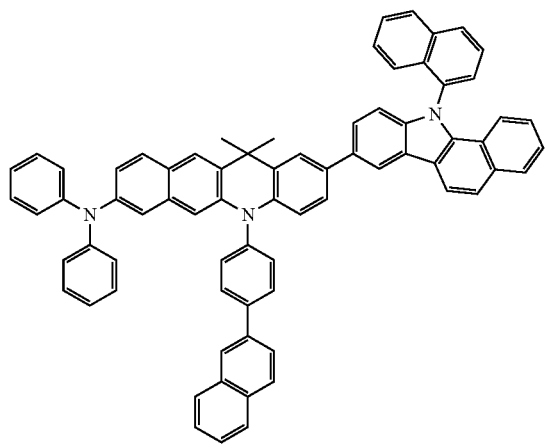
compound 136
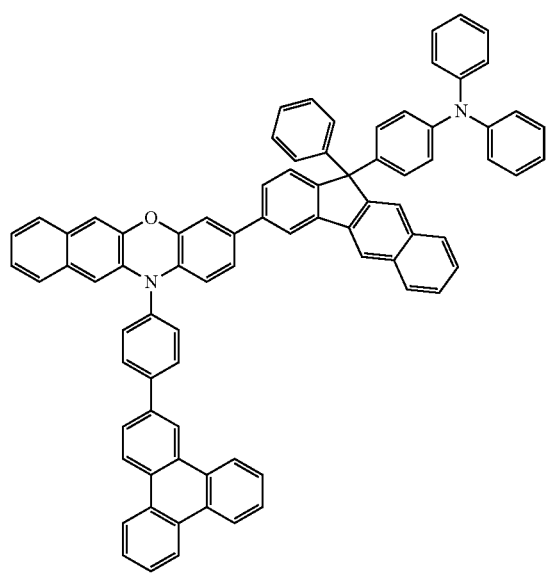
compound 137
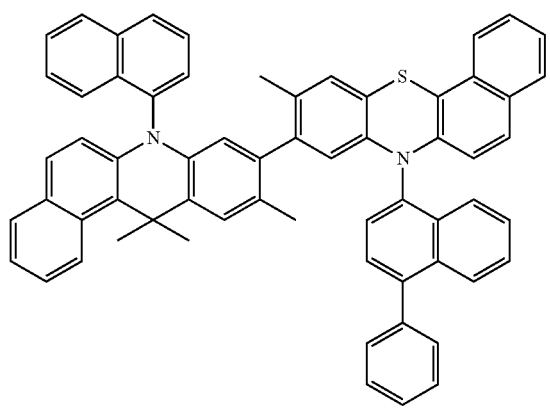
compound 138
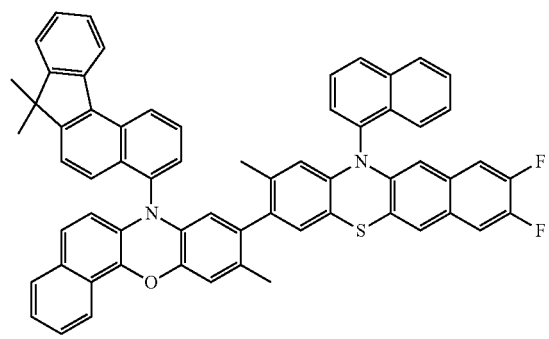
compound 139
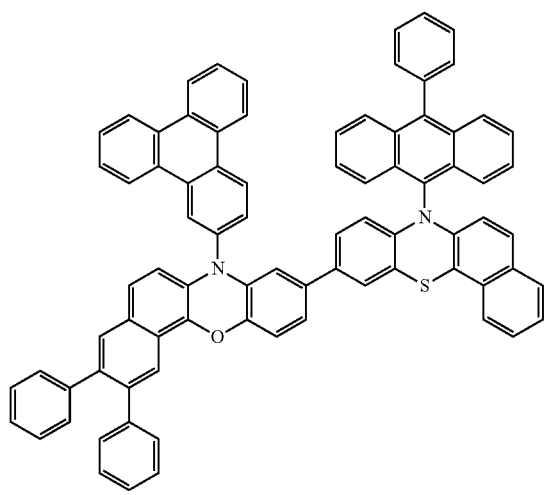

-continued
compound 140
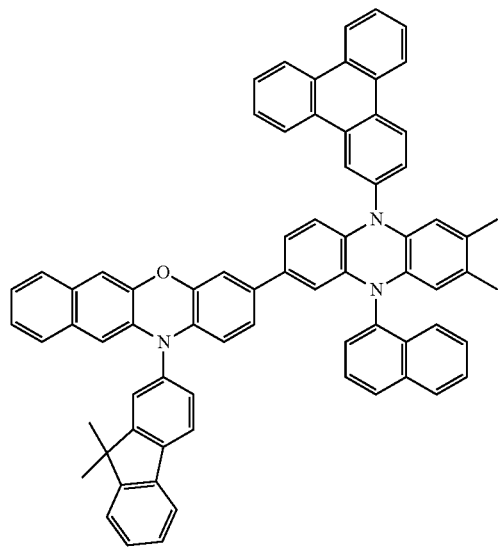
compound 141
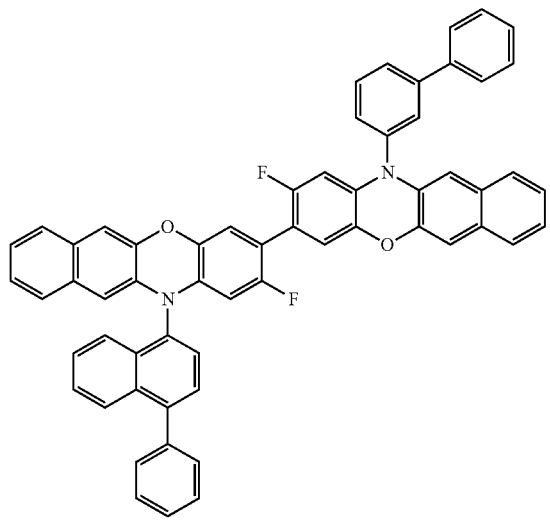
compound 142
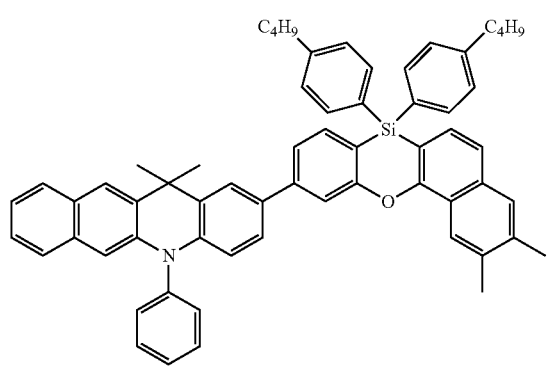
compound 143
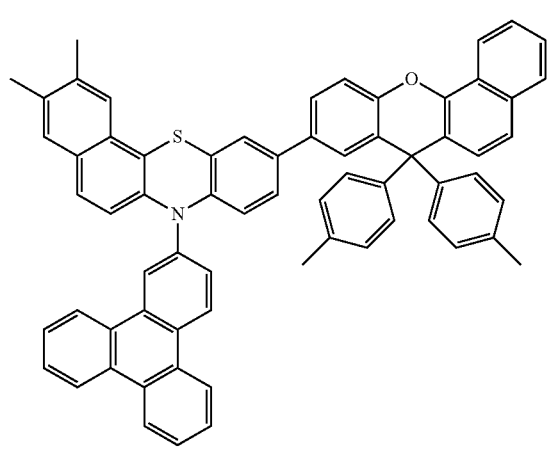
compound 144
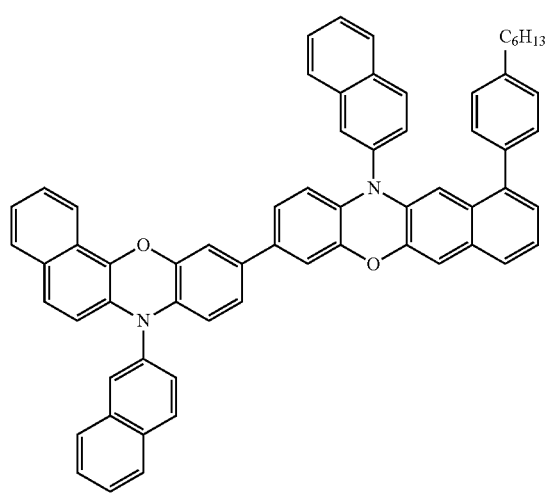
compound 145
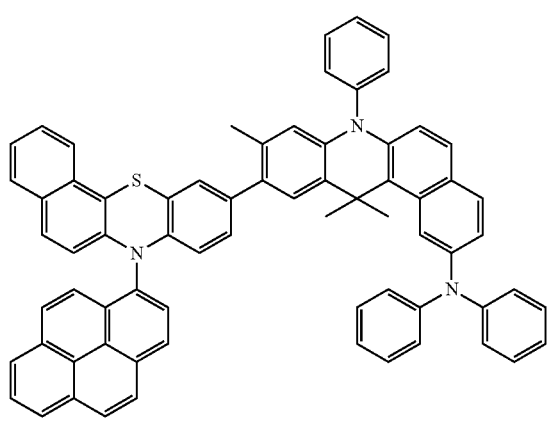

-continued
compound 146
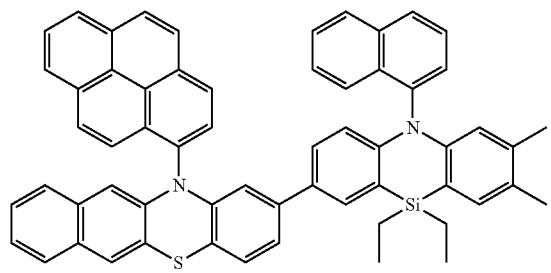
compound 147
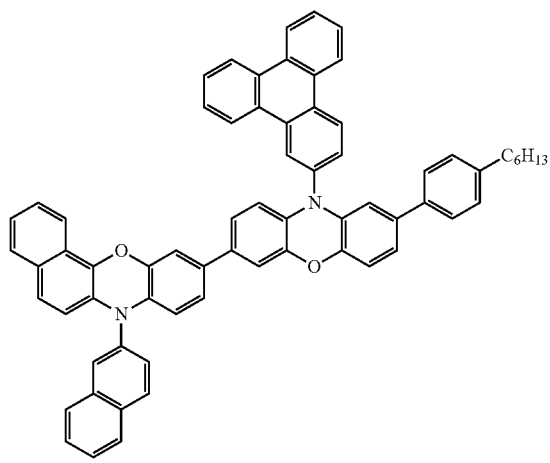
compound 148
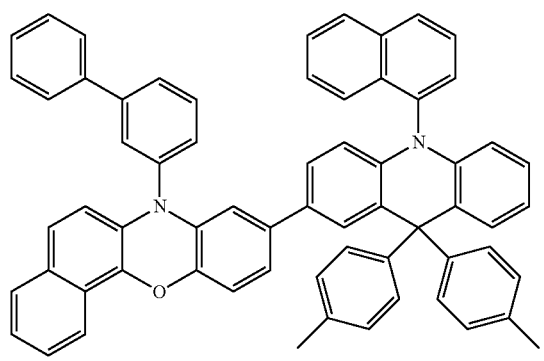
compound 149
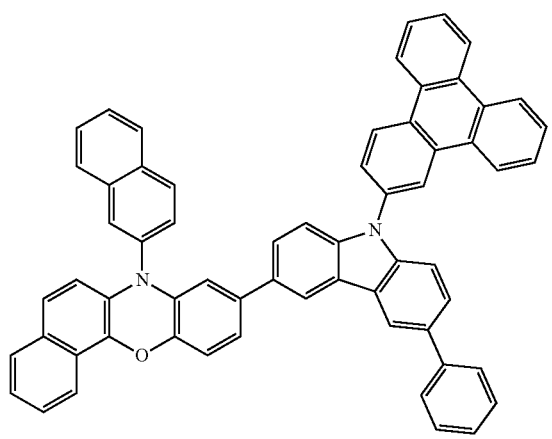
compound 150
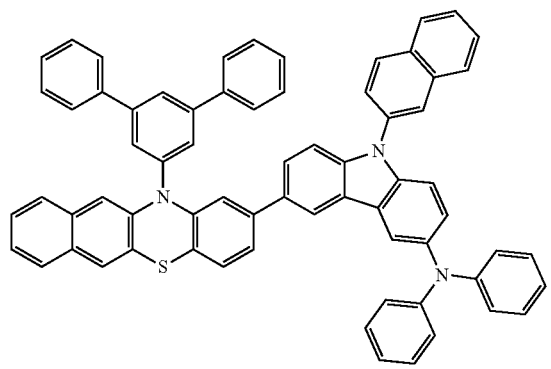
compound 151
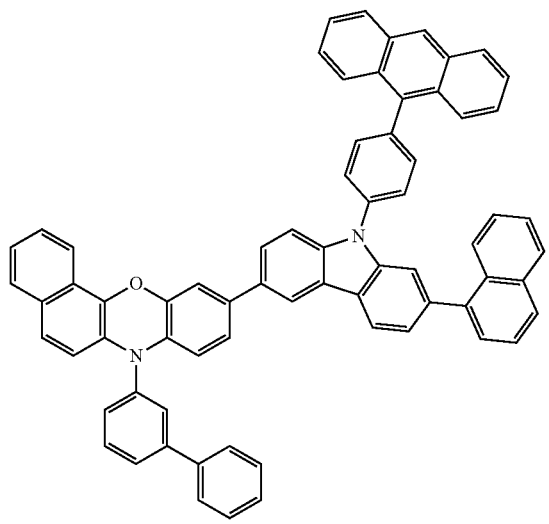

-continued
compound 152
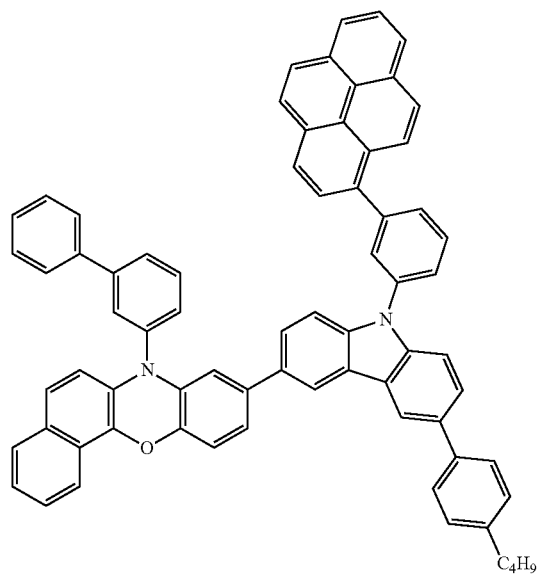
compound 153
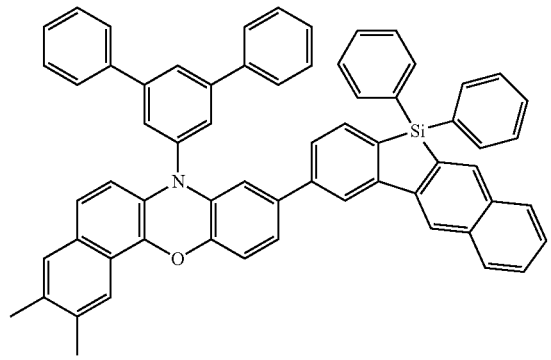
compound 154
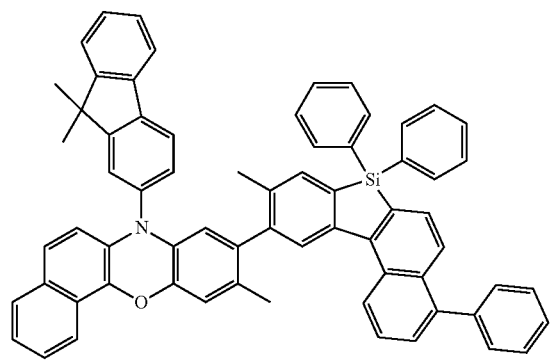
compound 155
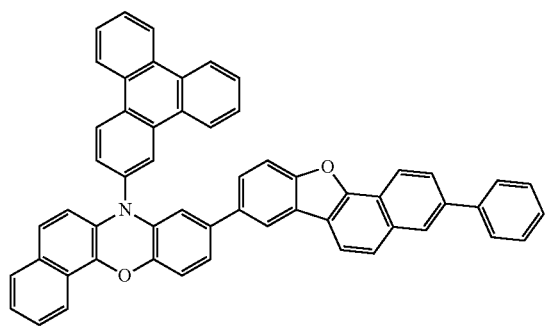
compound 156
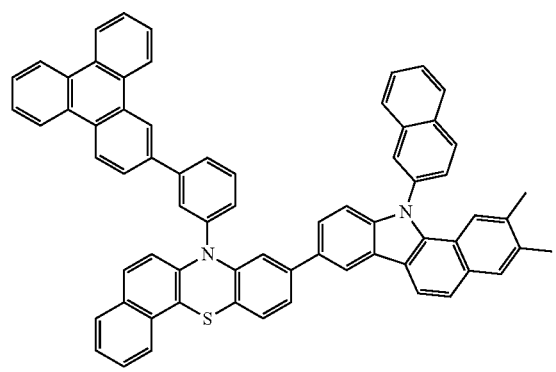
compound 157
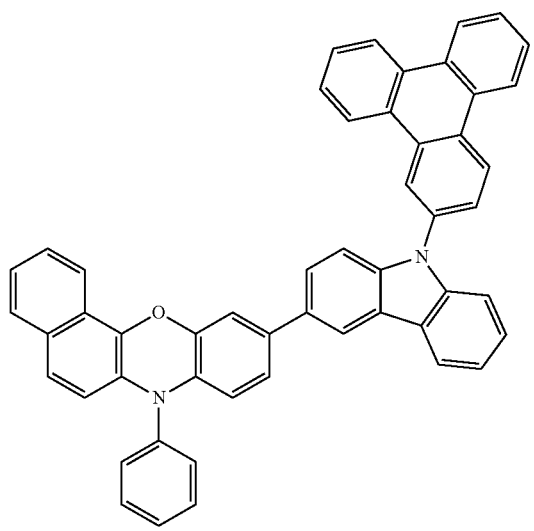

-continued
compound 158
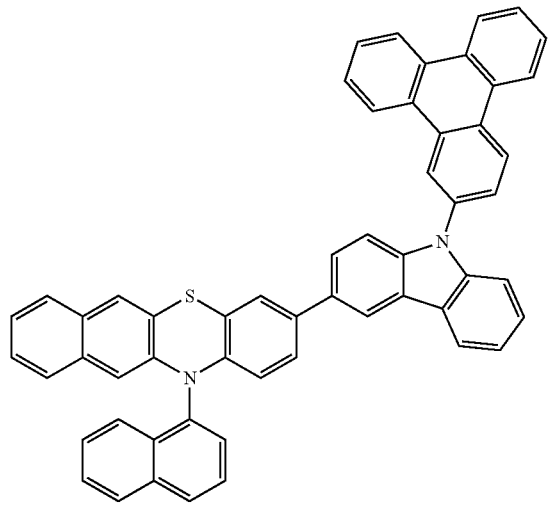
compound 159
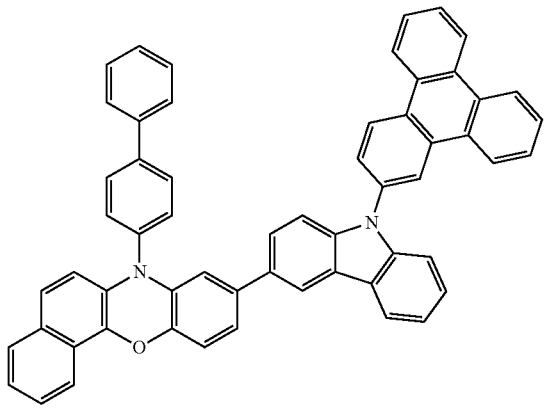
compound 160
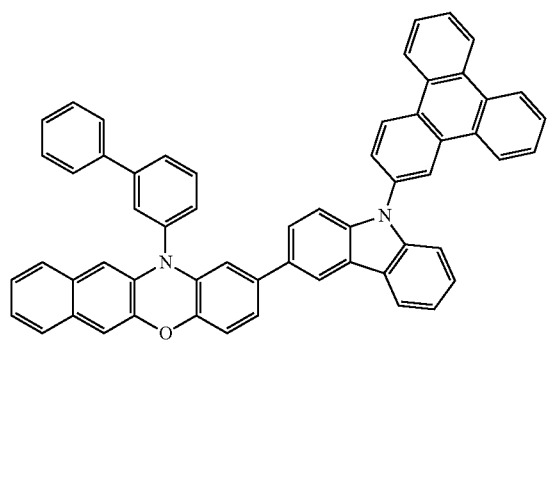
compound 161
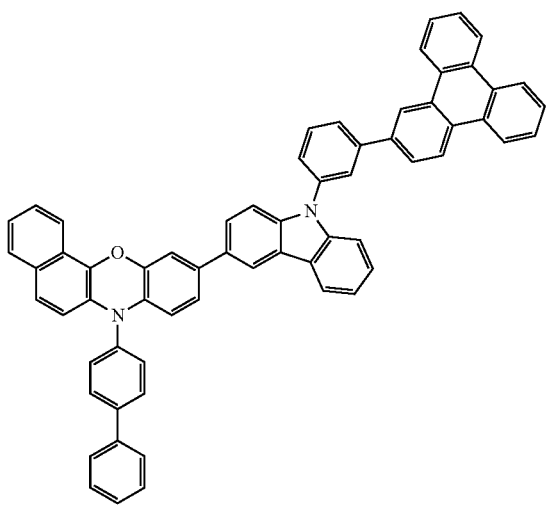
compound 162
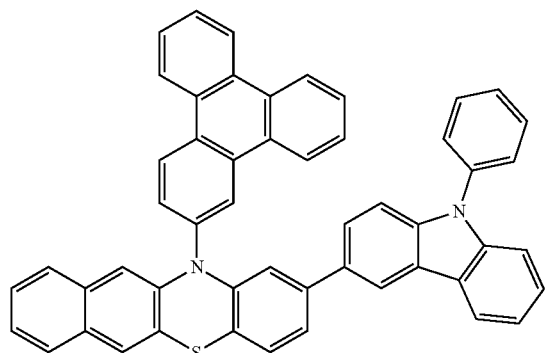
compound 163
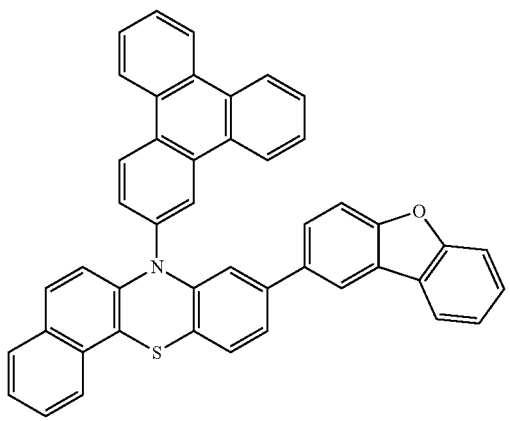

-continued
compound 164
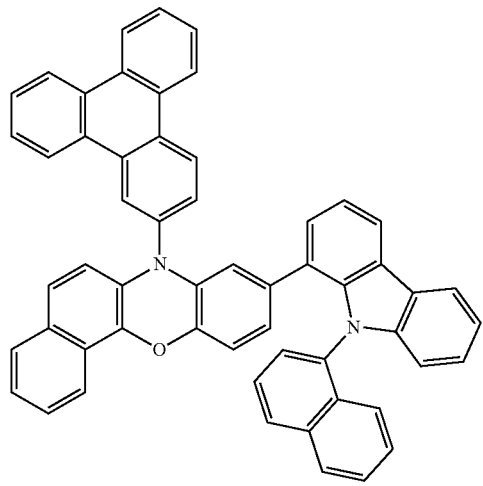
compound 165
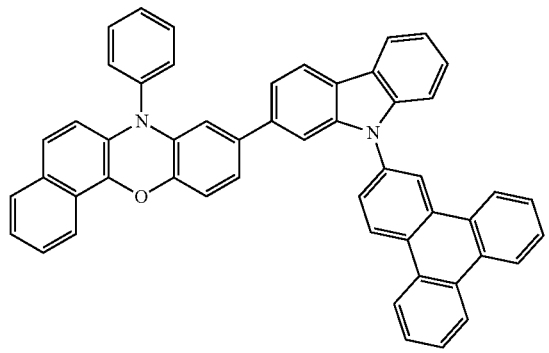
compound 166
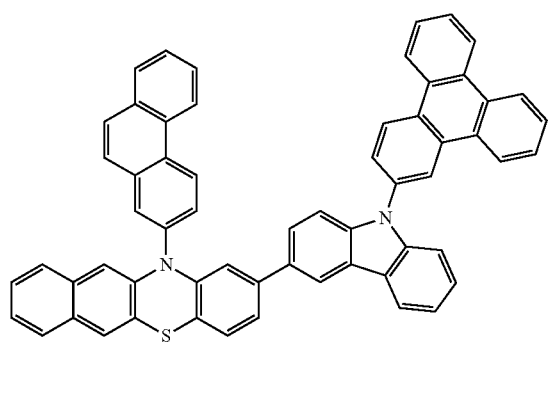
compound 167
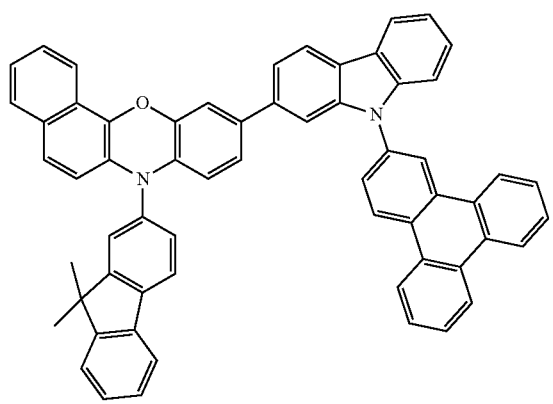
compound 168
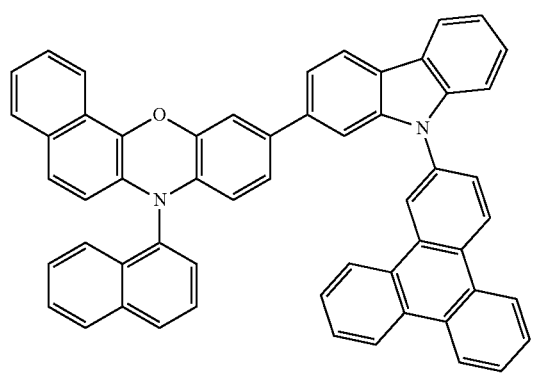
compound 169
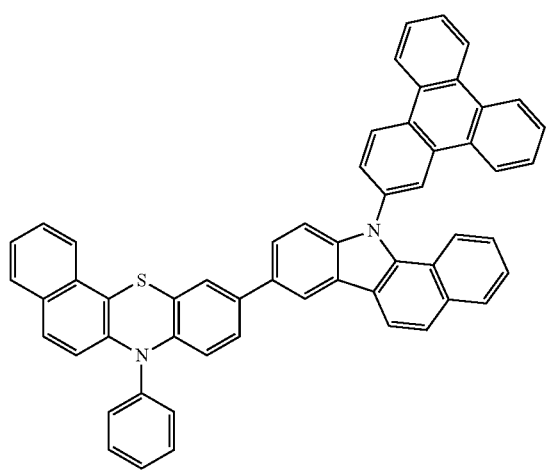

compound 170
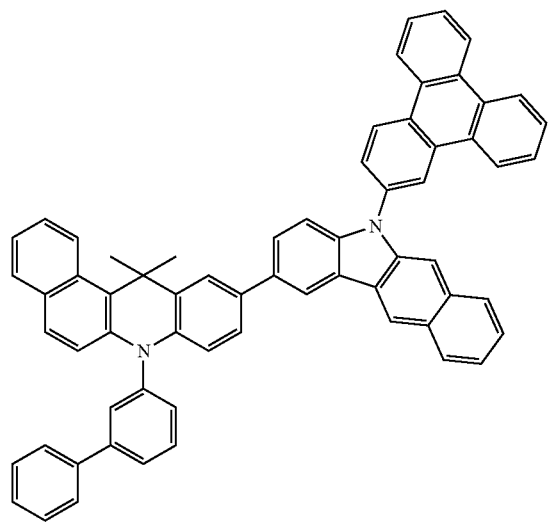
compound 171
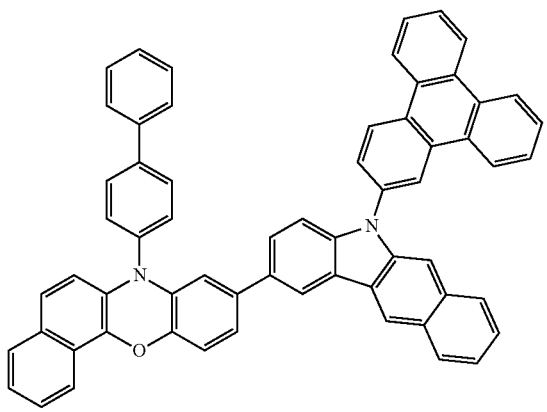
compound 172
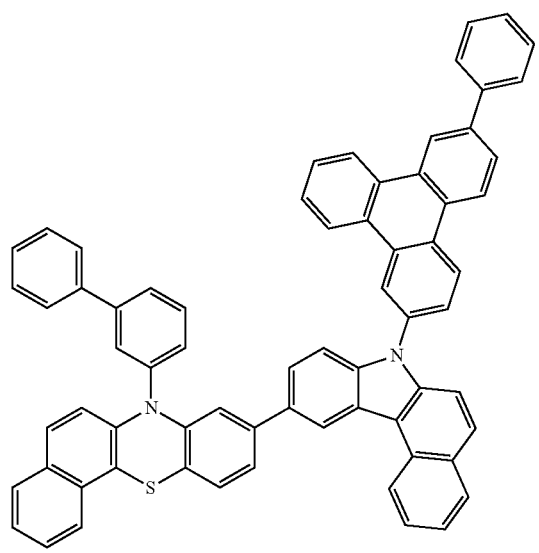
compound 173
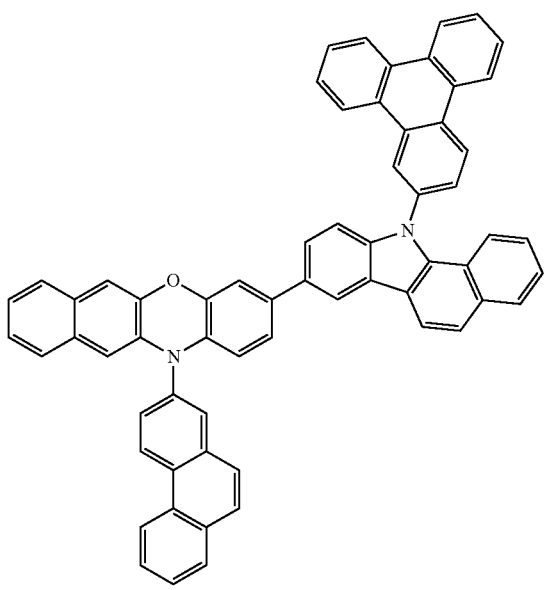

-continued
compound 174
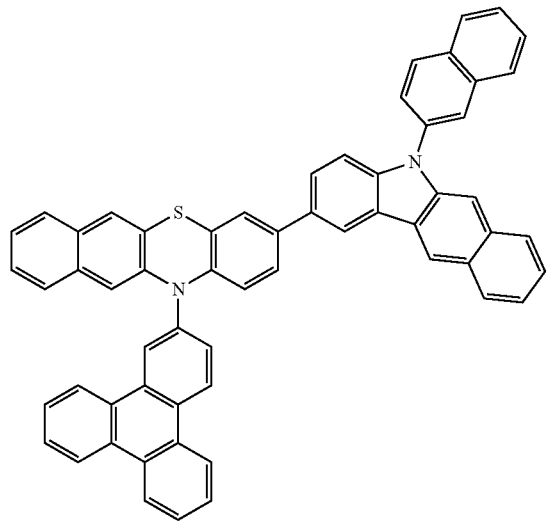
compound 175
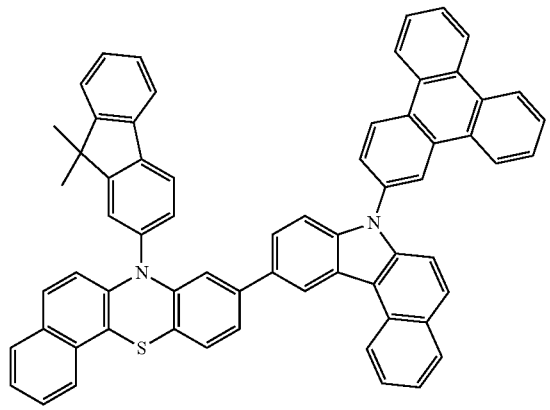
compound 176
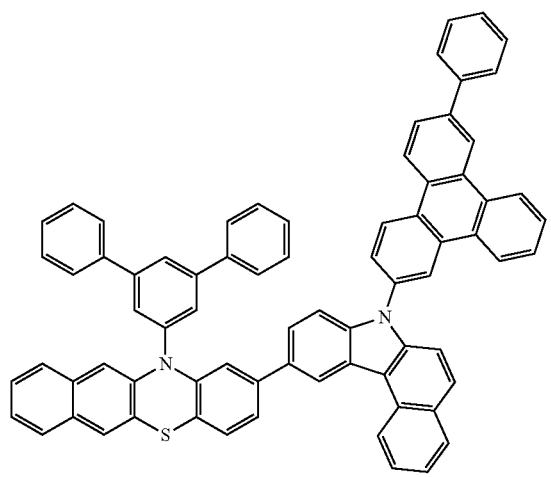
compound 177
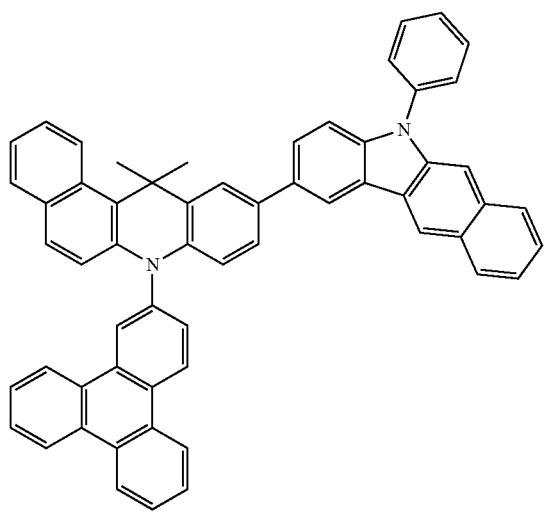
compound 178
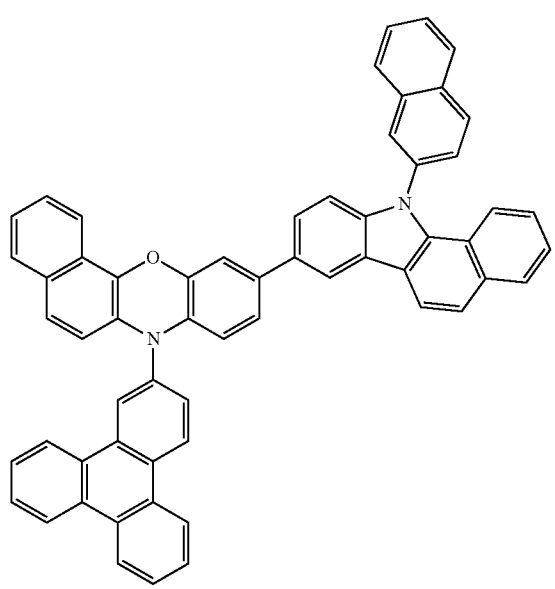
compound 179
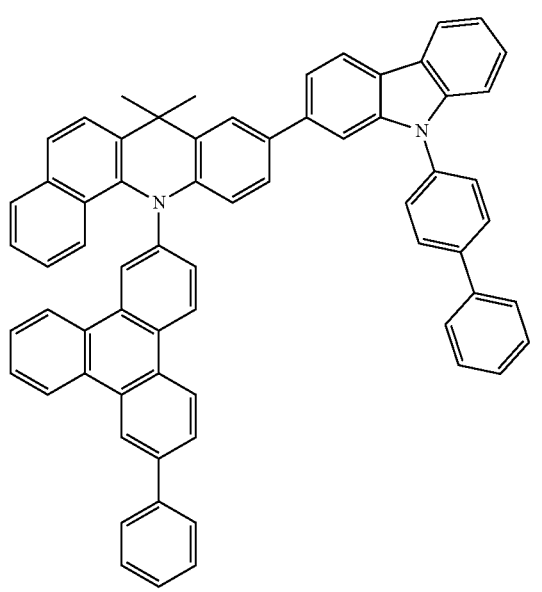

-continued
compound 180
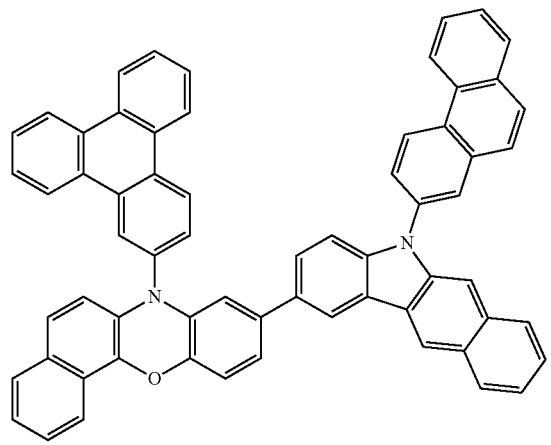
compound 181
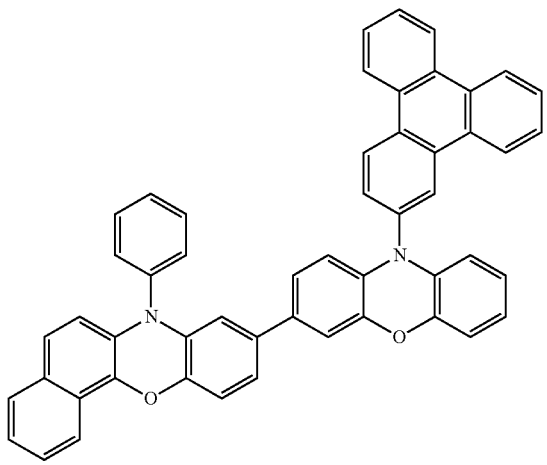
compound 182
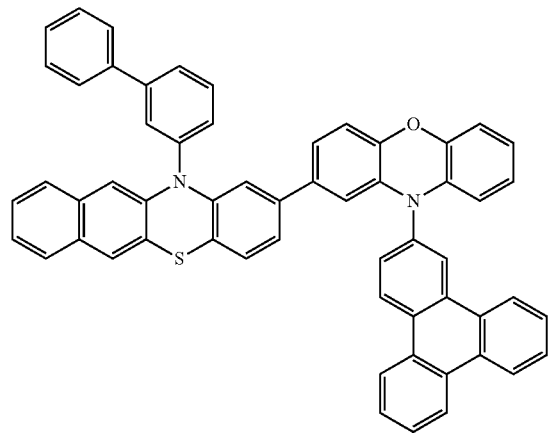
compound 183
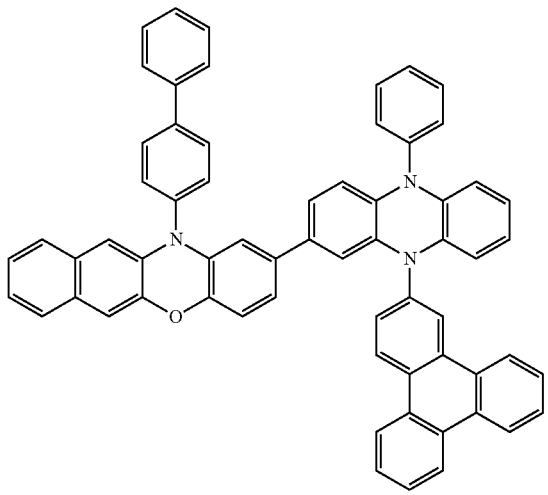
compound 184
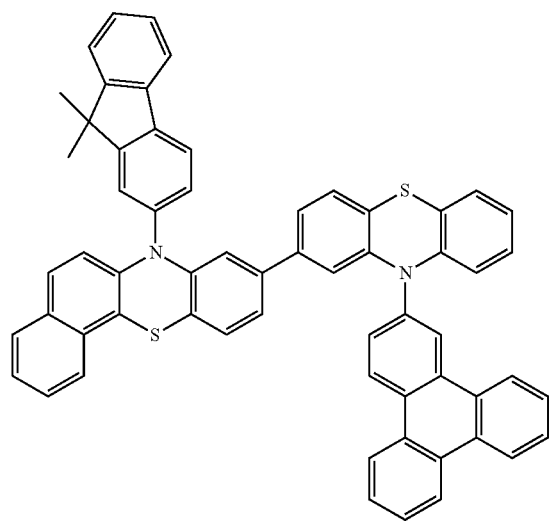
compound 185
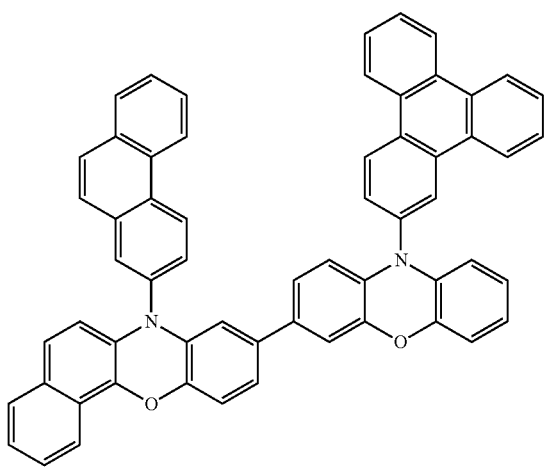

compound 186
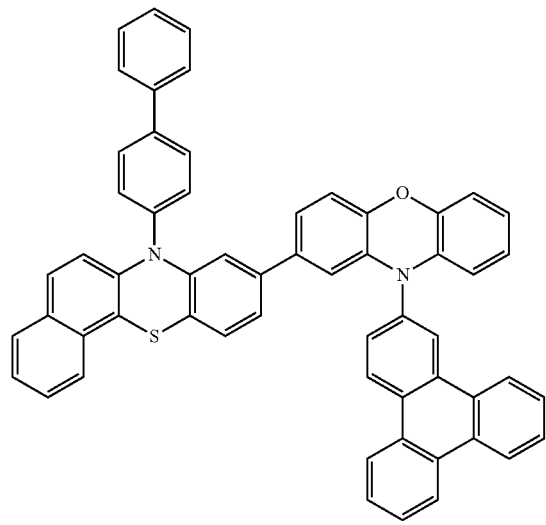
compound 187
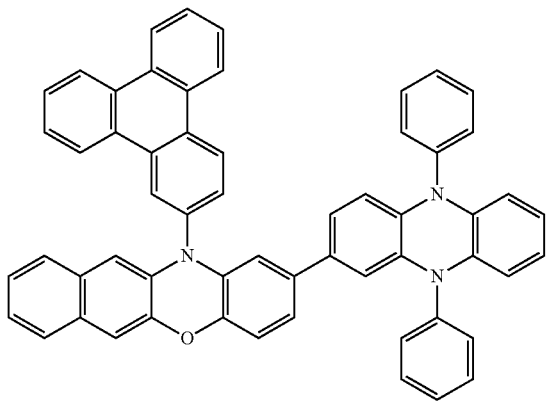
compound 188
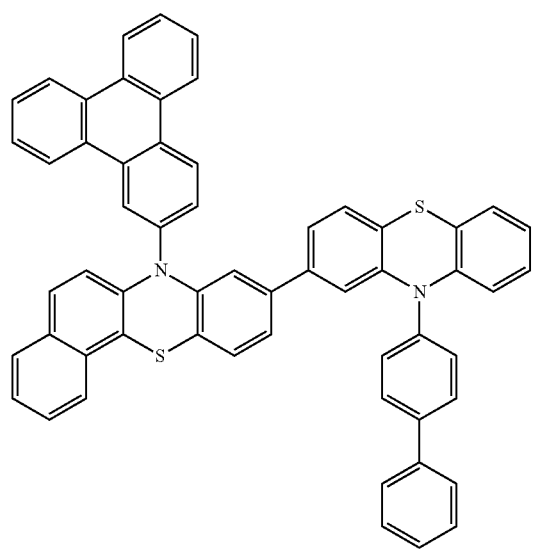
compound 189
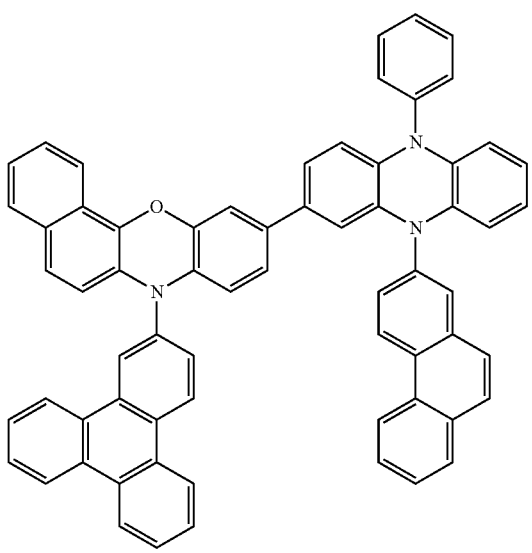

compound 190
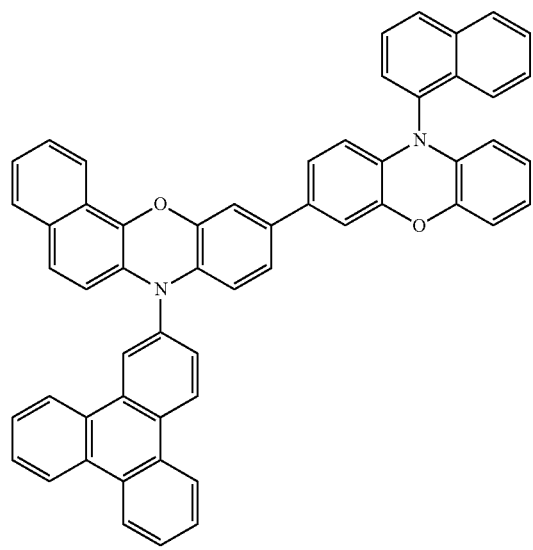
compound 191
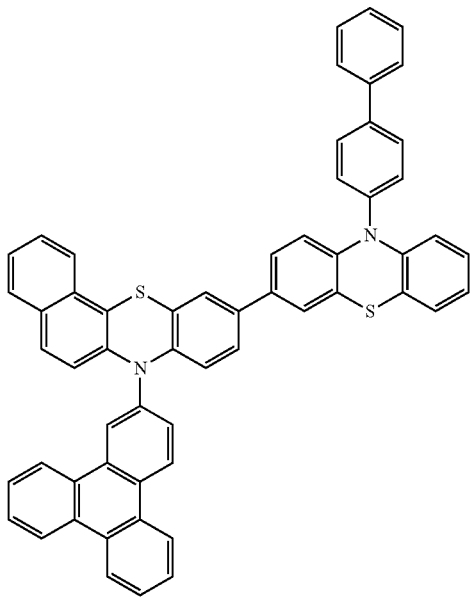
compound 192
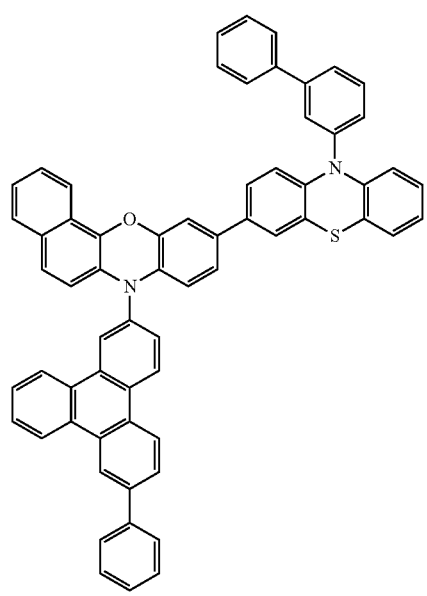
compound 193
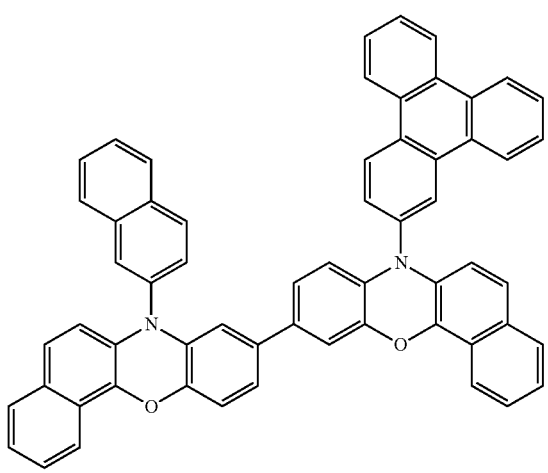

compound 194
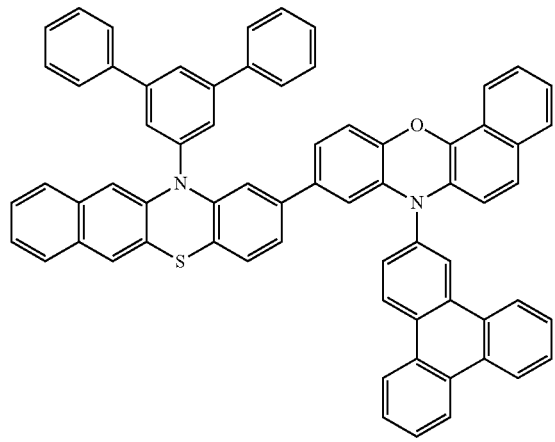
compound 195
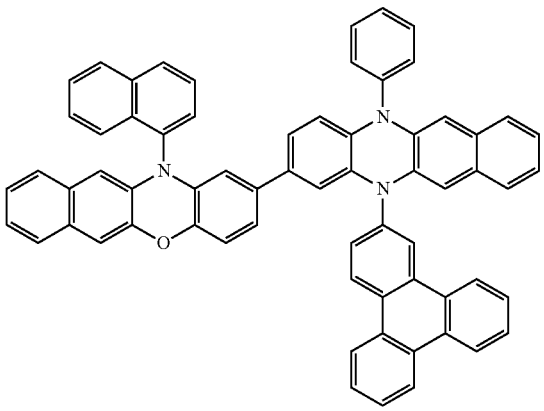
compound 196
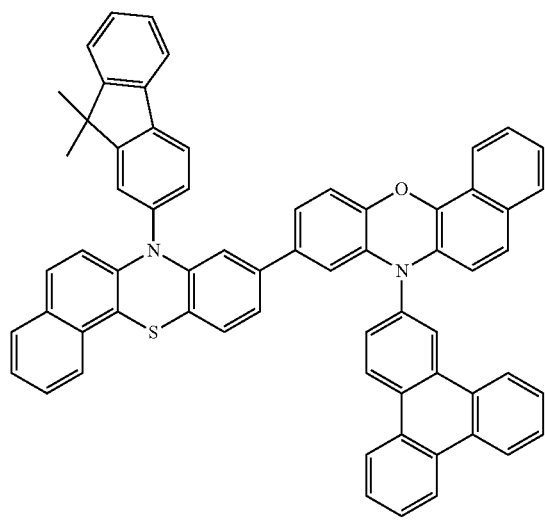
compound 197
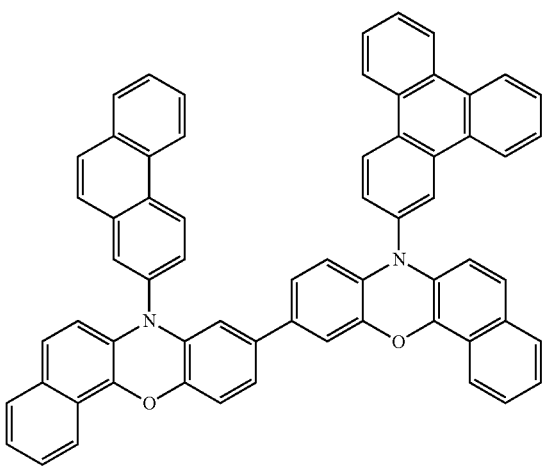
compound 198
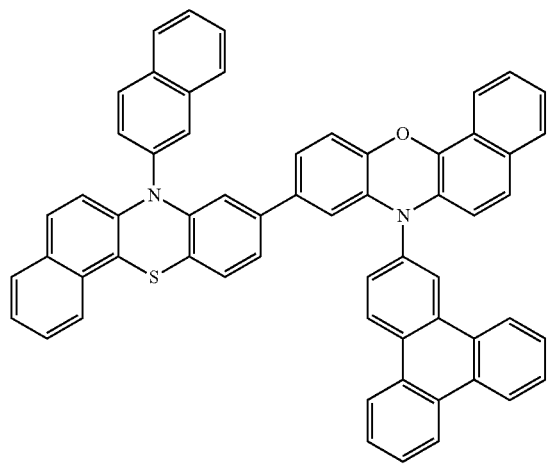
compound 199
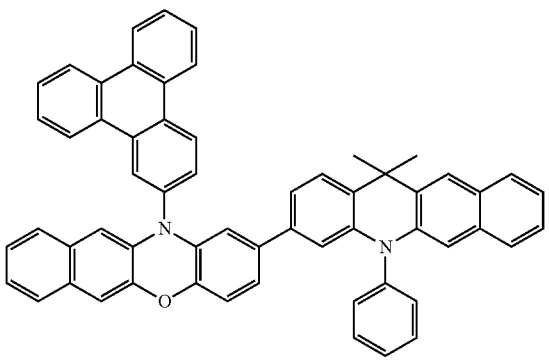

compound 200
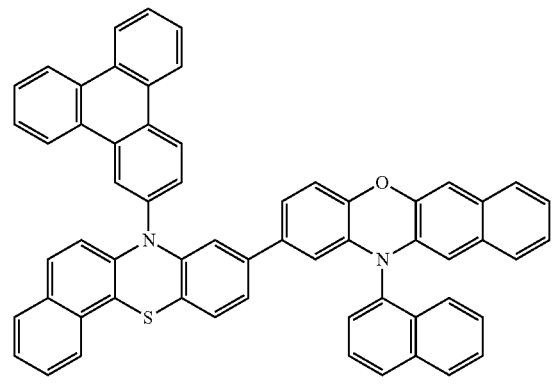
compound 201
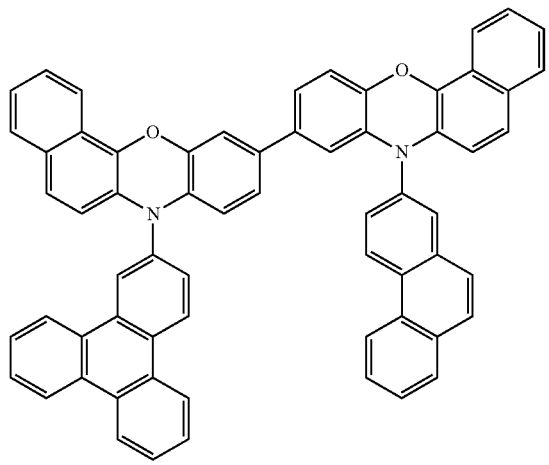
compound 202
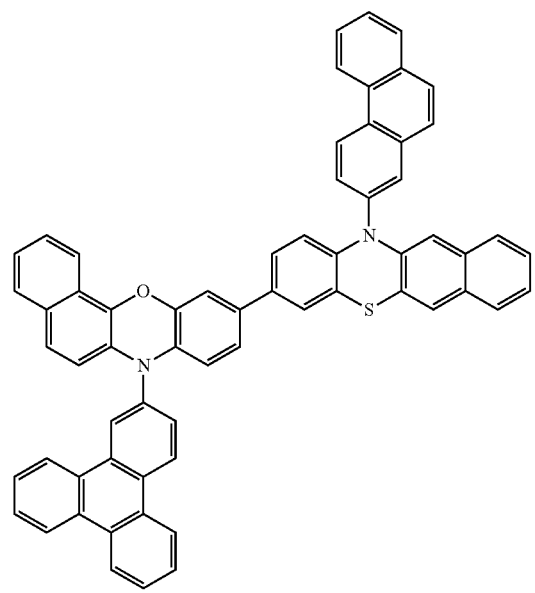
compound 203
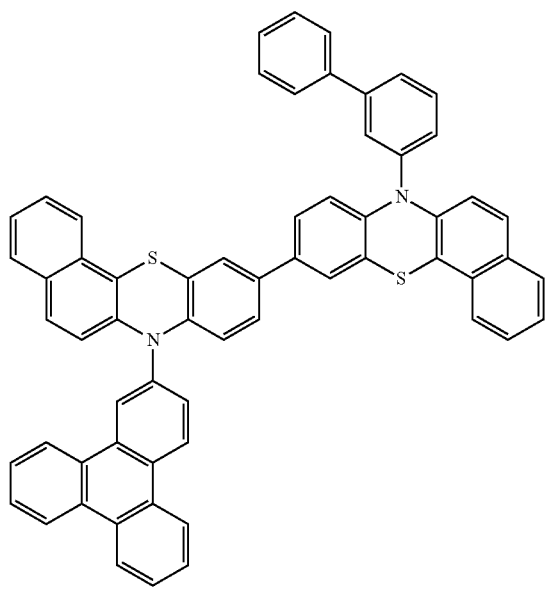

-continued
compound 204
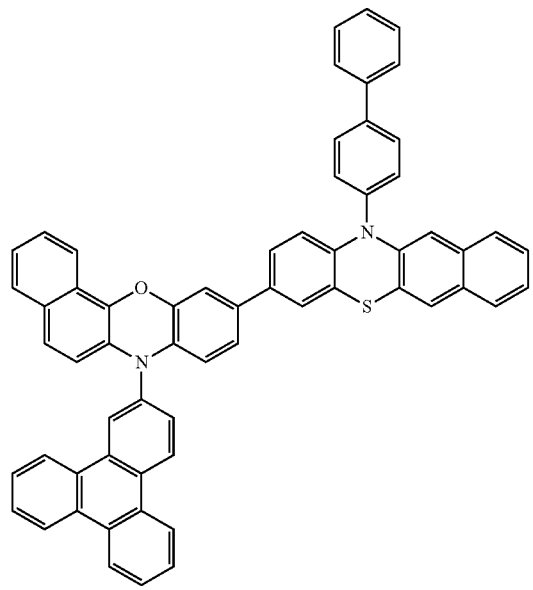
compound 205
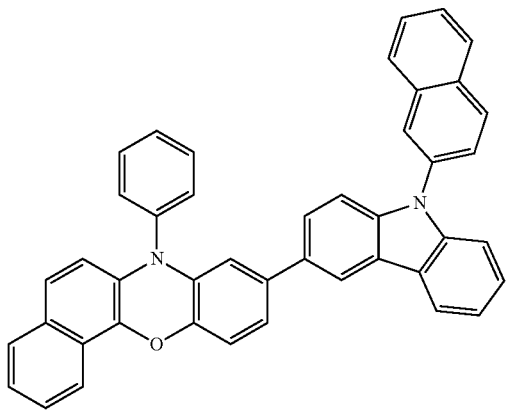
compound 206
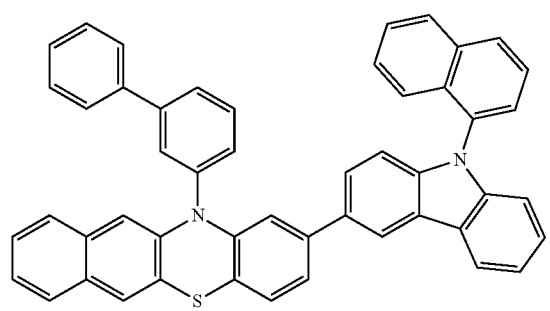
compound 207
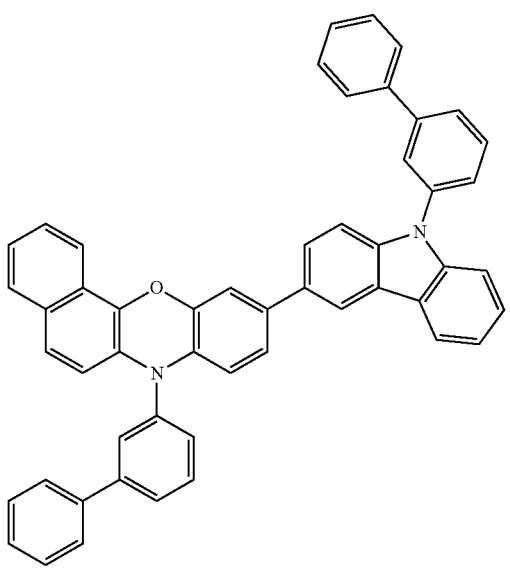

-continued
compound 208
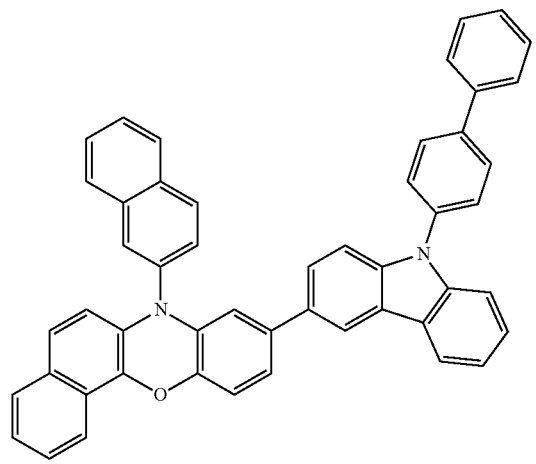
compound 209
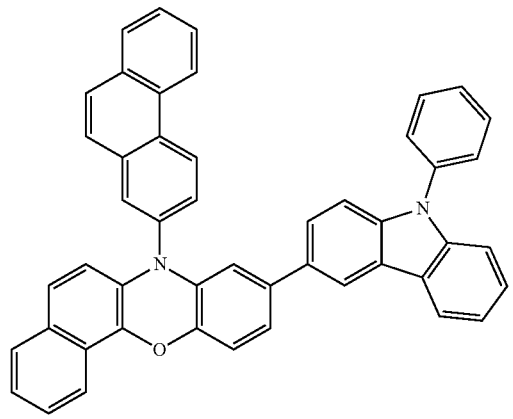
compound 210
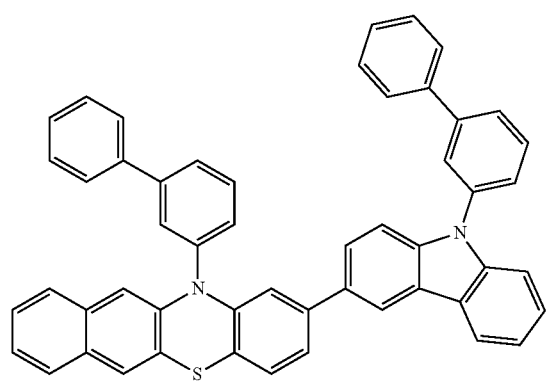
compound 211
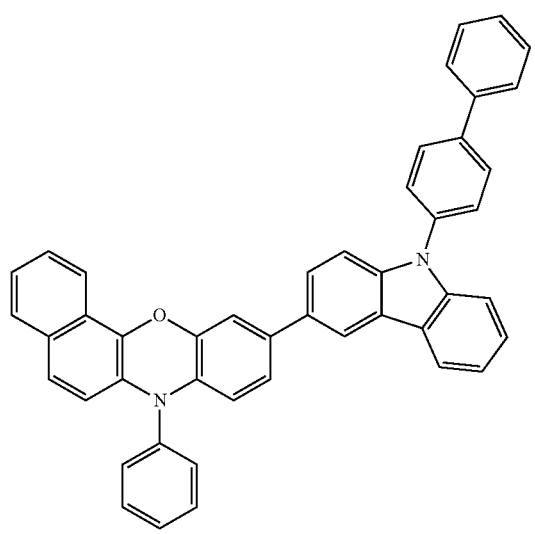
compound 212
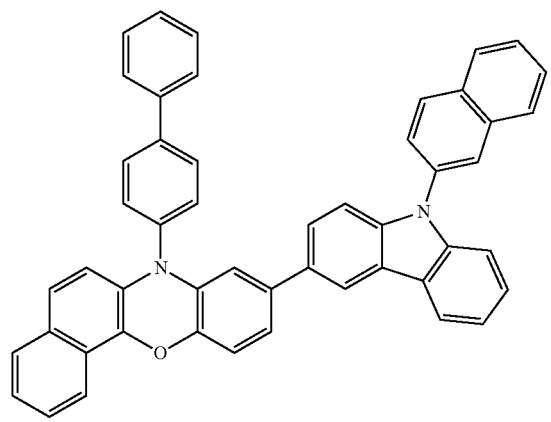
compound 213
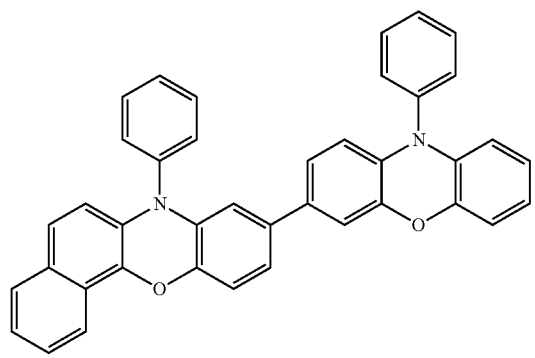

compound 214
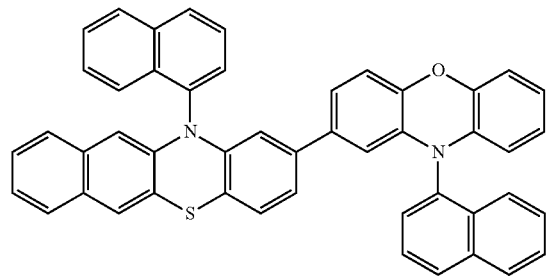
compound 215
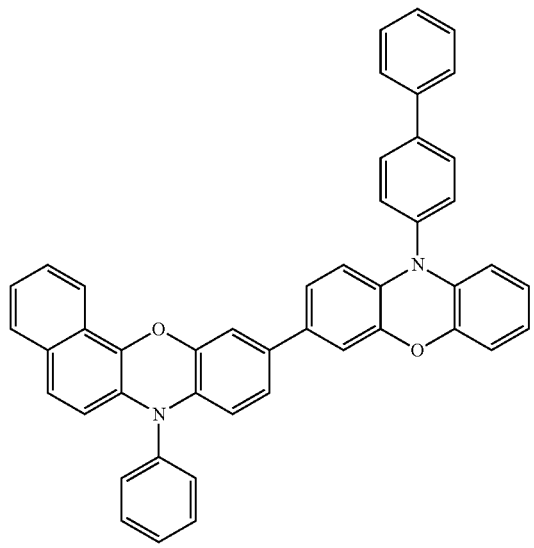
compound 216
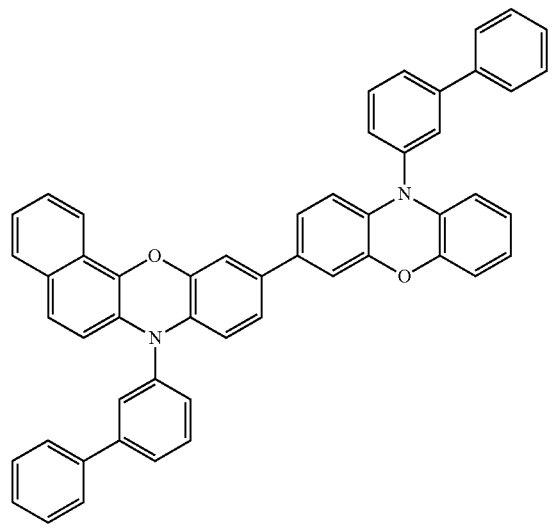
compound 217
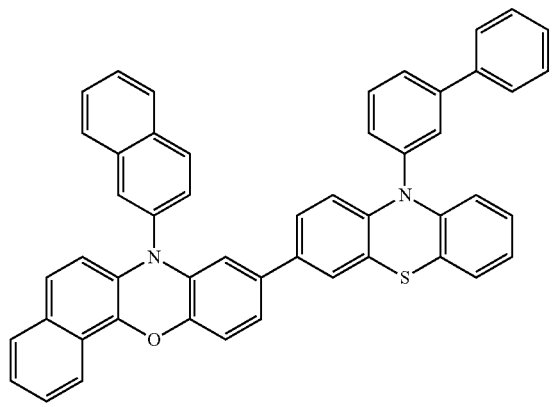

-continued
compound 218
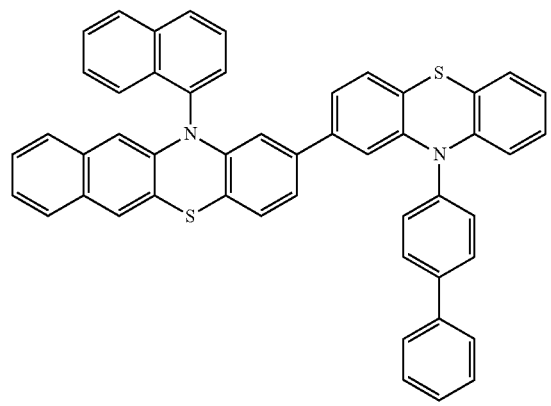
compound 219
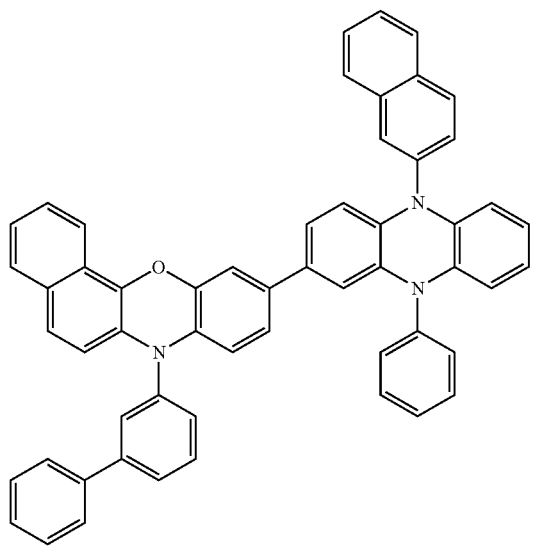
compound 220
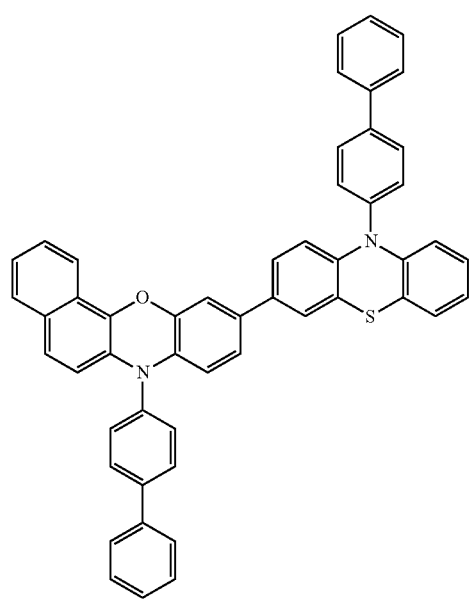
compound 221
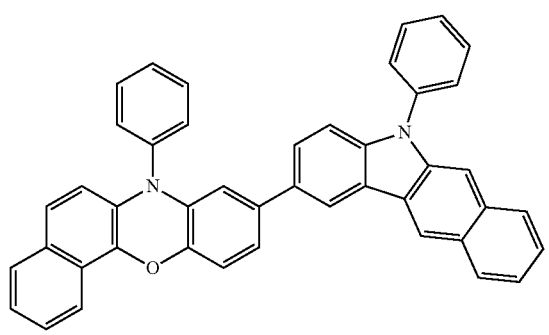

-continued
compound 222
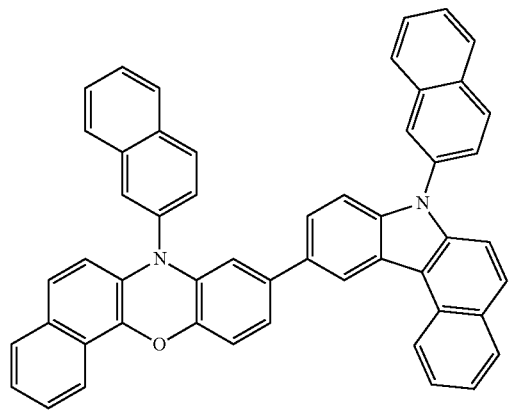
compound 223
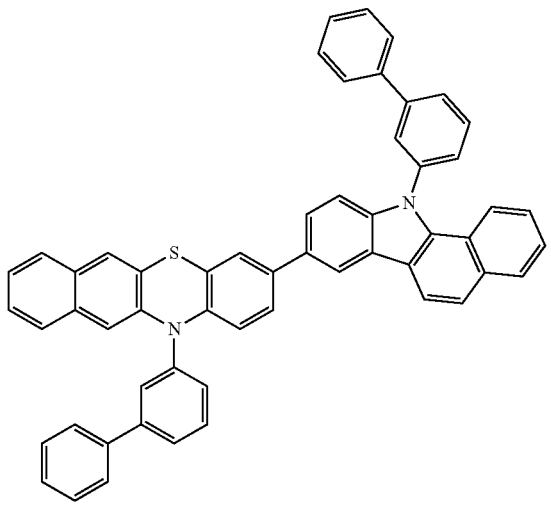
compound 224
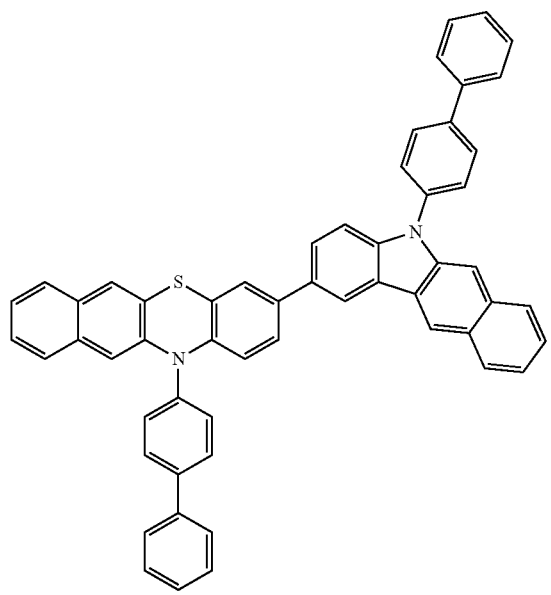
compound 225
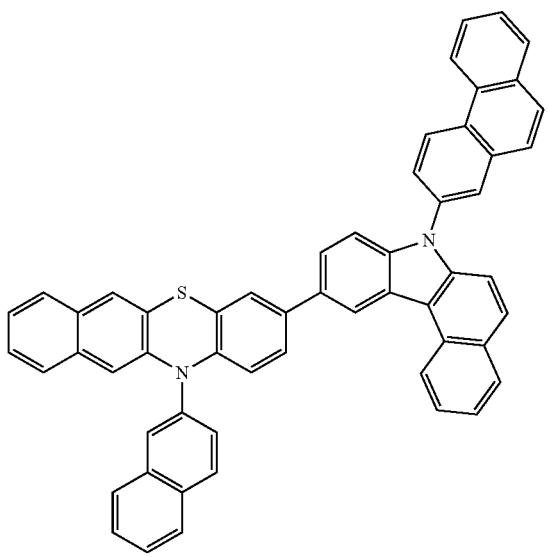
compound 226
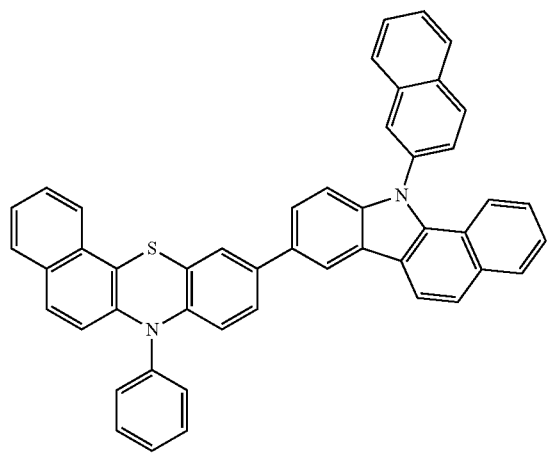
compound 227
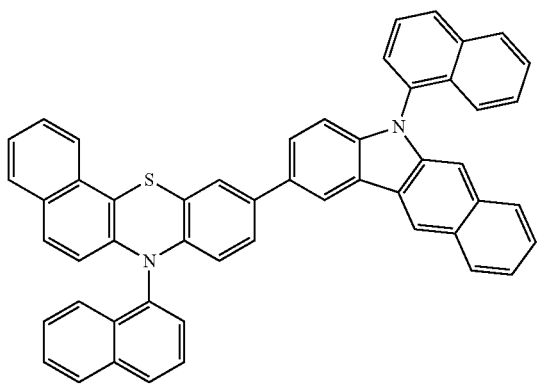

-continued
compound 228
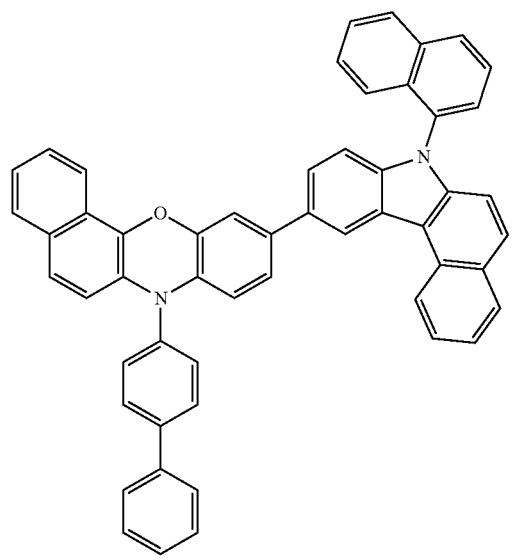
compound 229
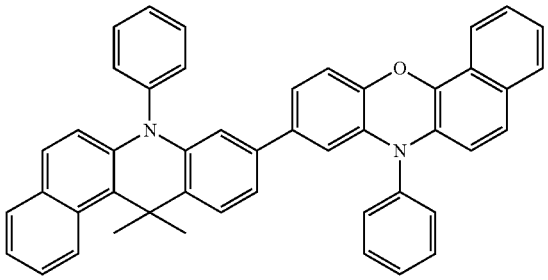
compound 230
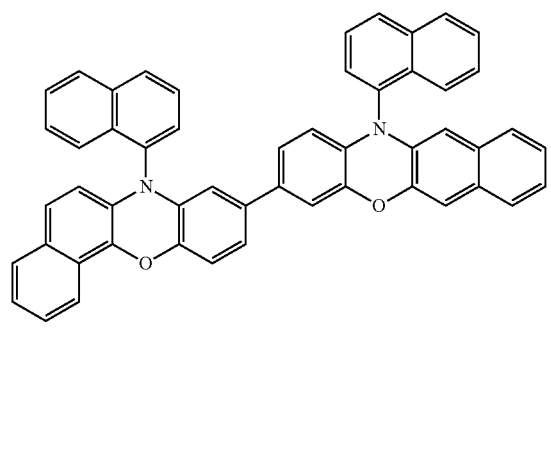
compound 231
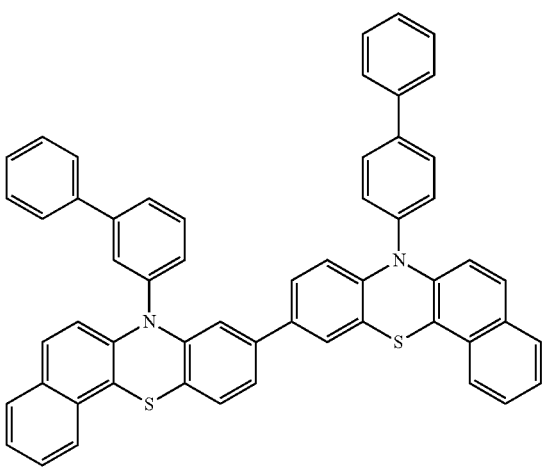
compound 232
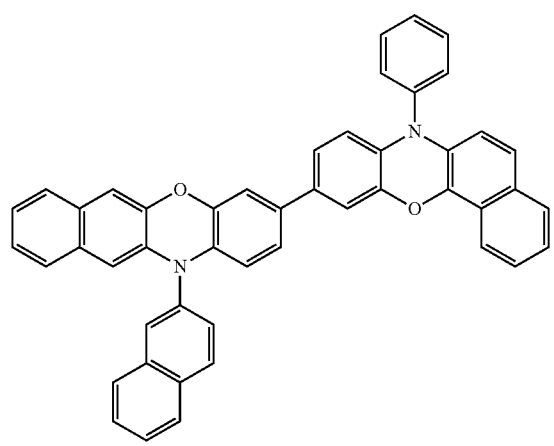
compound 233
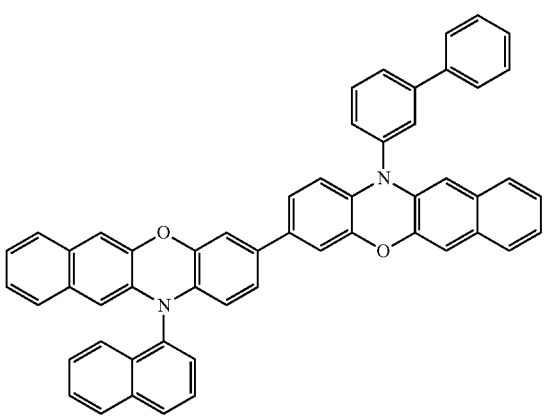

-continued
compound 234
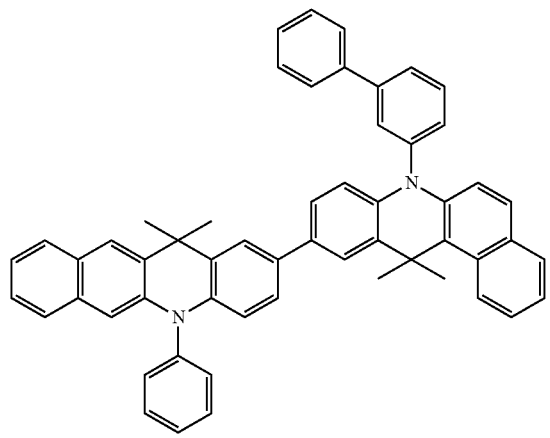
compound 235
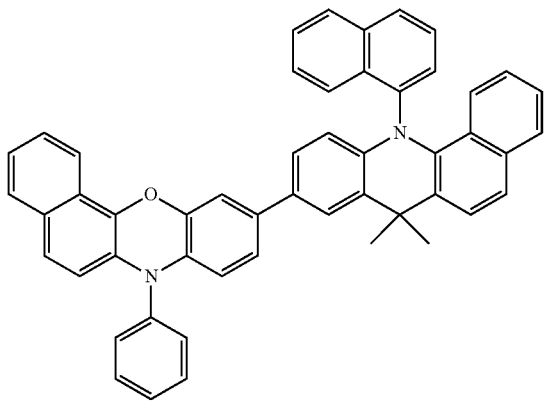
compound 236
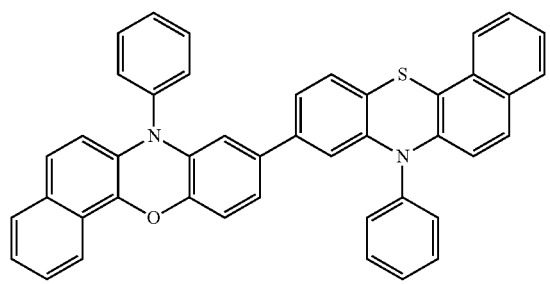
compound 237
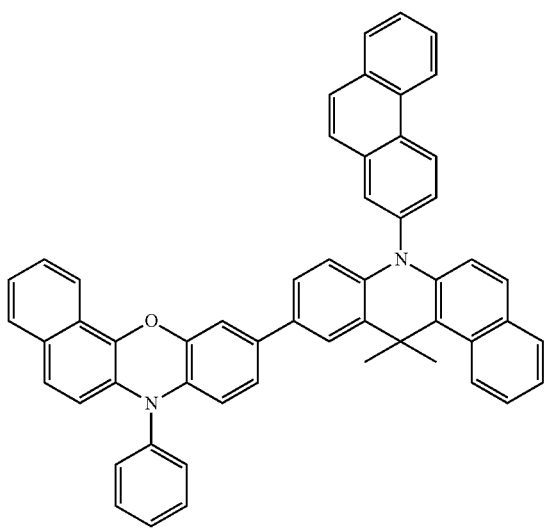
compound 238
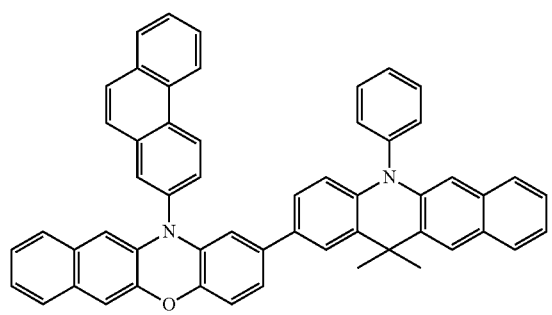
compound 239
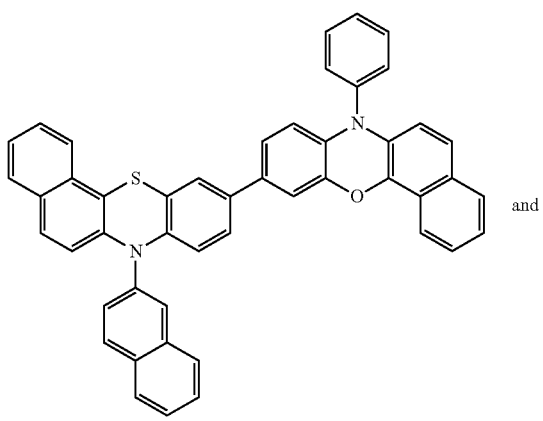
and -continued

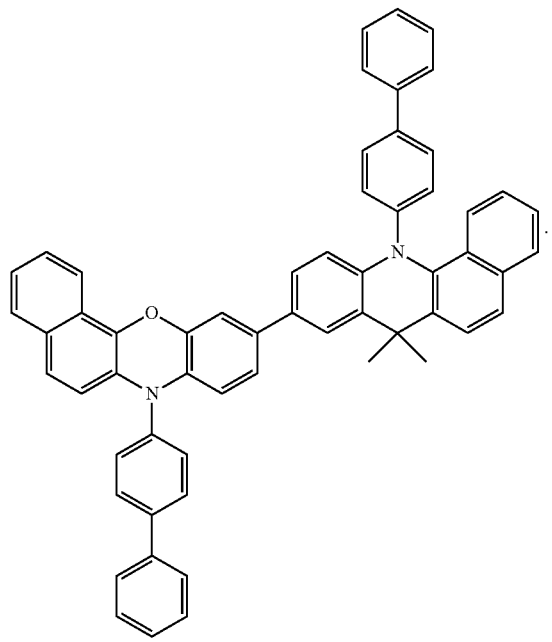

compound 240

Referring to FIG. 1, the first organic EL device 510 may comprise an anode 310, a cathode 380 and one or more organic layers 320, 330, 340E, 350, 360, 370 formed between the anode 310 and the cathode 380. From the bottom to the top, the one or more organic layers may comprise a hole injection layer 320, a hole transport layer 330, an emissive layer 340E, a hole blocking layer 350, an electron transport layer 360 and an electron injection layer 370.

The emissive layer 340E may comprise a 15% dopant D1 and the organic compound of formula (C) 340C doped with the dopant D1. The dopant D1 may be a green guest material for tuning the wavelength at which the emissive layer 340E emits light, so that the color of emitted light may be green. The organic compound of formula (C) may be a host 340C of the emissive layer 340E.

FIG. 2 is a cross-sectional view of an organic EL device without the organic compound of formula (C). Referring to FIG. 2, the organic EL device 400 may comprise an anode 310, a cathode 380 and one or more organic layers 320, 330, 340, 350, 360, 370 formed between the anode 310 and the cathode 380. From the bottom to the top, the one or more organic layers may comprise a hole injection layer 320, a hole transport layer 330, an emissive layer 340, a hole blocking layer 350, an electron transport layer 360 and an electron injection layer 370. The emissive layer 340 may comprise a 15% dopant D1 and an organic compound H1 doped with the dopant D1. The dopant D1 may be a green guest material. The organic compound H1 is a host of the emissive layer 340.

To those organic EL devices of FIG. 1 and FIG. 2, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

The I-V-B (at 1000 nits) test reports of those organic EL devices of FIG. 1 and FIG. 2 may be summarized in Table 1 below. The half-life is defined as the time that the initial luminance of 1000 cd/m² has dropped to half.

TABLE 1

(The "Comp." is short for "Compound")

| Host (H1 or 340C) | Dopant | Driving Voltage (V) | Current Efficiency (cd/A) | CIE (y) | Half-life (hours) |
|---|---|---|---|---|---|
| H1 | D1 | 5.1 | 18 | 0.53 | 350 |
| Comp. 3 | D1 | 3.9 | 34 | 0.55 | 650 |
| Comp. 5 | D1 | 3.8 | 36 | 0.54 | 700 |
| Comp. 6 | D1 | 3.7 | 37 | 0.53 | 720 |
| Comp. 7 | D1 | 4.4 | 28 | 0.52 | 480 |
| Comp. 10 | D1 | 4.0 | 33 | 0.55 | 630 |
| Comp. 22 | D1 | 4.5 | 27 | 0.54 | 440 |
| Comp. 26 | D1 | 3.7 | 36 | 0.54 | 680 |
| Comp. 27 | D1 | 2.9 | 44 | 0.54 | 900 |
| Comp. 37 | D1 | 3.8 | 35 | 0.53 | 690 |
| Comp. 48 | D1 | 4.6 | 25 | 0.56 | 430 |
| Comp. 59 | D1 | 3.2 | 42 | 0.55 | 920 |
| Comp. 74 | D1 | 2.9 | 45 | 0.53 | 1000 |
| Comp. 75 | D1 | 3.0 | 44 | 0.56 | 960 |
| Comp. 86 | D1 | 3.9 | 34 | 0.54 | 660 |
| Comp. 112 | D1 | 4.4 | 28 | 0.54 | 520 |
| Comp. 135 | D1 | 4.3 | 28 | 0.52 | 500 |
| Comp. 141 | D1 | 4.6 | 27 | 0.56 | 450 |
| Comp. 145 | D1 | 4.5 | 26 | 0.54 | 430 |
| Comp. 155 | D1 | 2.8 | 45 | 0.53 | 980 |
| Comp. 171 | D1 | 3.1 | 43 | 0.52 | 900 |
| Comp. 189 | D1 | 3.0 | 44 | 0.54 | 920 |
| Comp. 198 | D1 | 3.1 | 43 | 0.53 | 900 |
| Comp. 229 | D1 | 3.8 | 36 | 0.55 | 650 |
| Comp. 235 | D1 | 3.9 | 35 | 0.53 | 660 |

According to Table 1, in the first organic EL device 510, the organic compound of formula (C) comprised as a host 340C of FIG. 1 exhibits performance better than a prior art organic EL material (H1).

A method of producing the first organic EL device 510 of FIG. 1 and the organic EL device 400 of FIG. 2 is described.

ITO-coated glasses with 9~12 ohm/square in resistance and 120~160 nm in thickness are provided (hereinafter ITO substrate) and cleaned in a number of cleaning steps in an ultrasonic bath (e.g. detergent, deionized water).

Before vapor deposition of the organic layers, cleaned ITO substrates may be further treated by UV and ozone. All pre-treatment processes for ITO substrate are under clean room (class 100), so that an anode 310 may be formed.

One or more organic layers 320, 330, 340 (FIG. 2), 340E (FIG. 1), 350, 360, 370 are applied onto the anode 310 in order by vapor deposition in a high-vacuum unit ($10^{-7}$ Torr), such as resistively heated quartz boats. The thickness of the respective layer and the vapor deposition rate (0.1~0.3 nm/sec) are precisely monitored or set with the aid of a quartz-crystal monitor. It is also possible, as described above, each of the organic layers may comprise more than one organic compound. For example, an emissive layer 340E or 340 may be formed of a dopant and a host doped with the dopant. An emissive layer 340E or 340 may also be formed of a co-host and a host co-deposited with the co-host. This may be successfully achieved by co-vaporization from two or more sources. Accordingly, the compounds for the organic layers of the present invention are thermally stable.

Referring to FIG. 1 and FIG. 2, onto the anode 310, Dipyrazino[2,3-f:2,3-]quinoxaline-2,3,6,7,10,11-hexacarbonitrile (HAT-CN) may be applied to form a hole injection layer 320 having a thickness of about 20 nm in the organic EL device 510 or 400. N,N-Bis(naphthalene-1-yl)-N,N-bis(phenyl)-benzidine (NPB) may be applied to form a hole transporting layer 330 having a thickness of about 110 nm. Referring to FIG. 1 and FIG. 2, in the organic EL device 510 (FIG. 1) or 400 (FIG. 2), an emissive layer 340E or 340 may be formed to have a thickness of about 30 nm.

Referring to FIG. 2, in the organic EL device 400, 12-(4,6-diphenyl-1,3,5-triazin-2-yl)-10,10-dimethyl-10,12-dihydrophenanthro[9',10':5,6]indeno[2,1-b]carbazole (i.e., H1 of paragraph [0002]) may be applied to form a host H1 of an emissive layer 340 of FIG. 2. The emissive layer 340 may further comprise bis(2-phenylpyridinato)(2,4-diphenylpyridinato)iridium(III) as a dopant D1, also a green guest of the emissive layer 340. The doped emissive layer 340 may have a thickness of about 30 nm.

On the emissive layer 340, a compound HB1 may be a hole blocking material (HBM) to form a hole blocking layer 350. 2-(naphthalen-1-yl)-9-(4-(1-(4-(10-(naphthalene-2-yl) anthracen-9-yl)-phenyl)-1H-benzo[d]imidazol-2-yl)phenyl)-1,10-phenanthroline (ET1) may be applied as an electron transporting material to co-deposit with 8-hydroxyquinolato-lithium (LiQ) at a ratio of 1:1, thereby forming an electron transporting layer (ETL) 360 of the organic EL device 510 or 400. The electron transporting layer (ETL) 360 may have a thickness of about 35 nm. The organic compounds ET1, HB1, D1, NPB and HAT-CN for producing the organic EL device 400 or 510 in this invention may have the formulas as follows:

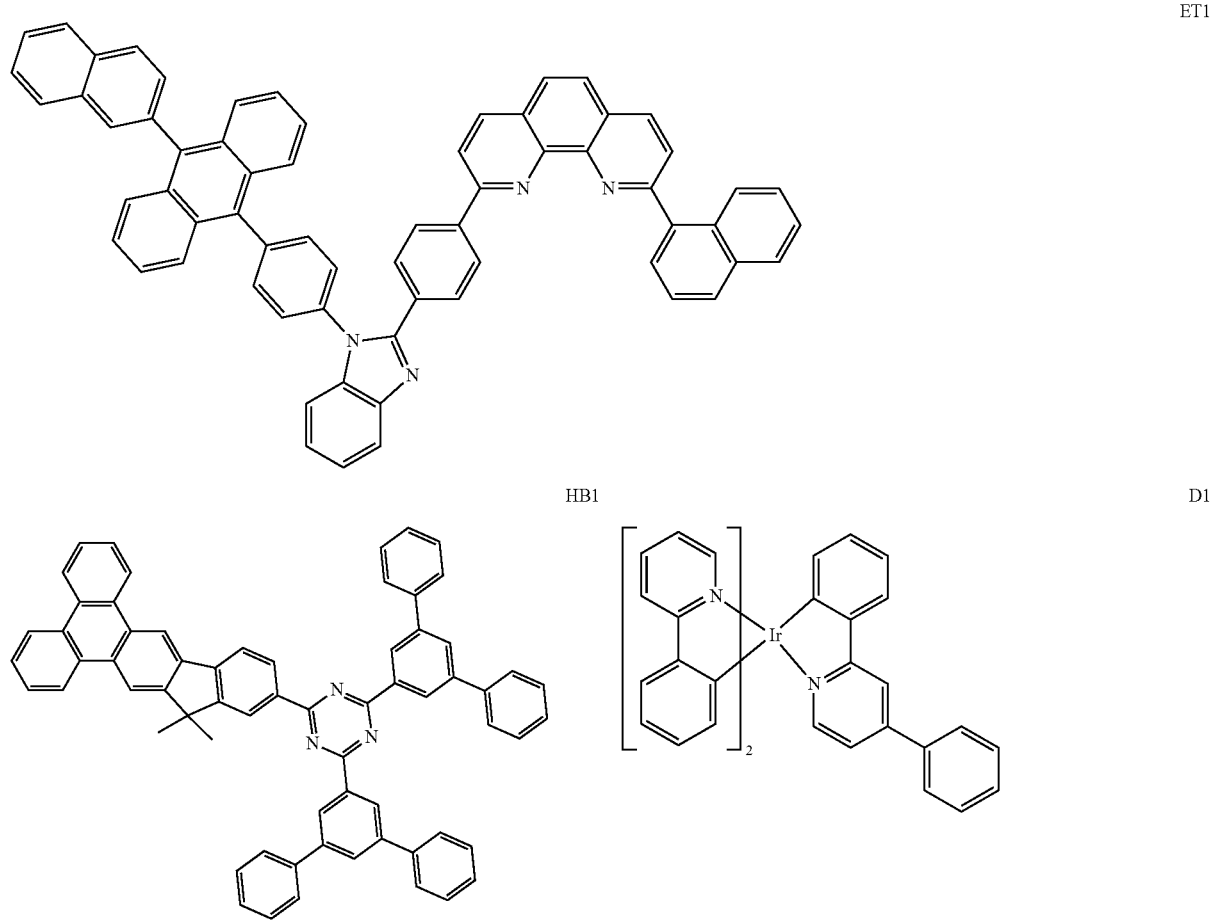

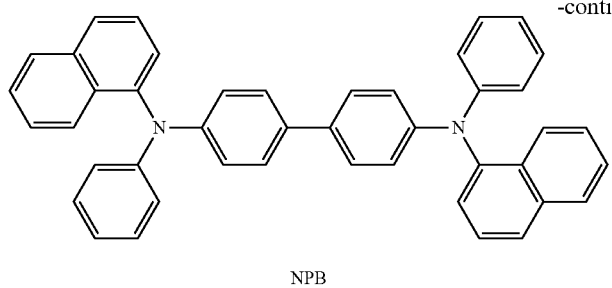

NPB

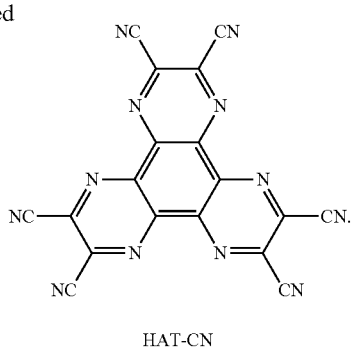

HAT-CN

Referring to FIG. 1 and FIG. 2, the organic EL device 510 or 400 may further comprise a low work function metal, such as Al, Mg, Ca, Li or K, as a cathode 380 by thermal evaporation. A low work function metal may help electrons injecting the electron transporting layer 360 from cathode 380. The cathode 380 may have a thickness of about 160 nm. Between the cathode 380 and the electron transporting layer 360, a thin electron injecting layer 370 of LiQ having a thickness of about 1 nm is introduced, to reduce the electron injection barrier and to improve the performance of the organic EL device 510 or 400. The material of the electron injecting layer 370 may alternatively be metal halide or metal oxide with low work function, such as LiF, MgO, or $Li_2O$.

In a third embodiment of the present invention, a second organic EL device using the organic compound of formula (C) is disclosed. The method of producing the second organic EL device 520 of FIG. 3 is substantially the same as the method of producing the organic EL device 400 of FIG. 2. The difference is that the hole blocking layer (HBL) 350C of FIG. 3 is made by using the organic compound of formula (C), rather than HB1.

To those organic EL devices of FIG. 3 and FIG. 2, EL spectra and CIE coordination are measured by using a PR650 spectra scan spectrometer. Furthermore, the current/voltage, luminescence/voltage, and yield/voltage characteristics are taken with a Keithley 2400 programmable voltage-current source. The above-mentioned apparatuses are operated at room temperature (about 25° C.) and under atmospheric pressure.

The I-V-B (at 1000 nits) test reports of those organic EL devices of FIG. 3 and FIG. 2 may be summarized in Table 2 below. The half-life of the fluorescent green-emitting organic EL device 520 or 400 is defined as the time that the initial luminance of 1000 cd/m has dropped to half.

TABLE 2

(The "Comp." is short for "Compound")

| Material for HBL 350 or 350C | Material for ETL 360 | Driving Voltage (V) | Current Efficiency (cd/A) | CIE (y) | Half-life (hours) |
| --- | --- | --- | --- | --- | --- |
| HB1 | ET1 | 5.1 | 18 | 0.53 | 350 |
| Comp.13 | ET1 | 4.3 | 23 | 0.52 | 430 |
| Comp.23 | ET1 | 4.4 | 24 | 0.55 | 440 |
| Comp.34 | ET1 | 4.0 | 27 | 0.56 | 520 |
| Comp.39 | ET1 | 4.0 | 26 | 0.54 | 510 |
| Comp.41 | ET1 | 4.3 | 24 | 0.55 | 430 |
| Comp.55 | ET1 | 4.4 | 23 | 0.52 | 420 |
| Comp.69 | ET1 | 4.1 | 25 | 0.55 | 500 |
| Comp.83 | ET1 | 4.7 | 21 | 0.54 | 400 |

TABLE 2-continued (The "Comp." is short for "Compound")

| Material for HBL 350 or 350C | Material for ETL 360 | Driving Voltage (V) | Current Efficiency (cd/A) | CIE (y) | Half-life (hours) |
| --- | --- | --- | --- | --- | --- |
| Comp.108 | ET1 | 4.2 | 25 | 0.53 | 480 |
| Comp.115 | ET1 | 4.5 | 22 | 0.52 | 410 |
| Comp.138 | ET1 | 4.8 | 22 | 0.54 | 380 |
| Comp.148 | ET1 | 4.9 | 20 | 0.52 | 380 |
| Comp.154 | ET1 | 4.8 | 21 | 0.54 | 390 |
| Comp.214 | ET1 | 4.0 | 27 | 0.53 | 510 |
| Comp.231 | ET1 | 4.1 | 26 | 0.55 | 500 |

According to Table 2, in the second organic EL device 520, the organic compound of formula (C) comprised as a hole blocking layer 350C of FIG. 3 exhibits performance better than a prior art hole blocking material (HB1 as a HBL 350 of FIG. 2).

Referring to FIG. 1 or FIG. 3, the organic EL device 510 or 520 of the present invention may alternatively be alighting panel or a backlight panel.

Detailed preparation of the organic compounds of the present invention will be clarified by exemplary embodiments below, but the present invention is not limited thereto. EXAMPLES 1 to 23 show the preparation of the organic compounds of the present invention.

Example 1

Synthesis of 9-bromo-7H-benzo[c]phenoxazine

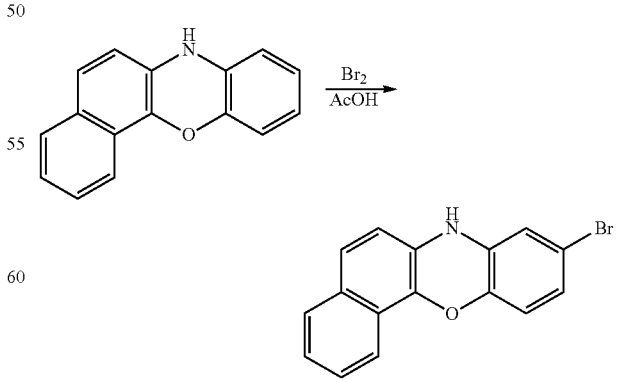

10 g (42.9 mmol) of 7H-benzo[c]phenoxazine was dissolved in 200 ml of acetic acid, and the mixture was allowed to cool to 0° C. 6.9 g (42.9 mmol) of bromine was dropped into the mixture, and then the mixture was stirred at room temperature for 12 hrs. After the reaction finished, the mixture was extracted with dichloromethane/H$_2$O, and the organic layer was removed under reduced pressure, and the crude product was purified by column chromatography, yielding 10.2 g of 9-bromo-7H-benzo[c]phenoxazine as yellow solid (76.2%). $^1$H NMR (CDCl$_3$, 400 MHz): chemical shift (ppm) 8.01 (d, 2H), 7.56 (dd, 1H), 7.43 (dd, 1H), 7.42-7.39 (m, 1H), 7.07-7.02 (m, 2H), 6.77-6.73 (m, 2H), 4.11 (s, H).

Synthesis of 9-bromo-7-phenyl-7H-benzo[c]phenoxazine

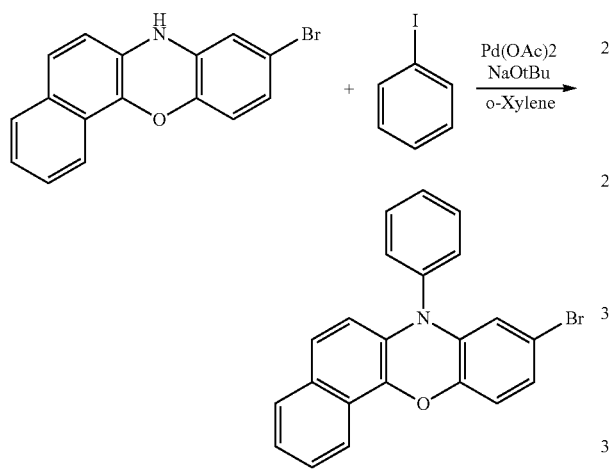

A mixture of 10.2 g (32.7 mmol) of 9-bromo-7H-benzo[c]phenoxazine, 6.7 g (32.7 mmol) of iodobenzene, 0.15 g (0.65 mmol) of Pd(OAc)$_2$, 4.7 g (49.1 mmol) of sodium tert-butoxide, and 200 ml of o-xylene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 10.3 g of 9-bromo-7-phenyl-7H-benzo[c]phenoxazine as yellow solid (81.1%). $^1$H NMR (CDCl$_3$, 400 MHz): chemical shift (ppm) 7.99 (d, 2H), 7.54 (dd, 1H), 7.39-7.34 (m, 2H), 7.22-7.19 (m, 2H), 7.02 (d, 1H), 6.91 (d, 1H), 6.81-6.77 (m, 2H), 6.66-6.61 (m, 3H).

Synthesis of 7-phenyl-9-(4,4,5,5-tetramethyl-1,3,2-dioxaborolan-2-yl)-7H-benzo[c]phenoxazine

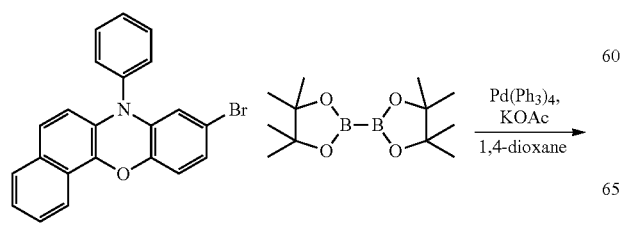

-continued

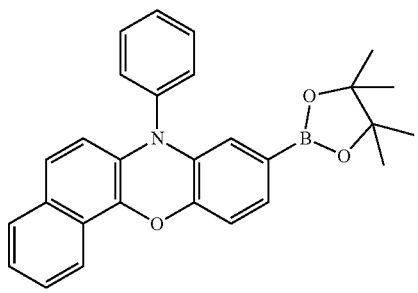

A mixture of 10.3 g (26.5 mmol) of 9-bromo-7-phenyl-7H-benzo[c]-phenoxazine, 8.08 g (31.8 mmol) of bis(pinacolato)diboron, 0.6 g (0.5 mmol) of Pd(Ph$_3$)$_4$, 3.9 g (39.8 mmol) of potassium acetate, and 150 ml of 1,4-dioxane was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 9 g of 7-phenyl-9-(4,4,5,5-tetramethyl-1,3,2-dioxaborolan-2-yl)-7H-benzo[c]phenoxazine as white solid (78%). $^1$H NMR (CDCl$_3$, 400 MHz): chemical shift (ppm) 8.01 (d, 2H), 7.55 (dd, 1H), 7.42-7.36 (m, 2H), 7.23-7.20 (m, 2H), 7.07-7.03 (m, 2H), 6.93 (d, 1H), 6.82-6.79 (m, 1H), 6.67-6.63 (m, 3H), 1.26 (s, 12H).

Synthesis of 9-(9-(naphthalen-2-yl)-9H-carbazol-3-yl)-7-phenyl-7H-benzo[c]phenoxazine (Compound 205)

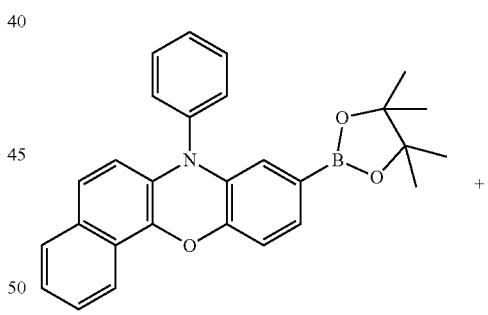

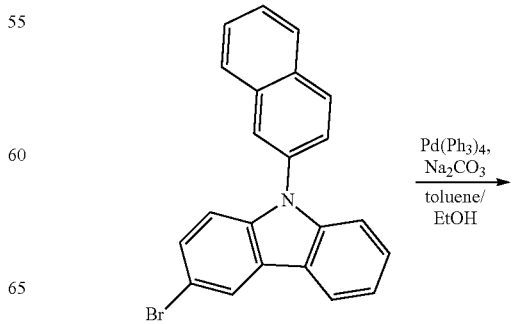

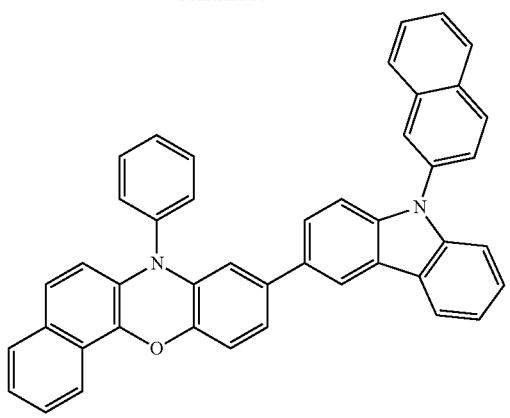

A mixture of 9 g (20.7 mmol) of 7-phenyl-9-(4,4,5,5-tetramethyl-1,3,2-dioxaborolan-2-yl)-7H-benzo[c]phenoxazine, 7.7 g (20.7 mmol) of 3-bromo-9-(naphthalen-2-yl)-9H-carbazole, 0.48 g (0.04 mmol) of Pd(Ph$_3$)$_4$, 20.7 ml of 2M Na$_2$CO$_3$, 100 ml of EtOH and 200 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 8.9 g of 9-(9-(naphthalen-2-yl)-9H-carbazol-3-yl)-7-phenyl-7H-benzo[c]phenoxazine as white solid (71.7%). $^1$H NMR (CDCl$_3$, 400 MHz): chemical shift (ppm) 8.20 (d, 1H), 8.13 (d, 1H), 8.03-7.96 (m, 6H), 7.84 (s, H), 7.76 (s, H), 7.65-7.59 (m, 3H), 7.50-7.46 (m, 2H), 7.38-7.32 (m, 4H), 7.22-7.18 (m, 2H), 7.09-7.04 (m, 2H), 6.95 (d, 1H), 6.86-6.81 (m, 2H), 6.65 (d, 2H).

Example 2

Synthesis of 7-phenyl-9-(10-phenyl-10H-phenoxazin-3-yl)-7H-benzo[c]phenoxazine (Compound 213)

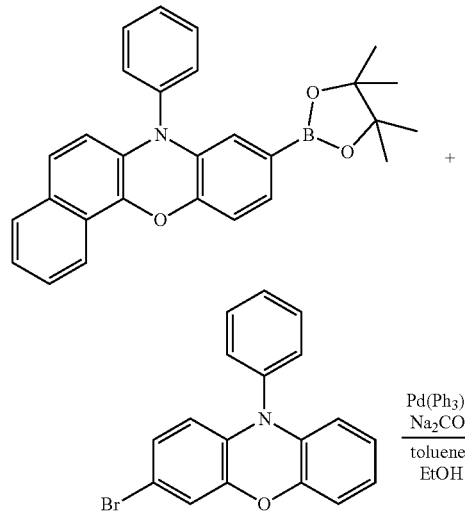

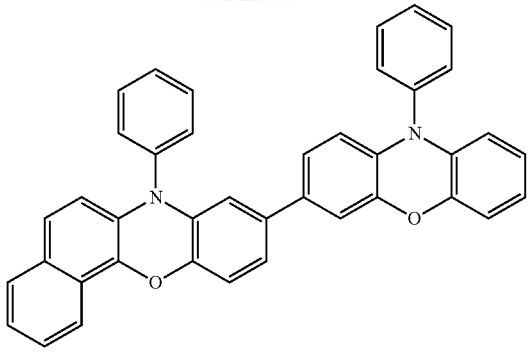

A mixture of 5 g (11.5 mmol) of 7-phenyl-9-(4,4,5,5-tetramethyl-1,3,2-dioxaborolan-2-yl)-7H-benzo[c]phenoxazine, 3.9 g (11.5 mmol) of 3-bromo-10-phenyl-10H-phenoxazine, 0.24 g (0.02 mmol) of Pd(Ph$_3$)$_4$, 11.5 ml of 2M Na$_2$CO$_3$, 50 ml of EtOH and 100 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 4.4 g of 7-phenyl-9-(10-phenyl-10H-phenoxazin-3-yl)-7H-benzo[c]phenoxazine as white solid (68%). $^1$H NMR (CDCl$_3$, 400 MHz): chemical shift (ppm) 8.03 (d, 2H), 7.58 (m, 1H), 7.45-7.38 (m, 2H), 7.29-7.21 (m, 6H), 7.13-7.08 (m, 2H), 6.98-6.92 (m, 3H), 6.85-6.79 (m, 4H), 6.68-6.61 (m, 6H).

Example 3

Synthesis of 7-phenyl-9-(5-phenyl-5H-benzo[b]carbazol-2-yl)-7H-benzo[c]phenoxazine (Compound 221)

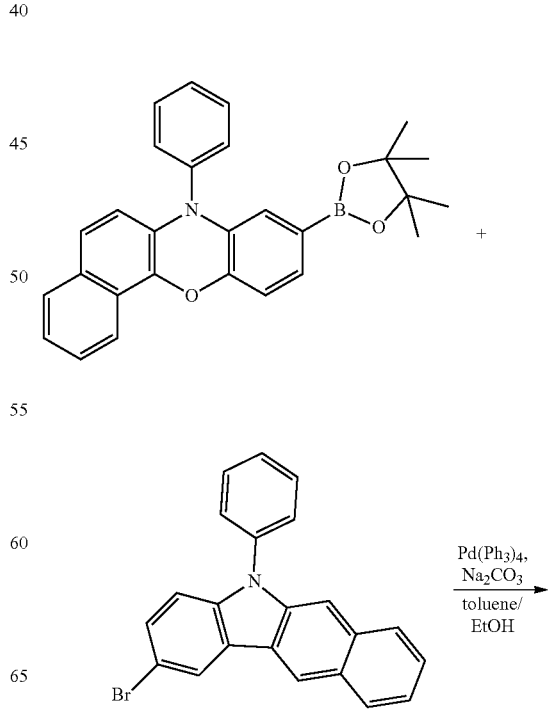

-continued

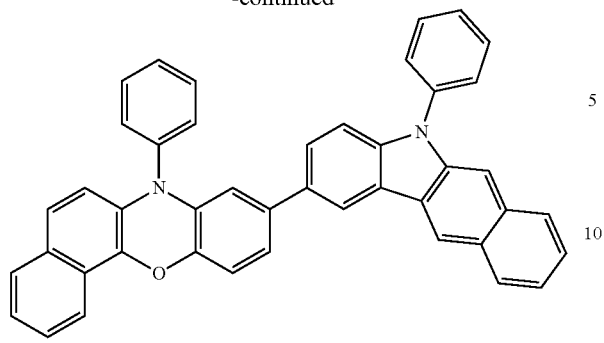

A mixture of 5 g (11.5 mmol) of 7-phenyl-9-(4,4,5,5-tetramethyl-1,3,2-dioxaborolan-2-yl)-7H-benzo[c]phenoxazine, 4.3 g (11.5 mmol) of 2-bromo-5-phenyl-5H-benzo[b]carbazole, 0.24 g (0.02 mmol) of Pd(Ph)$_4$, 11.5 ml of 2M Na$_2$CO$_3$, 50 ml of EtOH and 100 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 4.9 g of 7-phenyl-9-(5-phenyl-5H-benzo[b]carbazol-2-yl)-7H-benzo[c]phenoxazine as white solid (71%). $^1$H NMR (CDCl$_3$, 400 MHz): chemical shift (ppm) 8.19-8.15 (m, 3H), 8.01-7.95 (m, 3H), 7.79 (s, 1H), 7.69-7.65 (m, 2H), 7.57-7.50 (m, 6H), 7.43-7.36 (m, 4H), 7.22-7.20 (m, 2H), 7.10 (d, 1H), 7.03 (d, 1H), 6.94 (d, 1H), 6.83-6.78 (m, 2H), 6.61 (d, 2H).

Example 4

Synthesis of 7-phenyl-9-(7-phenyl-7H-benzo[c]phenothiazin-9-yl)-7H-benzo[c]phenoxazine (Compound 236)

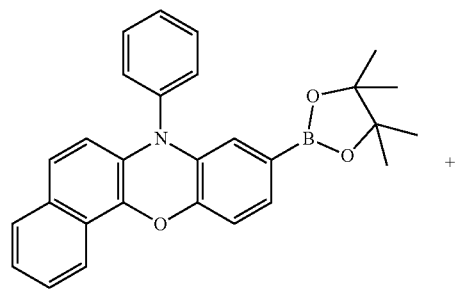

+

-continued

A mixture of 5 g (11.5 mmol) of 7-phenyl-9-(4,4,5,5-tetramethyl-1,3,2-dioxaborolan-2-yl)-7H-benzo[c]phenoxazine, 4.1 g (11.5 mmol) of 2-bromo-5-phenyl-5H-benzo[b]carbazole, 0.24 g (0.02 mmol) of Pd(Ph)$_4$, 11.5 ml of 2M Na$_2$CO$_3$, 50 ml of EtOH and 100 ml of toluene was degassed and placed under nitrogen, and then heated to reflux for 12 hrs. After the reaction finished, the mixture was allowed to cool to room temperature. Subsequently, the solvent was removed under reduced pressure, and the crude product was purified by column chromatography, yielding 4.3 g of 7-phenyl-9-(7-phenyl-7H-benzo[c]phenothiazin-9-yl)-7H-benzo[c]-phenoxazine as white solid (59.1%). $^1$H NMR (CDCl$_3$, 400 MHz): chemical shift (ppm) 8.18 (d, 2H), 8.01-7.97 (d, 2H), 7.69-7.66 (m, 2H), 7.53-7.51 (m, 1H), 7.43-7.37 (m, 2H), 7.25-7.18 (m, 6H), 7.11 (d, 1H), 7.02-6.96 (m, 4H), 6.88-6.81 (m, 4H), 6.65 (d, 4H).

Example 5-23

A series of intermediates and the product compounds are synthesized analogously, as follows.

| Ex. | Intermediate III | Intermediate IV | Product | Yield |
|---|---|---|---|---|
| 5 | | | | 69% |

-continued
| Ex. | Intermediate III | Intermediate IV | Product | Yield |
|---|---|---|---|---|
| 6 | 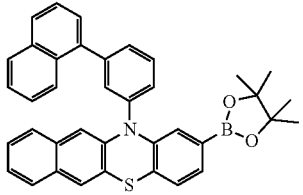 [SMILES: CC1(C)OB(c2ccc3c(c2)N(c2cccc(-c4cccc5ccccc45)c2)c2cc4ccccc4cc2S3)OC1(C)C] | 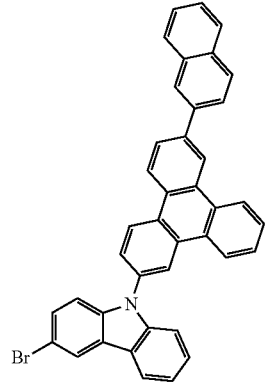 [SMILES: Brc1ccc2c(c1)c1ccccc1n2-c1ccc2c3ccc(-c4ccc5ccccc5c4)cc3c3ccccc3c2c1] | 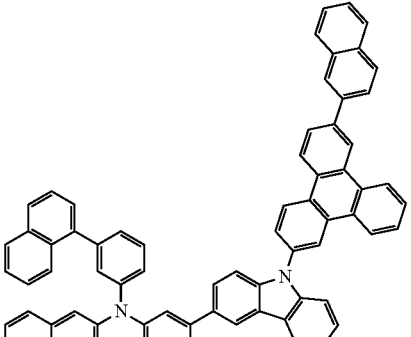 | 54% |
| 7 | 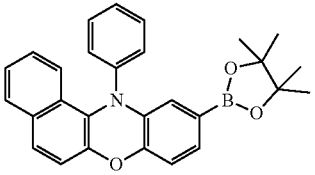 [SMILES: CC1(C)OB(c2ccc3c(c2)N(c2ccccc2)c2c(ccc4ccccc24)O3)OC1(C)C] | 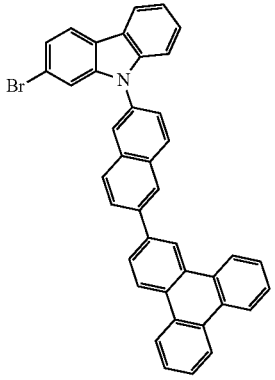 [SMILES: Brc1ccc2c3ccccc3n(-c3ccc4cc(-c5ccc6c7ccccc7c7ccccc7c6c5)ccc4c3)c2c1] | 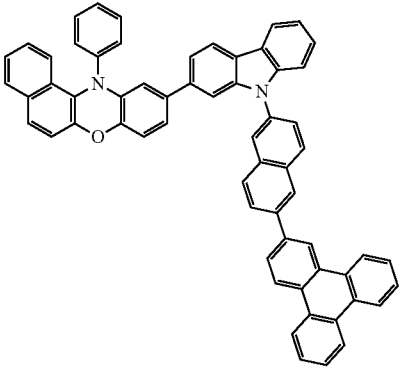 [SMILES: c1ccc(N2c3cc(-c4ccc5c6ccccc6n(-c6ccc7cc(-c8ccc9c%10ccccc%10c%10ccccc%10c9c8)ccc7c6)c5c4)ccc3Oc3ccc4ccccc4c32)cc1] | 48% |
| 8 | 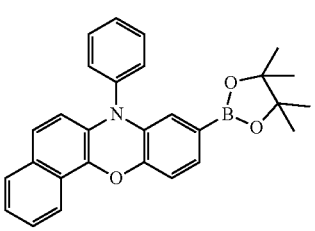 [SMILES: CC1(C)OB(c2ccc3c(c2)N(c2ccccc2)c2ccc4ccccc4c2O3)OC1(C)C] | 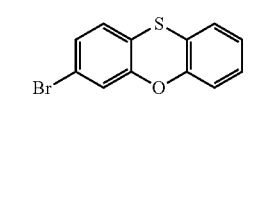 [SMILES: Brc1ccc2c(c1)Oc1ccccc1S2] | 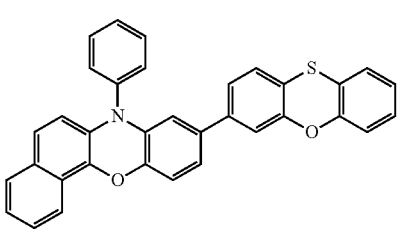 [SMILES: c1ccc(N2c3cc(-c4ccc5c(c4)Oc4ccccc4S5)ccc3Oc3c2ccc2ccccc32)cc1] | 62% |
| 9 | 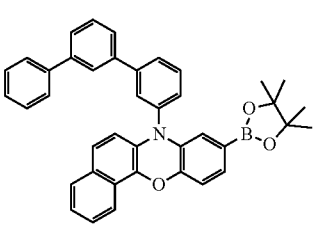 [SMILES: CC1(C)OB(c2ccc3c(c2)N(c2cccc(-c4cccc(-c5ccccc5)c4)c2)c2ccc4ccccc4c2O3)OC1(C)C] | 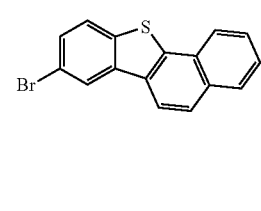 [SMILES: Brc1ccc2sc3c4ccccc4ccc3c2c1] | 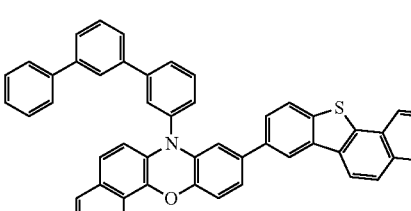 | 57% |
| 10 | 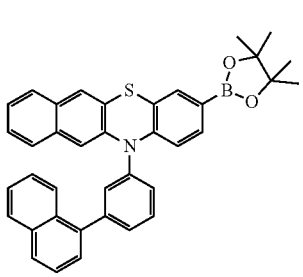 [SMILES: CC1(C)OB(c2ccc3c(c2)Sc2cc4ccccc4cc2N3c2cccc(-c3cccc4ccccc34)c2)OC1(C)C] | 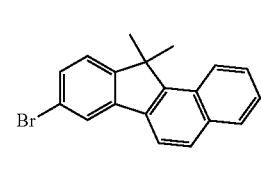 [SMILES: CC1(C)c2ccc(Br)cc2-c2ccc3ccccc3c21] | 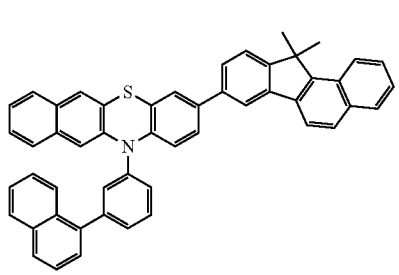 | 64% |

-continued

| Ex. | Intermediate III | Intermediate IV | Product | Yield |
|---|---|---|---|---|
| 11 | | | | 62% |
| 12 | | | | 51% |
| 13 | | | | 48% |
| 14 | | | | 41% |

-continued

| Ex. | Intermediate III | Intermediate IV | Product | Yield |
|---|---|---|---|---|
| 15 | | | | 49% |
| 16 | | | | 44% |
| 17 | | | | 51% |
| 18 | | | | 45% |

-continued

| Ex. | Intermediate III | Intermediate IV | Product | Yield |
|---|---|---|---|---|
| 19 | | | | 42% |
| 20 | | | | 51% |
| 21 | | | | 41% |
| 22 | | | | 50% |

| Ex. | Intermediate III | Intermediate IV | Product | Yield |
|---|---|---|---|---|
| 23 | | | | 47% |

When Q of formula (C) is a single bond, the organic compound may have the following formula:

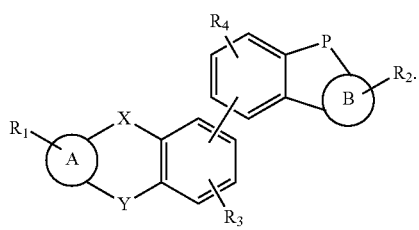

The same definition as described in the paragraph [0011] to paragraph [0027].

Obviously, many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. An organic compound is one of the following compounds:

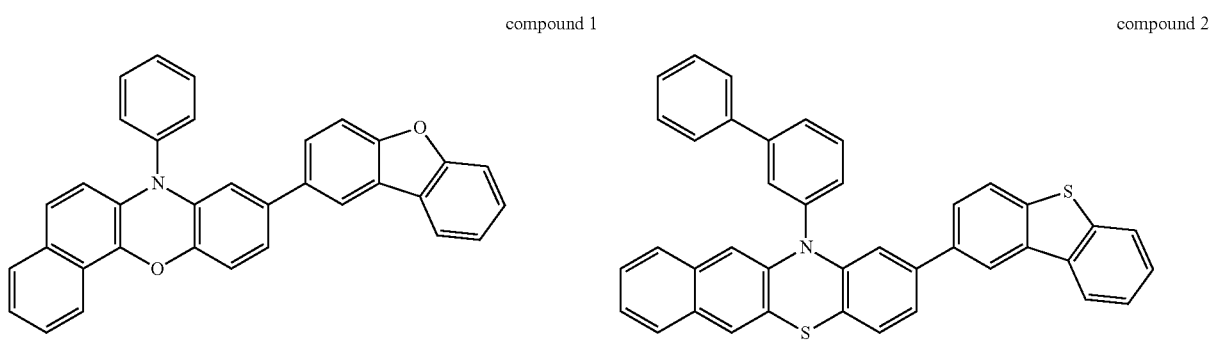

compound 1 compound 2

-continued
compound 3
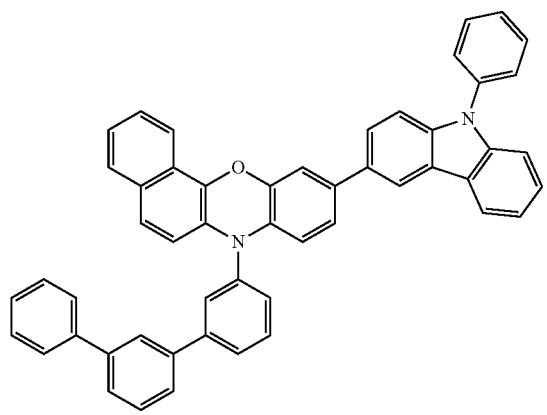
compound 4
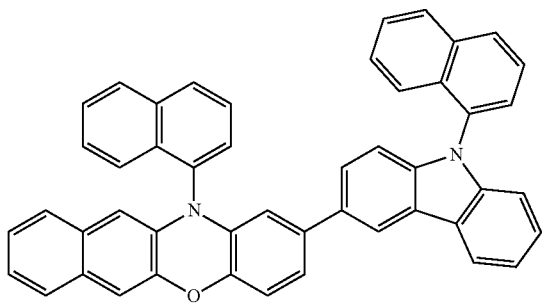
compound 5
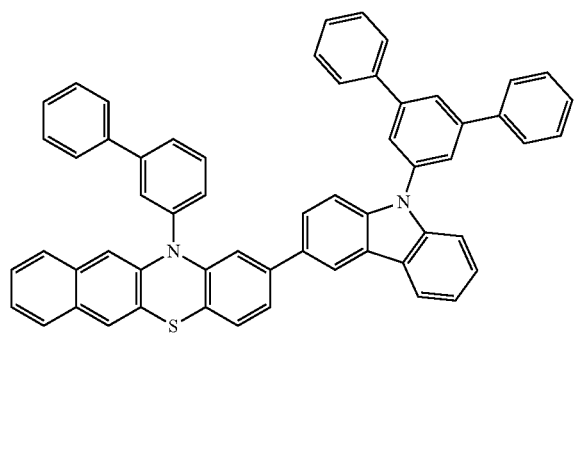
compound 6
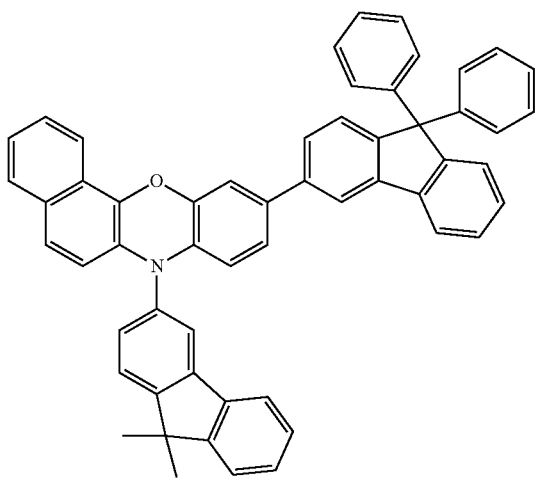
compound 7
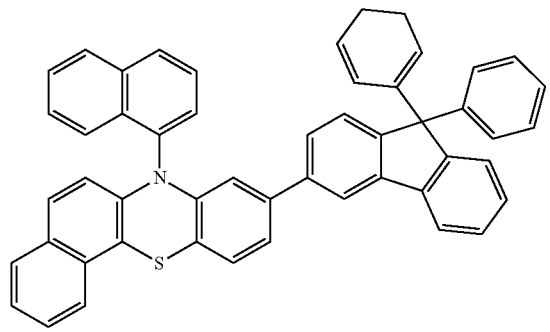
compound 8
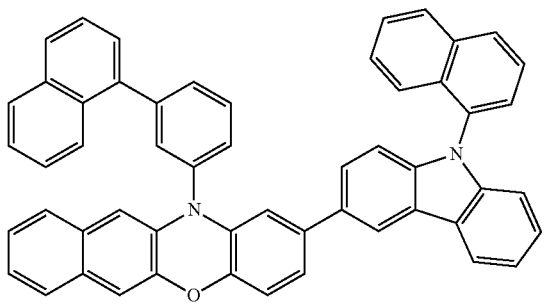

-continued
compound 9
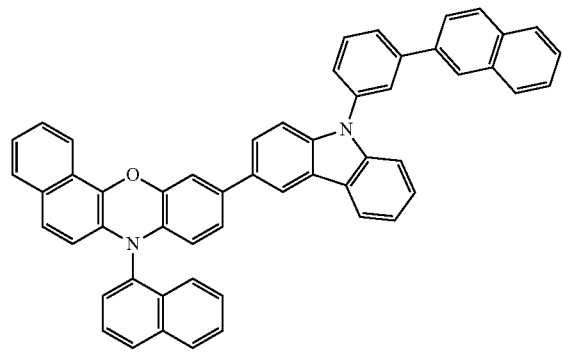
compound 10
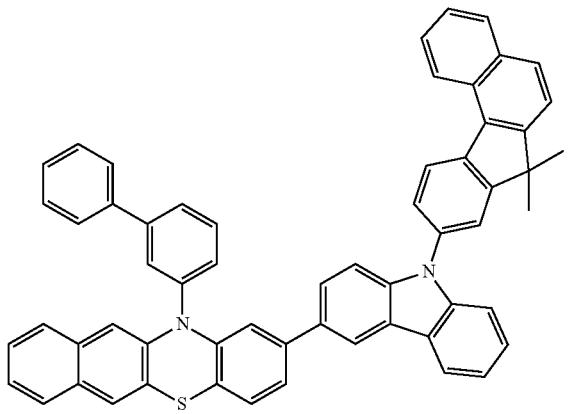
compound 11
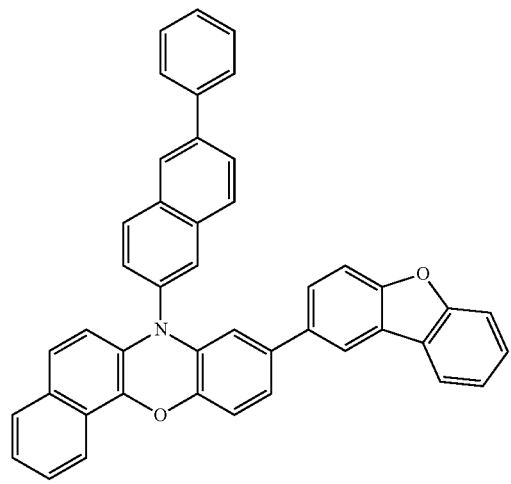
compound 12
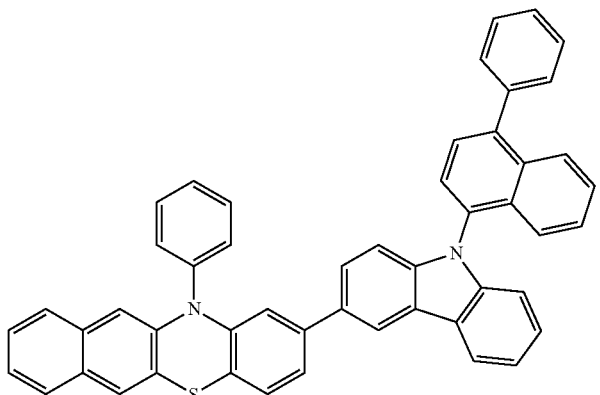
compound 13
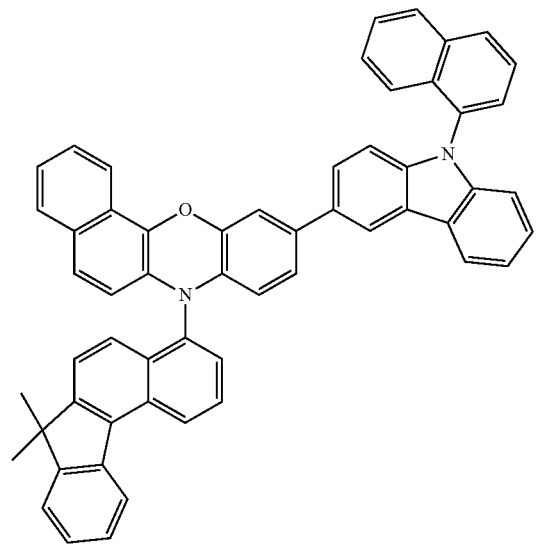
compound 14
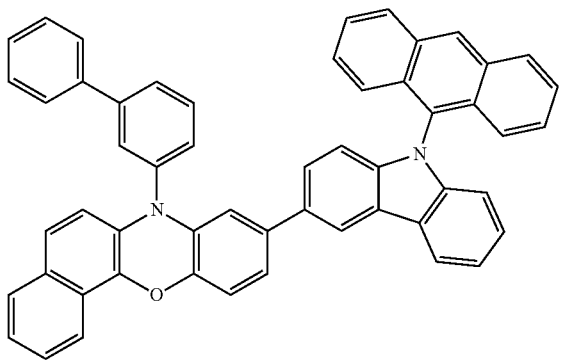

-continued
compound 15
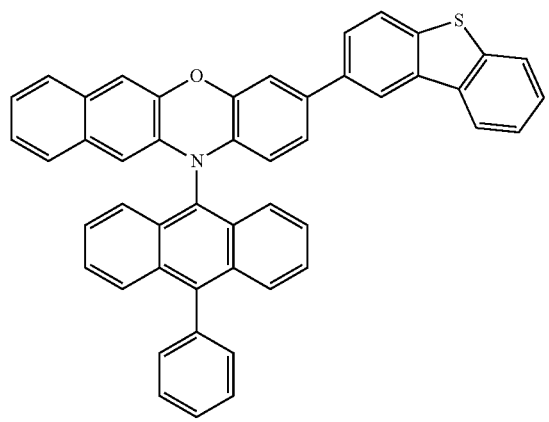
compound 16
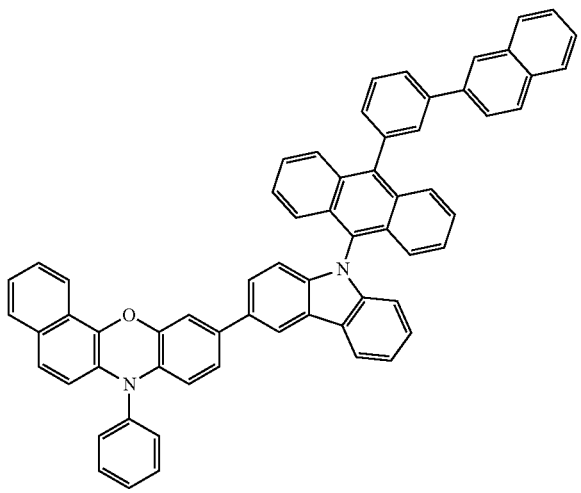
compound 17
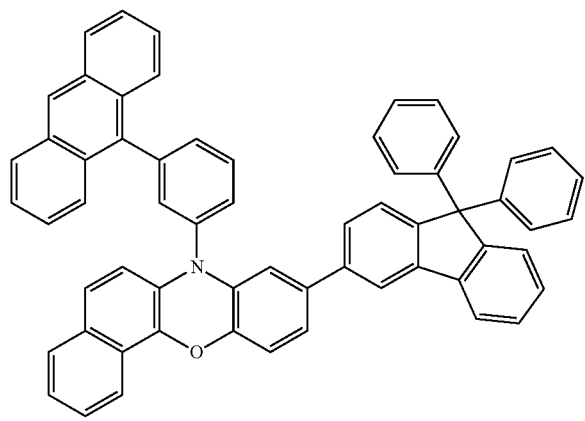
compound 18
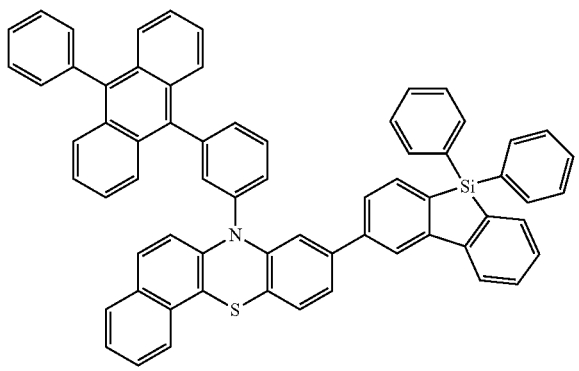
compound 19
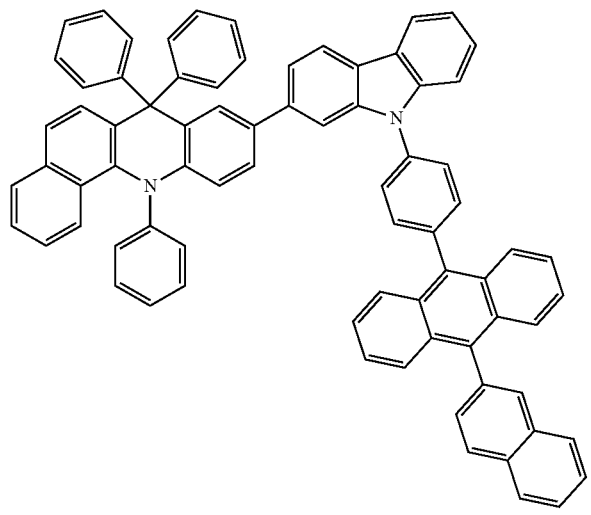
compound 20
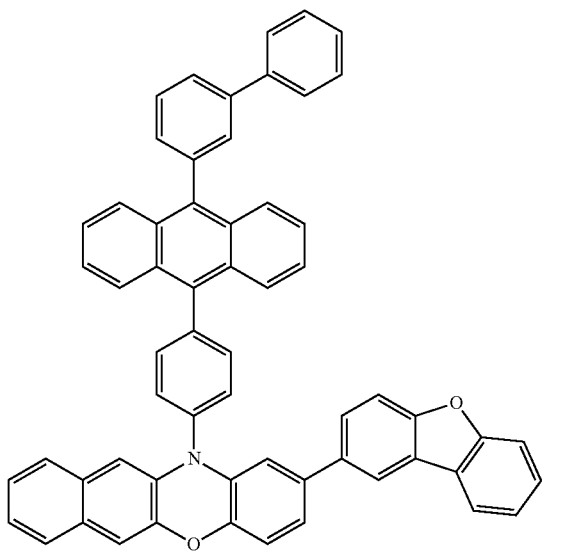

-continued
compound 21
compound 22
compound 23
compound 24
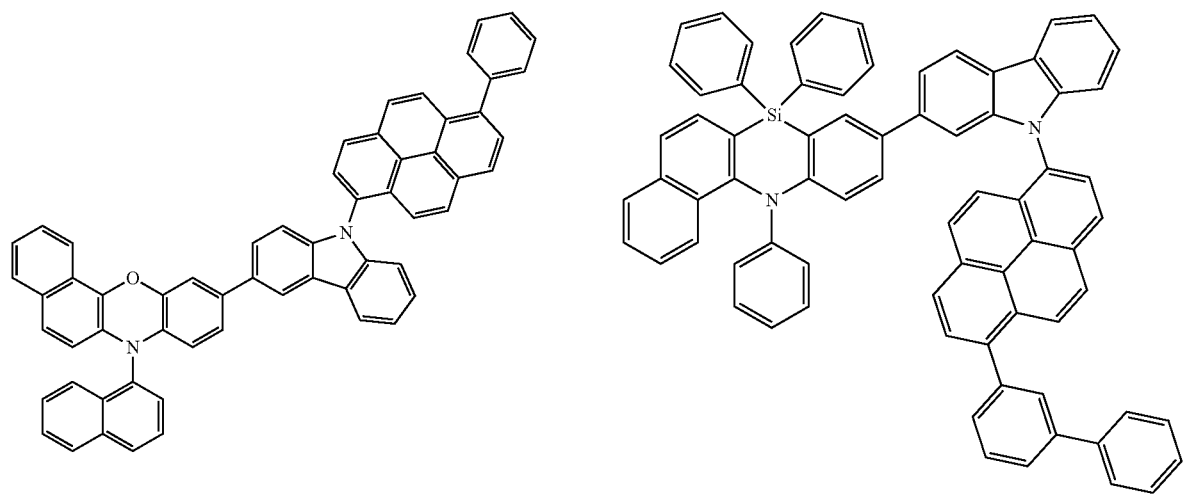
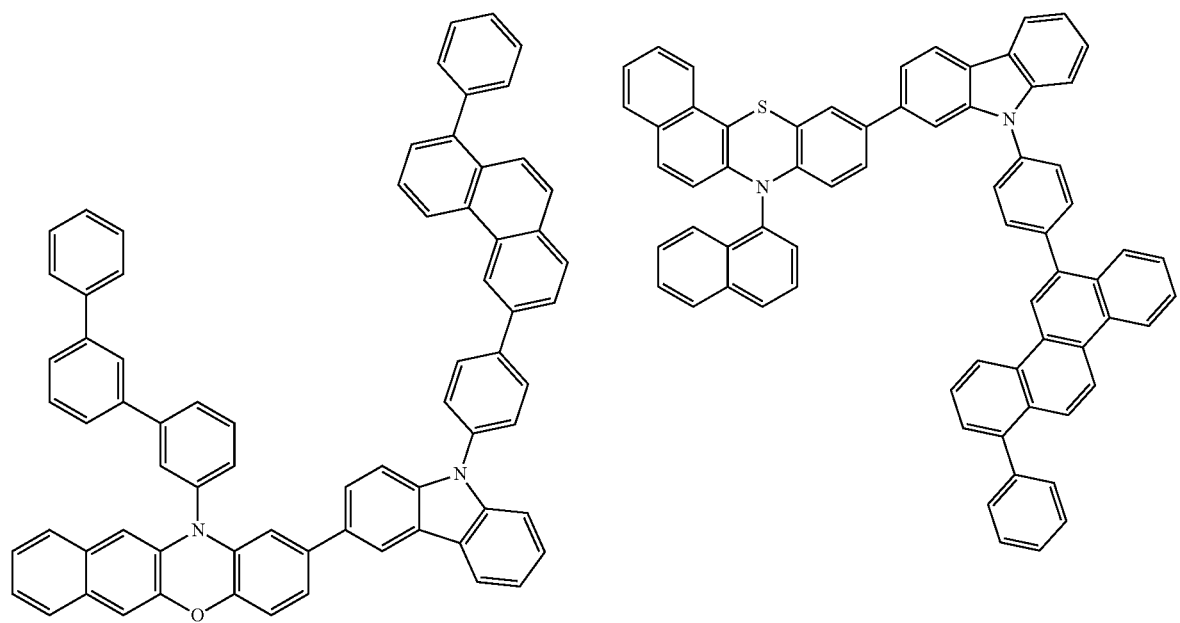

-continued
compound 25
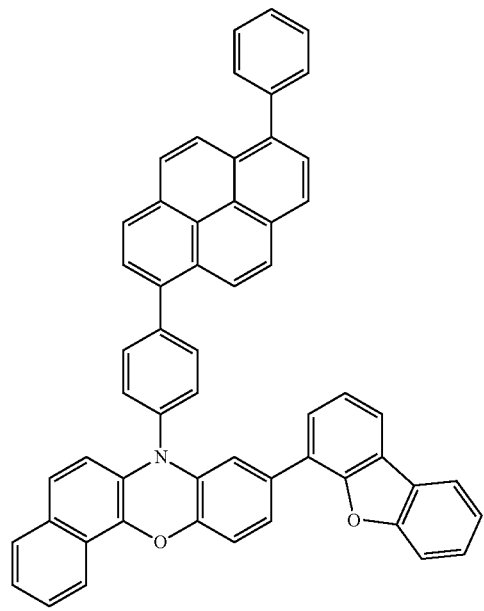
compound 26
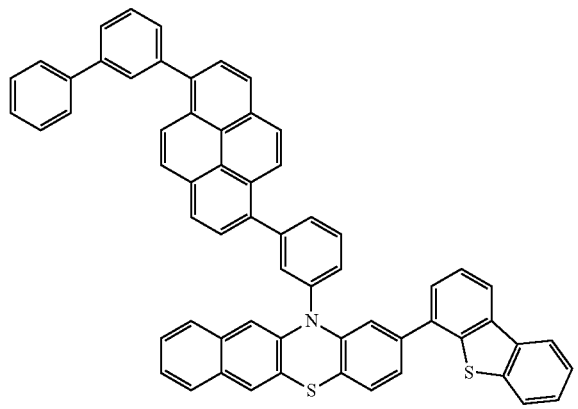
compound 27
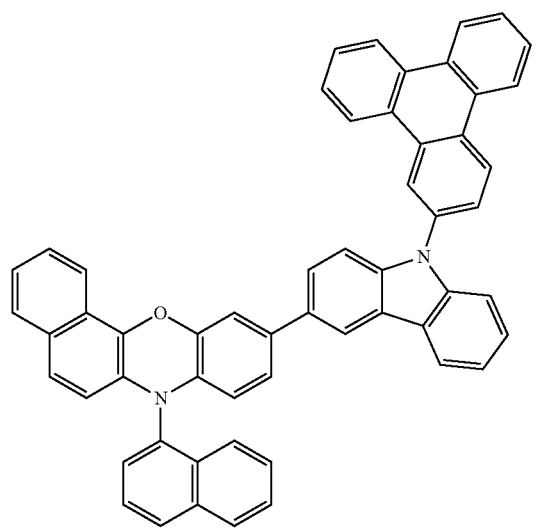
compound 28
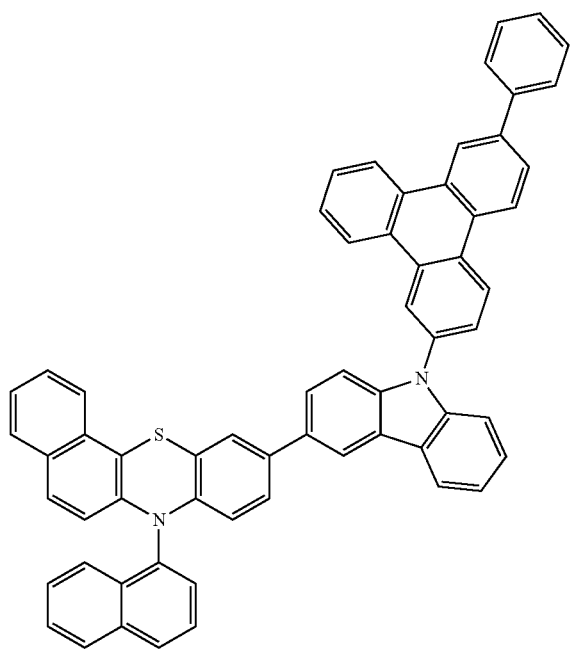

-continued
compound 29
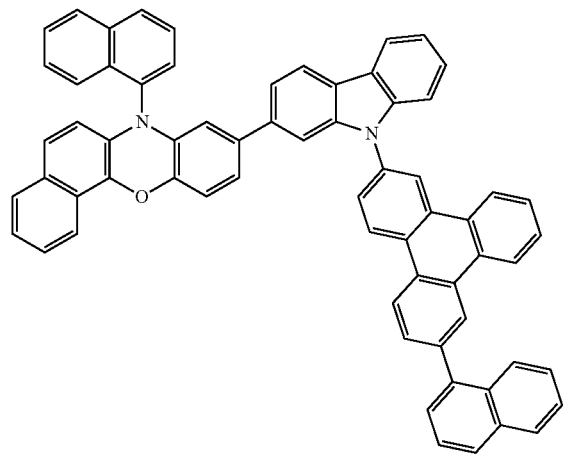
compound 30
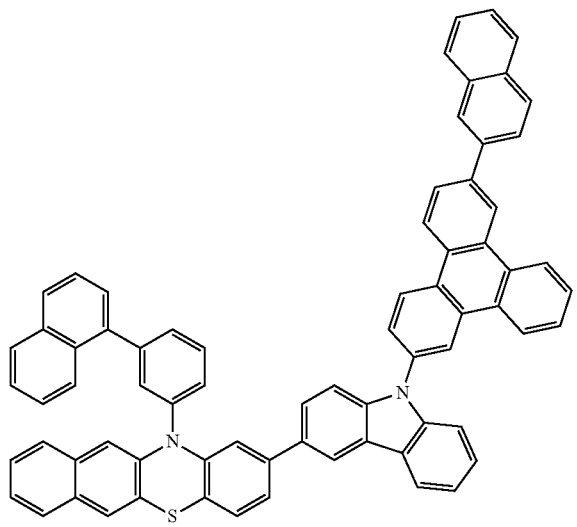
compound 31
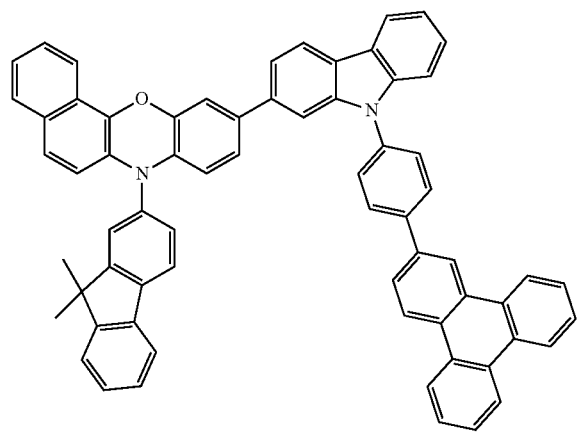
compound 32
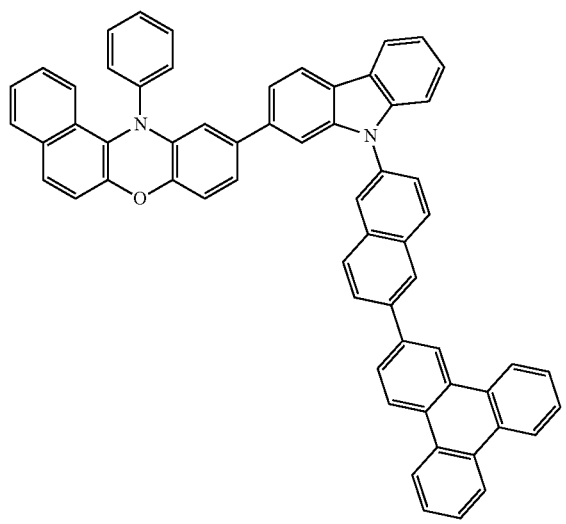
compound 33
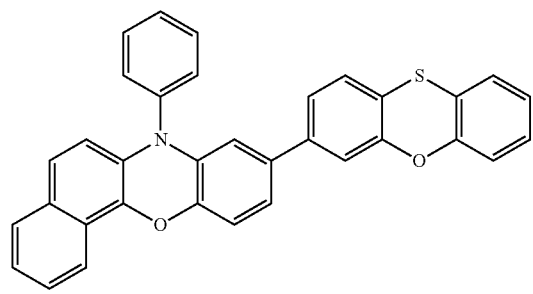
compound 34
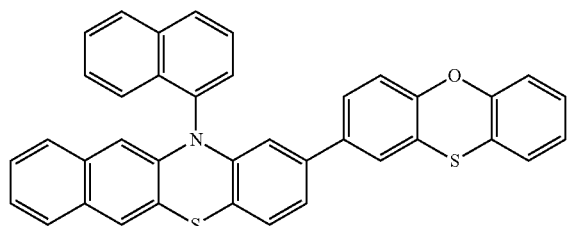

-continued
compound 35
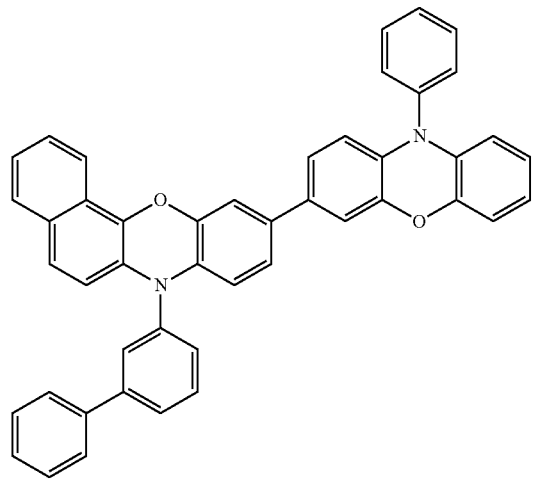
compound 36
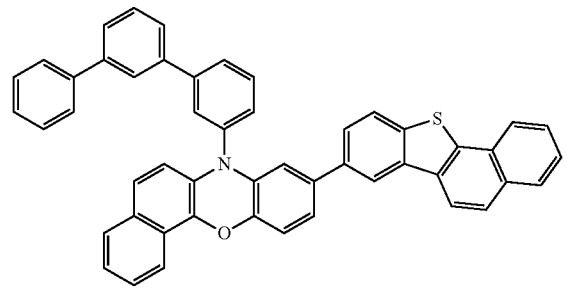
compound 37
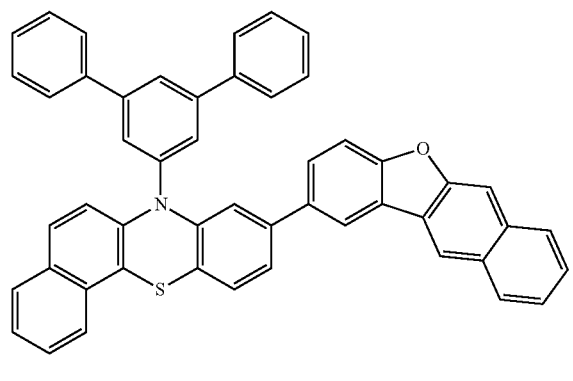
compound 38
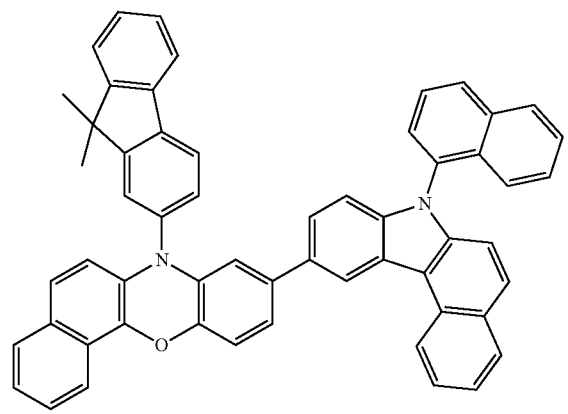
compound 39
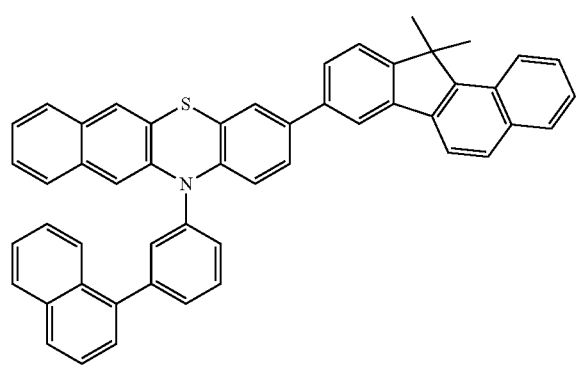 [SMILES: CC1(C)c2ccc(-c3ccc4c(c3)Sc3cc5ccccc5cc3N4c3cccc(-c4cccc5ccccc45)c3)cc2-c2ccc3ccccc3c21]
compound 40
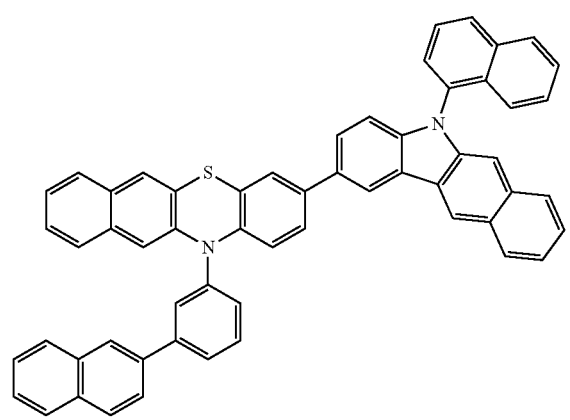

-continued
compound 41
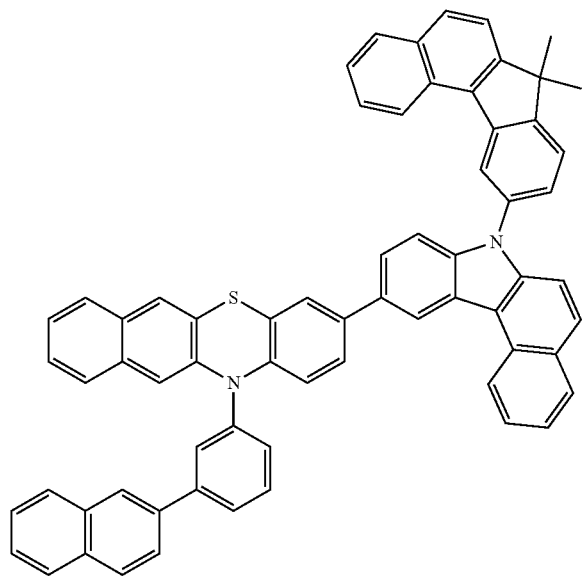
compound 42
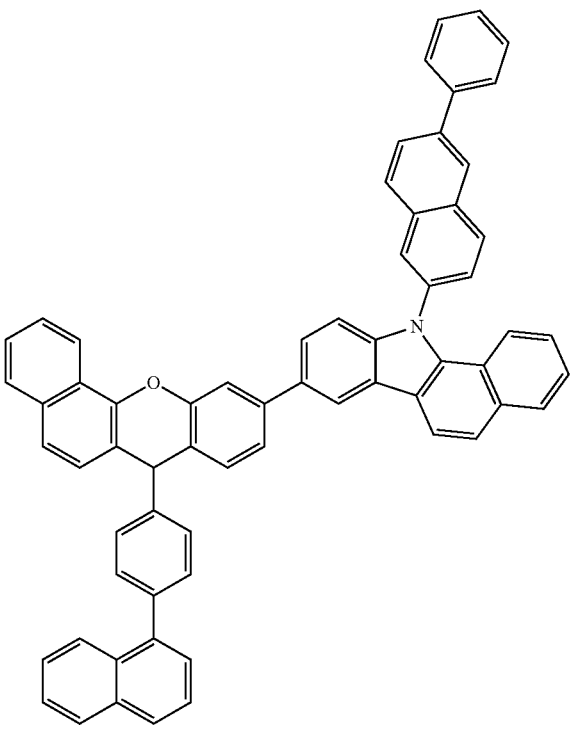
compound 43
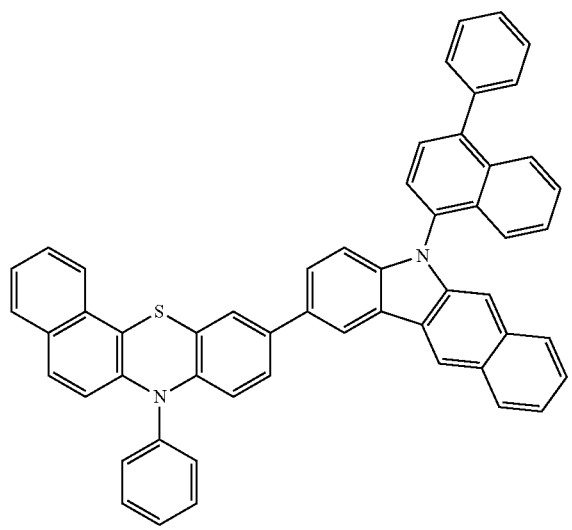
compound 44
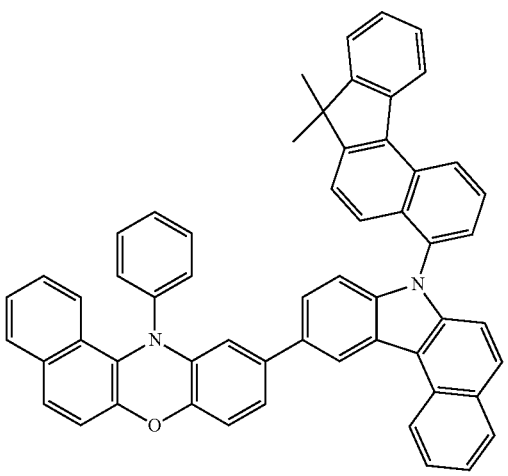 [SMILES: CC1(C)c2ccccc2-c2c1ccc1c(-n3c4ccc(-c5ccc6c(c5)N(c5ccccc5)c5c(ccc7ccccc57)O6)cc4c4c5ccccc5ccc43)cccc21]

compound 45
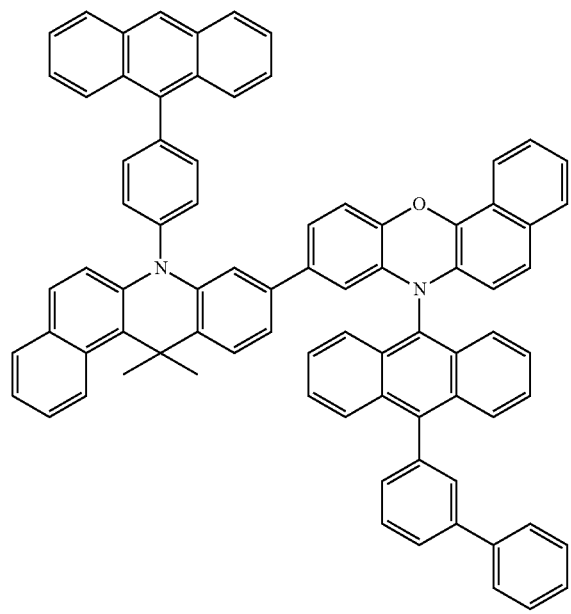
compound 46
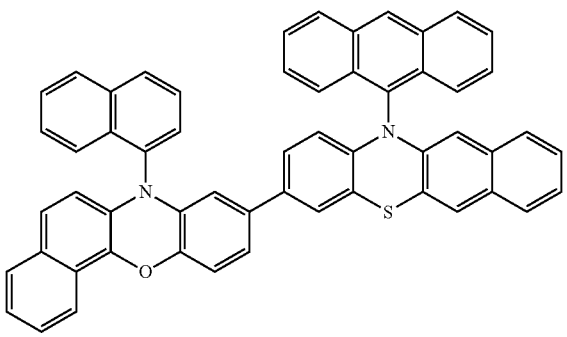
compound 47
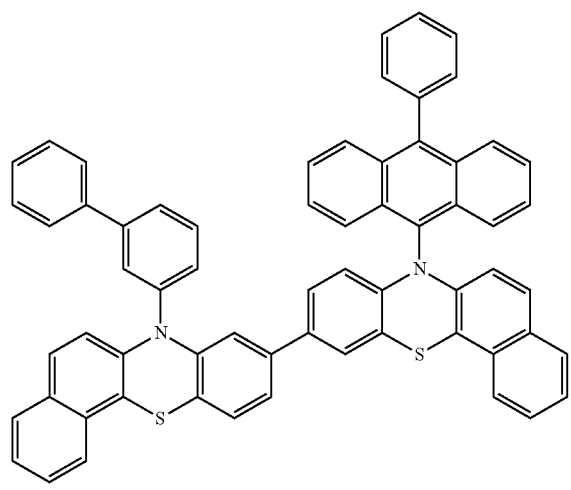
compound 48
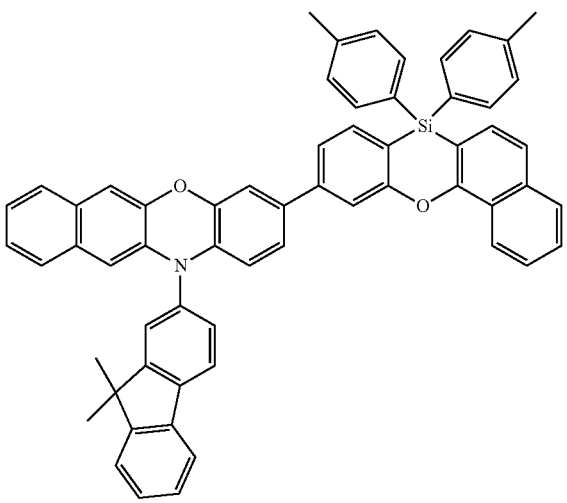

-continued
compound 49
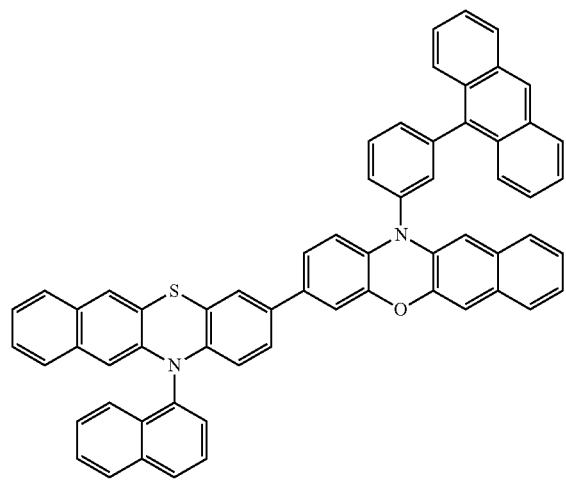
compound 50
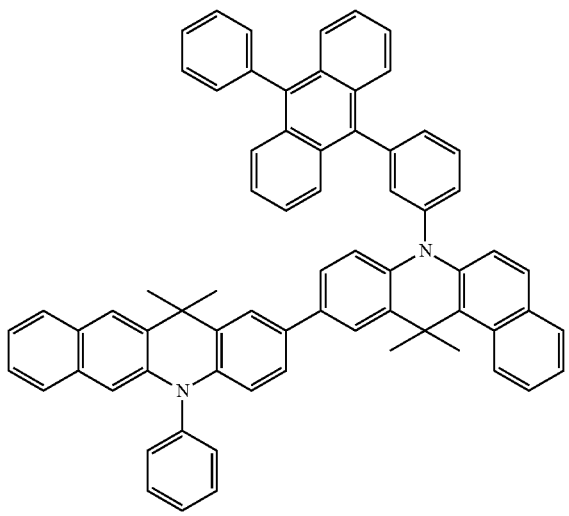 [SMILES: CC1(C)c2cc(-c3ccc4c(c3)C(C)(C)c3c(ccc5ccccc35)N4c3cccc(-c4c5ccccc5c(-c5ccccc5)c5ccccc45)c3)ccc2N(c2ccccc2)c2cc3ccccc3cc21]
compound 51
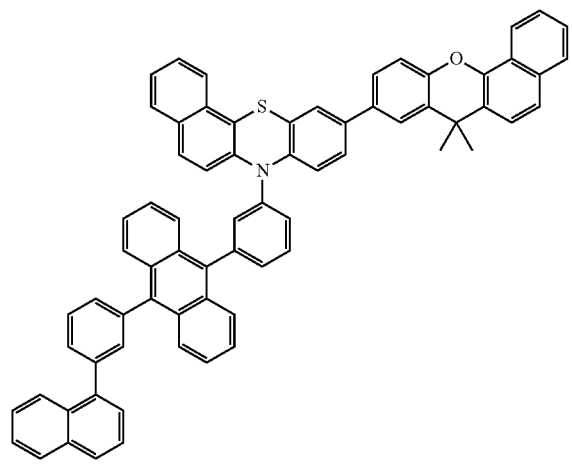
compound 52
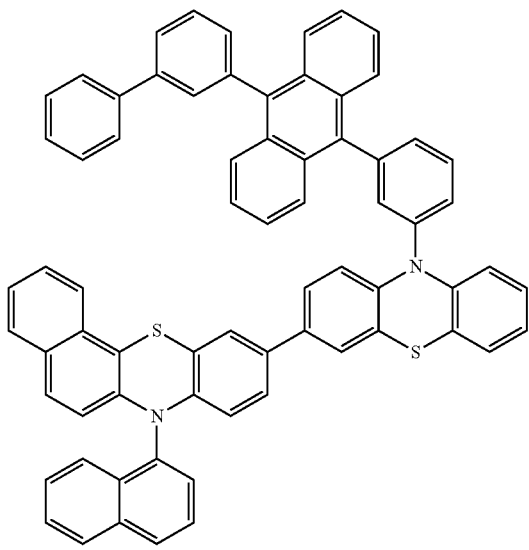

-continued
compound 53
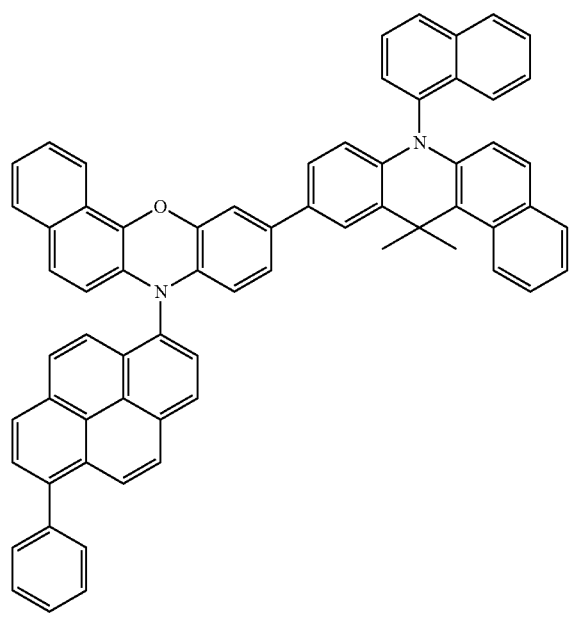
compound 54
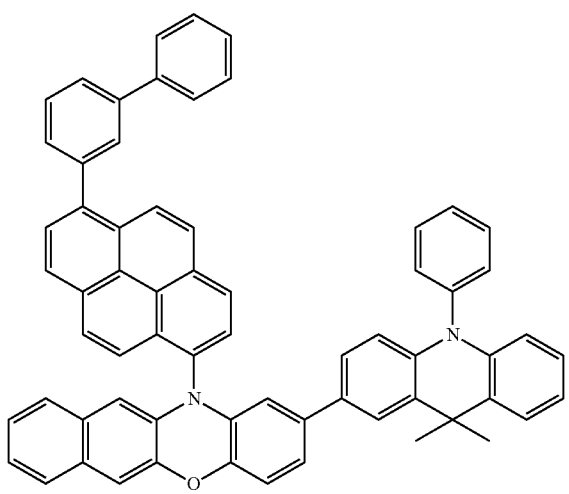
compound 55
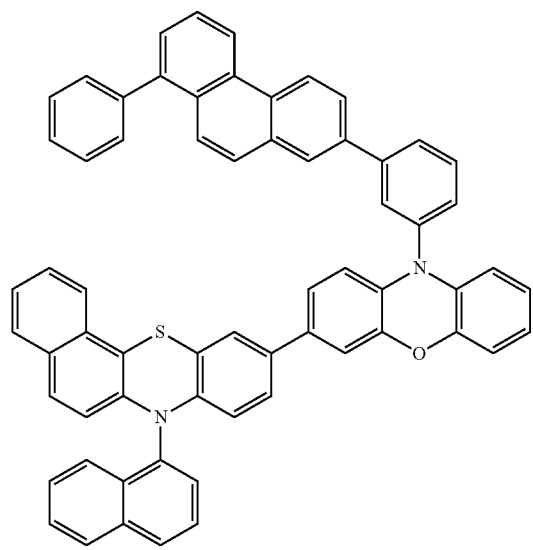
compound 56
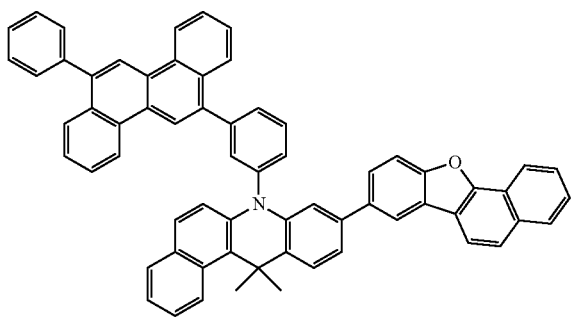

compound 57
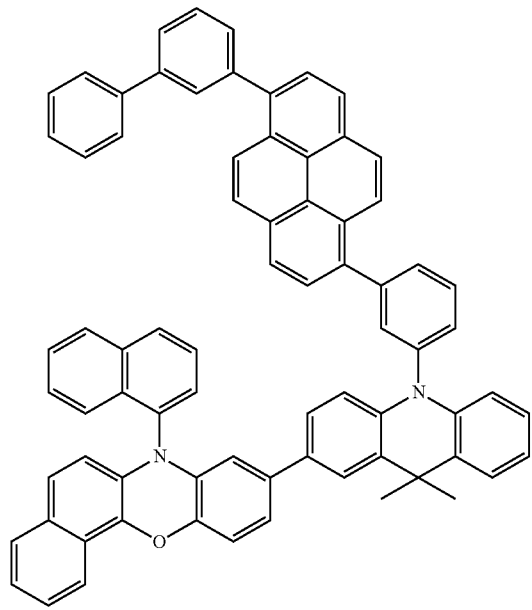
compound 58
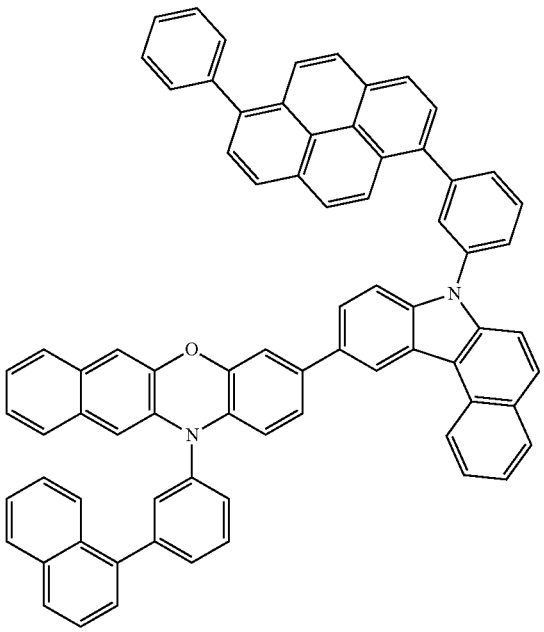
compound 59
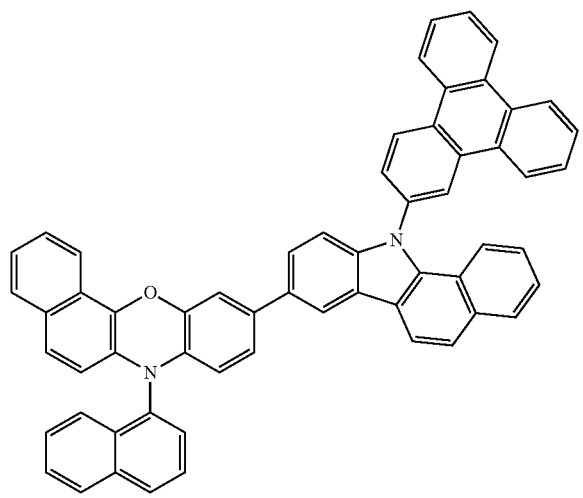
compound 60
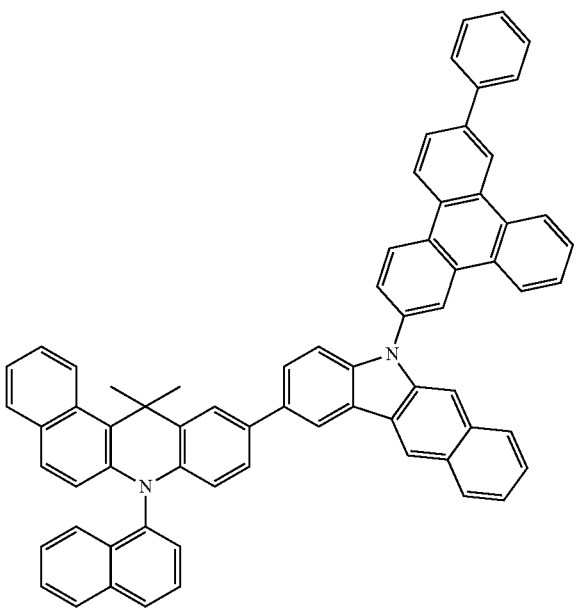

-continued
compound 61
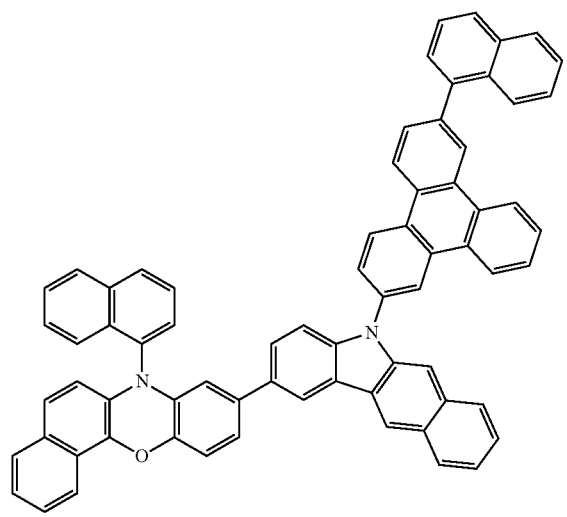
compound 62
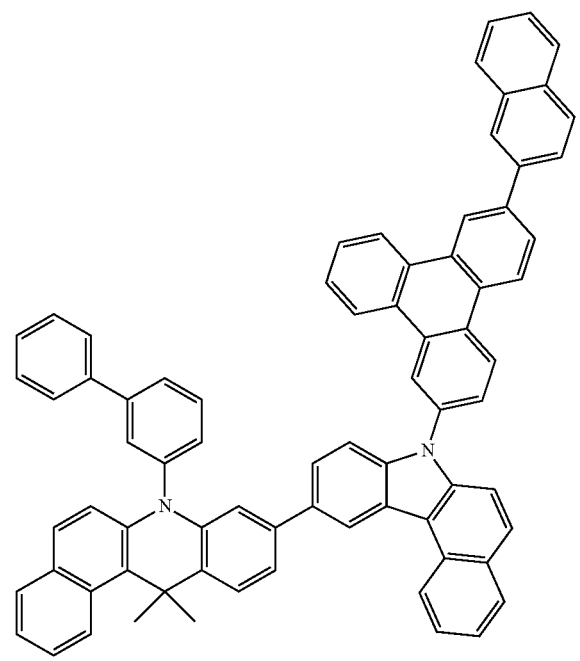
compound 63
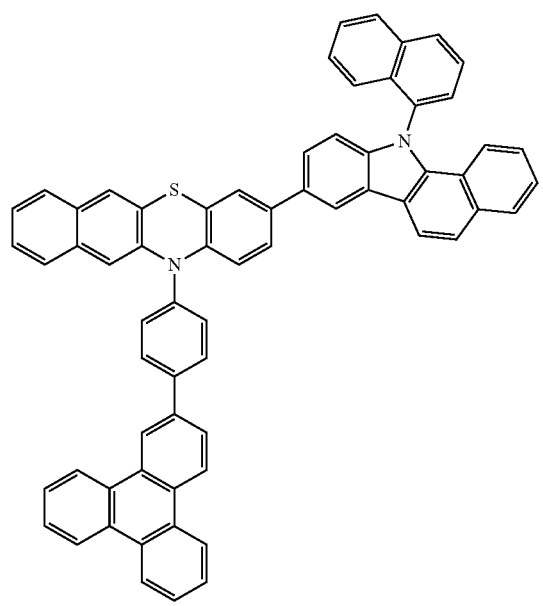
compound 64
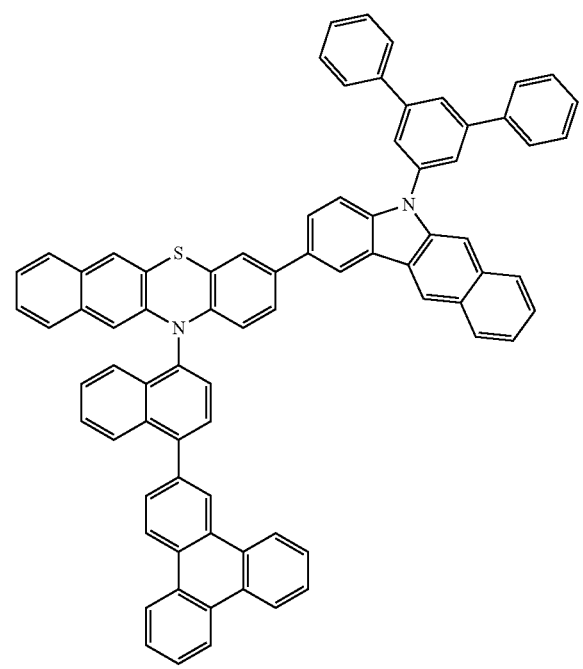

-continued
compound 65
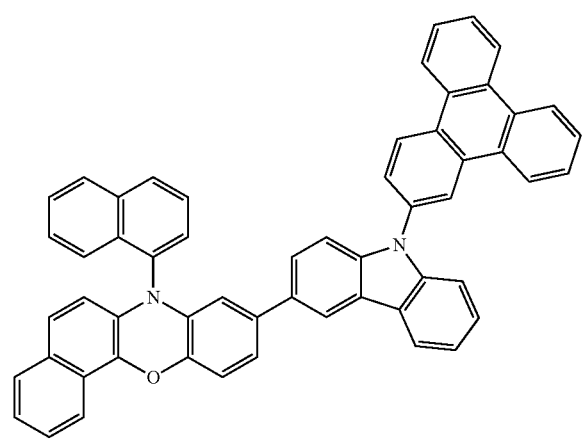
compound 66
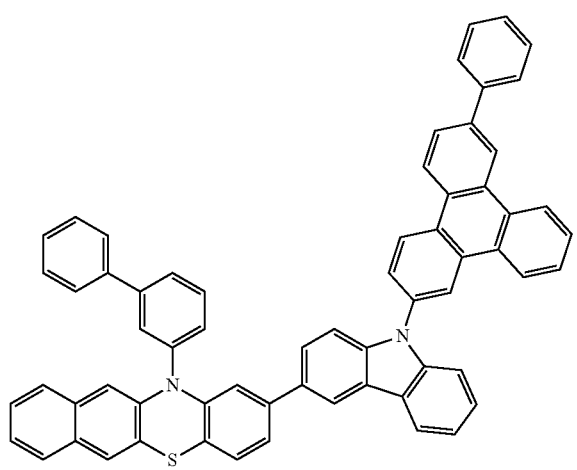
compound 67
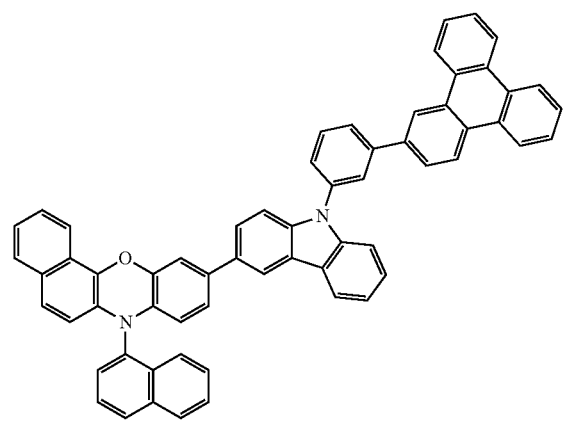
compound 68
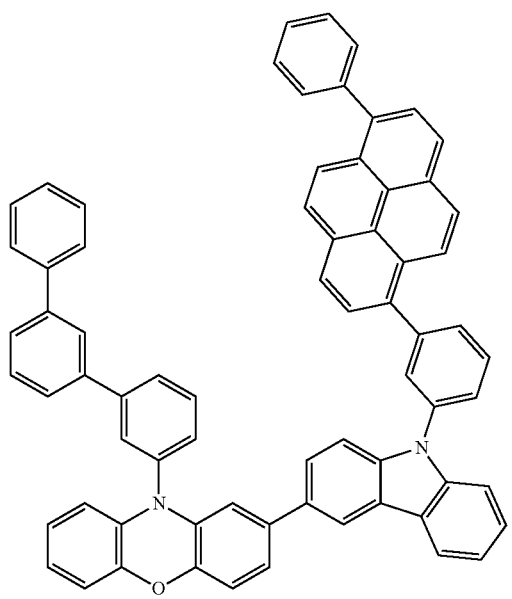
compound 69
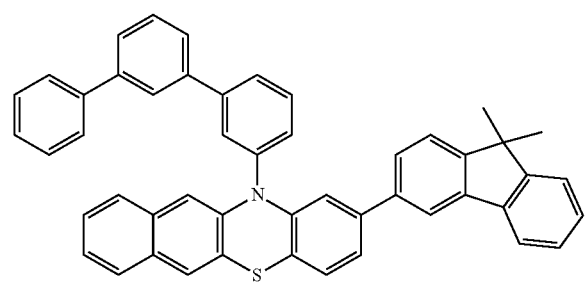
compound 70
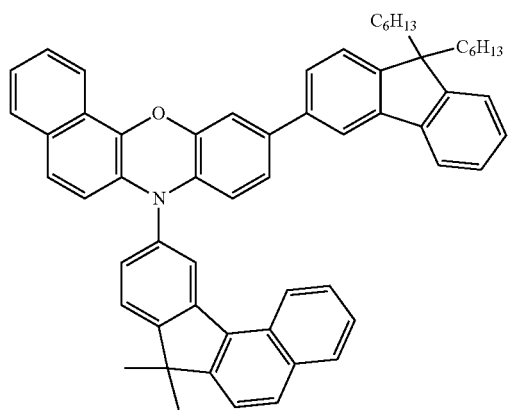

-continued
compound 71
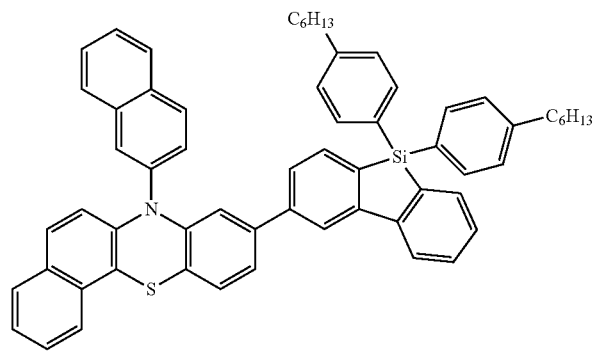
compound 72
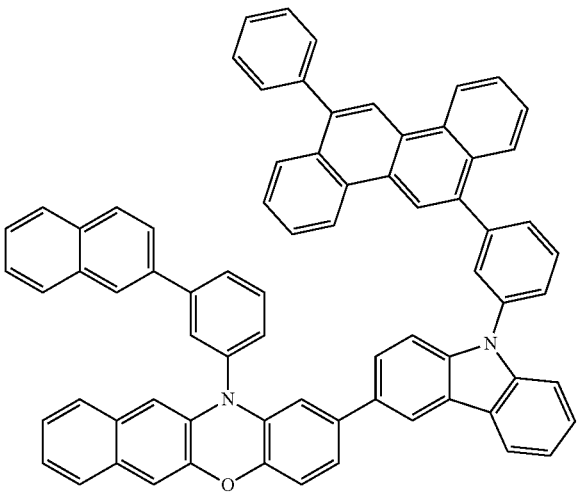
compound 73
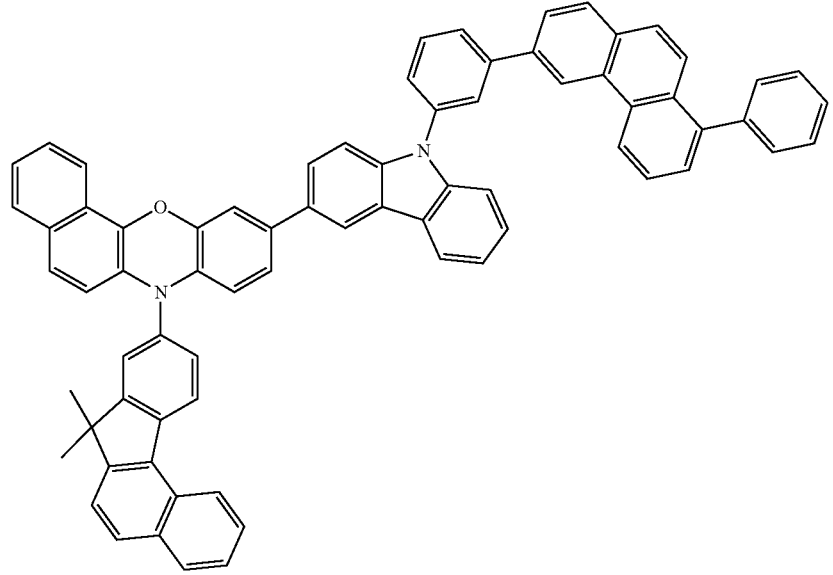
compound 74
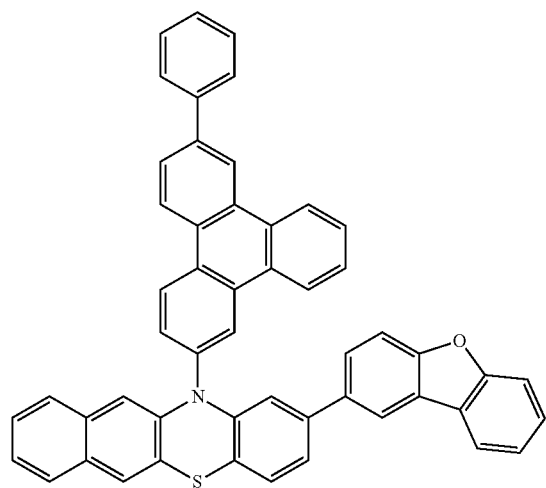
compound 75
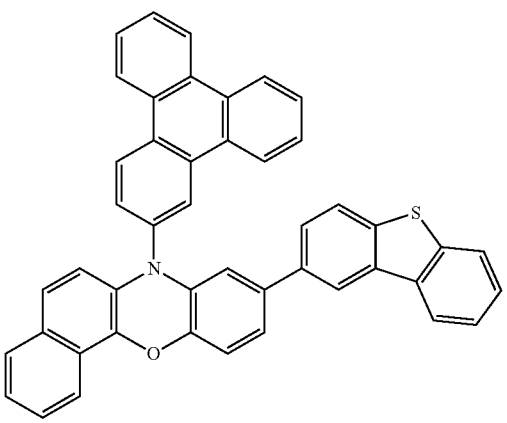

-continued
compound 76
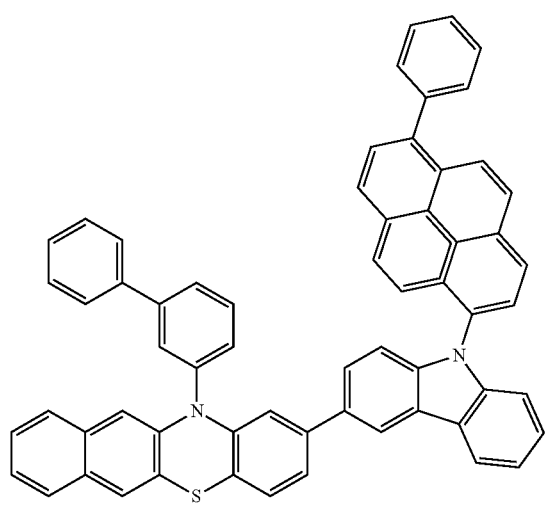
compound 77
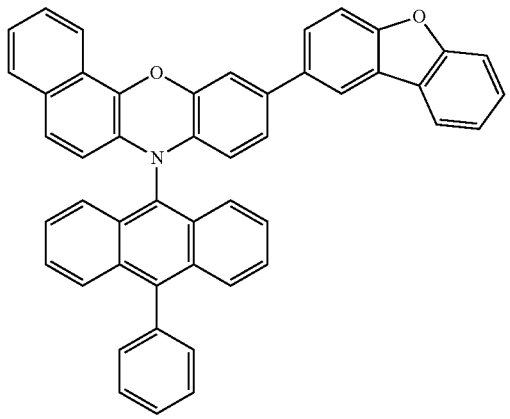
compound 78
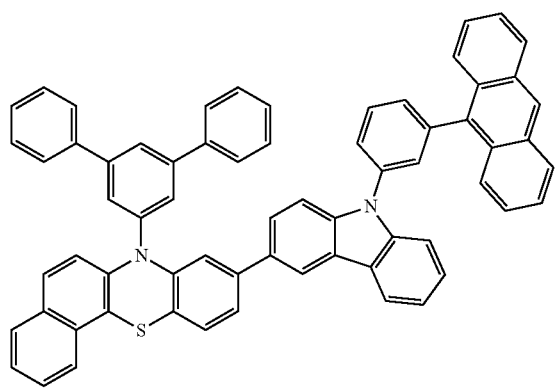
compound 79
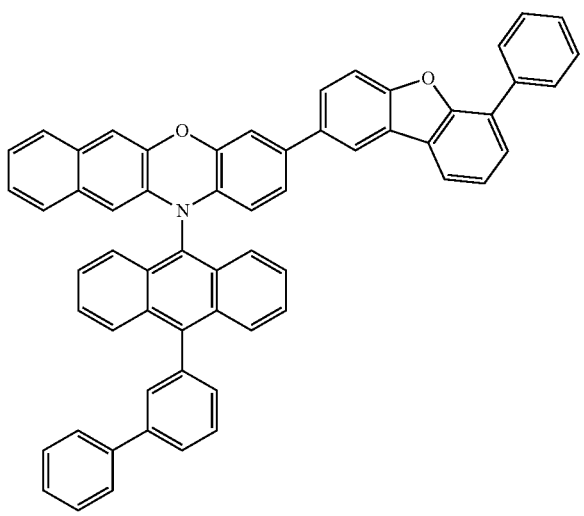
compound 80
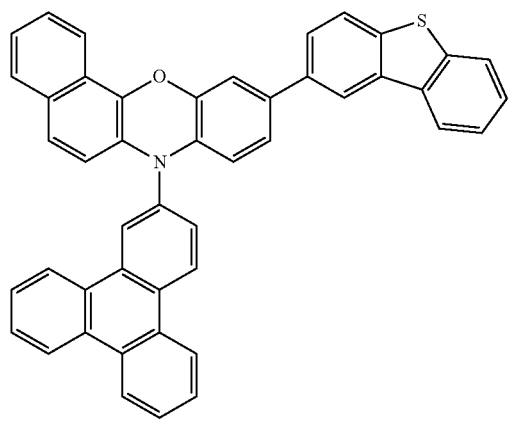
compound 81
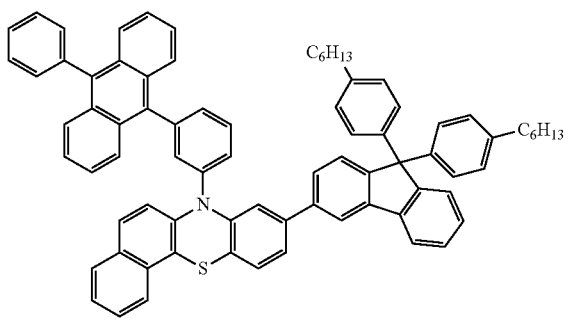

-continued
compound 82
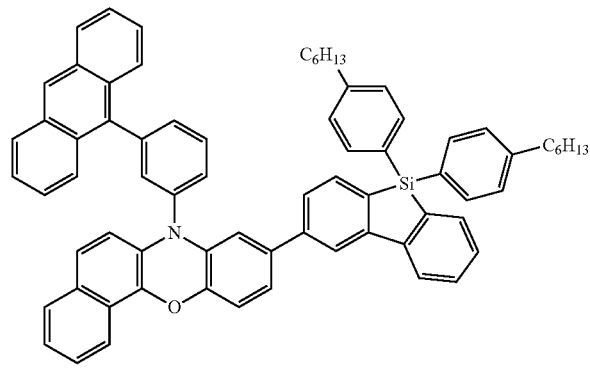
compound 83
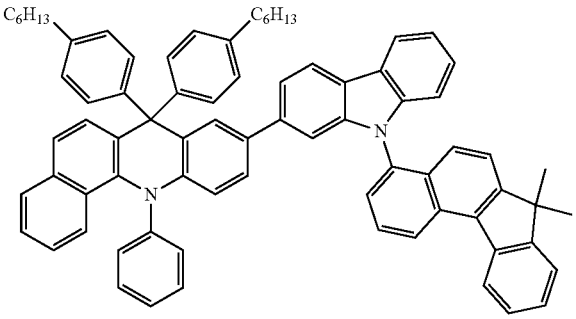
compound 84
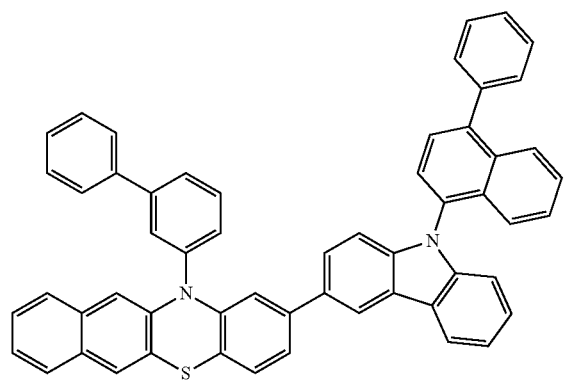
compound 85
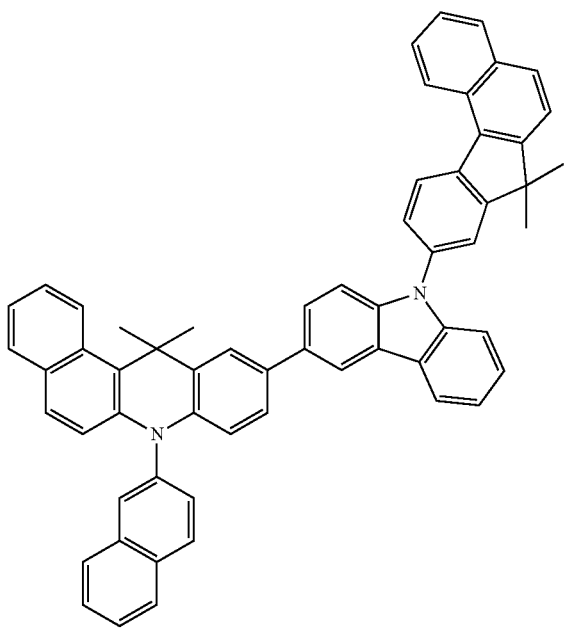
compound 86
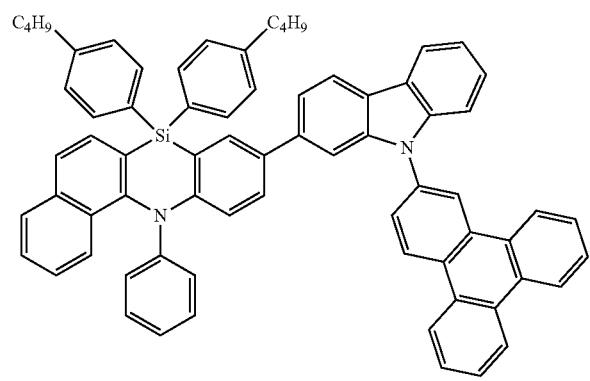
compound 87
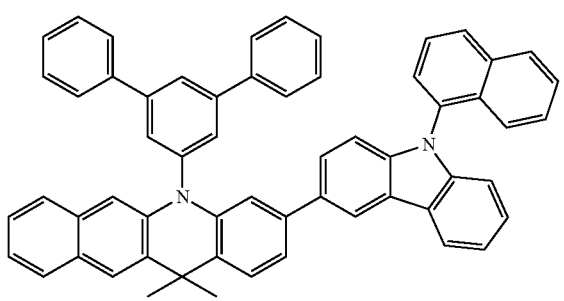

compound 88
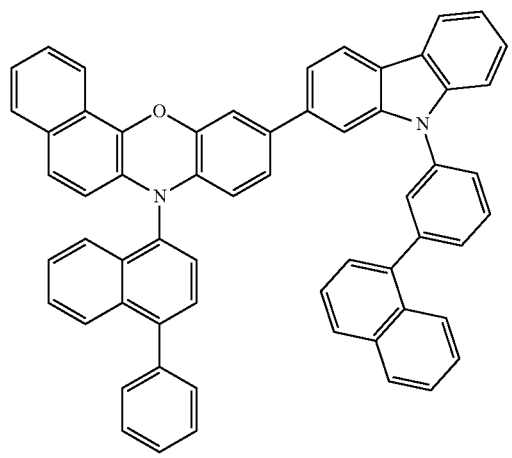
compound 89
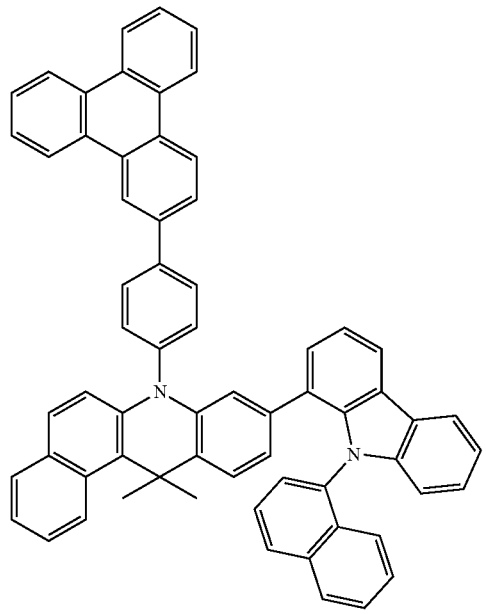
compound 90
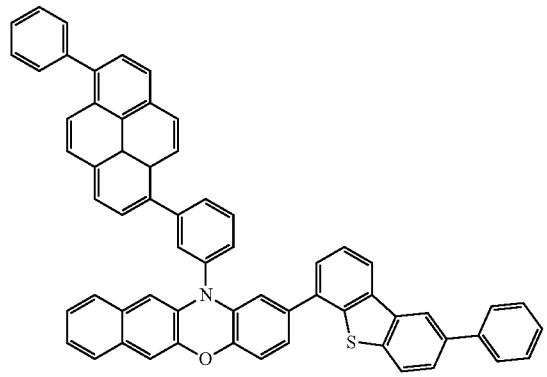
compound 91
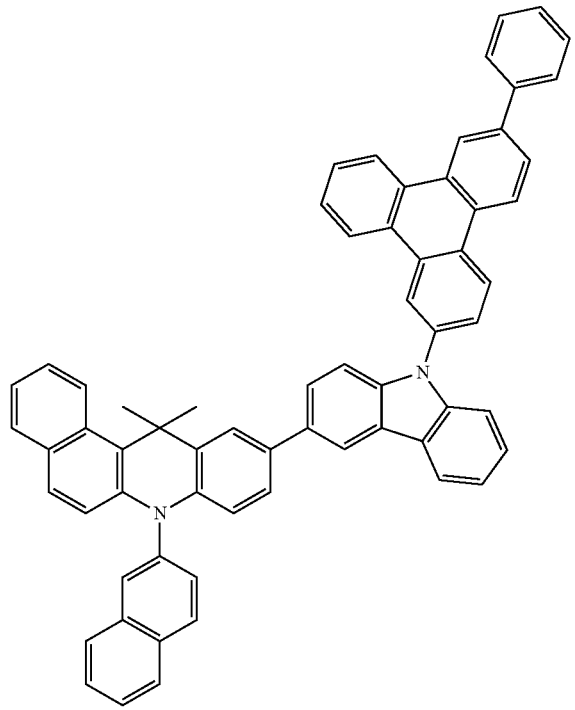

-continued
compound 92
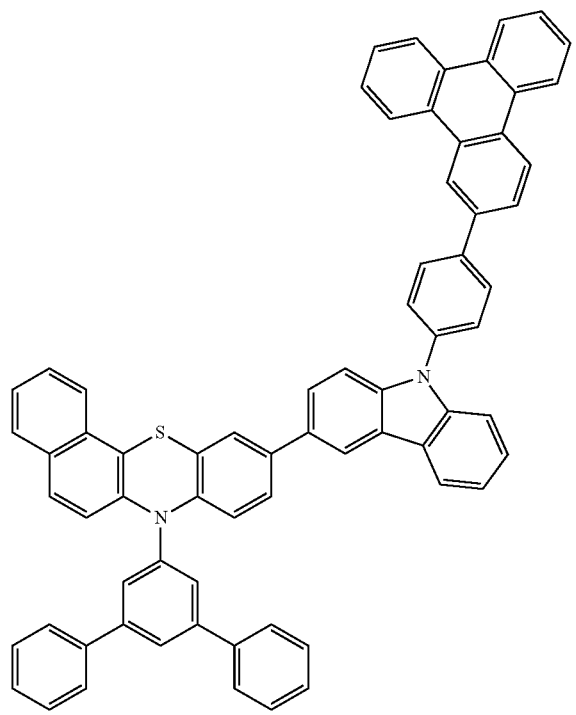
compound 93
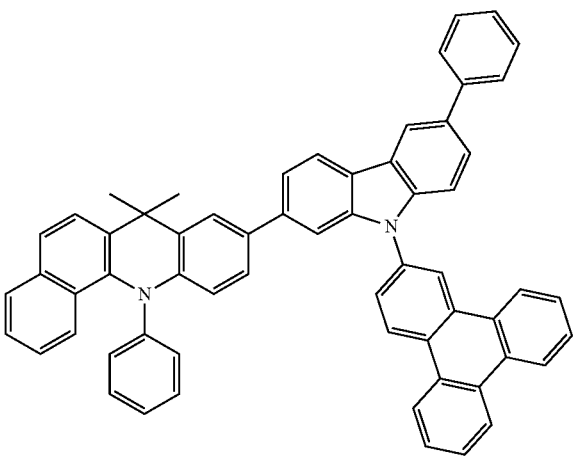
compound 94
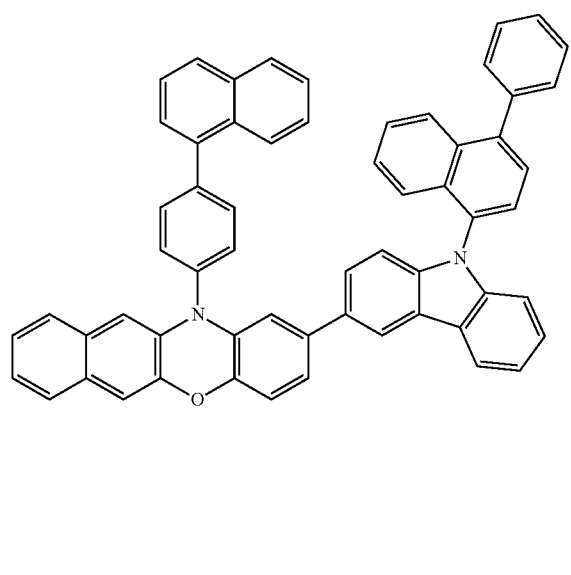
compound 95
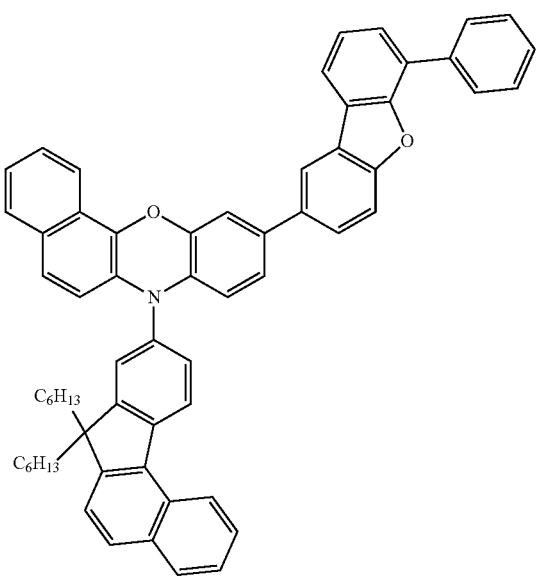

-continued
compound 96
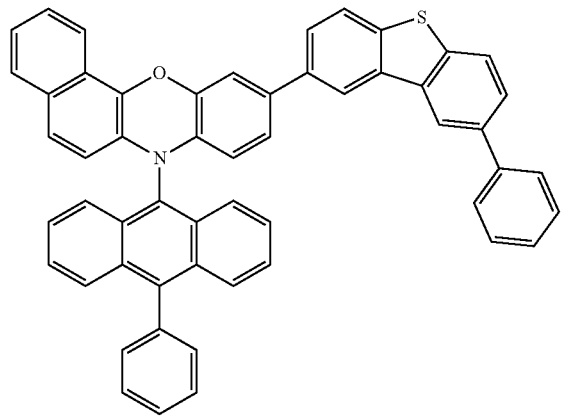
compound 97
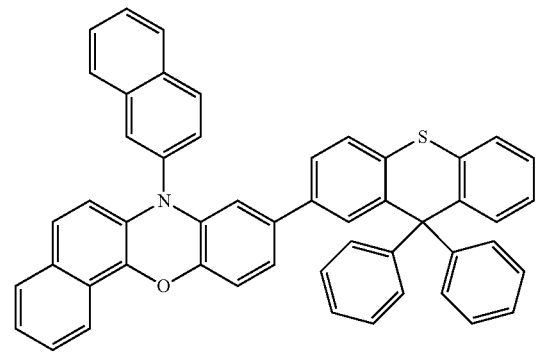
compound 98
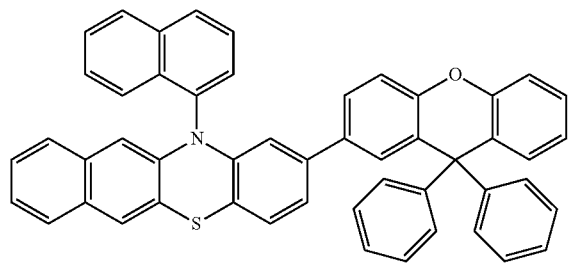
compound 99
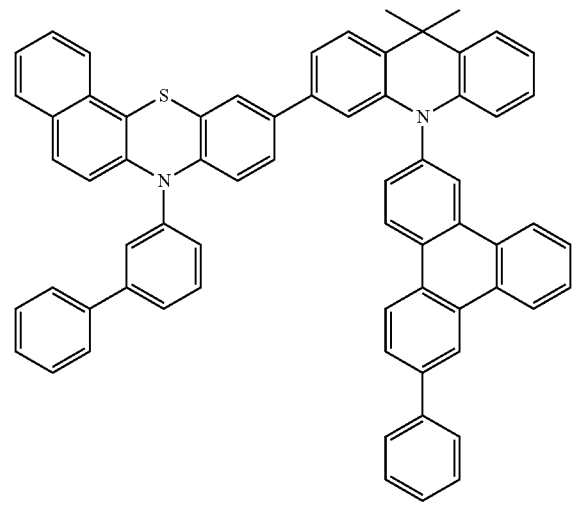 [SMILES: CC1(C)c2ccccc2N(c2ccc3c4ccc(-c5ccccc5)cc4c4ccccc4c3c2)c2cc(-c3ccc4c(c3)Sc3c(ccc5ccccc35)N4c3cccc(-c4ccccc4)c3)ccc21]
compound 100
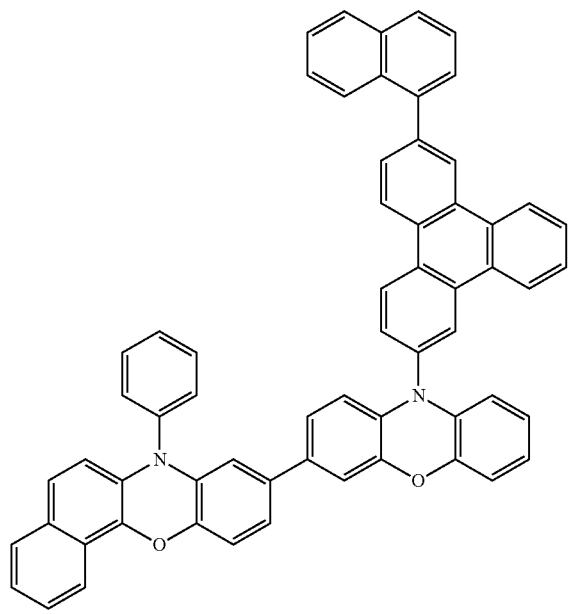
compound 101
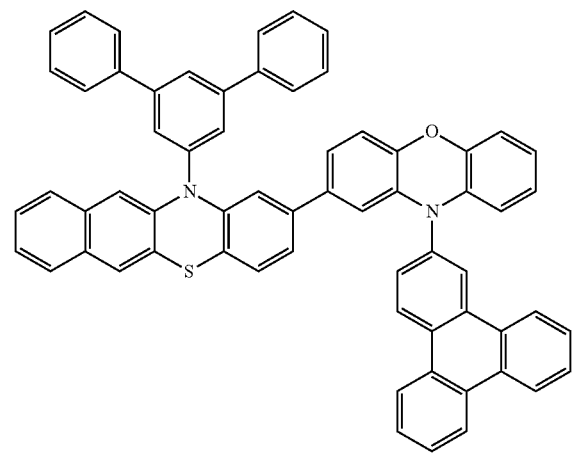

-continued
compound 102
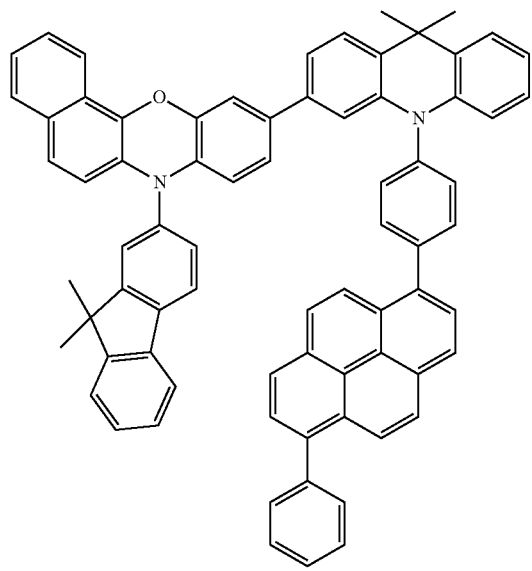
compound 103
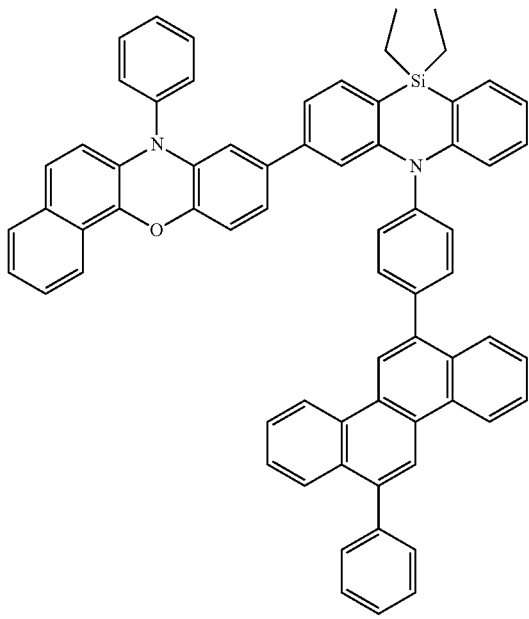
compound 104
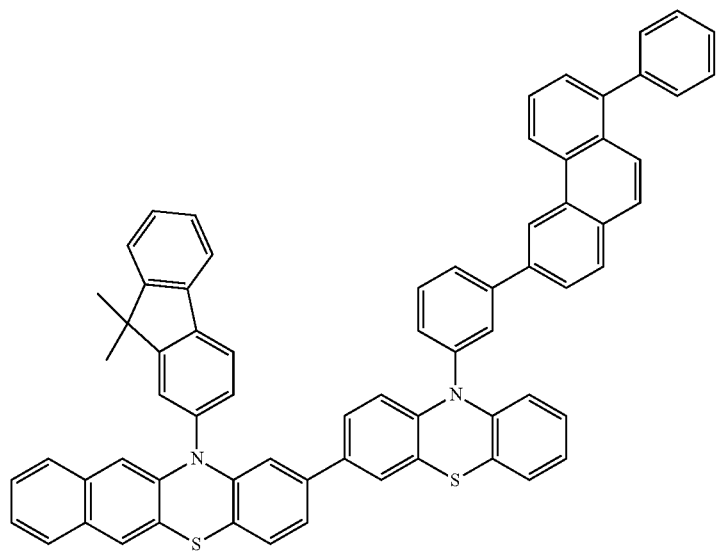
compound 105
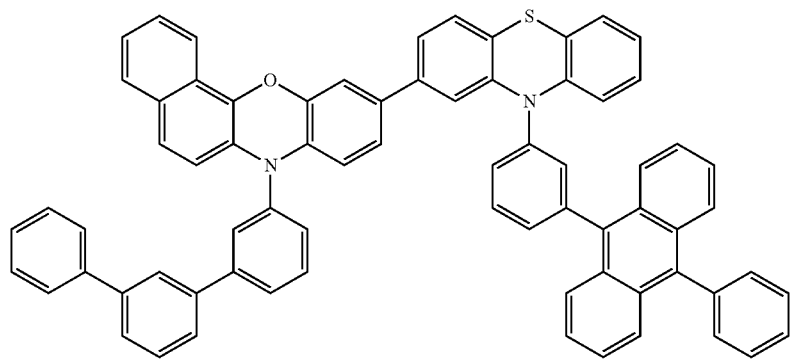

-continued
compound 106
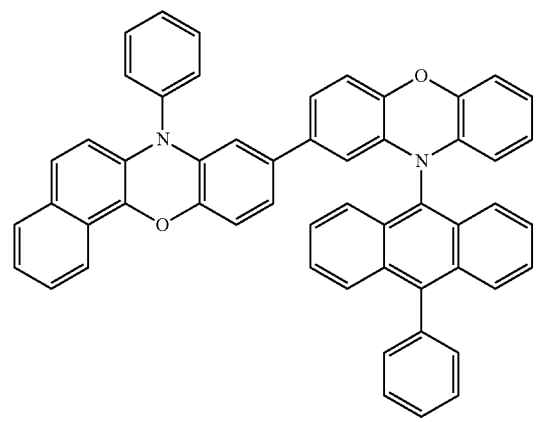
compound 107
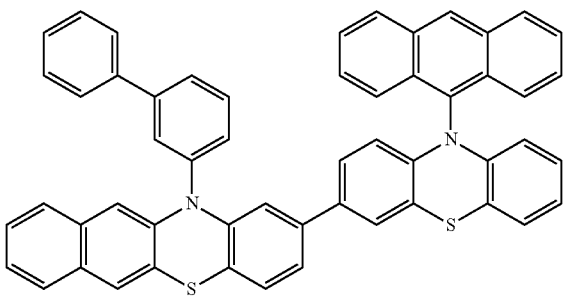
compound 108
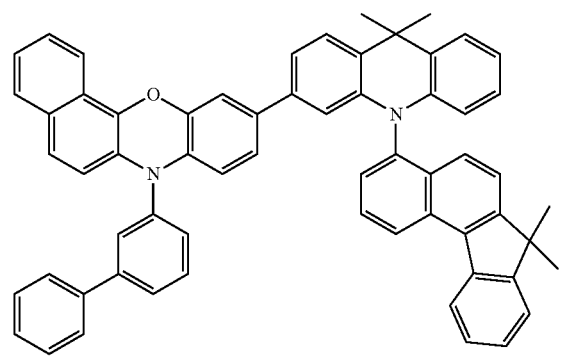
compound 109
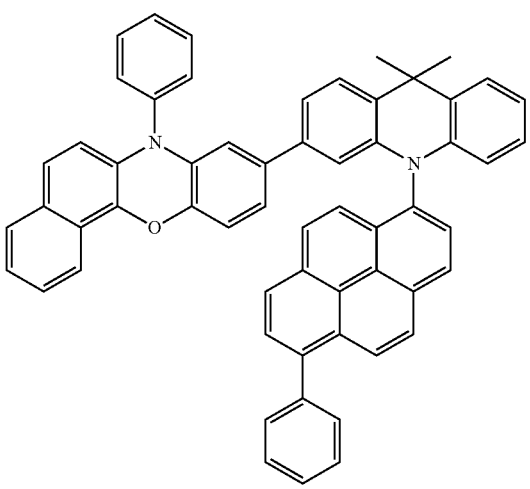
compound 110
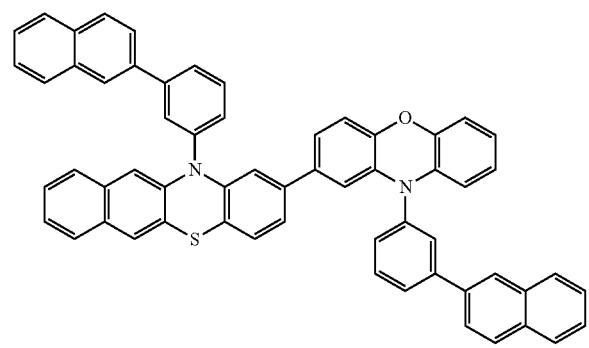
compound 111
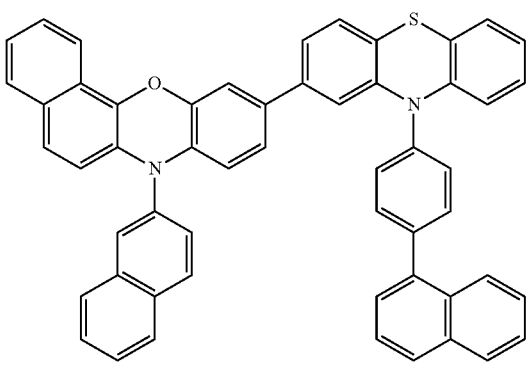

-continued
compound 112
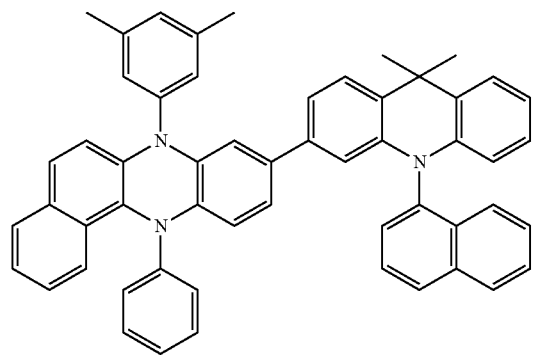
compound 113
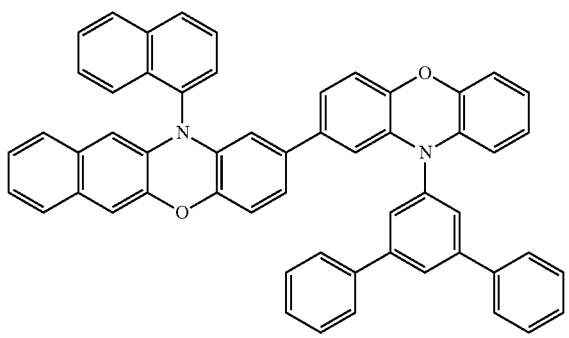
compound 114
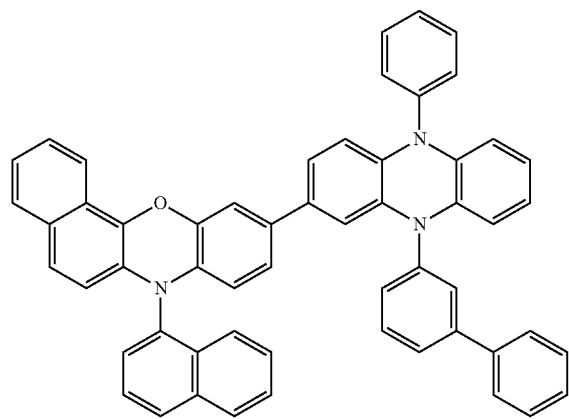
compound 115
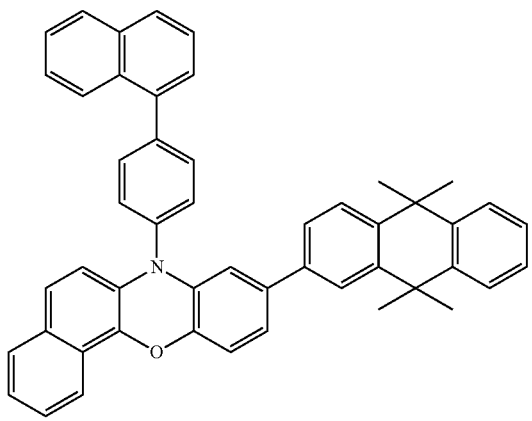
compound 116
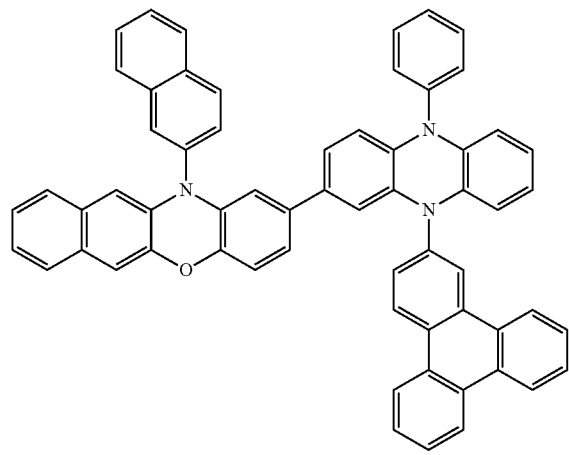
compound 117
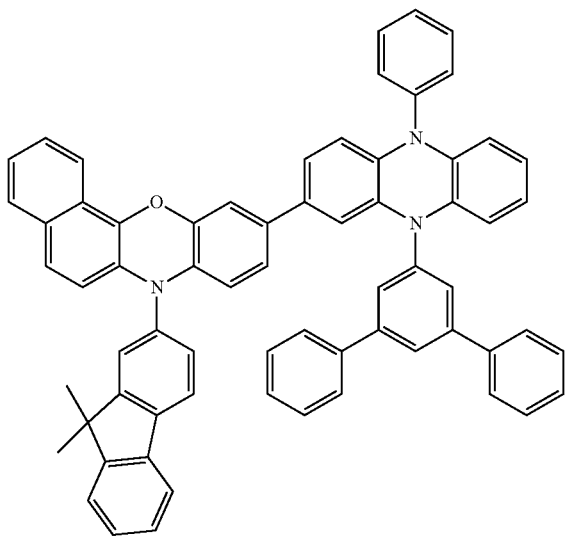

-continued
compound 118
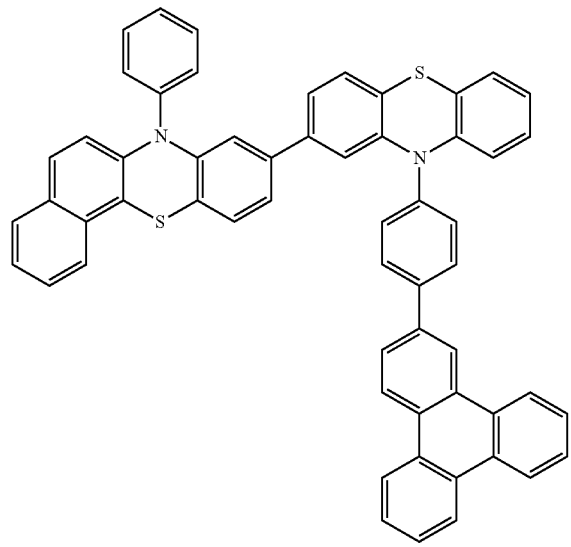
compound 119
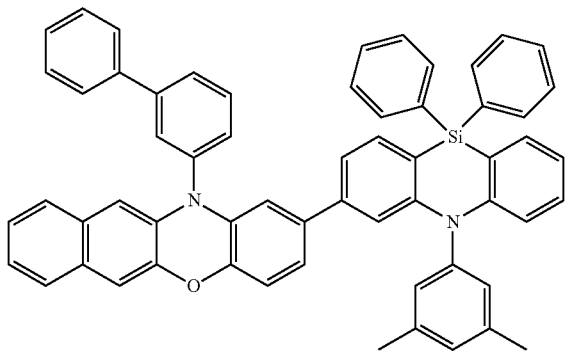
compound 120
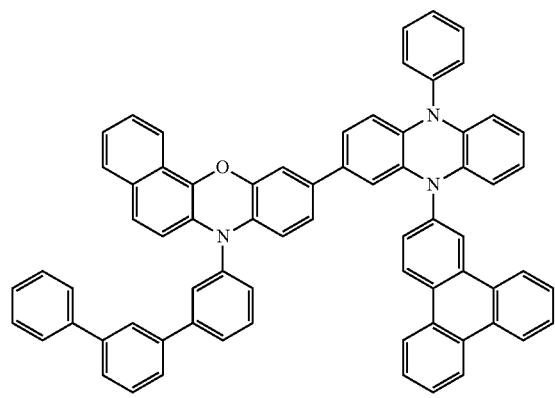
compound 121
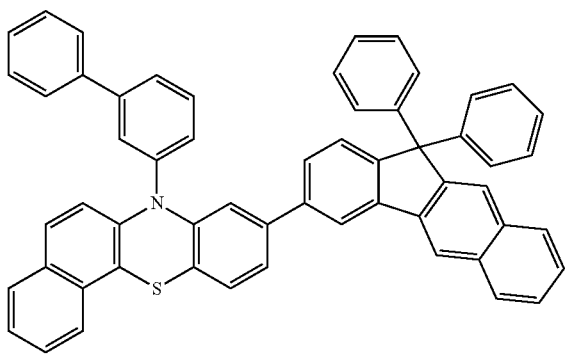
compound 122
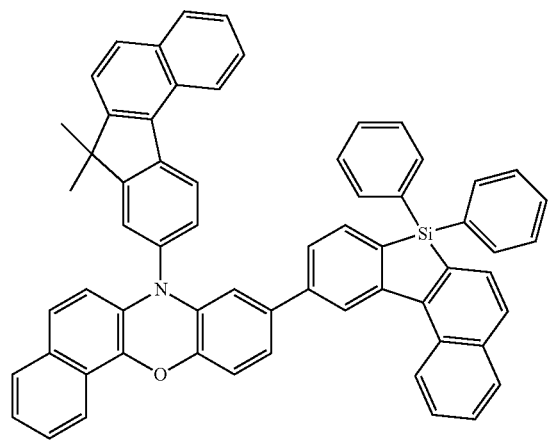

compound 123
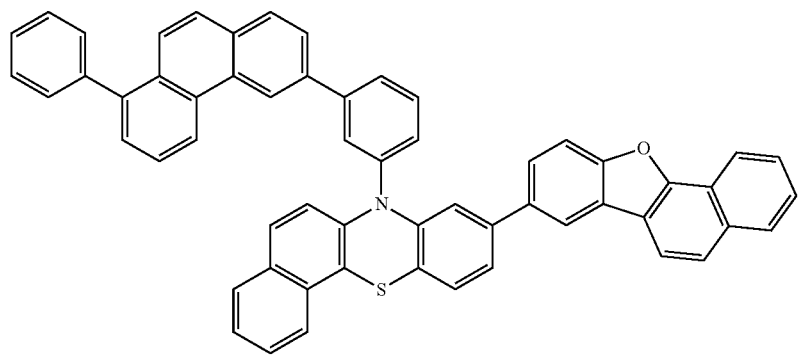
compound 124
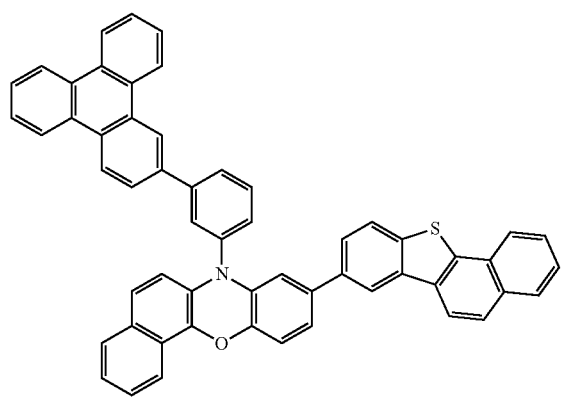
compound 125
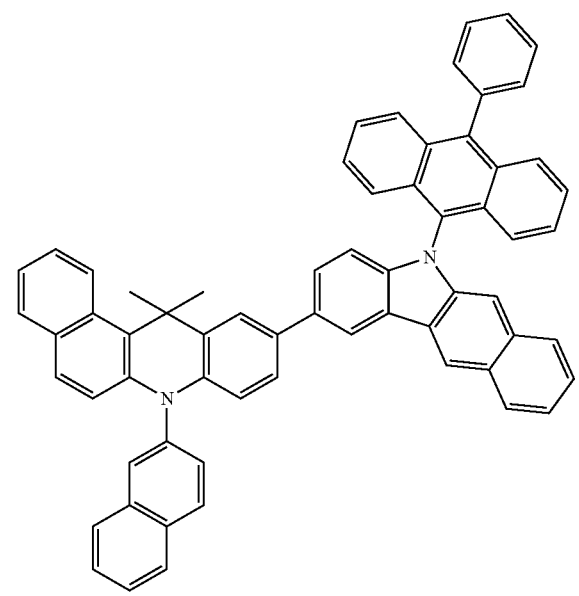 [SMILES: CC1(C)c2cc(-c3ccc4c(c3)c3cc5ccccc5cc3n4-c3c4ccccc4c(-c4ccccc4)c4ccccc34)ccc2N(c2ccc3ccccc3c2)c2ccc3ccccc3c21]
compound 126
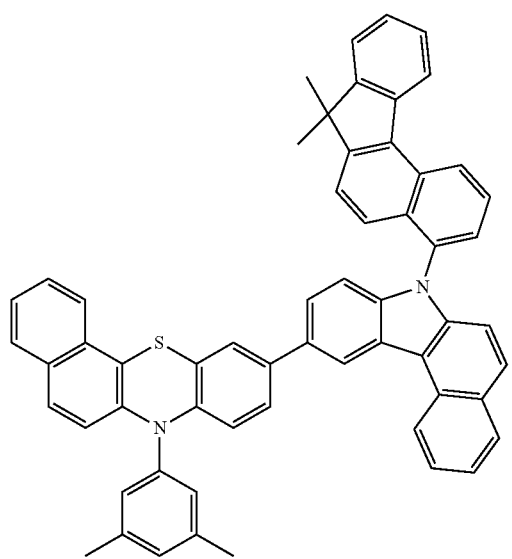
compound 127
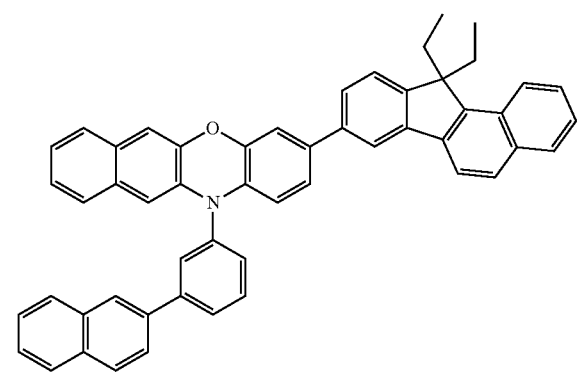

-continued
compound 128
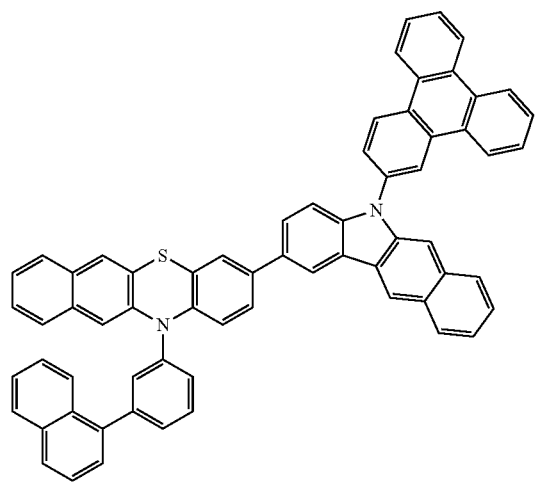
compound 129
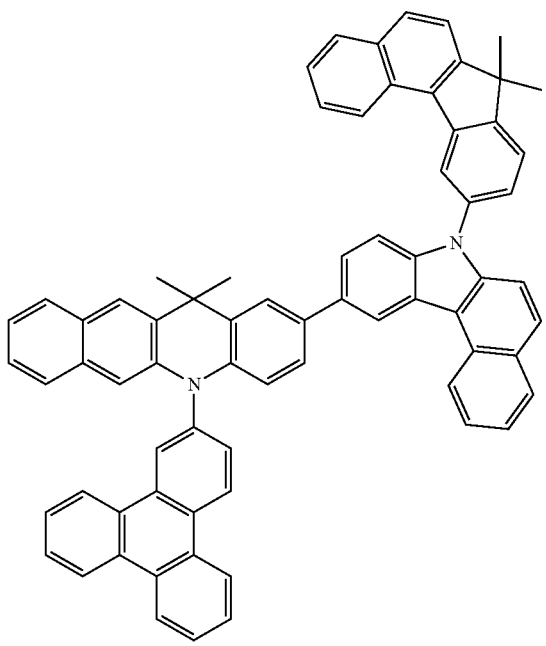
compound 130
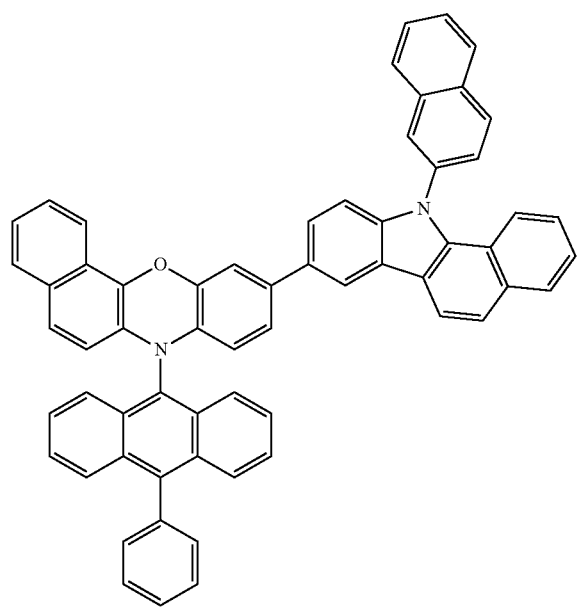
compound 131
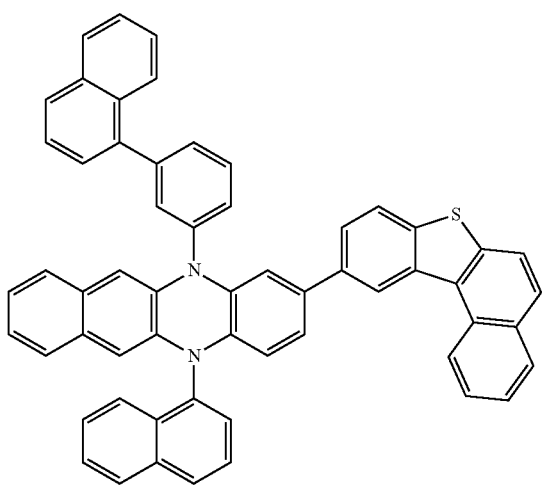

-continued
compound 132
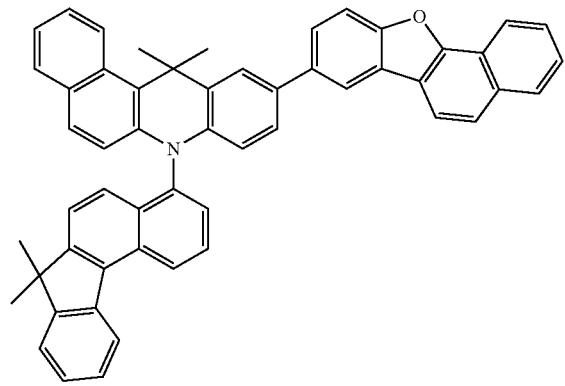
compound 133
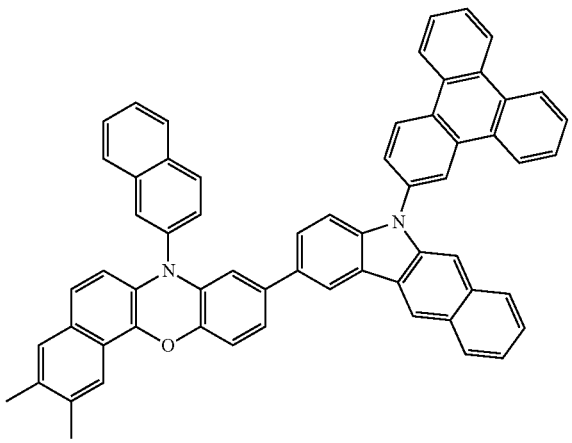
compound 134
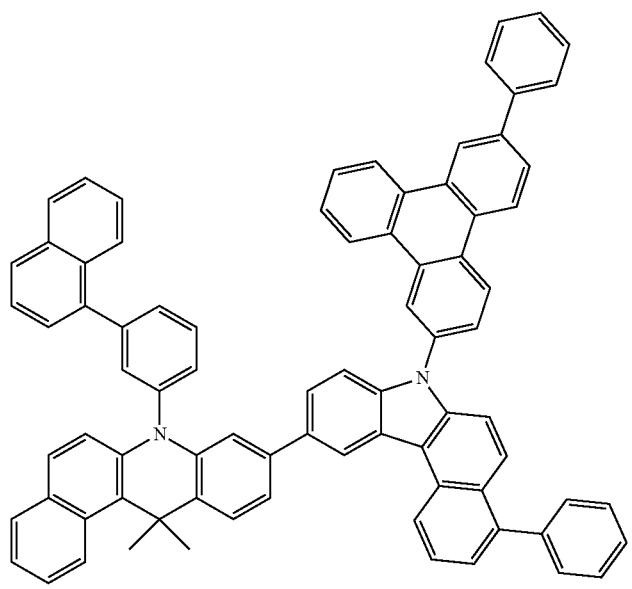
compound 135
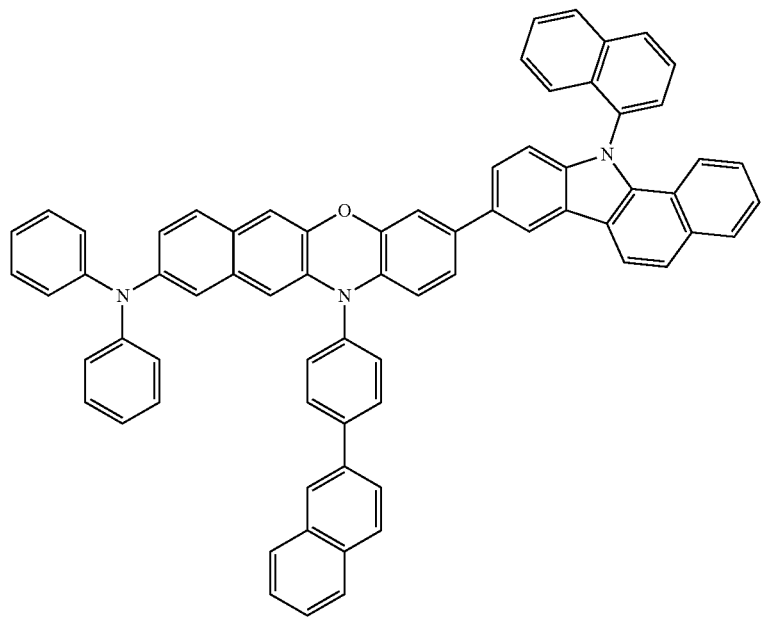

-continued
compound 136
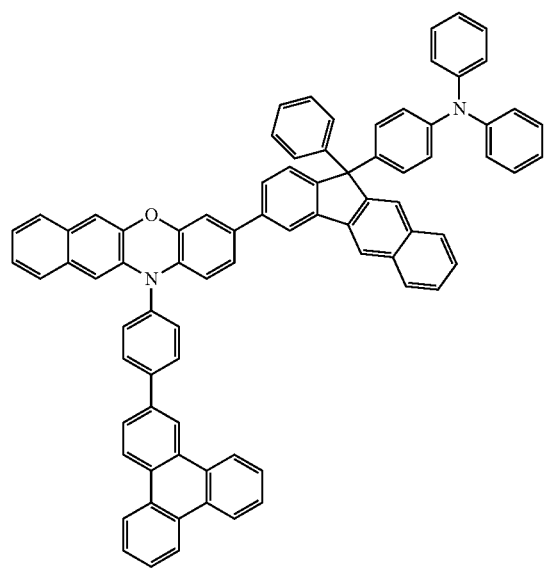
compound 137
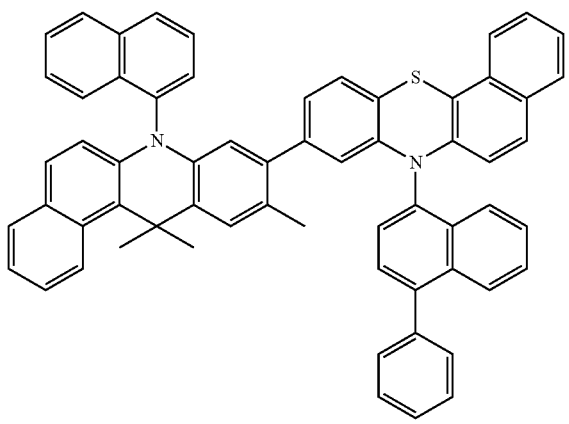
compound 138
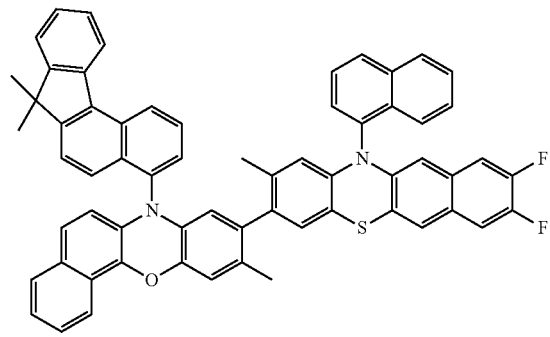
compound 139
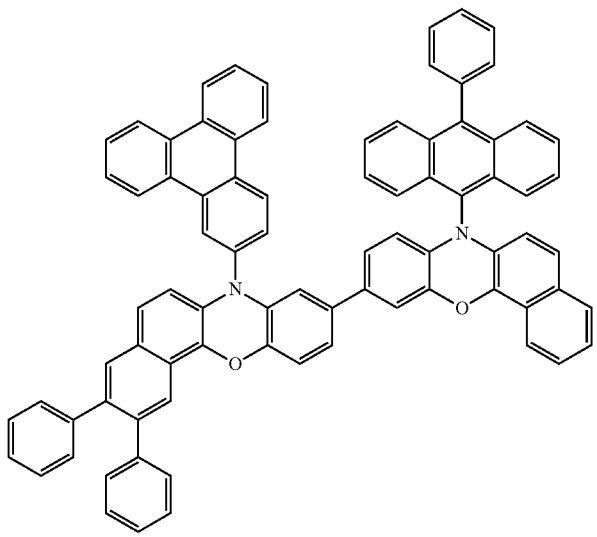

-continued
compound 140
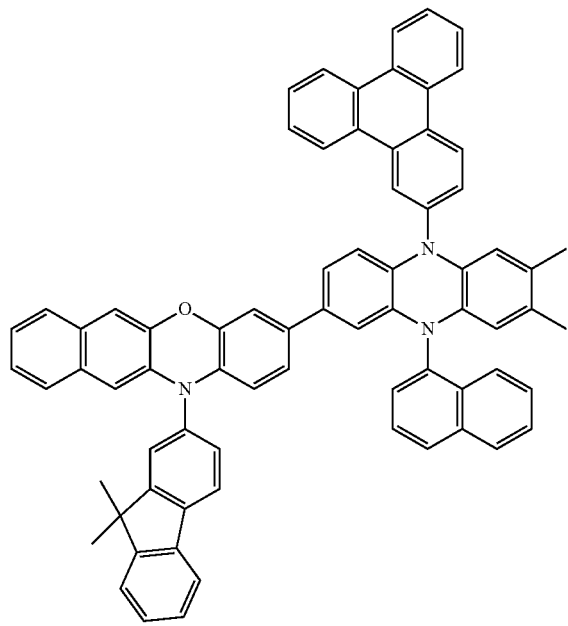
compound 141
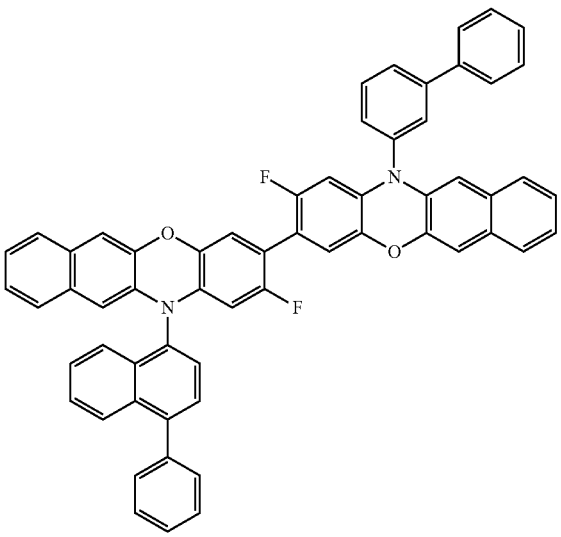
compound 142
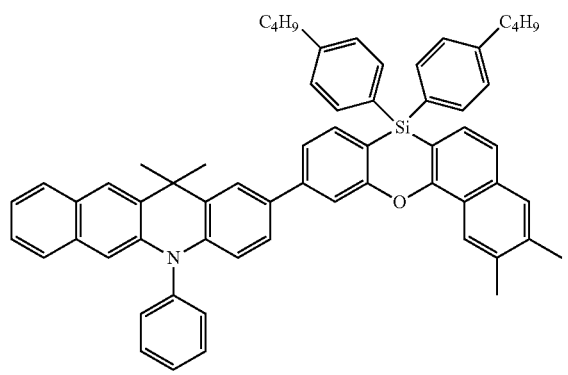
compound 143
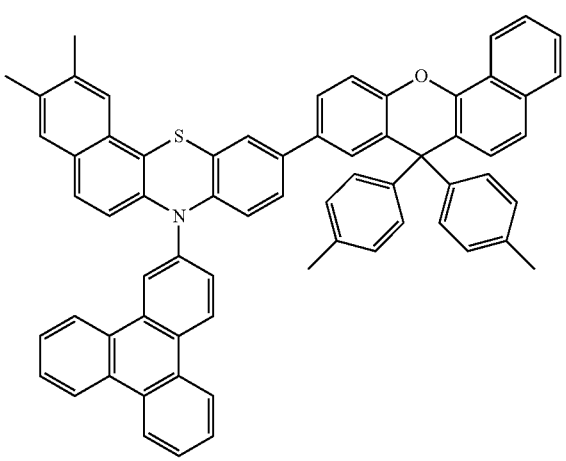
compound 144
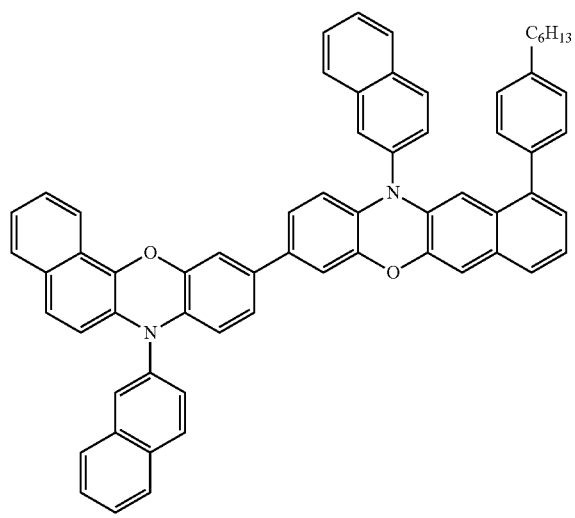
compound 145
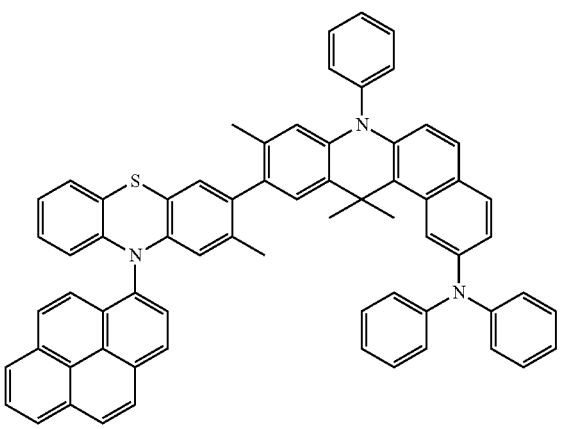

-continued
compound 146
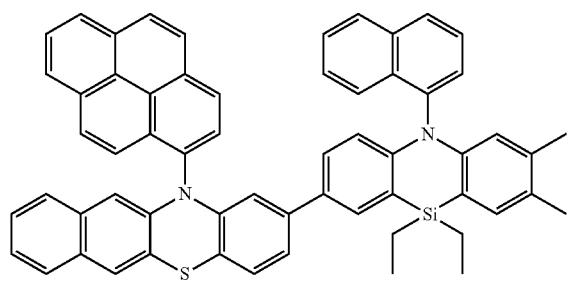
compound 147
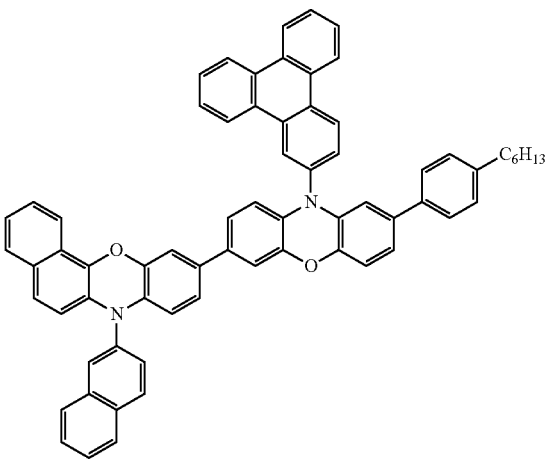
compound 148
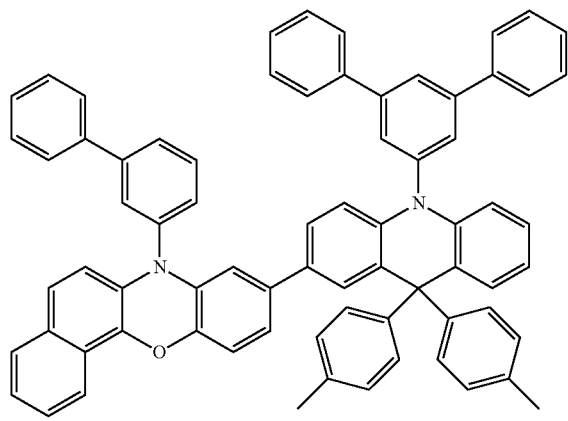
compound 149
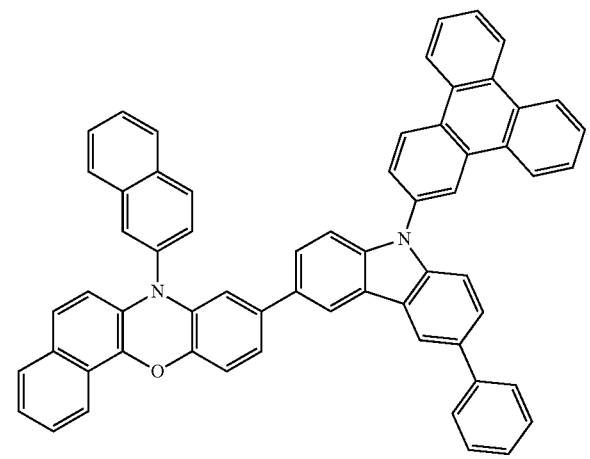
compound 150
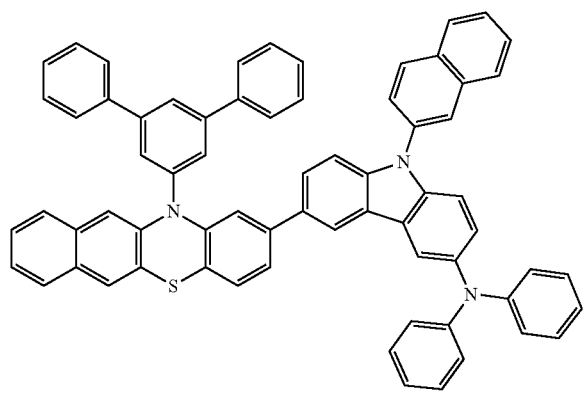
compound 151
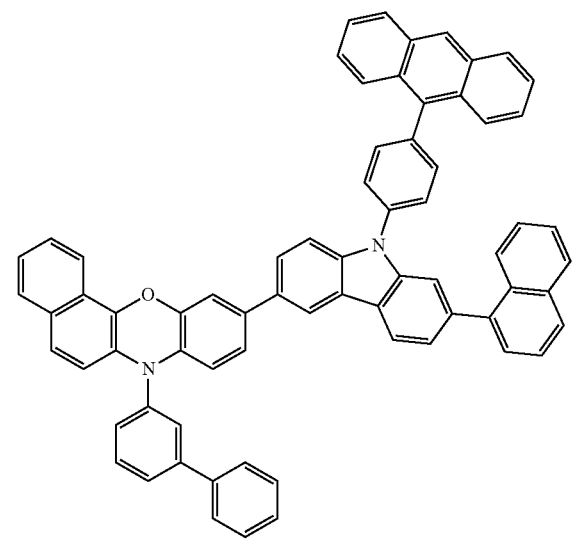

-continued
compound 152
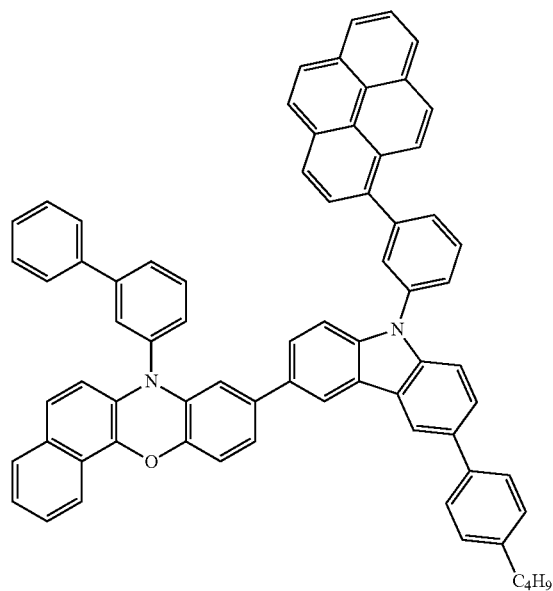
compound 153
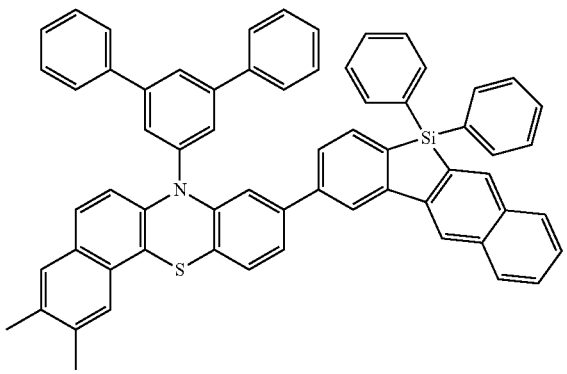
compound 154
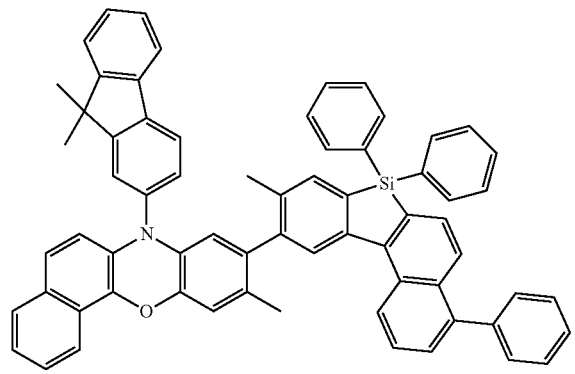
compound 155
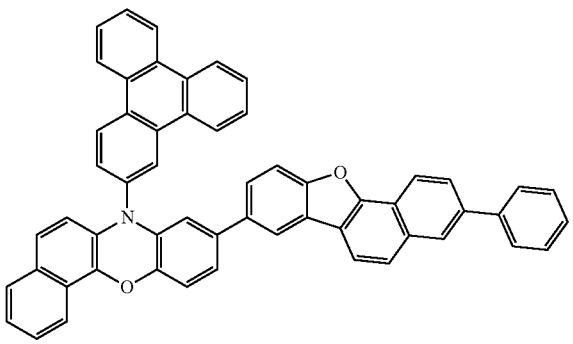
compound 156
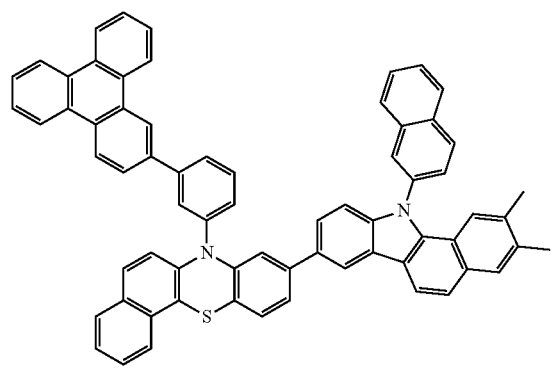
compound 157
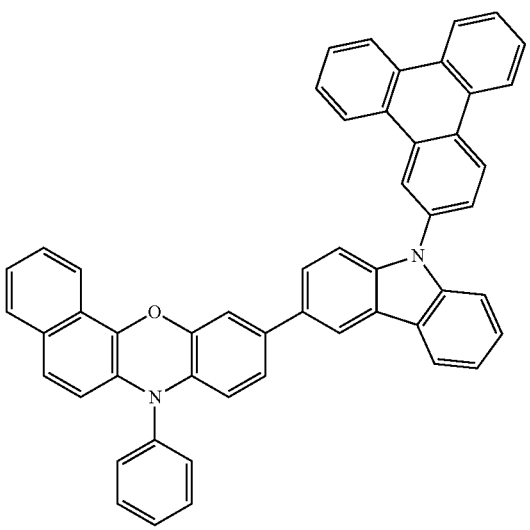

-continued
compound 158
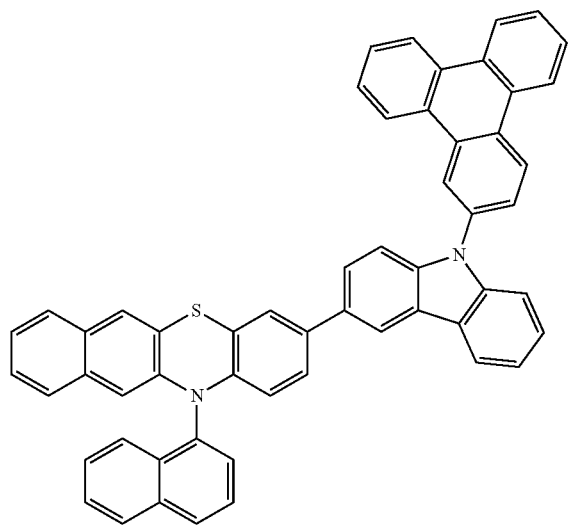
compound 159
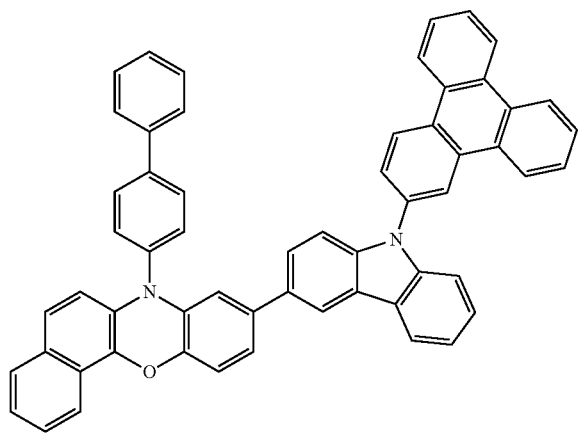 [SMILES: c1ccc(-c2ccc(N3c4cc(-c5ccc6c(c5)c5ccccc5n6-c5ccc6c7ccccc7c7ccccc7c6c5)ccc4Oc4c3ccc3ccccc43)cc2)cc1]
compound 160
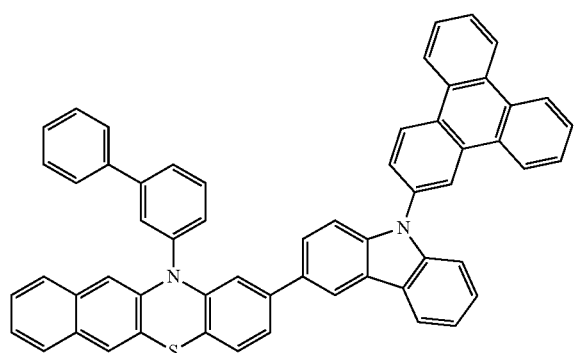
compound 161
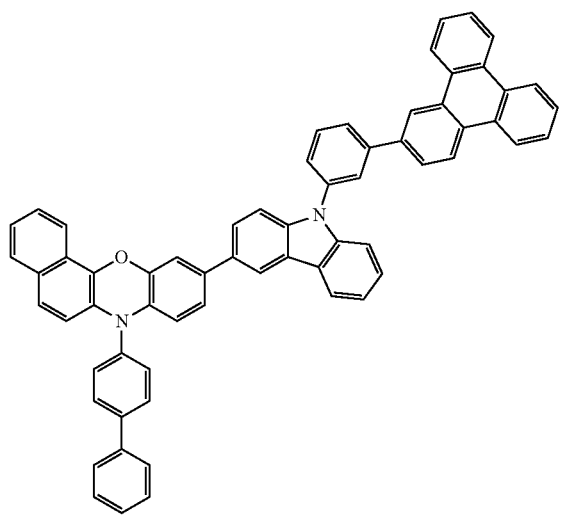
compound 162
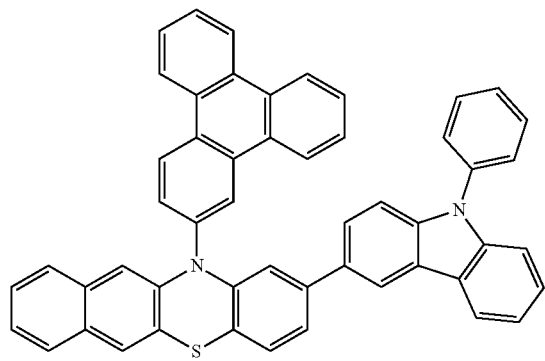 [SMILES: c1ccc(-n2c3ccccc3c3cc(-c4ccc5c(c4)N(c4ccc6c7ccccc7c7ccccc7c6c4)c4cc6ccccc6cc4S5)ccc32)cc1]
compound 163
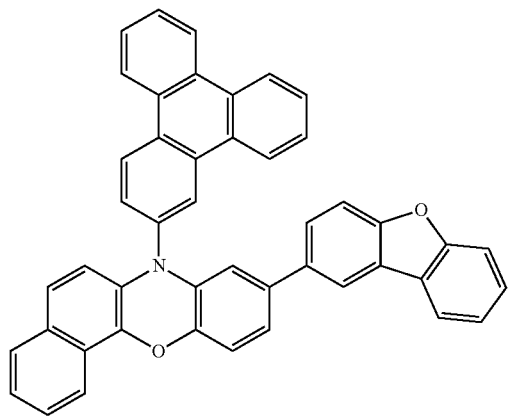

compound 164
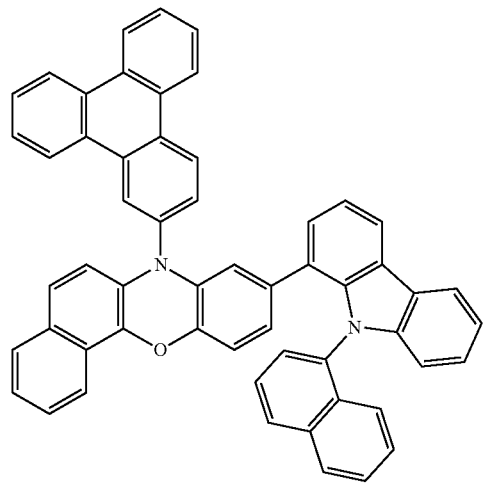
compound 165
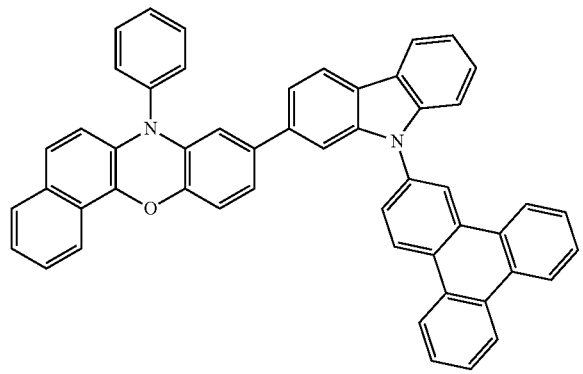
compound 166
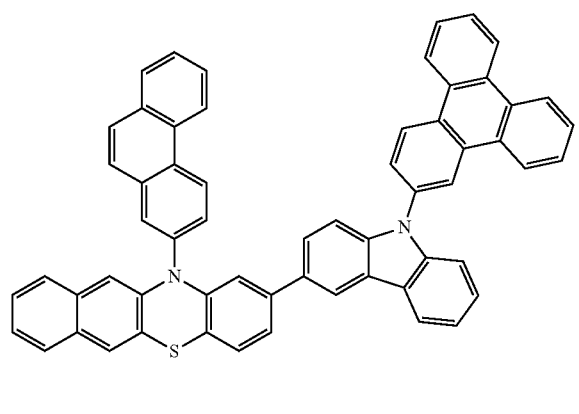
compound 167
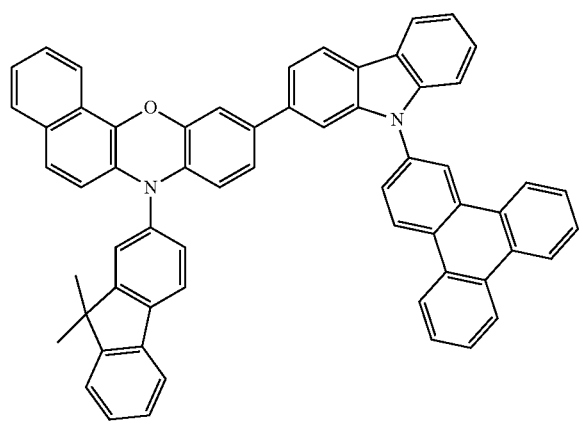
compound 168
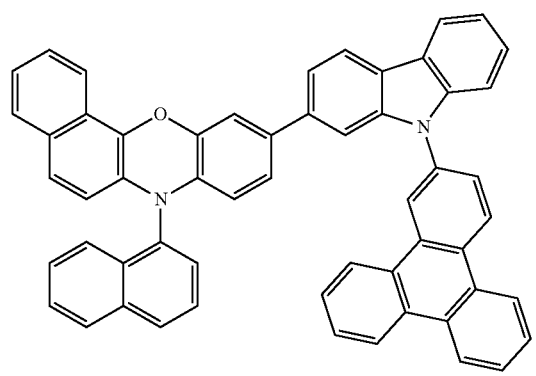
compound 169
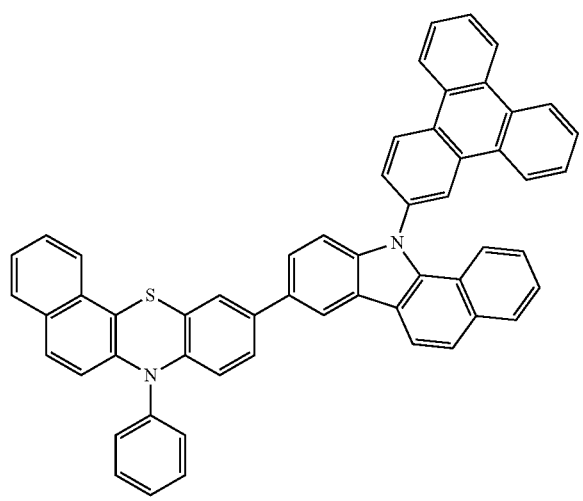 [SMILES: c1ccc(N2c3ccc(-c4ccc5c(c4)c4ccc6ccccc6c4n5-c4ccc5c6ccccc6c6ccccc6c5c4)cc3Sc3c2ccc2ccccc32)cc1]

compound 170
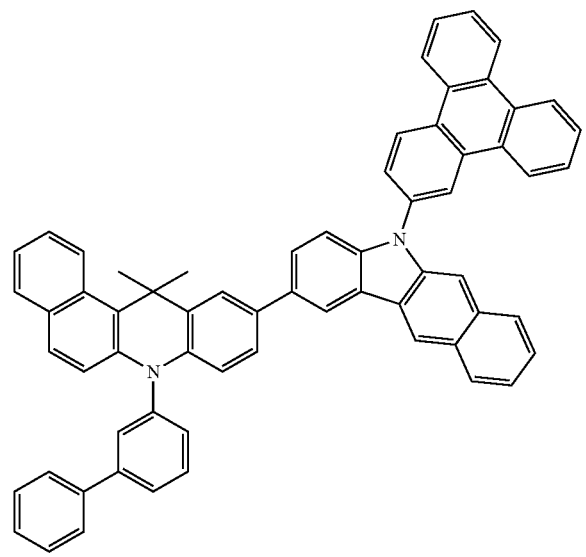
compound 171
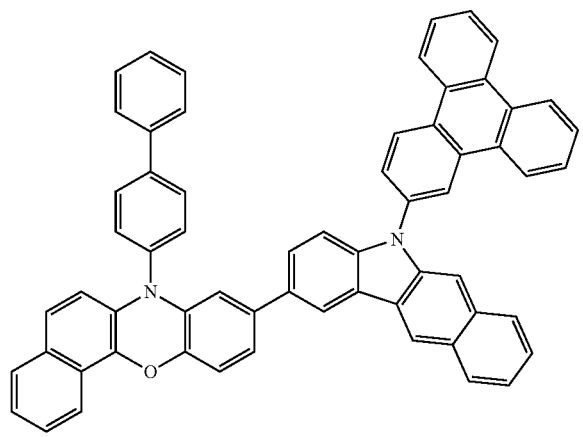
compound 172
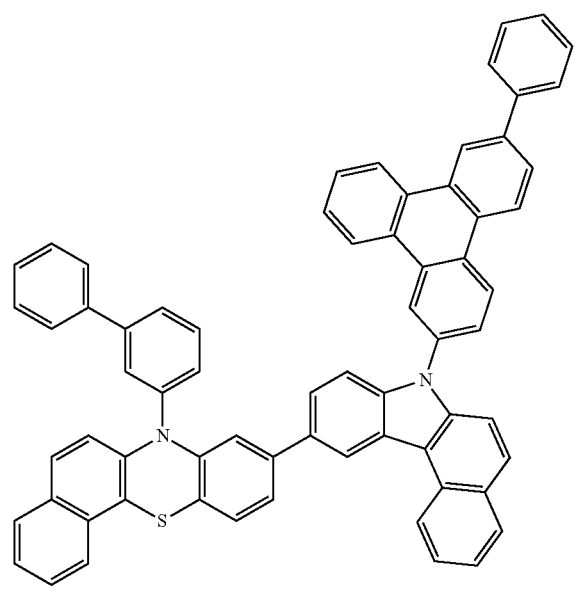
compound 173
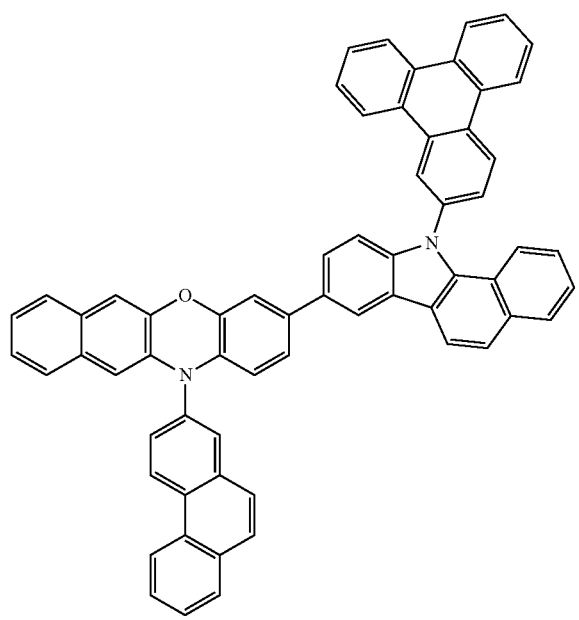

compound 174
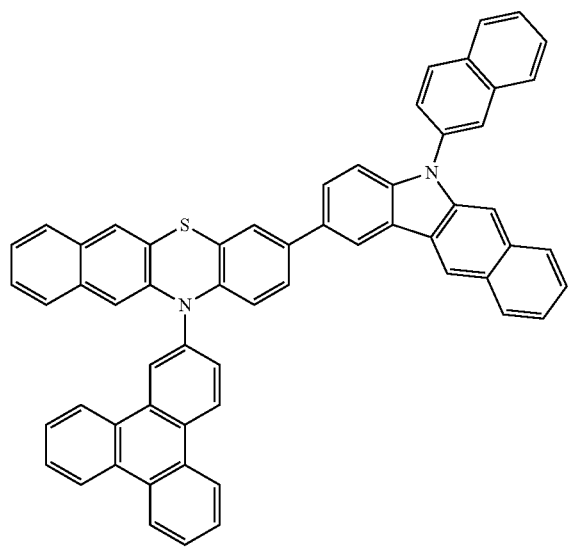
compound 175
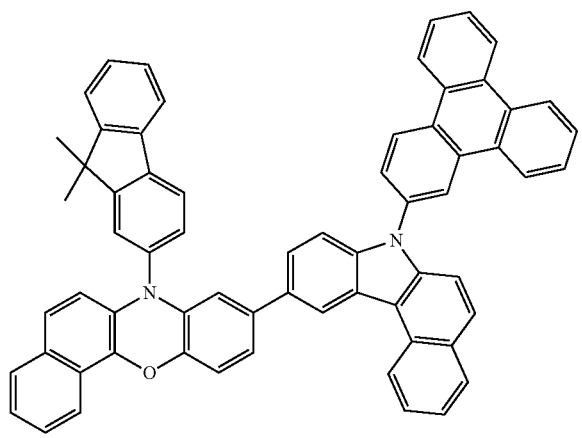
compound 176
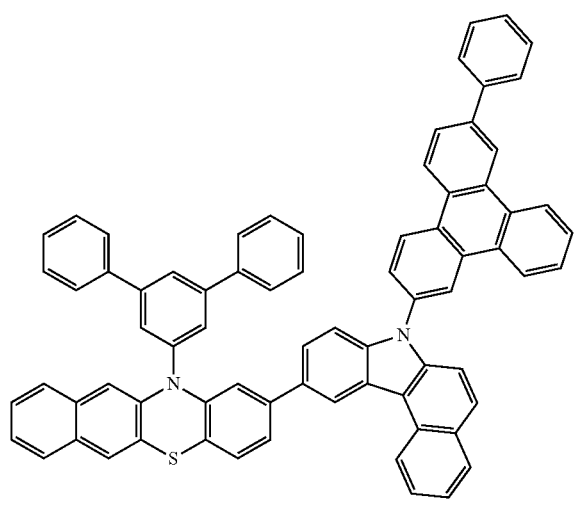
compound 177
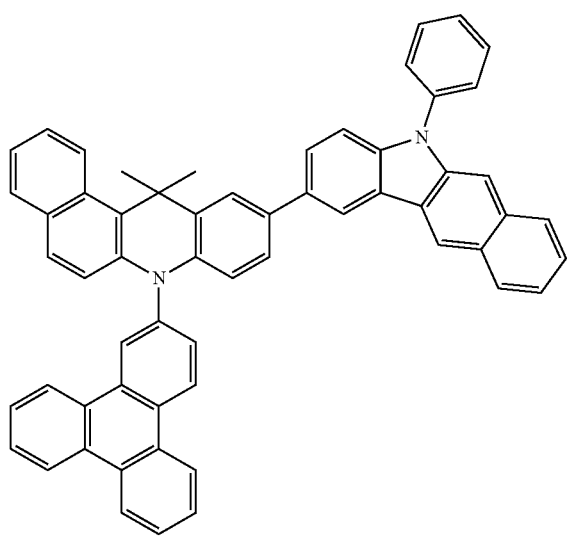

-continued
compound 178
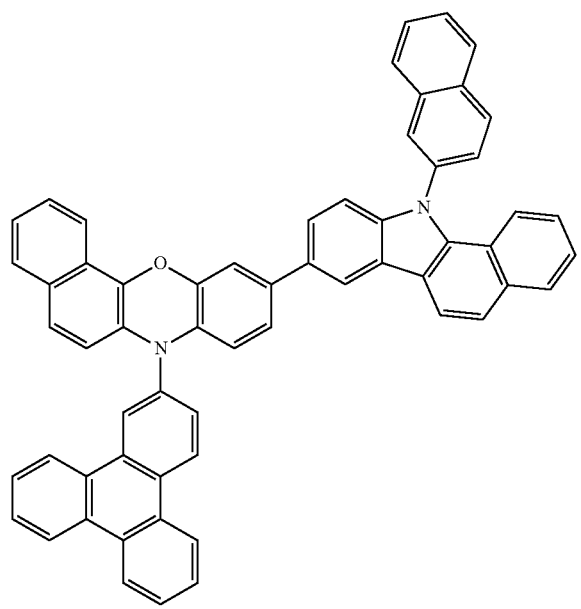
compound 179
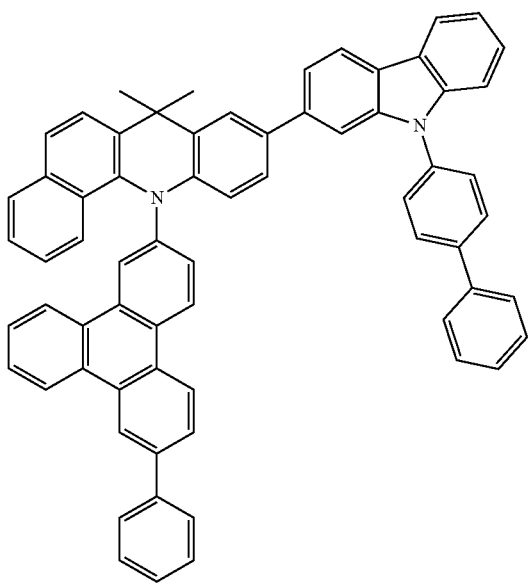
compound 180
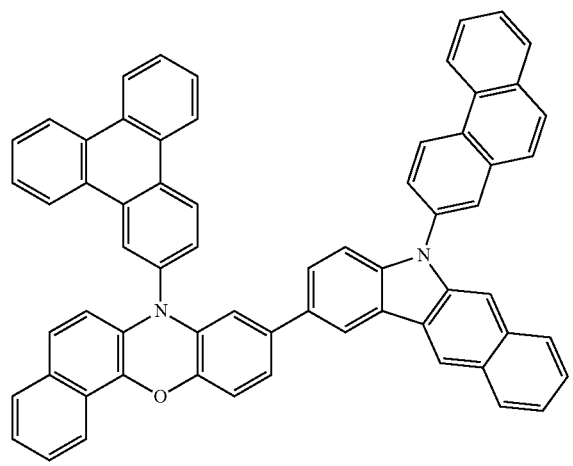
compound 181
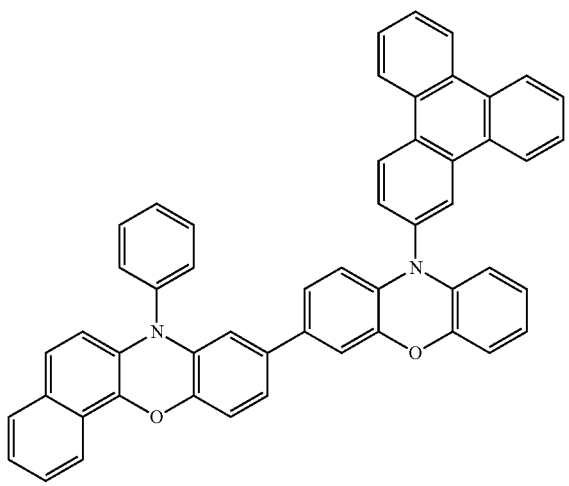
compound 182
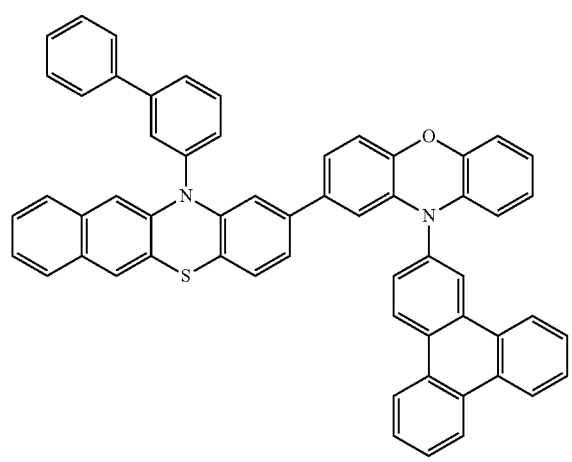
compound 183
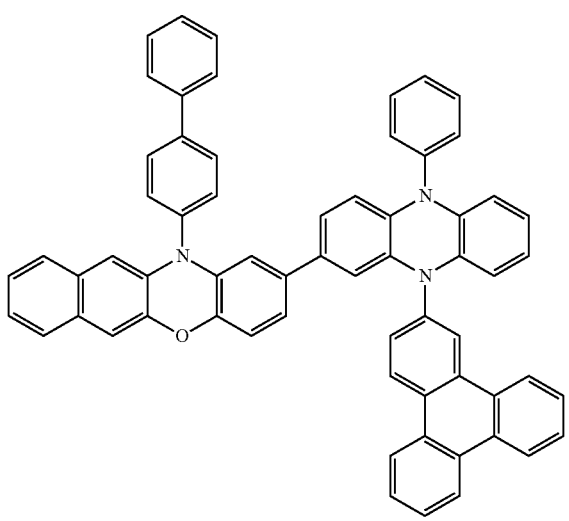

compound 184
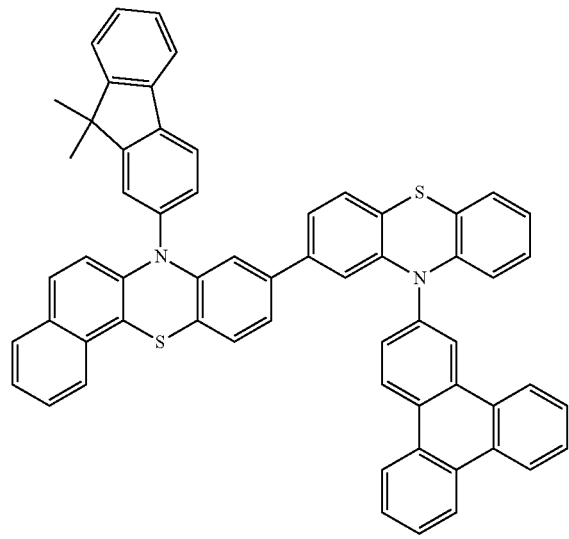 [SMILES: CC1(C)c2ccccc2-c2ccc(N3c4cc(-c5ccc6c(c5)N(c5ccc7c8ccccc8c8ccccc8c7c5)c5ccccc5S6)ccc4Sc4c3ccc3ccccc43)cc21]
compound 185
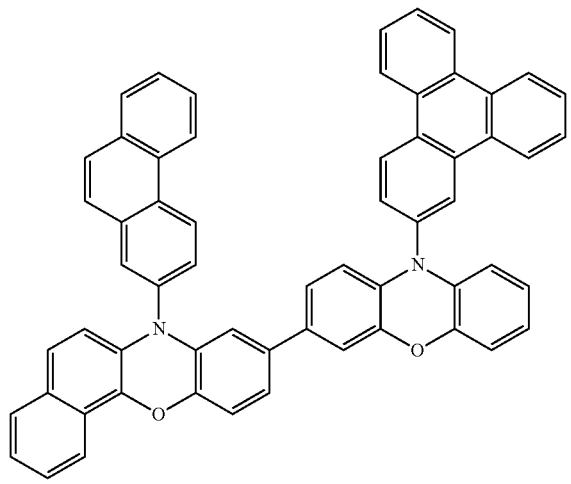
compound 186
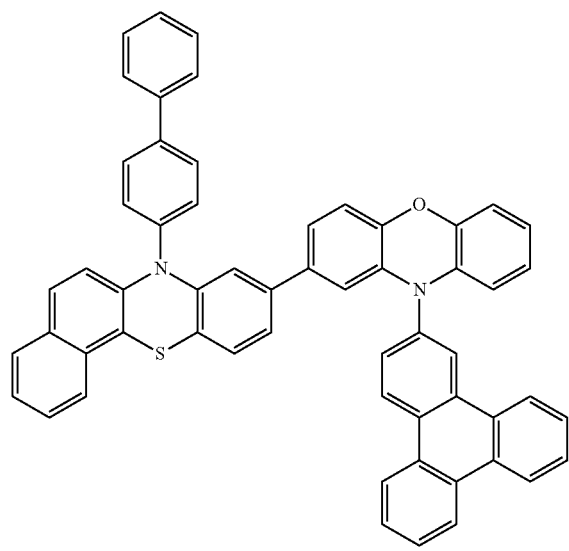
compound 187
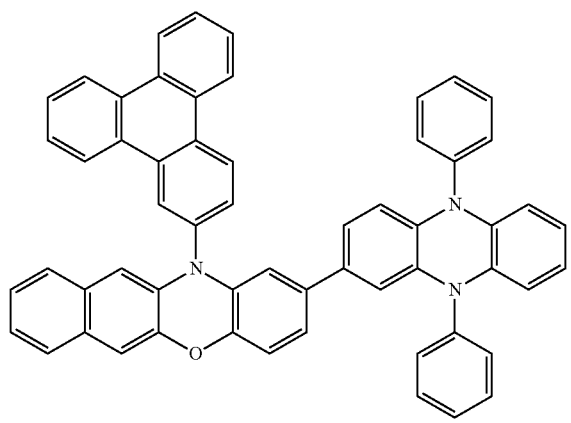

-continued
compound 188
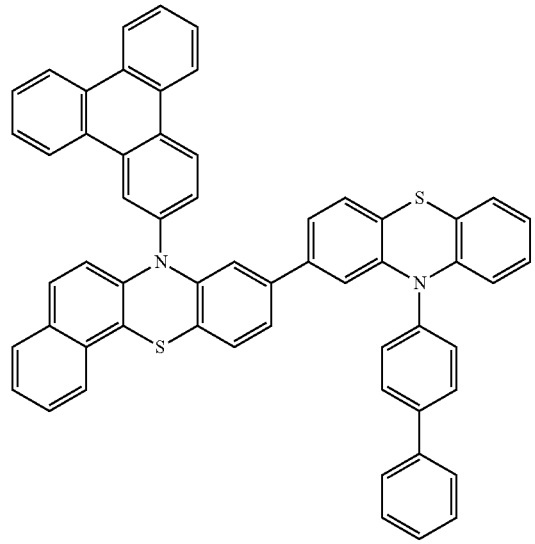
compound 189
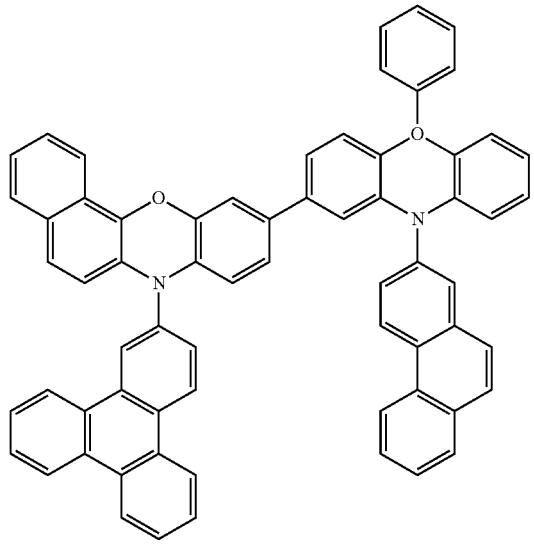
compound 190
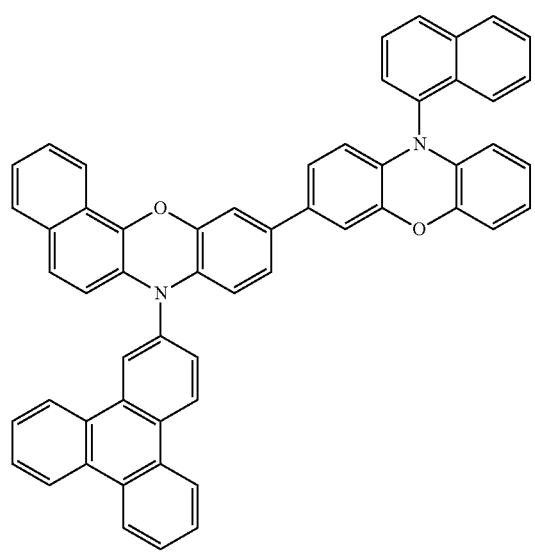
compound 191
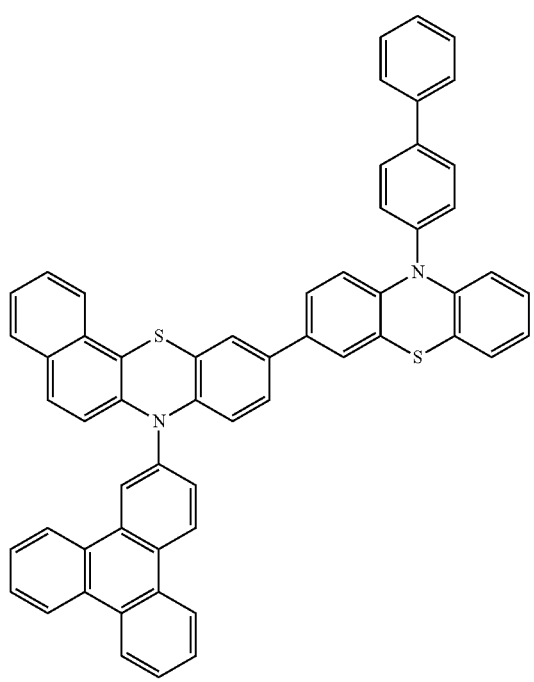

-continued
compound 192
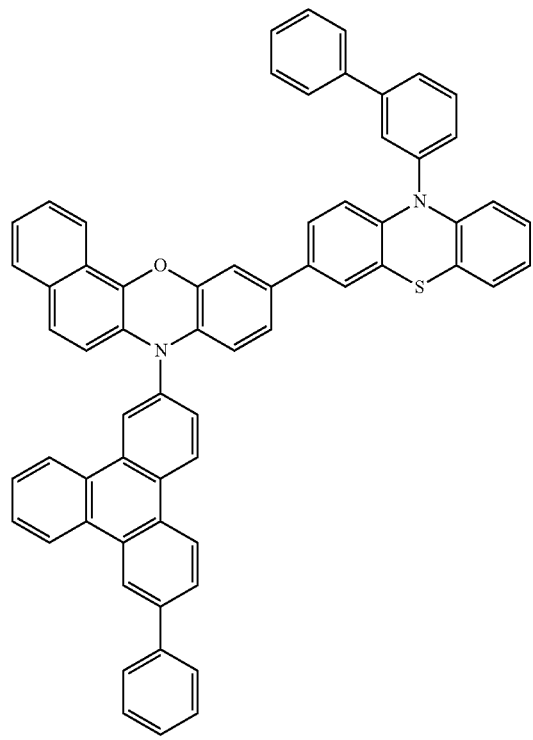
compound 193
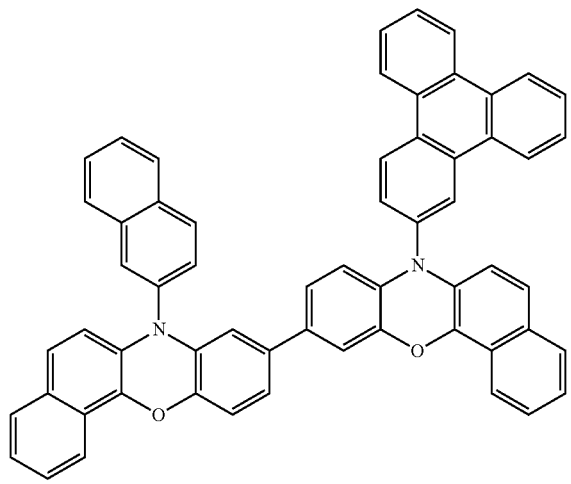
compound 194
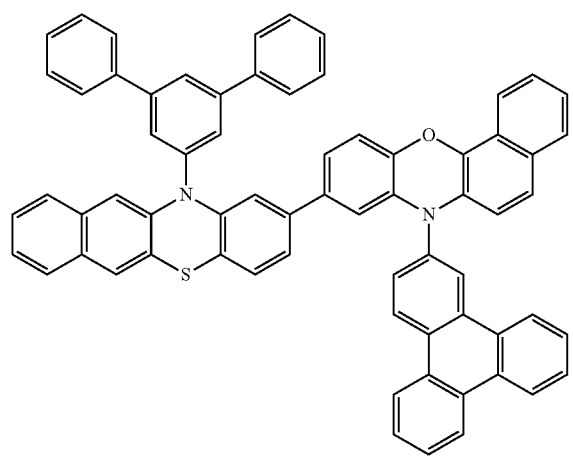
compound 195
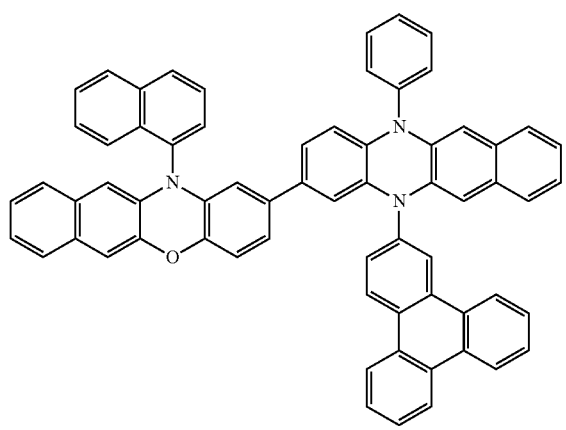 [SMILES: c1ccc(N2c3ccc(-c4ccc5c(c4)N(c4cccc6ccccc46)c4cc6ccccc6cc4O5)cc3N(c3ccc4c5ccccc5c5ccccc5c4c3)c3cc4ccccc4cc32)cc1]

compound 196
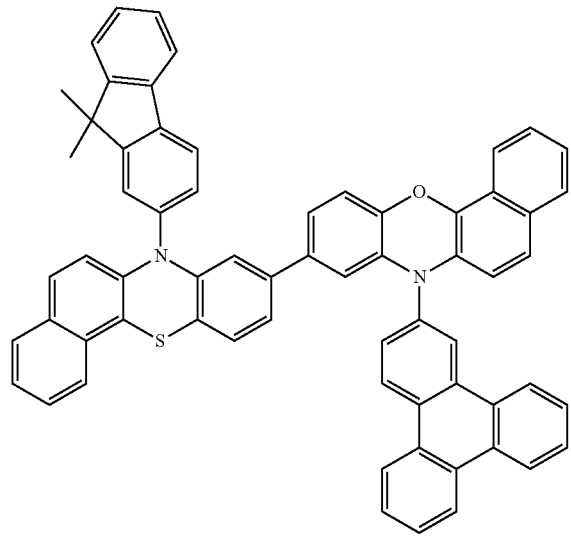
compound 197
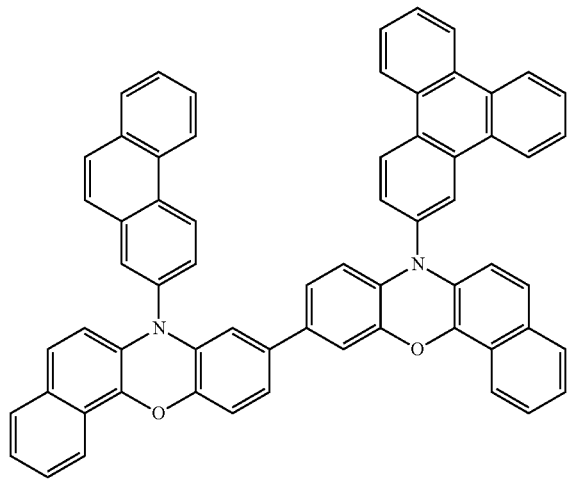
compound 198
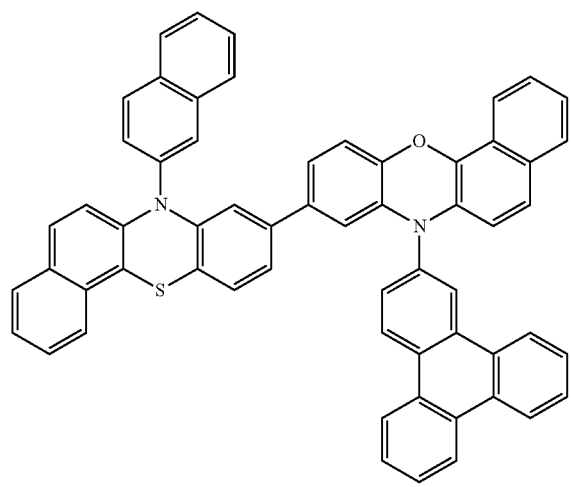
compound 199
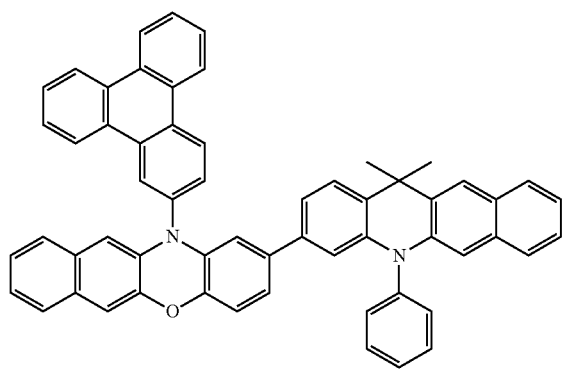
compound 200
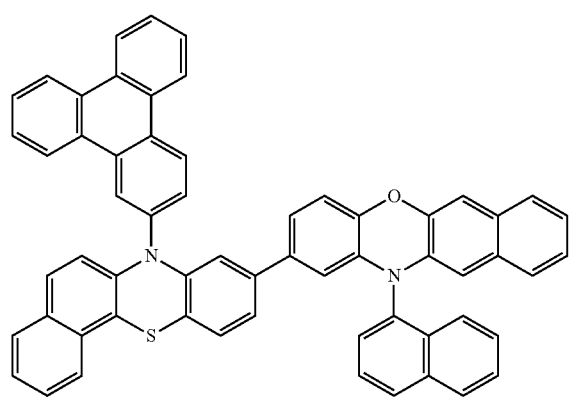
compound 201
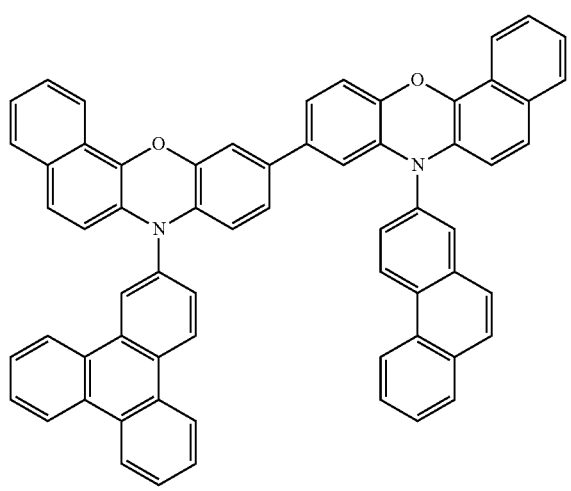

-continued
compound 202
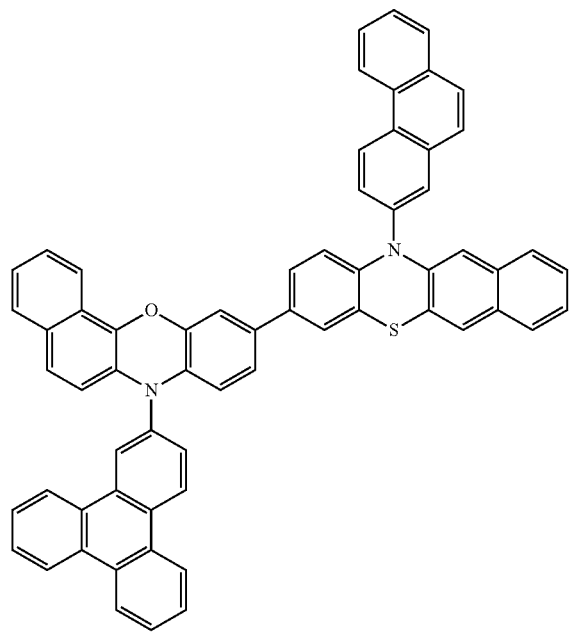
compound 203
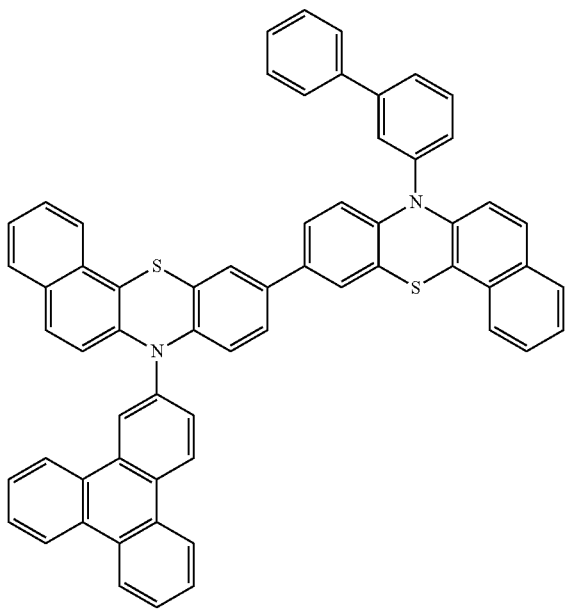
compound 204
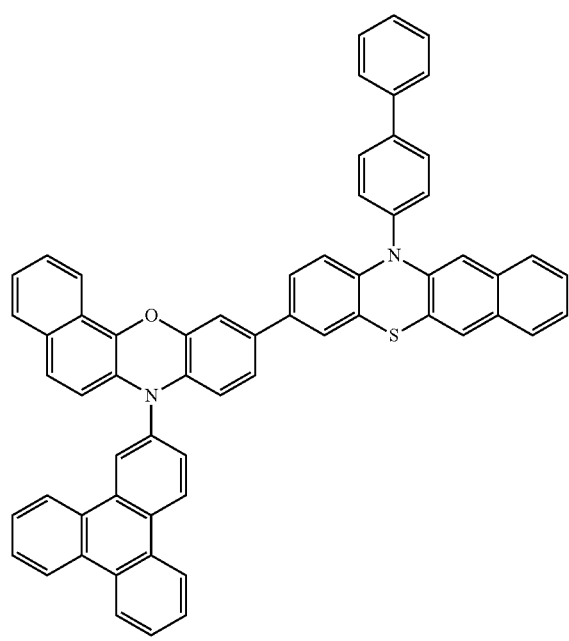
compound 205
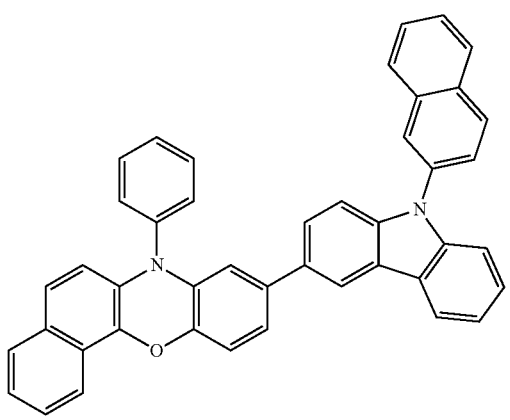

-continued
compound 206
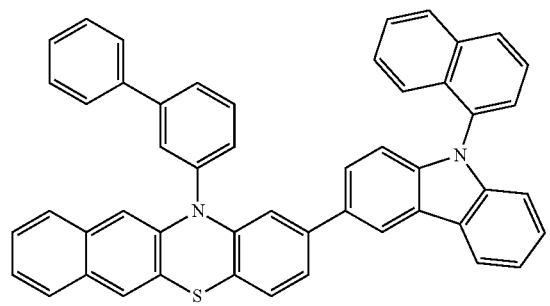
compound 207
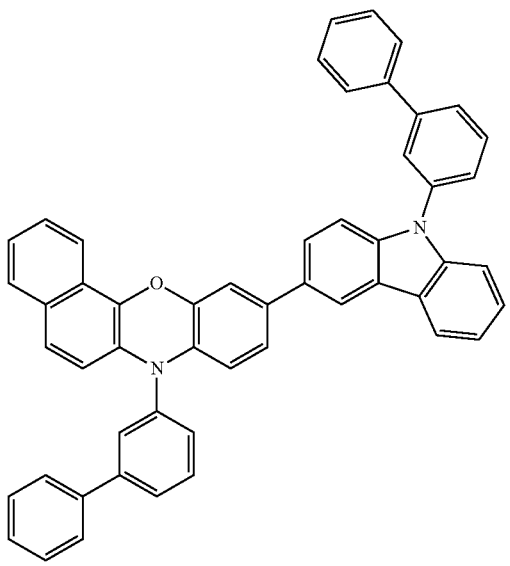
compound 208
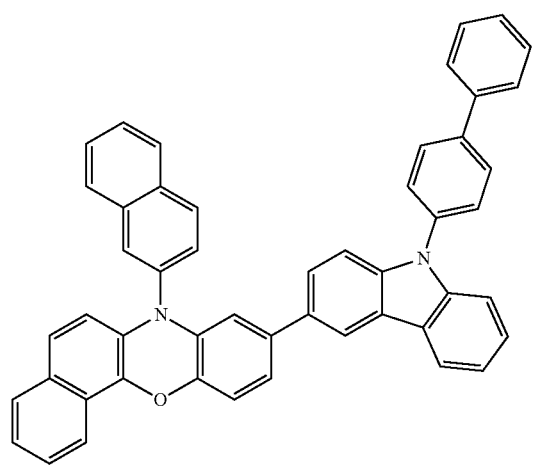
compound 209
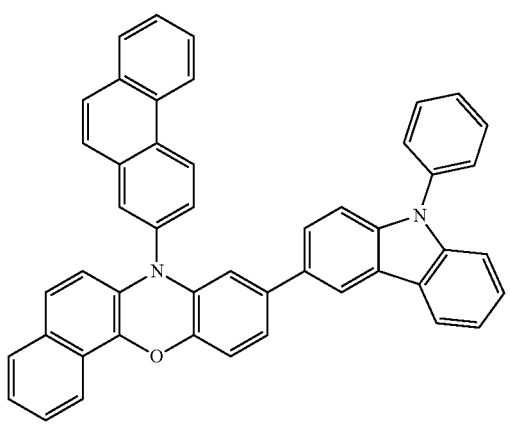
compound 110
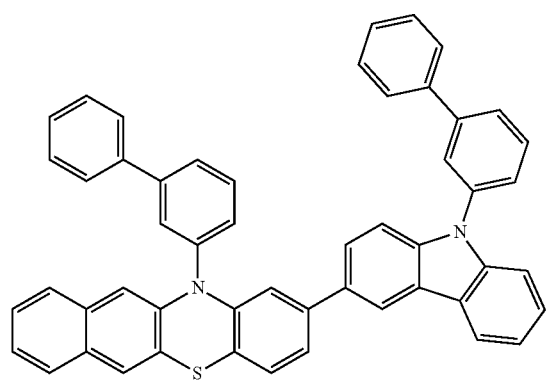
compound 211
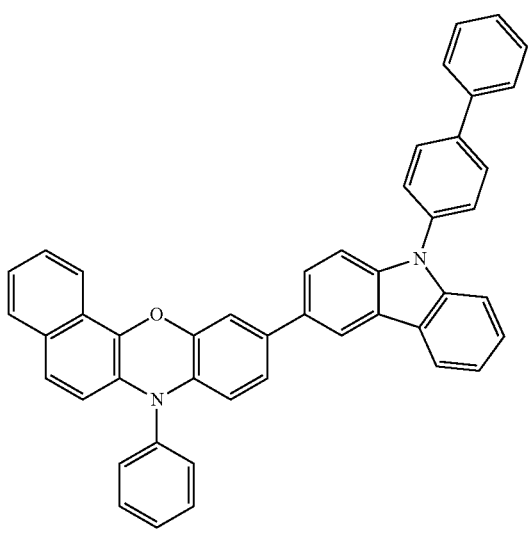

-continued
compound 212
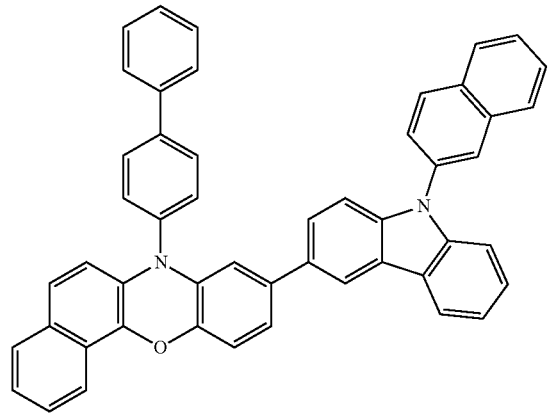
compound 213
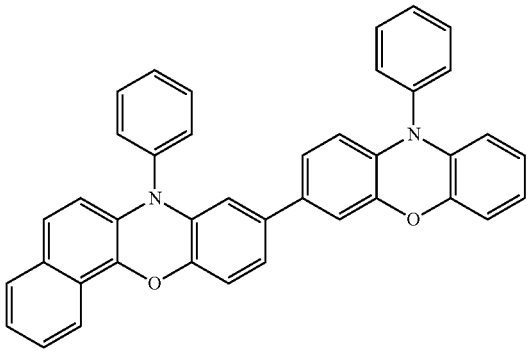
compound 214
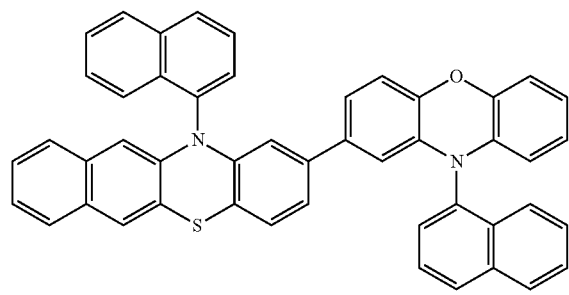
compound 215
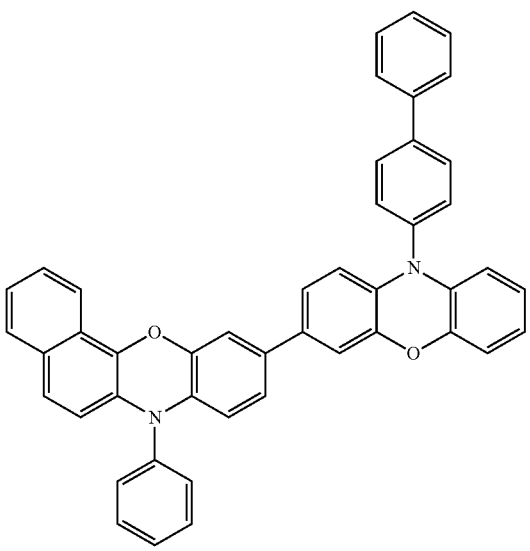
compound 216
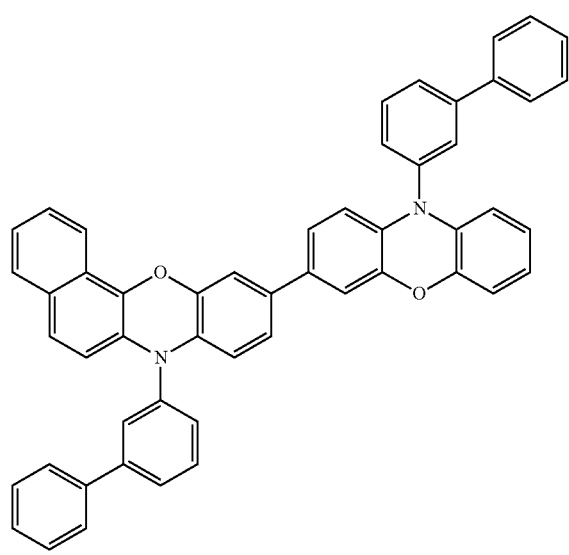
compound 217
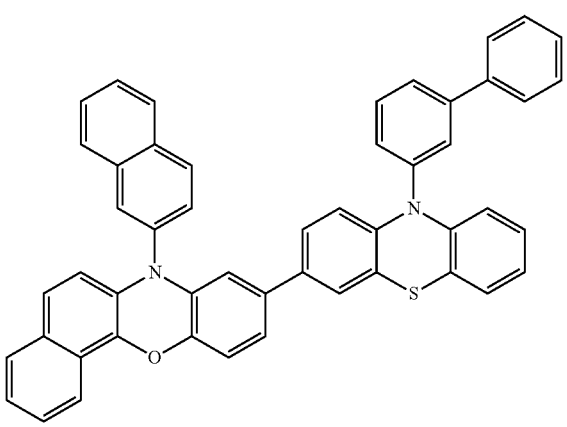

-continued
compound 218
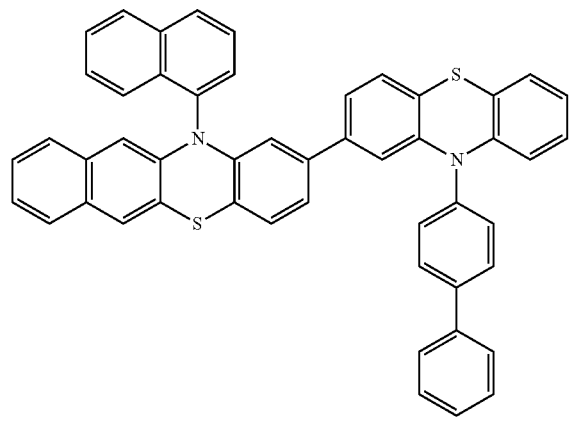
compound 219
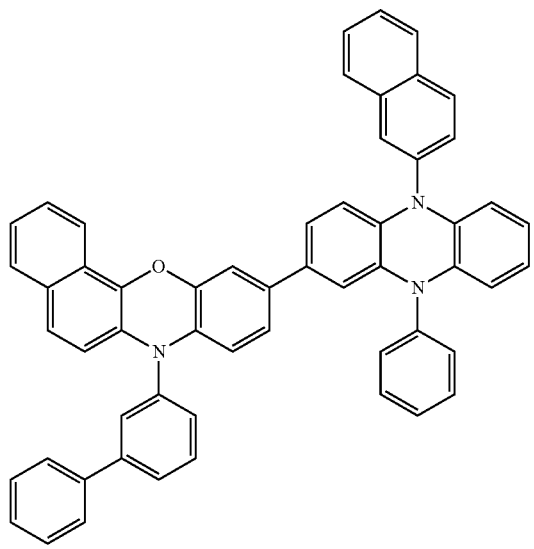 [SMILES: c1ccc(-c2cccc(N3c4ccc(-c5ccc6c(c5)N(c5ccccc5)c5ccccc5N6c5ccc6ccccc6c5)cc4Oc4c3ccc3ccccc43)c2)cc1]
compound 220
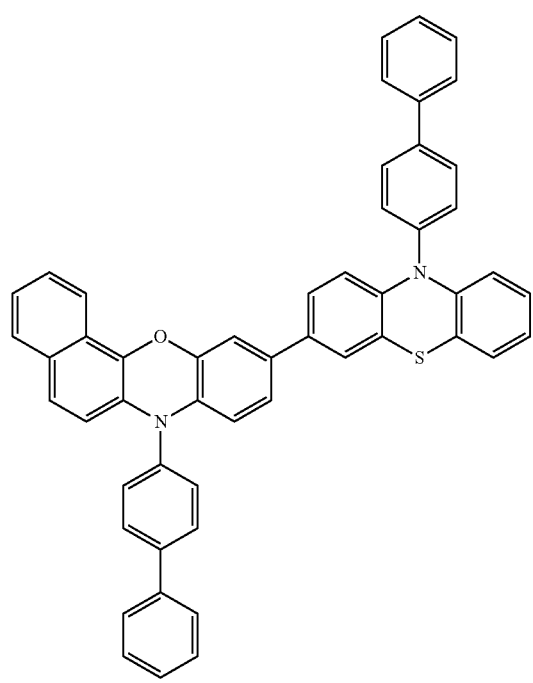
compound 221
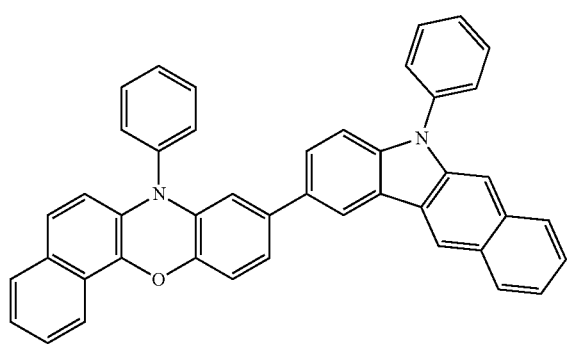

compound 222
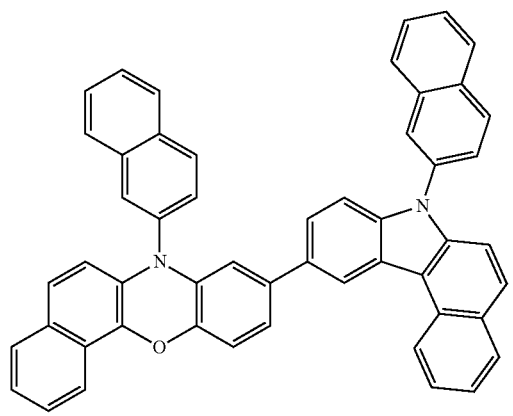
compound 223
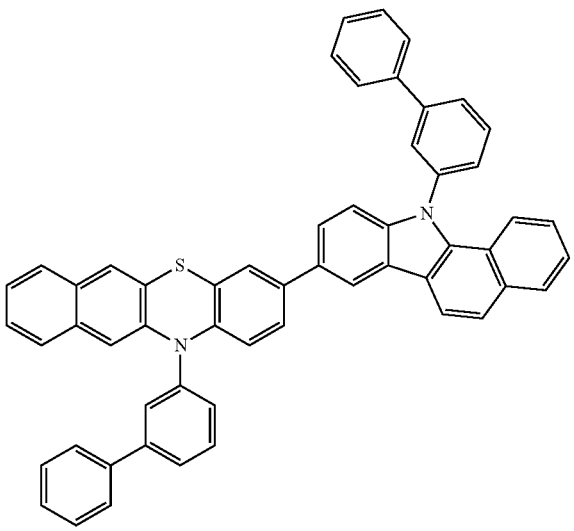
compound 224
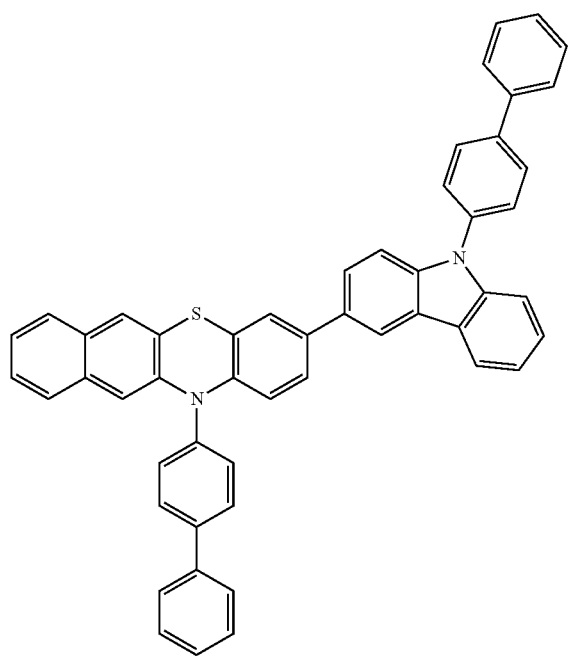
compound 225
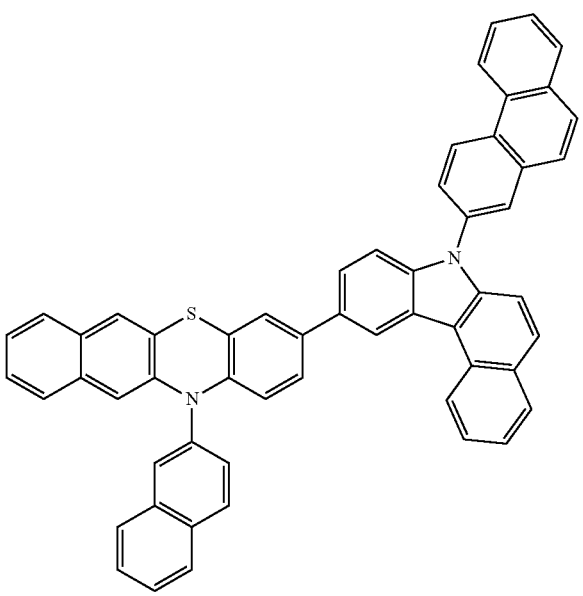

-continued
compound 226
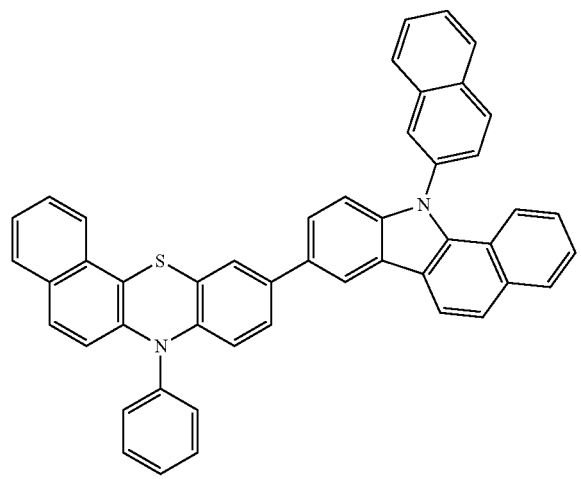
compound 227
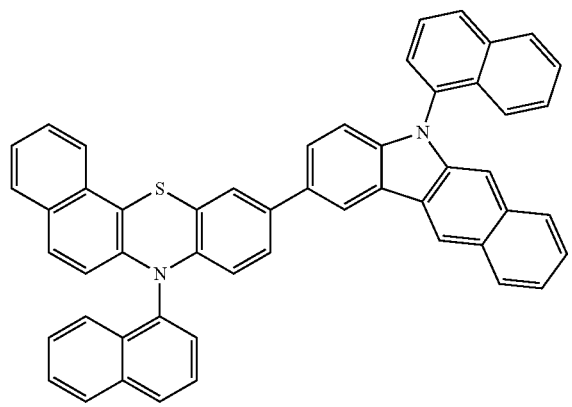
compound 228
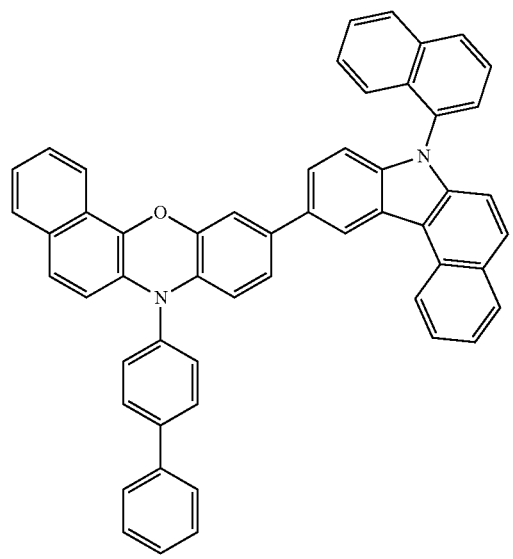
compound 229
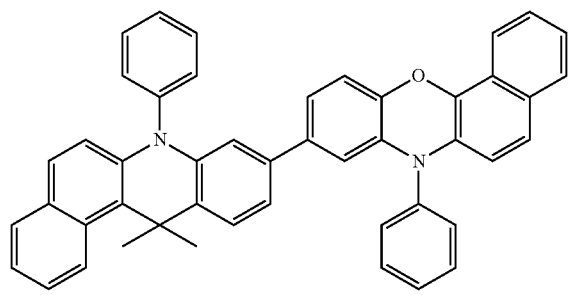
compound 230
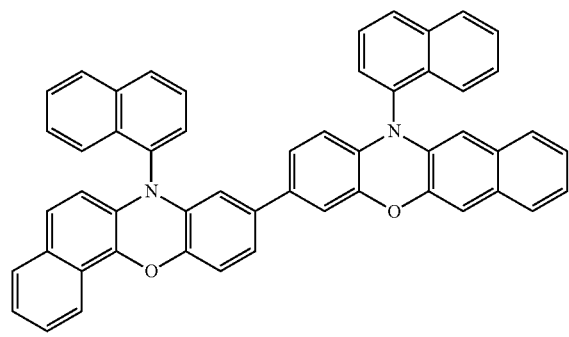
compound 231
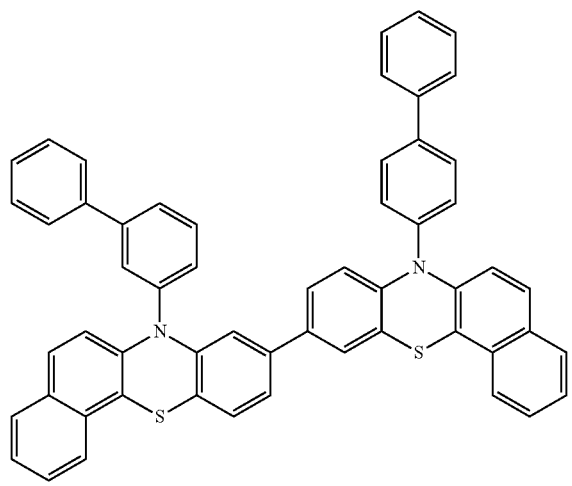

compound 232
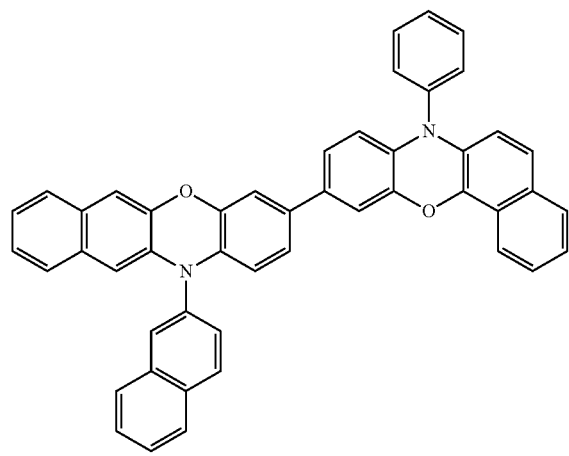
compound 233
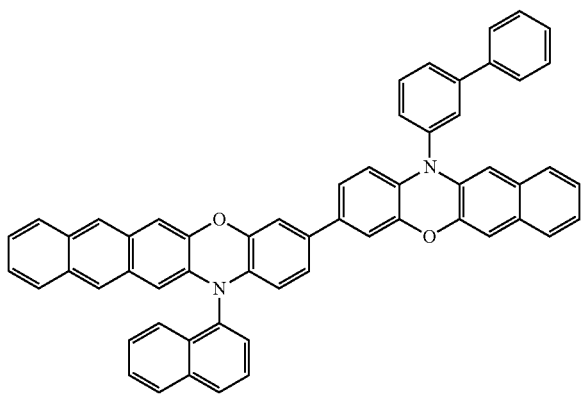
compound 234
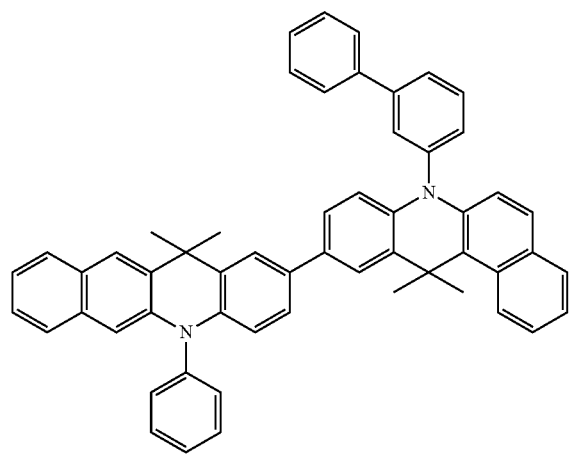
compound 235
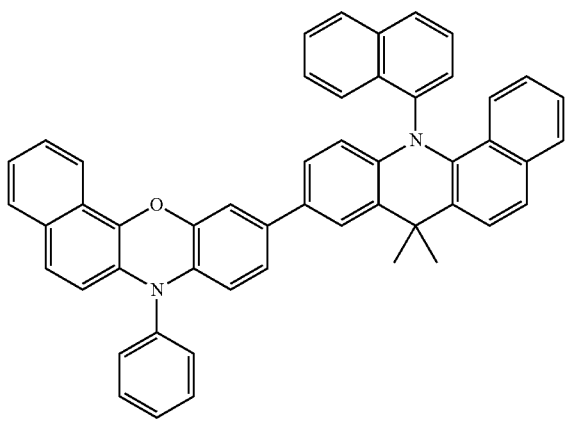
compound 236
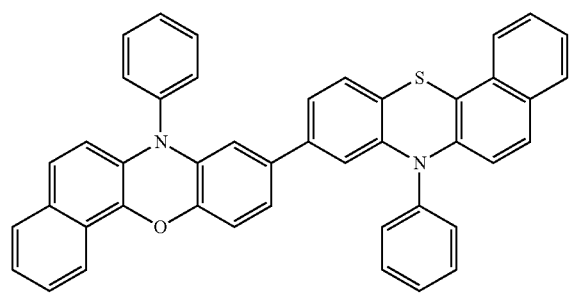
compound 237
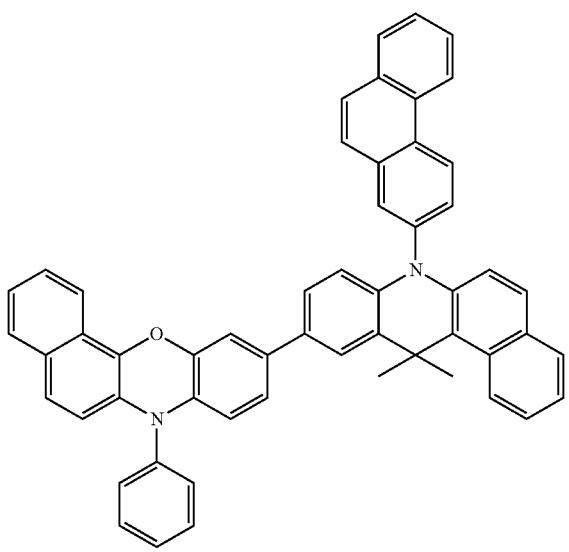

-continued compound 238

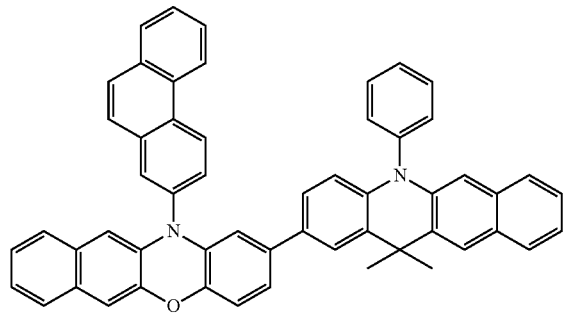

and compound 239

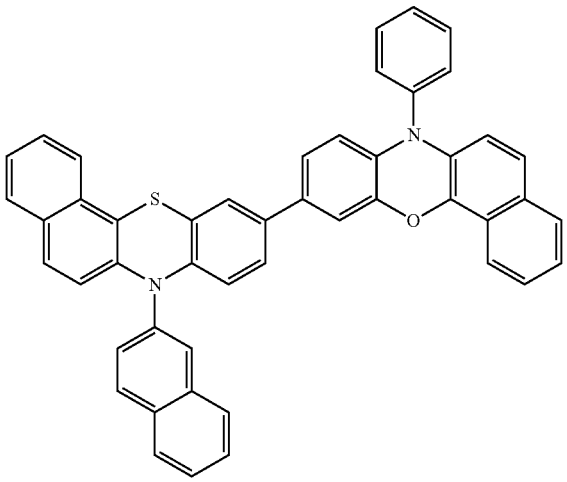

compound 240

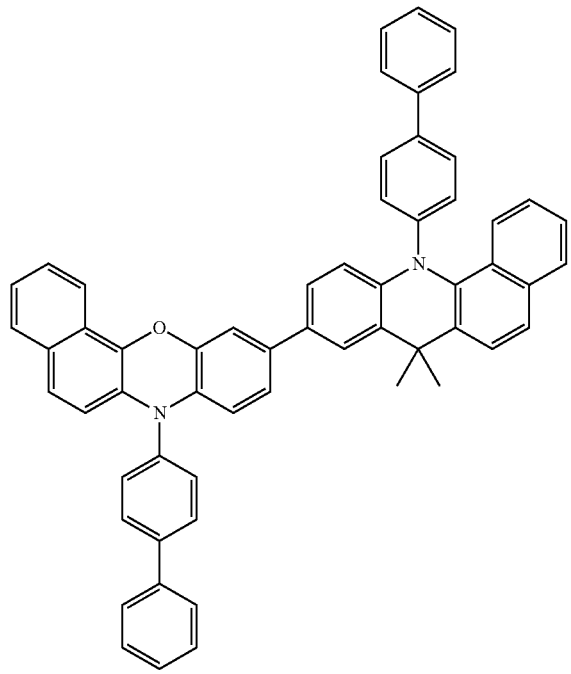 [SMILES: CC1(C)c2cc(-c3ccc4c(c3)Oc3c(ccc5ccccc35)N4c3ccc(-c4ccccc4)cc3)ccc2N(c2ccc(-c3ccccc3)cc2)c2c1ccc1ccccc21]

2. An organic electroluminescence device comprising an anode, a cathode and one or more organic layers formed between the anode and the cathode, wherein at least one of the organic layers comprises the organic compound according to claim 1.

3. The organic electroluminescence device according to claim 2, wherein the organic layers comprise an emissive layer having a host, and wherein the organic compound is comprised as the host.

4. The organic electroluminescence device according to claim 2, wherein the organic layers comprise a hole blocking layer, and wherein the organic compound of claim 1 is comprised as the hole blocking layer.

5. The organic electroluminescence device according to claim 2, wherein the organic electroluminescence device is a lighting panel.

6. The organic electroluminescence device according to claim 2, wherein the organic electroluminescence device is a backlight panel.

* * * * *